United States Patent
Jin et al.

(10) Patent No.: US 12,281,117 B2
(45) Date of Patent: Apr. 22, 2025

(54) SMALL MOLECULE IMMUNE AGONISTS AND IMMUNE TARGETING COMPOUNDS AND APPLICATION THEREOF

(71) Applicant: SHENZHEN UNIVERSITY, Guangdong (CN)

(72) Inventors: Guangyi Jin, Guangdong (CN); Zhulin Wang, Guangdong (CN); Li Tang, Guangdong (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 1235 days.

(21) Appl. No.: 17/044,659

(22) PCT Filed: Apr. 2, 2019

(86) PCT No.: PCT/CN2019/080945
§ 371 (c)(1),
(2) Date: Mar. 17, 2021

(87) PCT Pub. No.: WO2019/192454
PCT Pub. Date: Oct. 10, 2019

(65) Prior Publication Data
US 2021/0038605 A1   Feb. 11, 2021
US 2023/0148436 A2   May 11, 2023

(30) Foreign Application Priority Data

Apr. 3, 2018  (CN) .......................... 201810289351.7
Apr. 13, 2018 (CN) .......................... 201810331582.X

(51) Int. Cl.
A61K 31/52   (2006.01)
A61K 47/54   (2017.01)
(Continued)

(52) U.S. Cl.
CPC ............ *C07D 473/18* (2013.01); *A61K 31/52* (2013.01); *A61K 47/54* (2017.08); *A61K 47/545* (2017.08);
(Continued)

(58) Field of Classification Search
None
See application file for complete search history.

(56) References Cited

U.S. PATENT DOCUMENTS 8,357,374 B2   1/2013   Carson et al.
8,729,088 B2   5/2014   Carson et al.
(Continued)

FOREIGN PATENT DOCUMENTS

CN   101230064   7/2008
CN   101239980   8/2008
(Continued)

OTHER PUBLICATIONS

Gao et al., Sci Rep 6, 39598 (2016) (Year: 2016).*
(Continued)

*Primary Examiner* — Karl J Puttlitz
(74) *Attorney, Agent, or Firm* — Ballard Spahr LLP

(57) ABSTRACT

Provided is a series of homologous small molecule immune agonists and novel bifunctional immune targeting compounds having targeting and immune activation functions, which are obtained by coupling the small molecule immune agonists to targeting drugs. The resulting immune targeting compounds are beneficial for enhancing immune activation effects, and anti-tumor and other disease fighting effects of the targeting drug. The enhanced effect is produced from a synergy of immunological anti-tumor factors (such as IFN-γ) and inhibition at pathogenic targeting sites.

3 Claims, 30 Drawing Sheets

(51) Int. Cl.
  *A61K 47/64* (2017.01)
  *A61K 47/68* (2017.01)
  *A61P 35/00* (2006.01)
  *C07D 473/18* (2006.01)

(52) U.S. Cl.
  CPC .......... *A61K 47/64* (2017.08); *A61K 47/6803* (2017.08); *A61P 35/00* (2018.01)

(56) References Cited

U.S. PATENT DOCUMENTS

| | | |
|---|---|---|
| 8,790,655 B2 | 7/2014 | Carson et al. |
| 9,050,376 B2 | 6/2015 | Carson et al. |
| 2015/0284445 A1 | 10/2015 | Ida |
| 2018/0339987 A1 | 11/2018 | Jin et al. |

FOREIGN PATENT DOCUMENTS

| | | | |
|---|---|---|---|
| CN | 102439011 | | 5/2012 |
| CN | 102993265 | * | 3/2013 |
| CN | 105315281 | * | 10/2016 |
| CN | 106267188 | | 1/2017 |
| CN | 107281483 | | 10/2017 |
| CN | 107281484 | | 10/2017 |
| CN | 108379591 | | 8/2018 |
| CN | 101790380 | | 7/2020 |
| WO | WO 2010/093436 A2 | | 8/2010 |
| WO | WO 2018032793 | | 2/2018 |
| WO | WO 2018214699 | | 11/2018 |
| WO | WO 2018219266 | | 12/2018 |
| WO | WO 2019192454 | | 10/2019 |

OTHER PUBLICATIONS

Database Caplus Chemical Abstracts Service, Columbus, Ohio, US; Registry No. 1429327-81-0, Entered: Apr. 26, 2013 (Year: 2013).*

Search Report for Chinese Priority Application No. 201810331582X, dated Nov. 3, 2020.

International Search Report and Written Opinion mailed on Jun. 28, 2018 by the International Searching Authority for Patent Application No. PCT/CN2019/0801945, which was filed on Apr. 3, 2018 and published as WO 2019/192454 on Oct. 10, 2019 (Inventor—Jin et al.; Applicant—Shenzhen University) (16 pages).

* cited by examiner

SMALL MOLECULE IMMUNE AGONISTS AND IMMUNE TARGETING COMPOUNDS AND APPLICATION THEREOF

CROSS-REFERENCE TO RELATED APPLICATIONS

This application is a U.S. National Phase Application of International Application No. PCT/CN2019/080945, filed Apr. 2, 2019, which claims priority to Chinese Application No. 201810289351.7, filed Apr. 3, 2018, and Chinese Application No. 201810331582.X, filed Apr. 13, 2018, each of which are hereby incorporated by reference in their entirety.

FIELD OF THE INVENTION

The present invention relates to a series of small-molecule immune agonists which are homologues, and to immune targeted compounds which are obtained by conjugating the agonists with targeted drugs and their applications, belonging to the field of an interdisciplinary science covering medicinal chemistry and immunology.

BACKGROUND OF THE INVENTION

Toll-like receptors (TLRs) present an organism's first line of defense in the defense system (Kaisho, T. & Akira, S. Toll-like receptor function and signaling. J. Allergy Clin. Immunol. 117, 979-987 (2006); Miyake, K. Innate immune sensing of pathogens and danger signals by cell surface Toll-like receptors. Semin. Immunol. 19, 3-10 (2007)). In particular, toll-like receptor 7 (TLR7), which is activated by single-stranded RNAs (ssRNAs) as its natural ligand, plays a crucial role in the defense against invasions of ssRNA viruses (Blasius, A. L. & Beutler, B. Intracellular toll-like receptors. Immunity 32, 305-315 (2010)). Furthermore, TLR7 can be activated by artificially-synthesized small-molecule compounds to induce immunomodulation of the organism, and thus plays an important role in both anti-viral and anti-tumor therapies (Huju Chi, Chunman Li, Flora Sha Zhao, Li Zhang, Tzi Bun Ng, Guangyi Jin and Ou Sha. Anti-tumor Activity of Toll-Like Receptor 7 Agonists. Front Pharmacol. 2017 May 31; 8:304. doi:10.3389/fphar.2017.00304).

Tyrosine kinase inhibitors (TKIs), as the representatives of anti-tumor targeted therapeutic agents, can prolong the lives of patients; however, most patients will develop drug resistance within about one year or less. In order to address the drug resistance of TKIs, in earlier studies we had explored the combined administration of TKIs and TLR7 immune agonists in an attempt to achieve immune-targeted synergistic effects. Nevertheless, the laboratory results showed that the TKIs antagonized the immunostimulatory effects of TLR7 agonist on immunocytes and inhibited the production of immunostimulatory cytokines (Scientific Reports, 2016 Dec. 21; 6:39598.doi:10.1038/srep39598).

SUMMARY OF THE INVENTION

The objective of the present invention is on one hand to provide a series of small-molecule immune agonists having immunostimulatory effects and their applications, and on the other hand to provide immune targeted compounds obtained by conjugating said small-molecule immune agonists with targeted drugs and their applications.

In the first aspect, the present invention relates to small-molecule immune agonists of Formula (I), or isomers or pharmaceutically acceptable salts thereof:

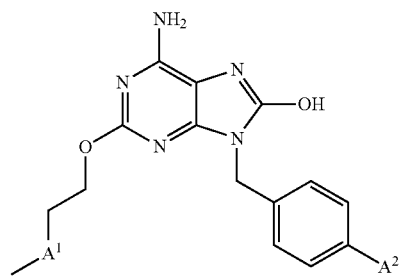

Formula (I)

wherein $A^1$ represents O or C;

$A^2$ represents a nitro, amino, isocyanate, alkyleneamino, alkylene isocyanate, or a group selected from Formula (II) or (III):

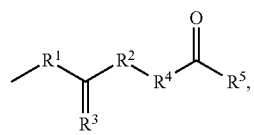

Formula (II)

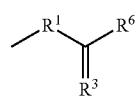

Formula (III)

wherein $R^1$ and $R^2$ each independently represent $(CH_2)_p(NH)_q$, where p is 0, 1 or 2, and q is 0, 1 or 2;

$R^3$ represents O or S;

$R^4$ represents $(CH_2)_x(C=O)_y(NH)_z[(CH_2)_2O]_r(CH_2)_s(C=C)_t$, where x is an integer ranging from 0 to 5; y is 0, 1 or 2; z is 0, 1 or 2; r is 0, 1, 2 or 3; s is an integer ranging from 0 to 5 and t is 0, 1 or 2, wherein when s≠0 and t=0, the carbon atom adjacent to the carbonyl group in $(CH_2)_s$ may be substituted by a group selected from —NHBoc, an amino group, —NHFmoc,

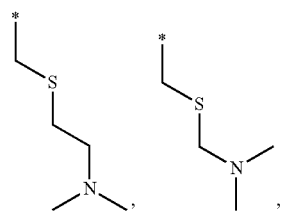

-continued
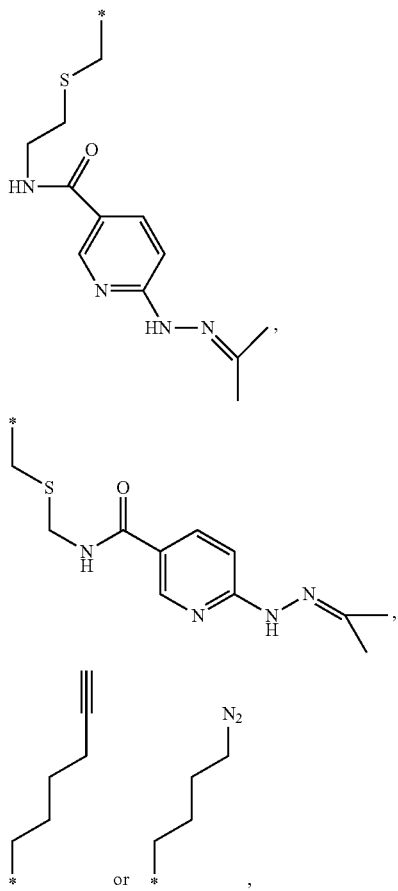
or forming a double bond with another carbon atom;
R⁵ represents a hydroxy, alkoxy, hydroxylamine, vinyl group or a group selected from:
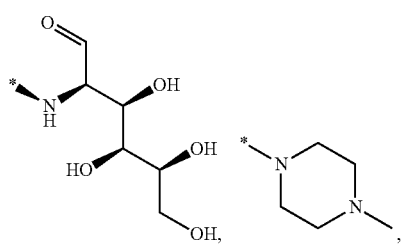
-continued
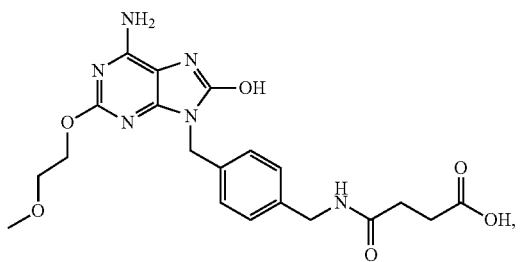
R⁶ represents alkyl or a group selected from:
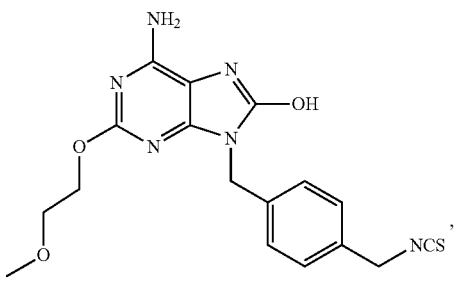
where * denotes the site linked to the carbon atom;
with the proviso that the following compounds are excluded:

-continued
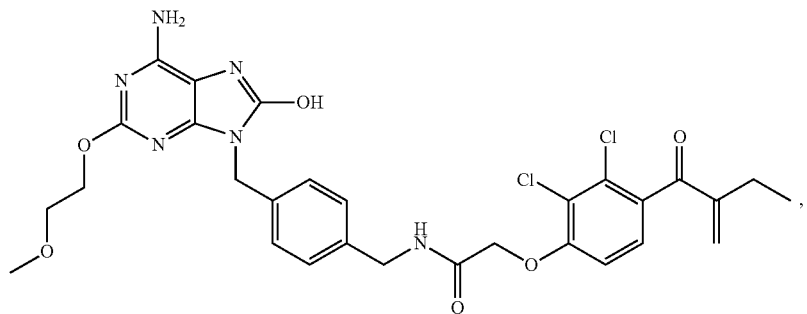
(SZU-103)
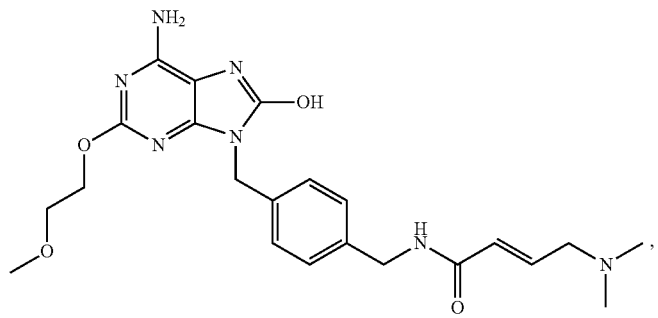 [SMILES: COCCOc1nc(N)c2nc(O)n(Cc3ccc(CNC(=O)CCCC(=O)O)cc3)c2n1]
(SZY-114)
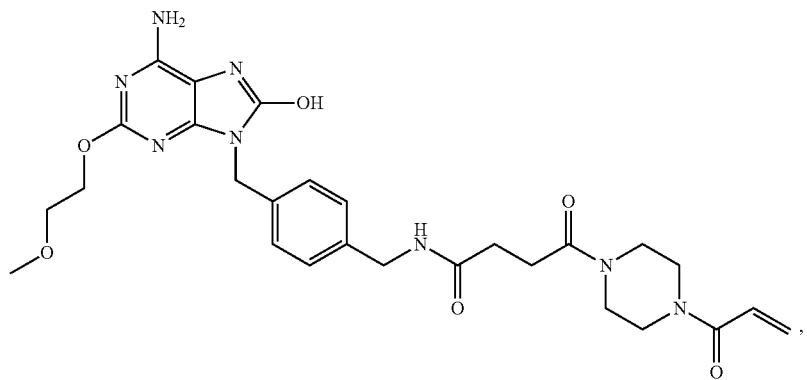
(SZU-117)
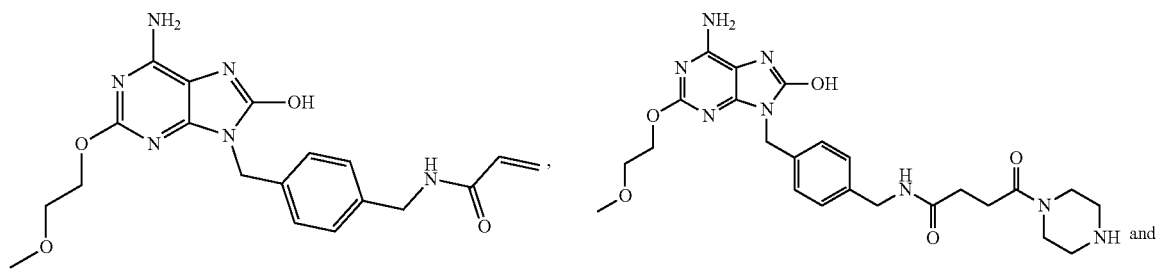
(SZU-122) (SZU-130)
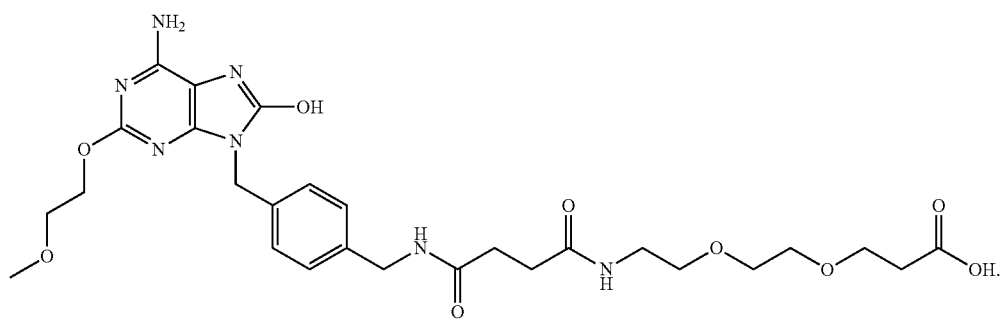 [SMILES: COCCOc1nc(N)c2nc(O)n(Cc3ccc(CNC(=O)CCC(=O)NCCOCCOCCC(=O)O)cc3)c2n1]
(SZU-106)

Preferably, the isomer is a geometric isomer or an enantiomer.

In a preferred embodiment, the present invention relates to small-molecule immune agonists of formula (I), or isomers or pharmaceutically acceptable salts thereof:

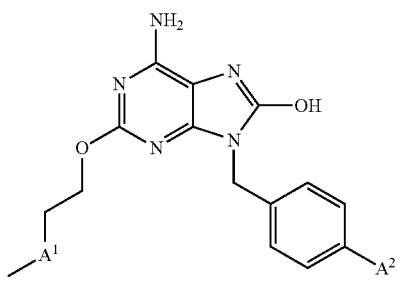

wherein $A^1$ represents O or C;

$A^2$ represents a nitro, amino, isocyanate, $C_1$-$C_6$ alkylene amino, $C_1$-$C_6$ alkylene isocyanate or a group selected from formula (II) or (III):

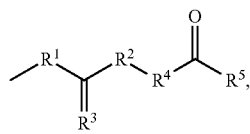

Formula (II)

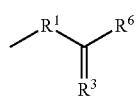

Formula (III)

wherein $R^1$ and $R^2$ each independently represent $(CH_2)_p(NH)_q$, where p is 0 or 1; and q is 0 or 1;

$R^3$ represents O or S;

$R^4$ represents $(CH_2)_x(C=O)_y(NH)_z[(CH_2)_2O]_r(CH_2)_s(C=C)_t$, where x is an integer ranging from 0 to 5; y is 0 or 1; z is 0 or 1; r is 0, 1, 2 or 3; s is an integer ranging from 0 to 5 and t is 0 or 1, wherein when s≠0 and t=0, the carbon atom adjacent to the carbonyl group in $(CH_2)_s$ may be substituted by a group selected from —NHBoc, an amino group, —NHFmoc,

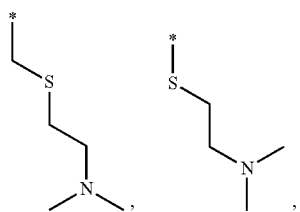

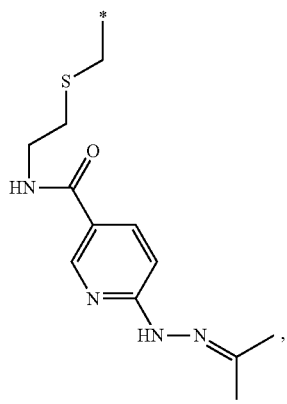

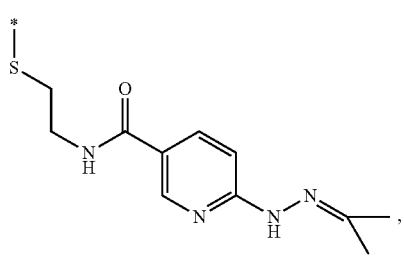

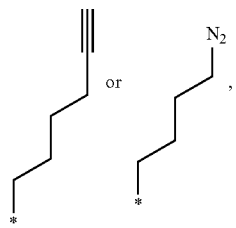

or forming a double bond with another carbon atom;

$R^5$ represents a hydroxyl, $C_1$-$C_6$ alkoxy, hydroxylamine, vinyl group or a group selected from:

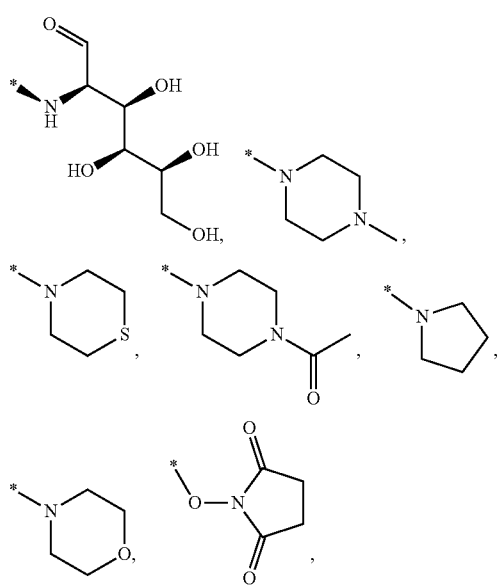

-continued
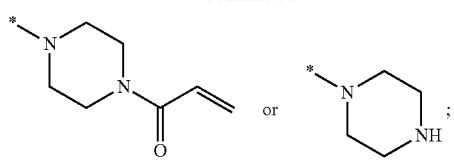
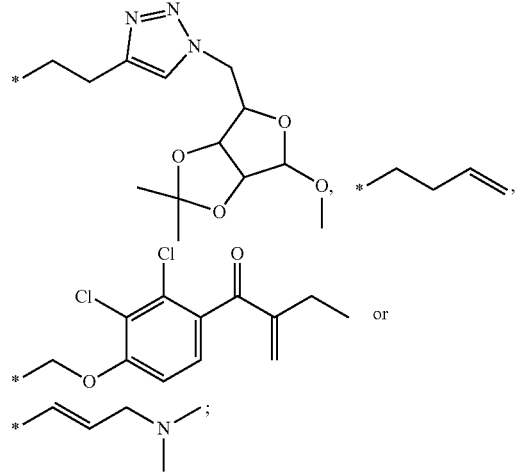
$R^6$ represents $C_1$-$C_6$ alkyl group or a group selected from:
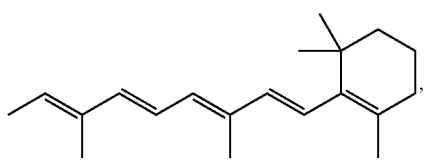
wherein * denotes the site linked to the carbon atom;
with the proviso that the following compounds are excluded:
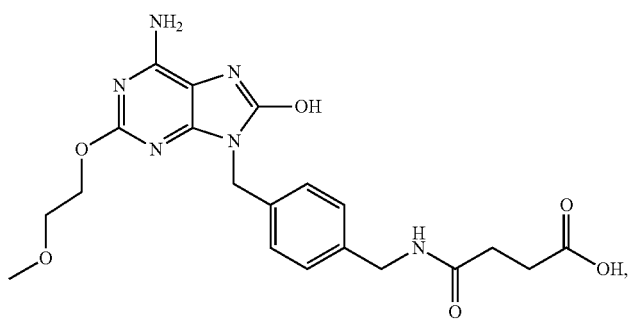
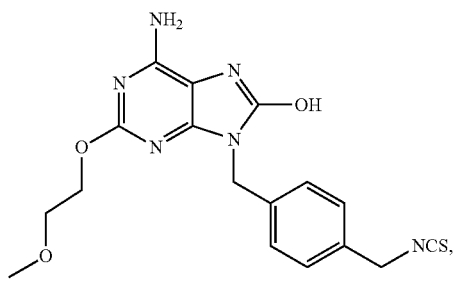
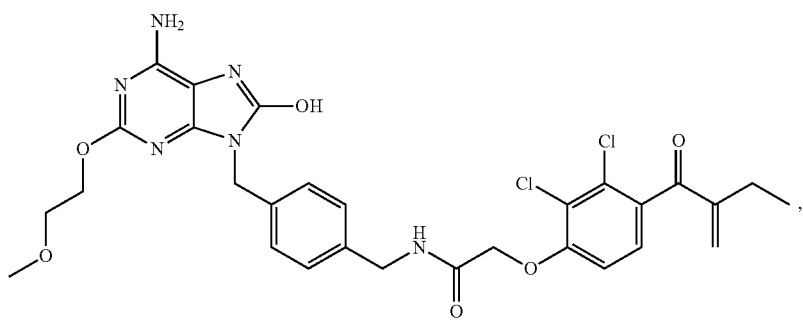

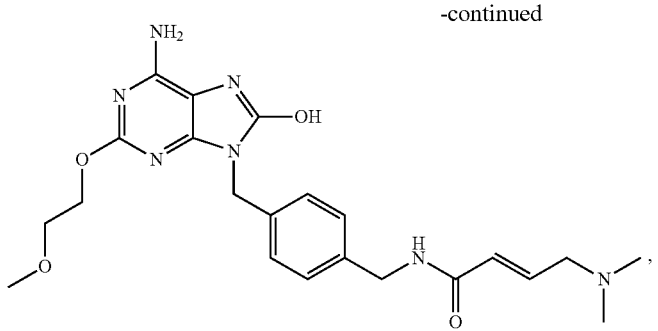
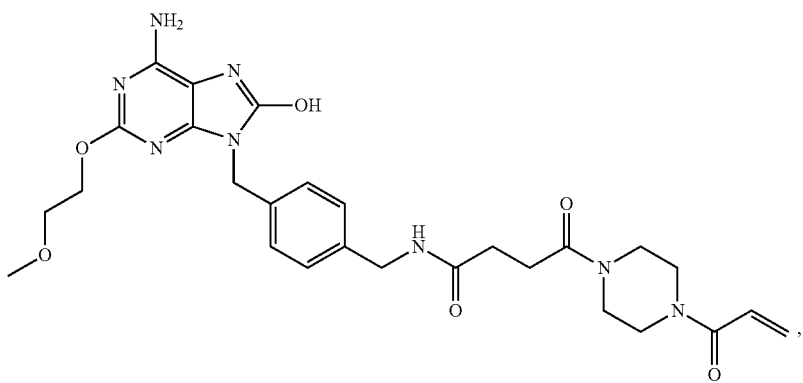
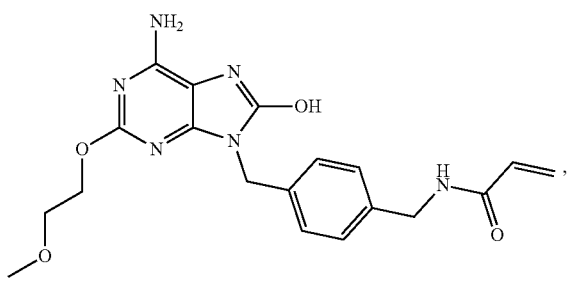
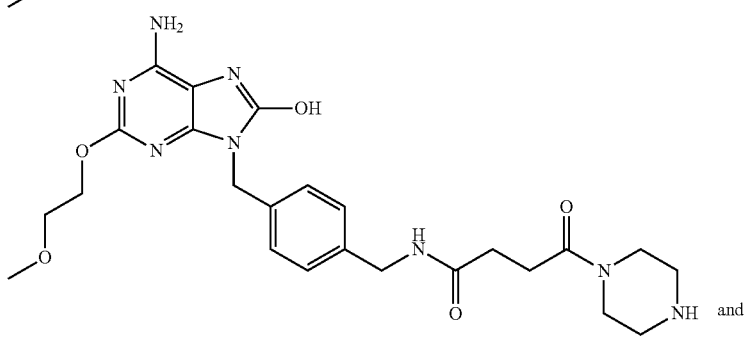
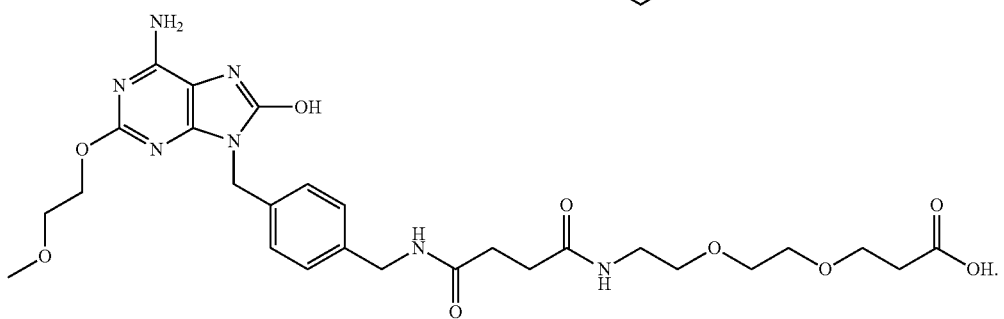

In a further preferred embodiment, the present invention relates to small-molecule immune agonists of Formula (I), or isomers or pharmaceutically acceptable salts thereof:

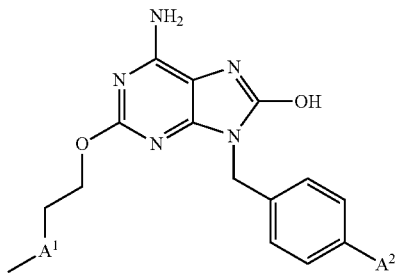

Formula (I)

wherein, $A^1$ represents O or C;

$A^2$ represents a nitro, amino, isocyanate, methylene amino, methylene isocyanate or a group selected from Formula (II) or Formula (III):

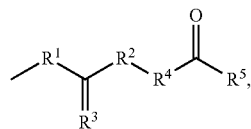

Formula (II)

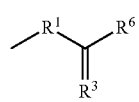

Formula (III)

wherein, $R^1$ and $R^2$ each independently represent $(CH_2)_p(NH)_q$, where p is 0 or 1, and q is 0 or 1;

$R^3$ represents O or S;

$R^4$ represents $(CH_2)_x(C=O)_y(NH)_z[(CH_2)_2O]_r(CH_2)_s(C=C)_t$, where x is an integer ranging from 0 to 5; y is 0 or 1; z is 0 or 1; r is 0, 1, 2 or 3; s is an integer ranging from 0 to 5 and t is 0 or 1, wherein when s≠0 and t=0, the carbon atom adjacent to the carbonyl group in $(CH_2)_s$ may be substituted by a group selected from —NHBoc, an amino group, —NHFmoc,

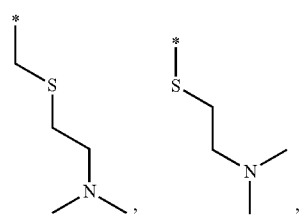

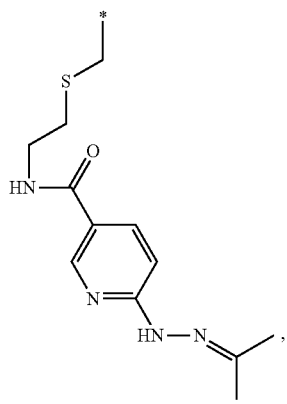

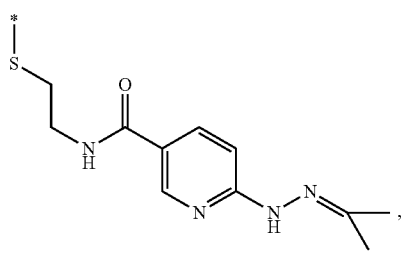

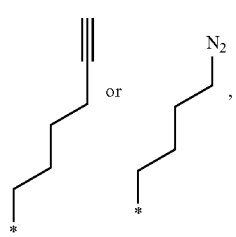

or forming a double bond with another carbon atom;

$R^5$ represents a hydroxyl, methoxy, hydroxylamine, vinyl group or a group selected from:

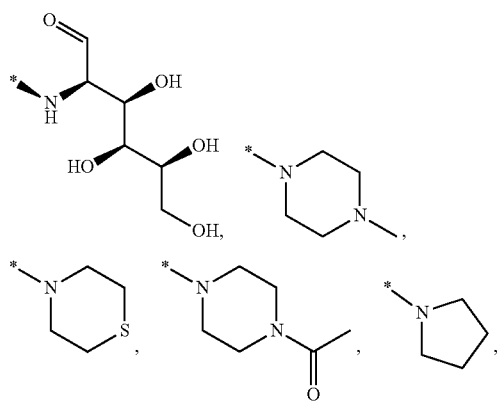

15
-continued
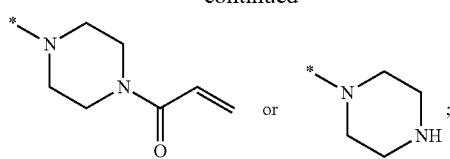
or
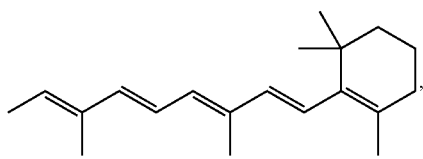
;
$R^6$ represents a methyl group or a group selected from:
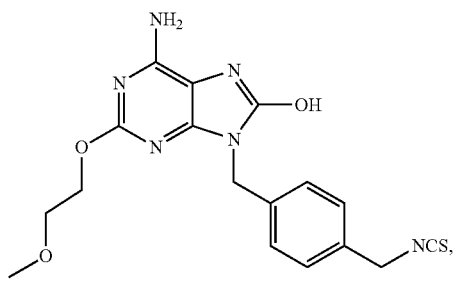
,
16
-continued
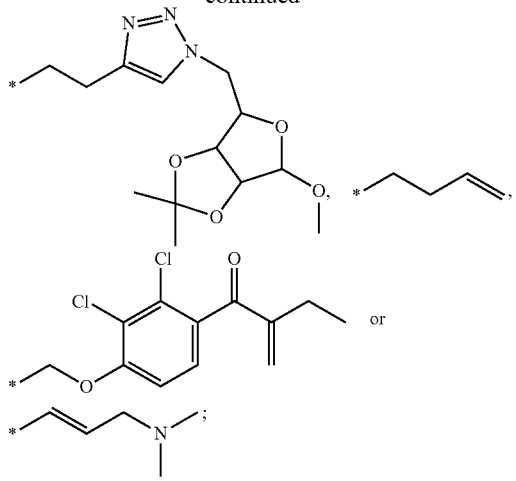
, *⌒⌒∥,
or
*⌒⌒N(CH3)2 ;
wherein * denotes the site linked to the carbon atom;
with the proviso that the following compounds are excluded:
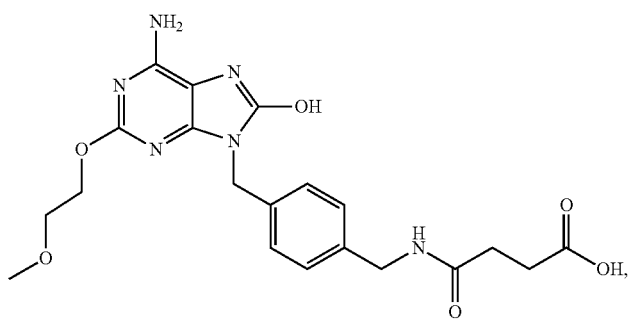
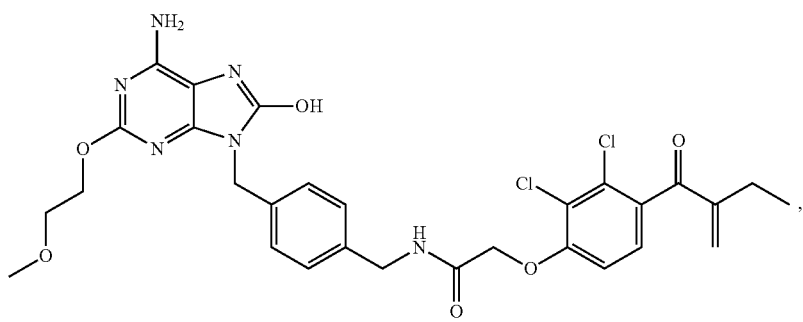

-continued
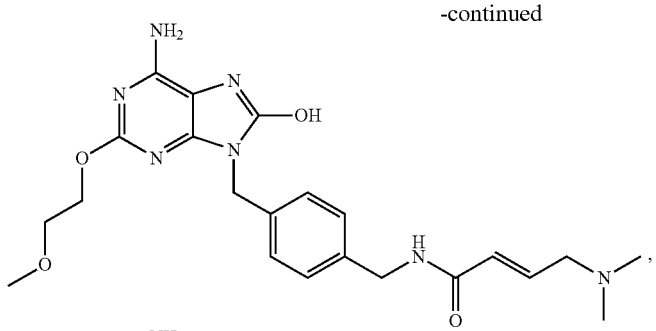
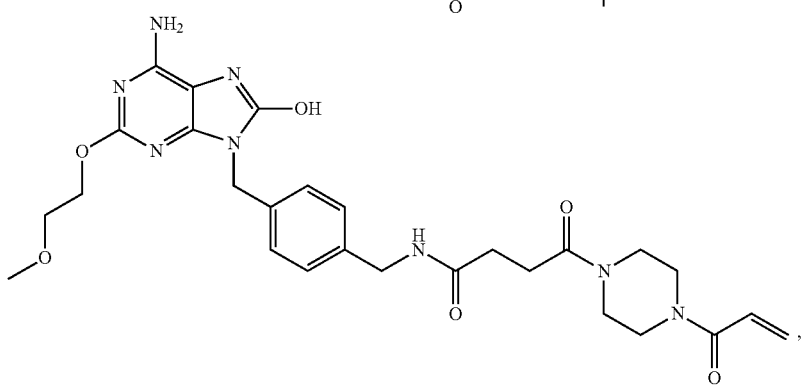
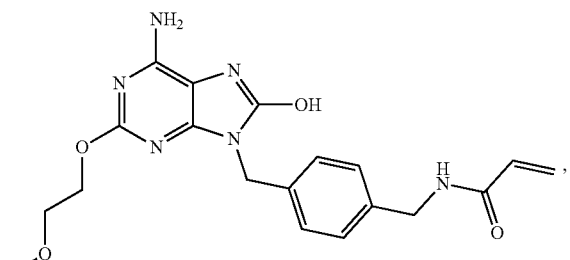
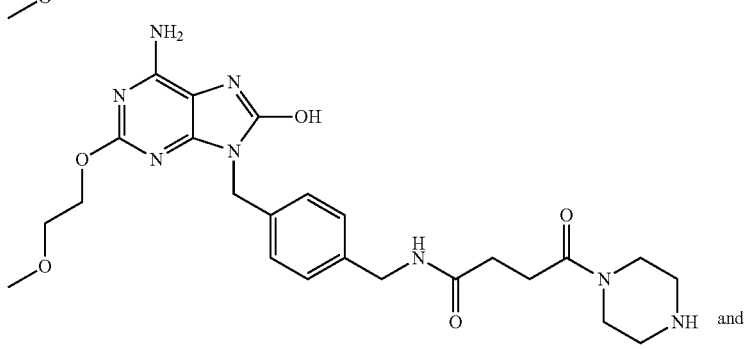
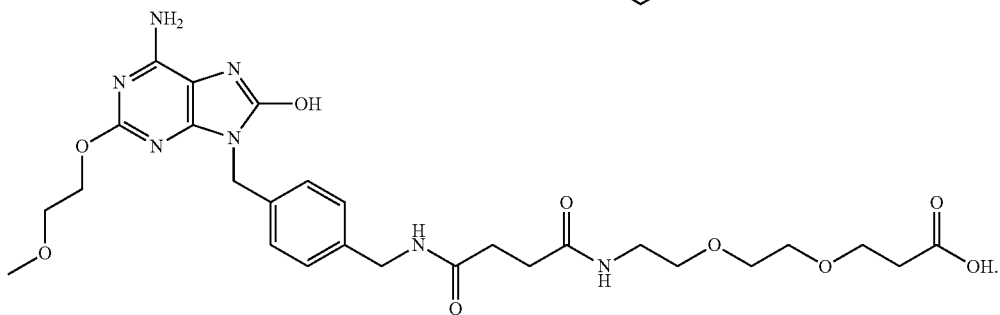
In a preferred embodiment, the present invention relates to small-molecule immune agonists of Formula (I), or isomers or pharmaceutically acceptable salts thereof, which are SZU-series compounds selected from the group consisting of (see Table 1 shown below for specific structural formulae): SZU-104, SZU-105, SZU-107, SZU-108, SZU-109, SZU-110, SZU-111, SZU-112, SZU-113, SZU-115, SZU-118, SZU-120, SZU-127, SZU-128, SZU-129, SZU-131, SZU-132, SZU-133, SZU-134, SZU-135, SZU-136, SZU-137, SZU-138, SZU-139, SZU-140, SZU-142, SZU-143, SZU-144, SZU-145, SZU-149, SZU-158, SZU-159, SZU-160, SZU-161, SZU-162, SZU-163, SZU-166 and SZU-171, or pharmaceutically acceptable salts thereof.

In the second aspect, the present invention relates to immune targeted compounds or pharmaceutically acceptable salts thereof, which are formed by covalently conjugating the small-molecule immune agonists or an addition product formed from the immune agonists and mercapto-containing polypeptides such as glutathione, with targeted drugs or antibodies, and represented by the following general formula:

(TLA)$_n$-L-(Tar)$_m$ wherein, TLA represents small-molecule immune agonists or their addition products with mercapto-containing polypeptides such as glutathione; Tar represents targeted drugs or antibodies; n and m each independently represent a numerical value ranging from 1 to 5; L represents a linker, which is linear or branched alkyl or polyethylene glycol chain, and both ends of L are covalently linked to TLA and/or Tar directly or via additional groups.

In a preferred embodiment, the small-molecule immune agonists comprise the small-molecule immune agonists as described in the first aspect of the present invention and compounds selected from the group consisting of:

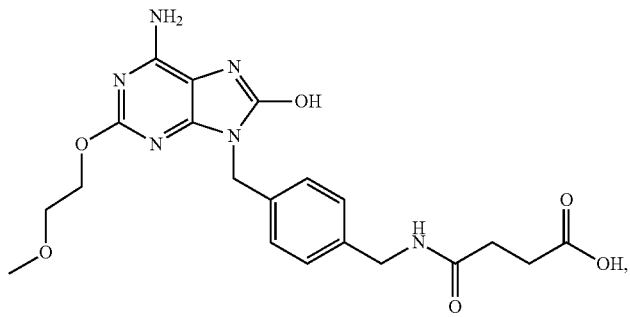

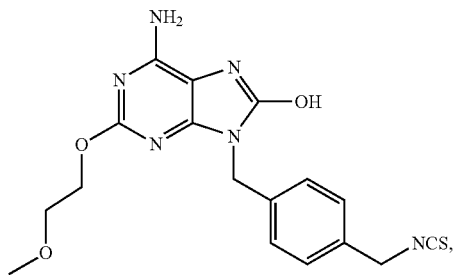

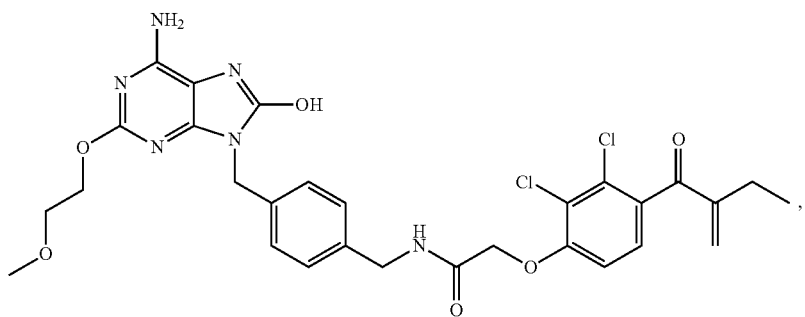

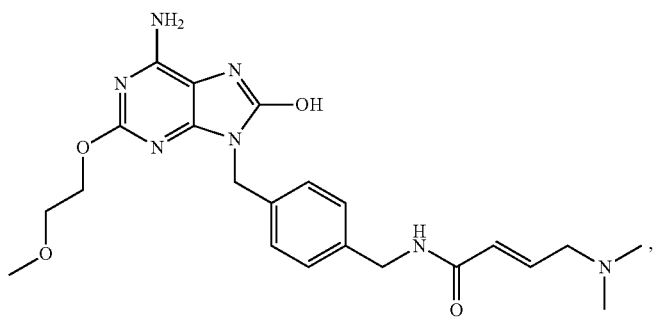

-continued

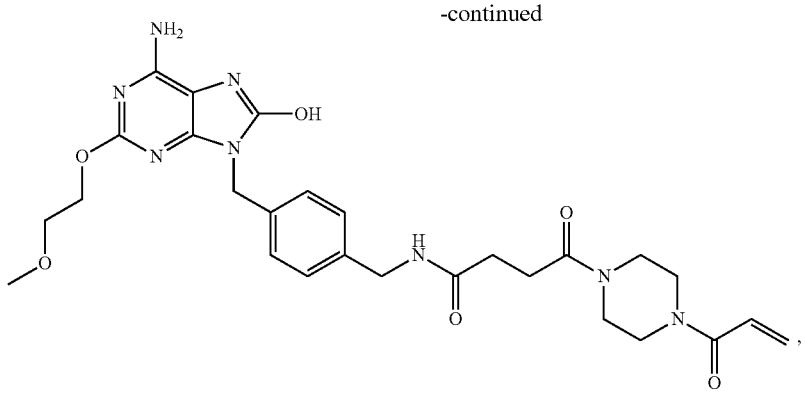

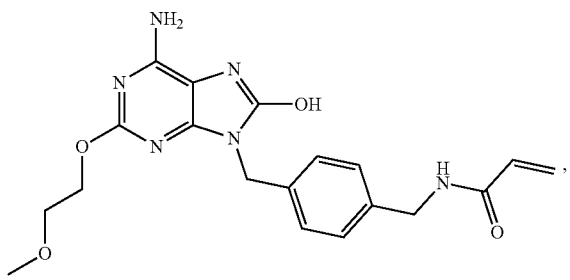

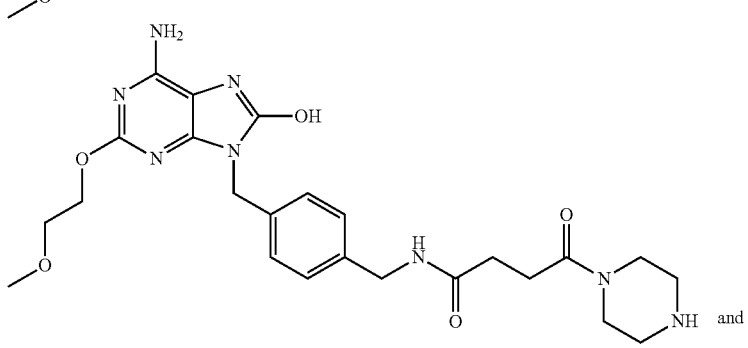

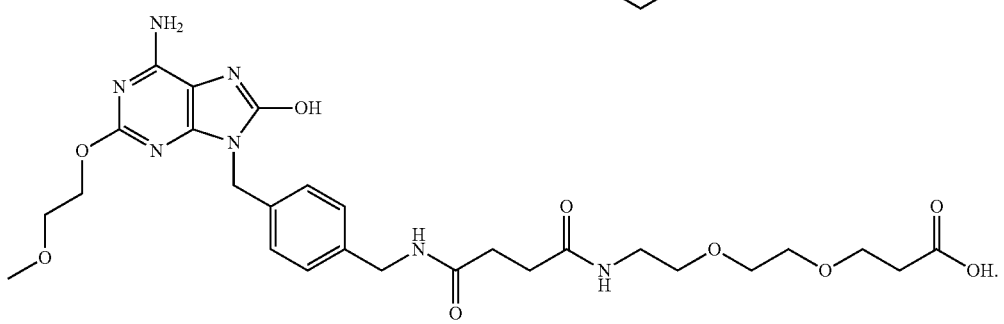

In a preferred embodiment, the small-molecule immune agonists are SZU-series compounds selected from the group consisting of (see Table 1 shown below for specific structural formulae): SZU-102, SZU-104, SZU-105, SZU-106, SZU-107, SZU-108, SZU-109, SZU-110, SZU-111, SZU-112, SZU-113, SZU-115, SZU-118, SZU-120, SZU-127, SZU-128, SZU-129, SZU-131, SZU-132, SZU-133, SZU-134, SZU-135, SZU-136, SZU-137, SZU-138, SZU-139, SZU-140, SZU-142, SZU-143, SZU-144, SZU-145, SZU-149, SZU-158, SZU-159, SZU-160, SZU-161, SZU-162, SZU-163, SZU-166, SZU-171, SZU-101, SZU-103, SZU-114, SZU-117, SZU-122 and SZU-130, or pharmaceutically acceptable salts thereof.

In a preferred embodiment, the TLA represents compounds selected from the group consisting of (see Table 3 shown below for specific structural formulae): SZU-103-GSH, SZU-114-GSH, SZU-117-GSH, SZU-122-GSH, SZU-127-GSH, SZU-133-GSH, SZU-138-GSH and SZU-144-GSH.

In a preferred embodiment, the Tar represents at least one compound selected from the group consisting of: Dasatinib, Imatinib, Saracatinib, Ponatinib, Nilotinib, Danusertib, AT9283Degrasyn, Bafetinib, kw-2449, nyp-bhg712, dcc-2036, GZD824, GNF-2, PD173955, GNF-5, Bosutinib, Gefitinib, Erlotinib, Sunitinib, Ruxolitinib, Tofacitinib, Lapatinib, Vandetanib, Sorafenib, Sunitinib, Axitinib, Nintedanib, Regorafenib, Pazopanib, Lenvatinib, Crizotinib, Ceritinib, Cabozantinib, DWF, Afatinib, Ibrutinib, Niraparib, Palbociclib, B43, KU004, Foreinib, KRCA-0008, PF-06439015, PF-06463922, Canerlinib, GSA-10, GW2974, GW583340, W24002, CP-380736, D2667, Mubritinib, PD153035, PD168393, Pelitinib, PF-06459988, PF06672131, PF-6422899, PKI166, ReveromycinA, Tyrphostin1, tyrphostin23, lyrphostin51, Tyrphostin AG528, Tyrphostin AG658, Tyrphostin AG825, Tyrphostin AG835, Tyrphostin AG1478, Tyrphostin RG13022, Tyrphostin RG14620, B178, GSK1838705A, PD-161570, PD173074, SU-5402, Roslin2, Picropodophyllotoxin, PQ401, i-ometyrphostin, AG538, GNF5837, GW441756, Tyrphostin, AG879, DMPQ, jnj-10198409, PLX647, Trapidil, TyrphostinA9, Tyrhostin, AG370, Lestaurtinib, DMH4, Eldanamvcin, Genistein, Gw2580, HerbimycinA, Lavendustin, CMidostaurin, nvp-bhg712, PD158780, pd-166866, pf-0627334, PP2, RPL, SU11274, SU5614, Symadex, Tyrphostin AG34, Tyrphostin AG974, Tyrphostin AG1007, UNC2881, Honokiol, SU1498, SKLB1002, cp-547632, jk-p3, KRN633, sc-1, ST638, SU 5416, Sulochrin, Tyrphostin SU1498, rociletinib, Dacomitinib, Tivantinib, Neratinib, Masitinib, Vatalanib, Icotinib, xl-184, osi-930, AB1010, Quizartinib, AZD9291, Tandutinib, HM61713, Brigantinib, Vemurafenib(plx-4032), Semaxanib, AZD2171, Crenolanib, Damnacanthal, Fostamatinib, Motesanib, Radotinib, osi-027, Linsitinib, BIX02189, PF-431396, PND-1186, PF-03814735, PF-431396, sirollmus, temsirolimus, everolimus, deforolimus, Zotarolimus, BEZ235, INK128, Omipalisib, AZD8055, MHY1485, PI-103, KU-0063794, ETP-46464, GDC0349, XL388, WYE-354, WYE-132, GiSK1059615, WAY-600, PF-04691502, wYE-687, PP121, BGT226, AZD2o014, PP242, CH5132799, P529, GDC0980, GDC-0994, XMD82, Ulixertinib, FR180204, SCH772984, Trametinib, PD184352, PD98059, Selumetinib, PD325901, U0126, Pimasertinib, tak-733, AZD8330, Binimetinib, PD318088, SL-327, Refametinib, gdc-0623, Cobimetinib, bl-847325, Adaphostin, GNF2, PPYA, aim-100, ASP 3026, LFM, Toceranib, JQ1, Niraparib, Fuzuopali, palbociclib, ARS-853, ARS-1620, Chlorazol-violet N (Direct violet N), miRNA-21, PreS, Zidovudine, Lenvatinib, LY-364947, ARS-1620 or Reparixin, EGFR inhibitors, TKI, BRD4 inhibitors, KRAS pathway-related target inhibitors, BRAF inhibitors, BTK Inhibitors, PARP inhibitors, PD-L1 inhibitors (including antibodies and small-molecules), PD-1 inhibitors (including antibodies and small-molecules), OX40 agonists (including antibodies and small-molecules), CD122 antibodies, CD3 antibodies, CD19 inhibitors, CD20 inhibitors, MUC1 inhibitors, MUC16 inhibitors, CDK4/6 inhibitors, TGF-β inhibitors, CXCR inhibitors, CCL and CXCL chemokine inhibitors and miRNAs.

In a further preferred embodiment, the Tar represents at least one of the compounds selected from the group consisting of: TKI, EGFR inhibitors, KRAS inhibitors, BRAF inhibitors, BTK inhibitors, BRD4 inhibitors, PD-L1 inhibitors, PD-1 inhibitors, OX40 agonists, PARP inhibitors and CDK4/6 inhibitors.

In a preferred embodiment, L is

In a preferred embodiment, the additional groups include amides, alkoxy bonds, alkylthio bonds, substituted amine groups, quaternary amine salts, heterocycles formed by Click reaction, amino acid groups that are dissociable by proteases, ureido or thiourea groups.

In a preferred embodiment, the immune targeted compounds or pharmaceutically acceptable salts thereof are SZU-series compounds selected from the group consisting of (see Table 4 shown below for specific structural formulae): SZU-116, SZU-119, SZU-124, SZU-125, SZU-146, SZU-147, SZU-168, SZU-169, SZU-174, SZU-175, SZU-176, SZU-177, SZU-178, SZU-179, SZU-180, SZU-181, SZU-158-PD-L1, SZU-158-OX40, SZU-158-PD-1 or SZU-136-miRNA21, or pharmaceutically acceptable salts thereof.

In the third aspect, the present invention relates to use of the small-molecule immune agonists of formula (I) or isomers or pharmaceutically acceptable salts thereof according to the first aspect of the present invention, compounds SZU-101, SZU-103, SZU-114, SZU-117, SZU-122 and SZU-130 (see Table 2 shown below for specific structural formulae) and the immune targeted compounds or pharmaceutically acceptable salts thereof according to the second aspect of the present invention, in the manufacture of a medicament that participates in immunomodulation.

In the fourth aspect, the present invention relates to use of the small-molecule immune agonists of formula (I) or isomers or pharmaceutically acceptable salts thereof according to the first aspect of the present invention, compounds SZU-101, SZU-103, SZU-114, SZU-117, SZU-122 and SZU-130 and the immune targeted compounds or pharmaceutically acceptable salts thereof according to the second aspect of the present invention, in the manufacture of a medicament as an anti-tumor or anti-viral drug or for eliminating target proteins.

The present invention further relates to use of a compound SZU-136-miRNA21 and analogues thereof in the manufacture of a medicament for immunologically targeting RNA, wherein the compound SZU-136-miRNA21 and analogues thereof are useful as small molecular RNAs for immune targeting; and the medicament may be present in various dosage forms, including solid preparations, liquid preparations, and conjugates formed from the medicament with various vehicles or crystalline hydrates of the medicament.

The present invention further relates to use of compounds SZU-179, SZU-180 and SZU-181 in the manufacture of a medicament as anti-AIDS and anti-hepatitis B agents, wherein the compounds SZU-179, SZU-180 and SZU-181 are useful as antiviral immune targeted compound.

The present invention further relates to use of compounds SZU-161 and SZU-162 for determining the conjugation degree of the small-molecule immune agonists conjugated with protein drugs and cells, wherein the compounds SZU-161 and SZU-162 are useful as small-molecule immune agonists with specific ultraviolet absorption.

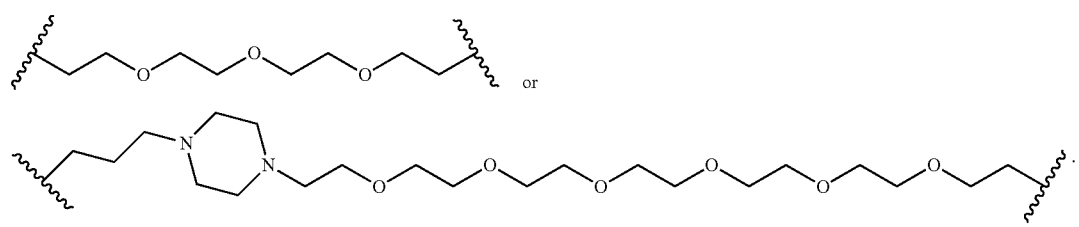

The present invention further relates to use of compounds SZU-116 and SZU-124 in observing and studying the cellular absorption and distribution in vivo of proteins or targeted drugs, wherein compounds SZU-116 and SZU-124 are conjugated with proteins or targeted drugs, and are useful as compounds with optical tracking properties of chromogenic indicators for small-molecule immune agonists. After having been conjugated with proteins or targeted drugs, they can show the cellular absorption and distribution in vivo of proteins or targeted drugs in real time.

The present invention further relates to use of compounds SZU-114, SZU-117, SZU-122, SZU-127, SZU-133, SZU-138, and SZU-143 in the manufacture of a medicament with dual immune targeted functions, wherein the compounds SZU-114, SZU-117, SZU-122, SZU-127, SZU-133, SZU-138, and SZU-143 are conjugated with targeted drugs or antibodies.

Persons skilled in the art have surprisingly found that the small-molecule immune agonists of the present invention per se have immunostimulatory effects. Furthermore, it is well-known to the skilled persons that the combined application of TKI and TLR7 immune agonist will cause TKIs to antagonize the activation of TLR7 agonists on immunocytes, thereby inhibiting the production of immunostimulatory cytokines. However, by covalent conjugation of the TKIs as the targeted drugs with TLR7 small-molecule immune agonists, the inventors have surprisingly found that such covalently conjugated compounds not only maintain or improve the immunostimulatory effects of the small-molecule immune agonists, but also enhance the anti-tumor effects of the targeted drugs. The immune targeted compounds obtained by the method of the present invention are of great significance for the long-term and high-effective treatment of tumors.

The novel small-molecule immune agonists that have immunostimulatory effects and can be conjugated with targeted drugs to form immune targeted compounds with targeting action as described above are shown in Table 1 below:

TABLE 1

| Serial No. | Structural Formula | Molecular weight |
|---|---|---|
| SZU-104 | | 632.74 |
| SZU-105 | | 532.62 |
| SZU-107 | | 647.58 |

TABLE 1-continued
| Serial No. | Structural Formula | Molecular weight |
|---|---|---|
| SZU-112 | 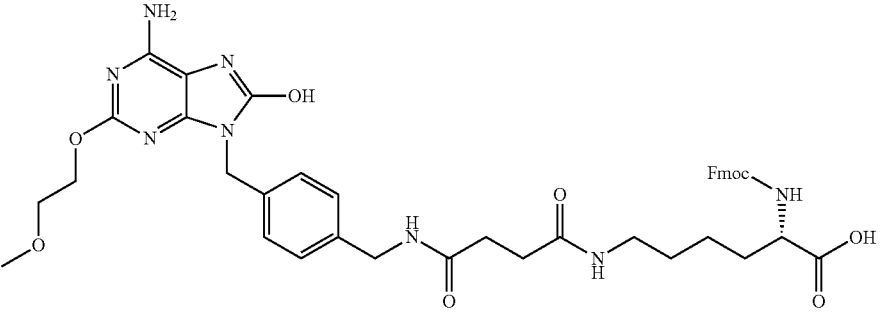 | 794.87 |
| SZU-113 | 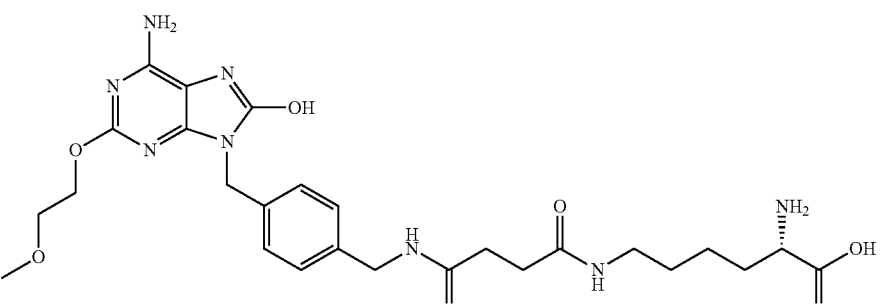 | 572.62 |
| SZU-108 | 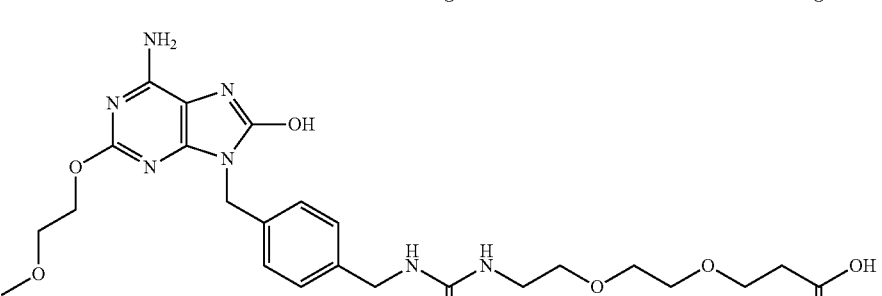 | 563.63 |
| SZU-109 | 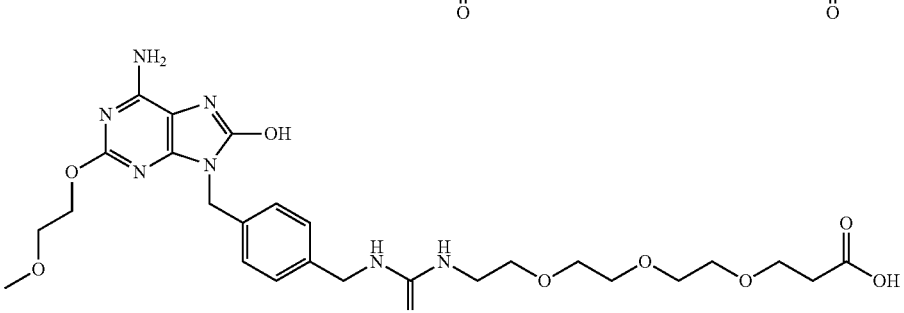 | 607.68 |
| SZU-110 | 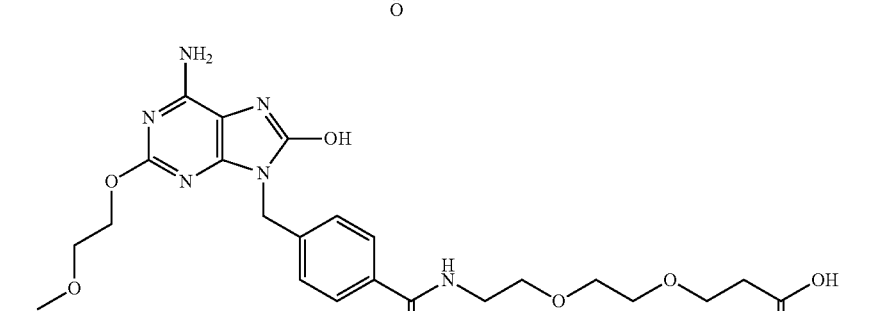 | 518.53 |

TABLE 1-continued

| Serial No. | Structural Formula | Molecular weight |
|---|---|---|
| SZU-111 | | 562.58 |
| SZU-144 | | 442.43 |
| SZU-133 | | 442.43 |
| SZU-138 | | 456.46 |

TABLE 1-continued

| Serial No. | Structural Formula | Molecular weight |
|---|---|---|
| SZU-134 | | 458.48 |
| SZU-135 | | 430.42 |
| SZU-158 | | 561.63 |
| SZU-159 | | 547.63 |

TABLE 1-continued

| Serial No. | Structural Formula | Molecular weight |
|---|---|---|
| SZU-161 | | 707.80 |
| SZU-162 | | 694.77 |
| SZU-115 | | 581.63 |

TABLE 1-continued

| Serial No. | Structural Formula | Molecular weight |
|---|---|---|
| SZU-160 | | 598.62 |
| SZU-127 | | 626.80 |
| SZU-145 | | 617.62 |
| SZU-143 | | 456.43 |

TABLE 1-continued

| Serial No. | Structural Formula | Molecular weight |
|---|---|---|
| SZU-149 | | 358.35 |
| SZU-163 | | 328.37 |
| SZU-166 | | 354.36 |
| SZU-139 | | 653.70 |
| SZU-128 | | 526.60 |

TABLE 1-continued

| Serial No. | Structural Formula | Molecular weight |
|---|---|---|
| SZU-129 | | 529.62 |
| SZU-131 | | 554.61 |
| SZU-132 | | 497.56 |
| SZU-120 | | 513.56 |

TABLE 1-continued

| Serial No. | Structural Formula | Molecular weight |
|---|---|---|
| SZU-118 | | 459.46 |
| SZU-136 | | 424.45 |
| SZU-142 | | 344.37 |
| SZU-140 | | |
| SZU-137 | | |

TABLE 1-continued

| Serial No. | Structural Formula | Molecular weight |
|---|---|---|
| SZU-171 | (structure) | |

Other small-molecule immune agonists that have immunostimulatory effects and can be conjugated with targeted drugs to form immune targeted compounds with targeting action are shown in Table 2 below:

TABLE 2

| Serial No. | Structural Formula | Molecular weight |
|---|---|---|
| SZU-101 | (structure) | |
| SZU-102 | | |
| SZU-103 | (structure) | |
| SZU-114 | (structure) | 455.52 |

TABLE 2-continued

| Serial No. | Structural Formula | Molecular weight |
|---|---|---|
| SZU-117 | | 566.62 |
| SZU-122 | | 398.42 |
| SZU-130 | | 512.57 |
| SZU-106 | | 603.63 |

Among such compounds, the structural formulae of compounds SZU-103, SZU-114, SZU-117, SZU-122 and SZU-130 and their preparation processes have been disclosed in the Chinese Patent Application CN107281483A; and the structural formulae of compounds SZU-102 and SZU-106 and their preparation processes have been disclosed in the Chinese Patent Application CN106267188A, wherein compound 1 corresponds to compound SZU-102 and compound 19 corresponds to compound SZU-106.

Some small-molecule immune agonists listed in Tables 1 and 2 can form addition products with mercapto-containing polypeptides such as glutathione (GSH), which can target glutathione transferase, result in improved therapeutic efficacy on diseases by acting synergistically with chemotherapy drugs, irreversible TKI targeted drugs and other irreversible targeted drugs, and eliminate drug resistance, while activating immunological effects. One of the addition products, SZU-117-GSH formed by reacting SZU-117 with glutathione via a synthesis process as shown in the following scheme, is illustrated as an example. Examples of the addition products formed from the small-molecule immune agonists and GSH are shown in Table 3:
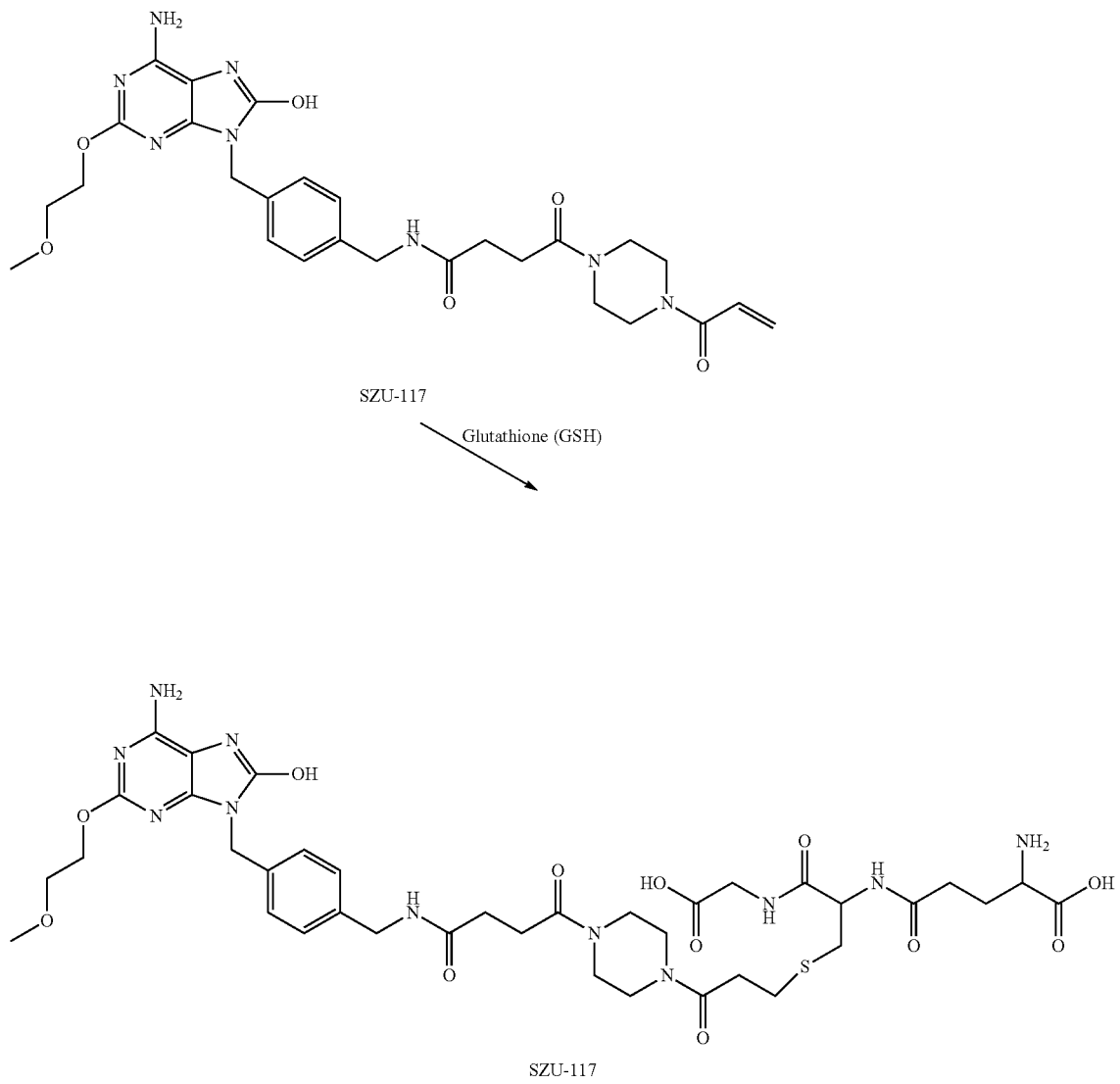
TABLE 3
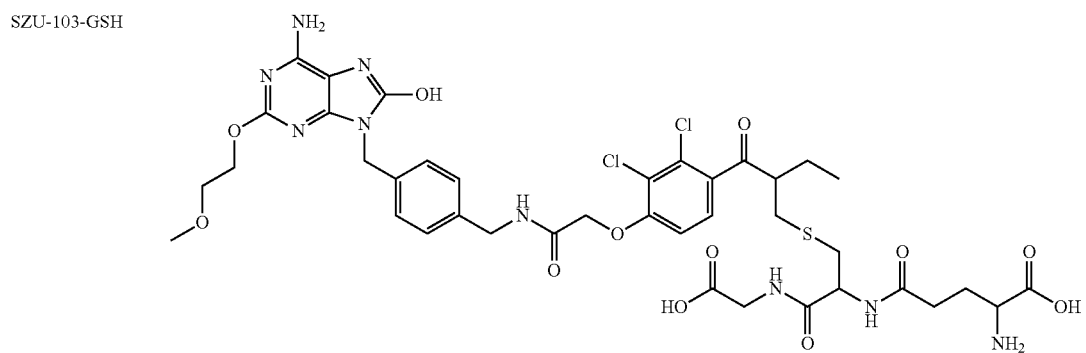

TABLE 3-continued
SZU-114-GSH
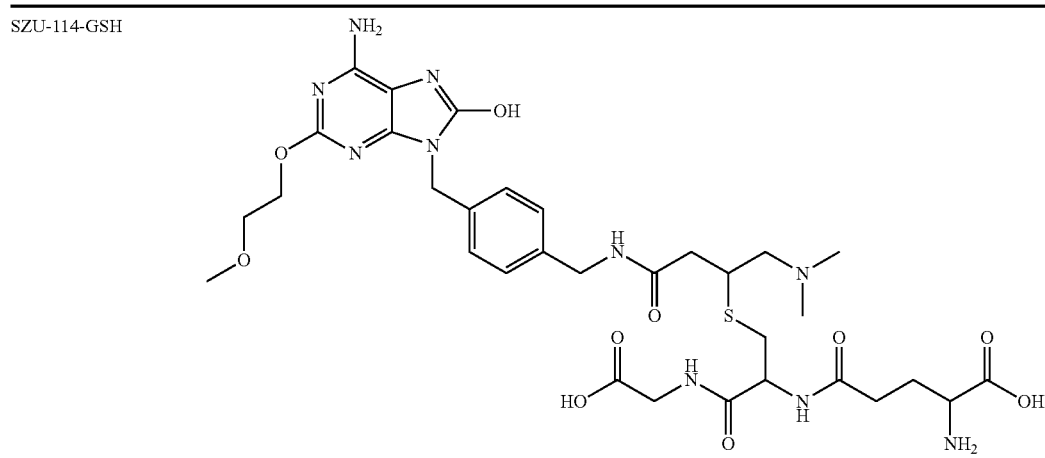
SZU-117-GSH
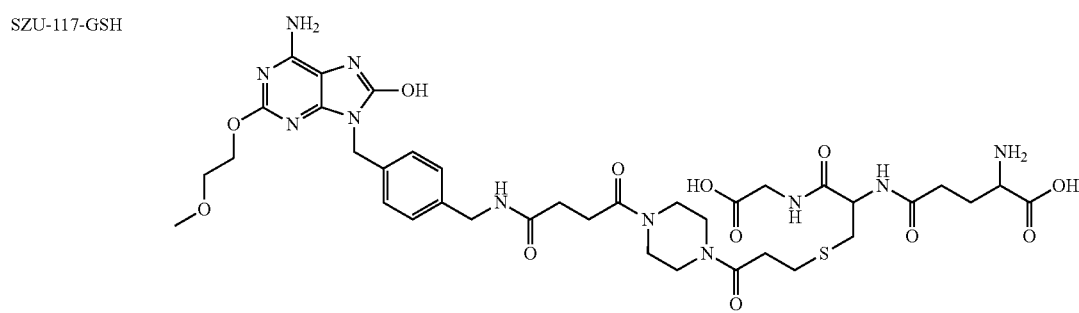
SZU-122-GSH
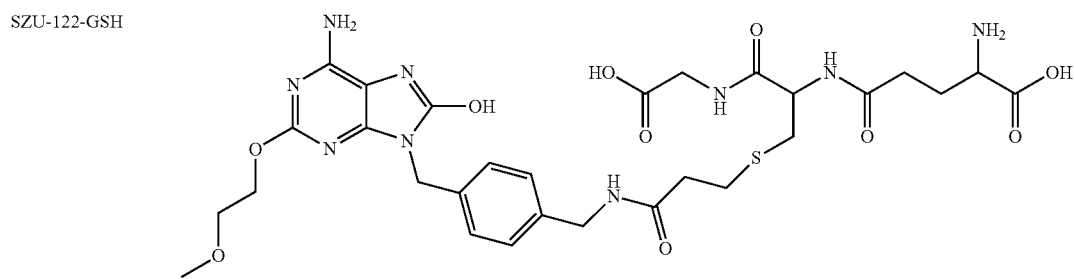
SZU-127-GSH
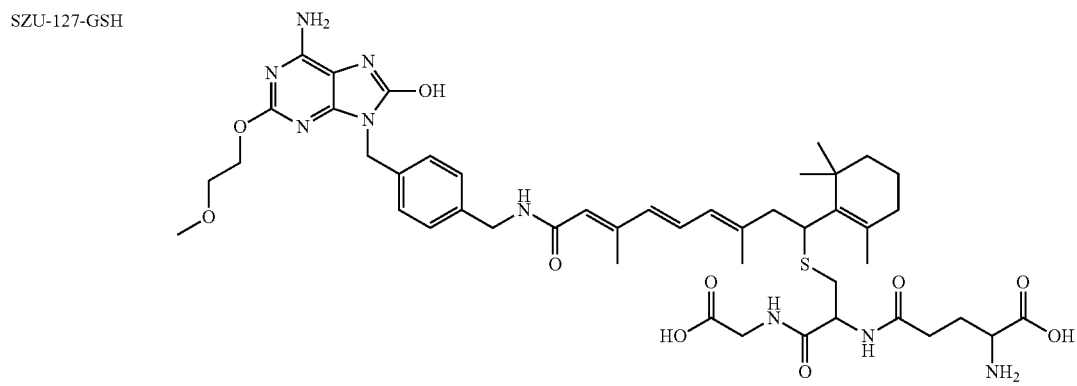

TABLE 3-continued
SZU-133-GSH
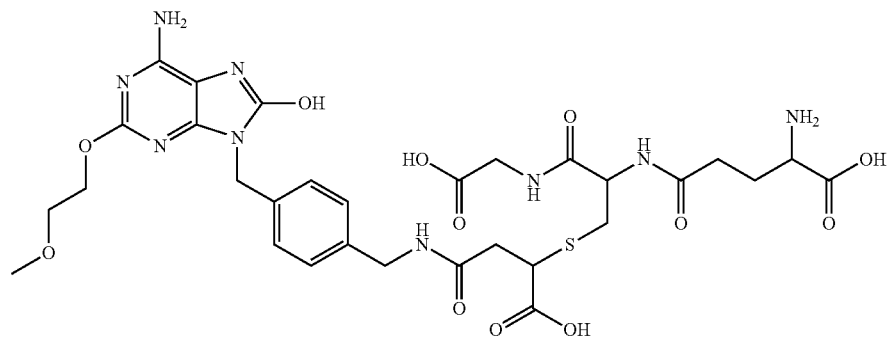 [SMILES: COCCOc1nc(N)c2nc(O)n(Cc3ccc(CNC(=O)CC(SCC(NC(=O)CCC(N)C(=O)O)C(=O)NCC(=O)O)C(=O)O)cc3)c2n1]
SZU-138-GSH
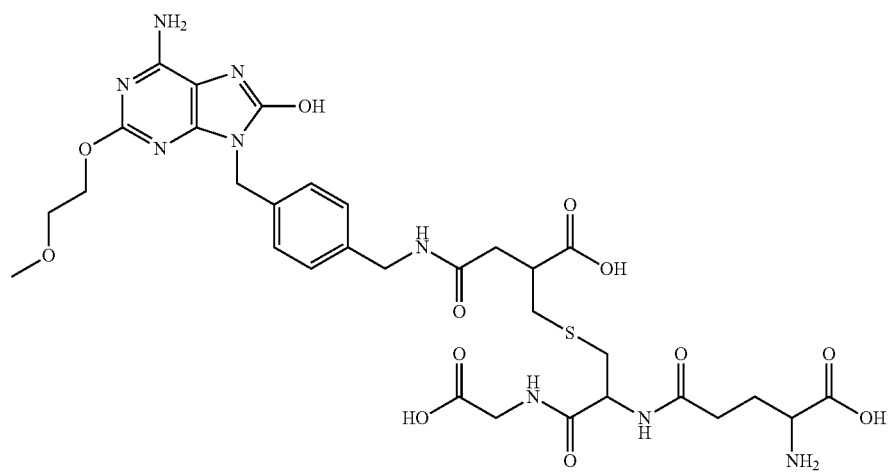 [SMILES: COCCOc1nc(N)c2nc(O)n(Cc3ccc(CNC(=O)CC(CSCC(NC(=O)CCC(N)C(=O)O)C(=O)NCC(=O)O)C(=O)O)cc3)c2n1]
SZU-144-GSH
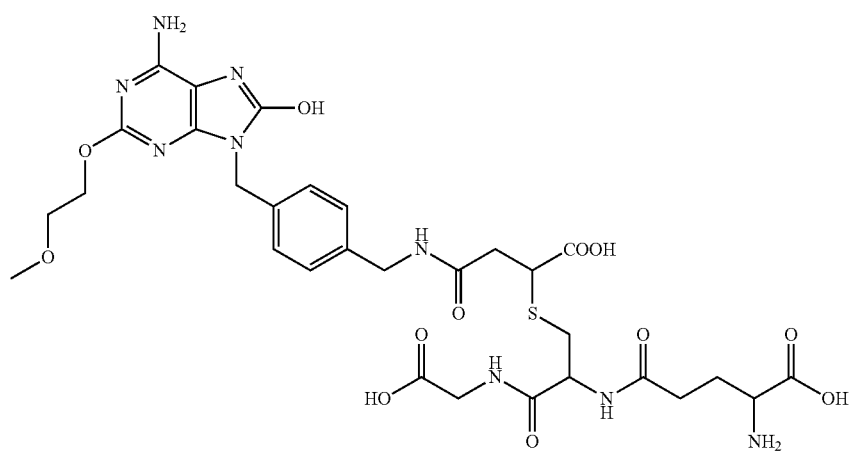 [SMILES: COCCOc1nc(N)c2nc(O)n(Cc3ccc(CNC(=O)CC(SCC(NC(=O)CCC(N)C(=O)O)C(=O)NCC(=O)O)C(=O)O)cc3)c2n1]

Other mercapto-containing compounds include, for example, 2-methylamino ethanethiol and

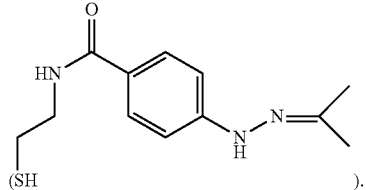

(SZU-033T).

The small-molecule immune agonists listed in Tables 1 and 2 and the compounds formed from some small-molecule immune agonists and GSH listed in Table 3 can be conjugated with targeted drugs to give bi-functional immune targeted compounds with immune targeting effects. The immune targeted compounds obtained are shown in Table 4 below:

TABLE 4

| Serial No. | Structural Formula | Molecular weight |
|---|---|---|
| SZU-116 | | 1393.63 |
| SZU-119 | | 1001.56 |
| SZU-124 | | 1189.27 |

TABLE 4-continued

| Serial No. | Structural Formula | Molecular weight |
| --- | --- | --- |
| SZU-125 | | 801.95 |
| SZU-146 | | 618.58 |
| SZU-147 | | 746.83 |

TABLE 4-continued
| Serial No. | Structural Formula | Molecular weight |
|---|---|---|
| SZU-169 | 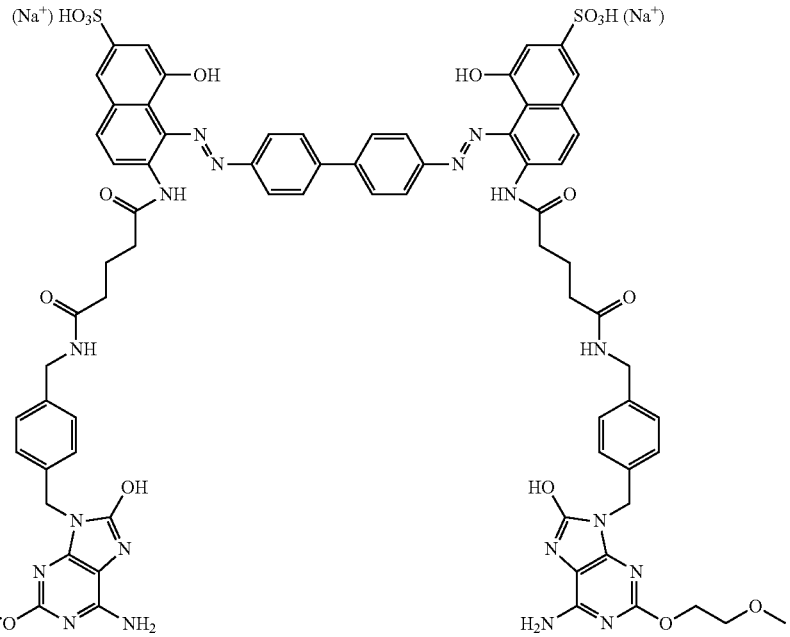 | 1565.61 |
| SZU-174 | 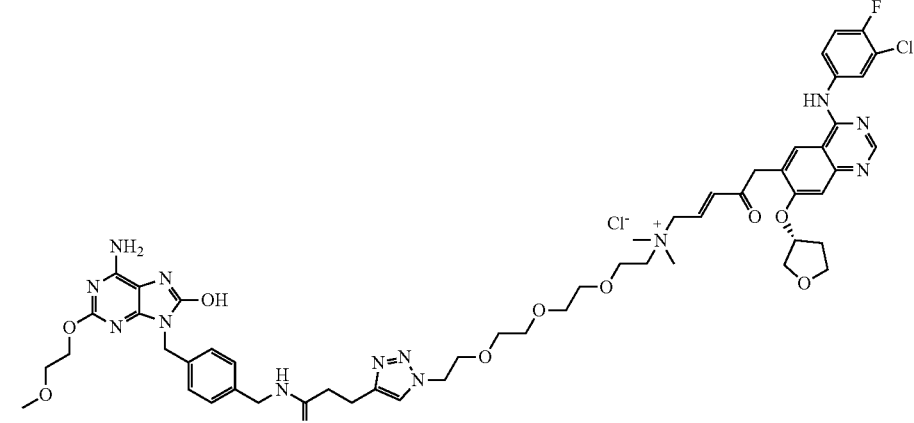 | 1148.07 |
| SZU-175 | 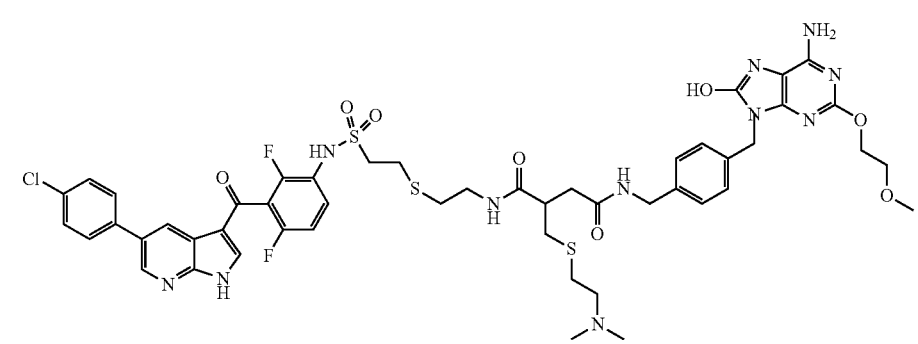 | 1094.67 |

TABLE 4-continued

| Serial No. | Structural Formula | Molecular weight |
|---|---|---|
| SZU-168 | | 905.39 |
| SZU-176 | | 869.97 |
| SZU-177 | | 992.05 |
| SZU-179 | | 848.86 |

TABLE 4-continued
| Serial No. | Structural Formula | Molecular weight |
|---|---|---|
| SZU-158-PD-L1 | 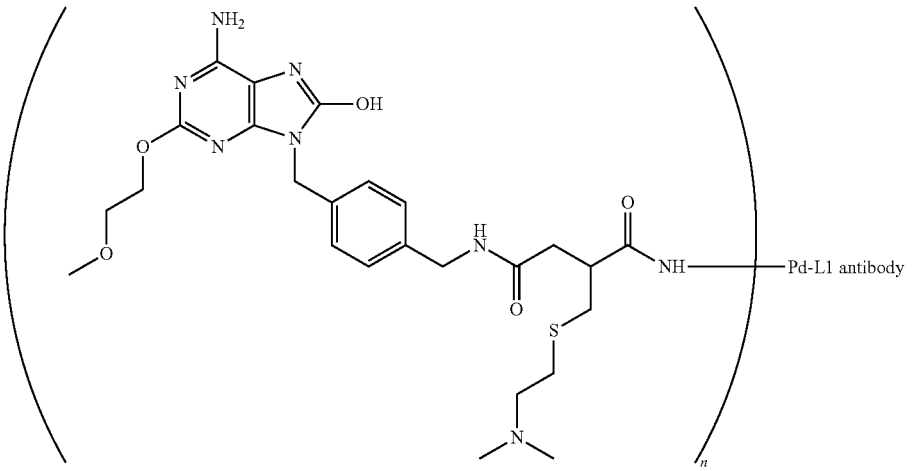 | |
| SZU-158-OX40 | 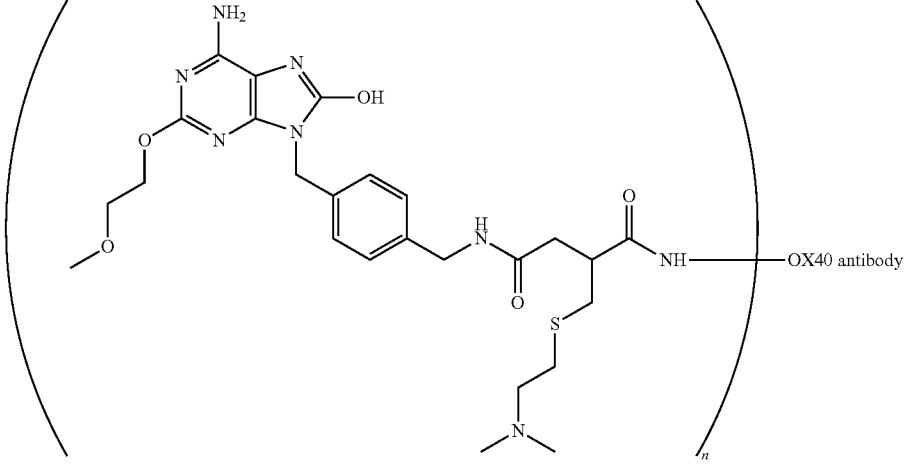 | |
| SZU-158-PD-1 | 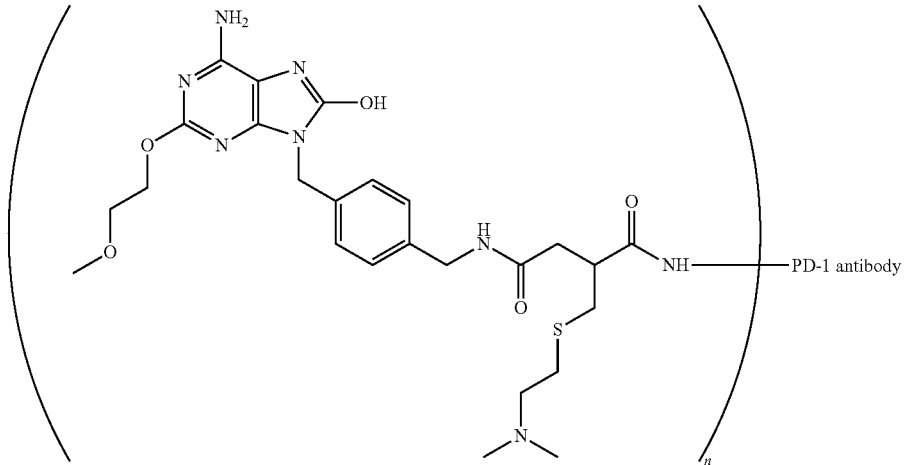 | |

TABLE 4-continued
| Serial No. | Structural Formula | Molecular weight |
|---|---|---|
| SZU-178 | 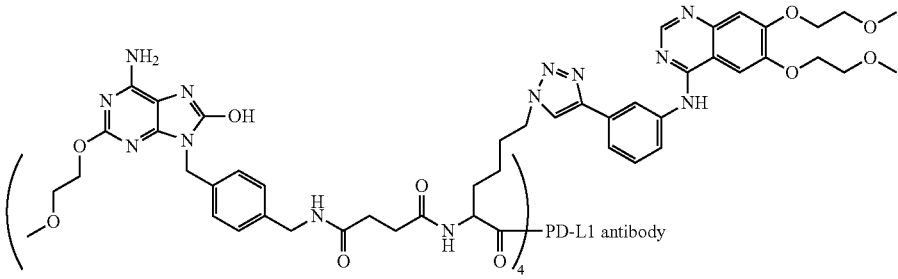 | |
| SZU-180 | 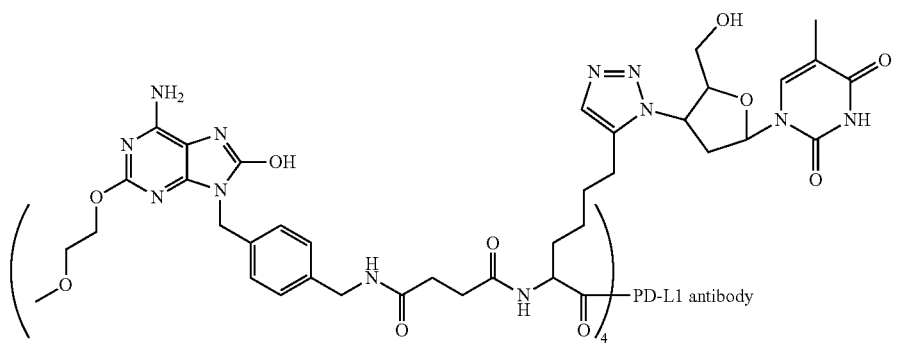 | |
| SZU-181 | 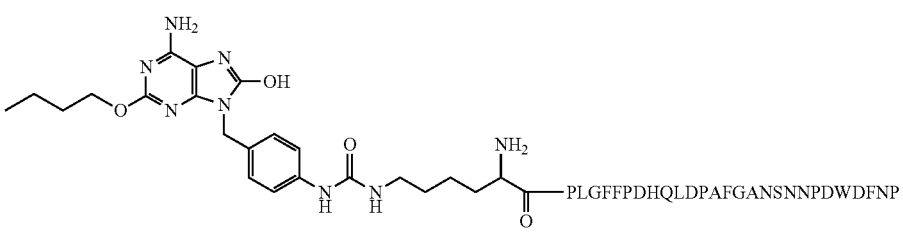 | 3512.80 |
| SZU-136-miR NA21 | 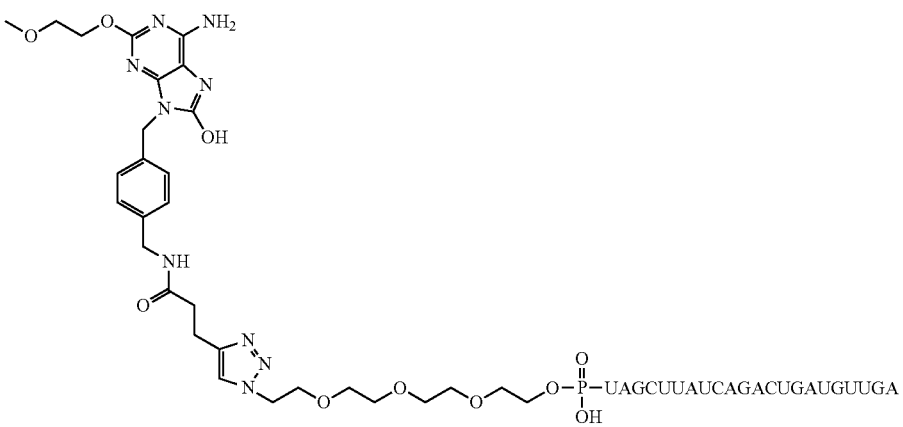 | |

Small-molecule immune agonists are conjugated with targeted drugs to form immune targeted compounds via synthesis schemes shown below:
Small-molecule immune agonists may be conjugated with targeted drugs via Synthesis Scheme I:
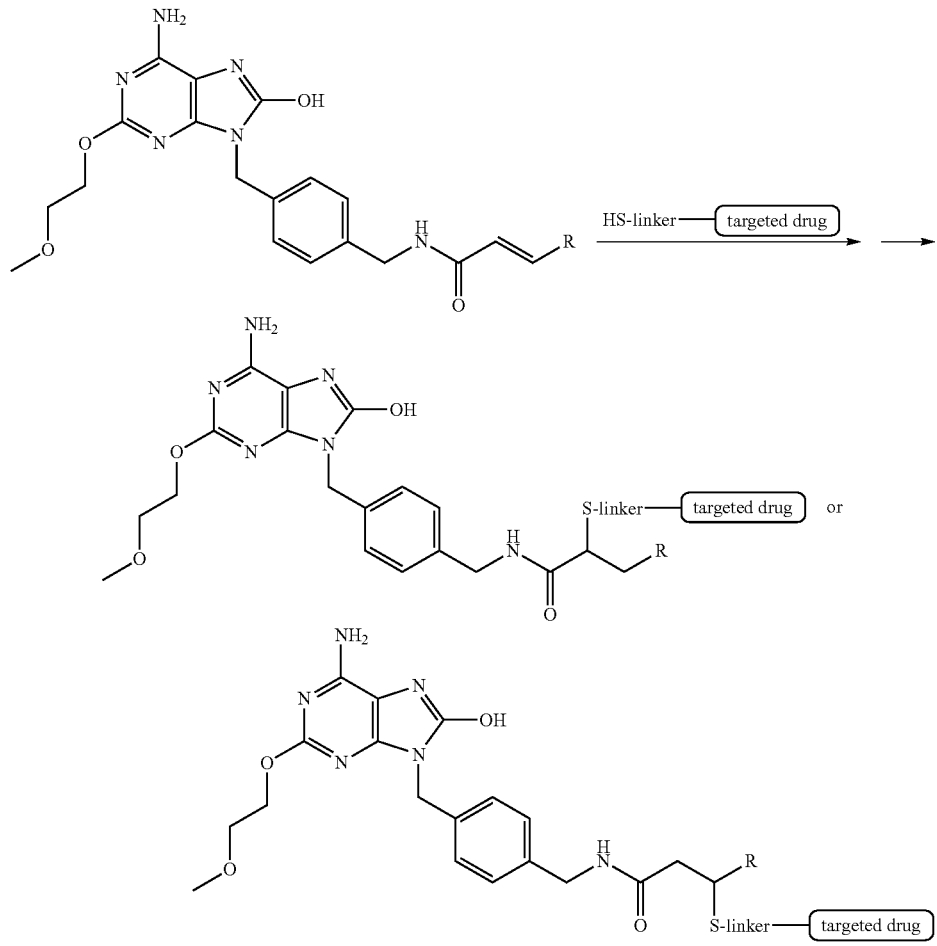
Small-molecule immune agonists (using SZU-137 as an example) may be conjugated with targeted drugs via Synthesis Scheme II:
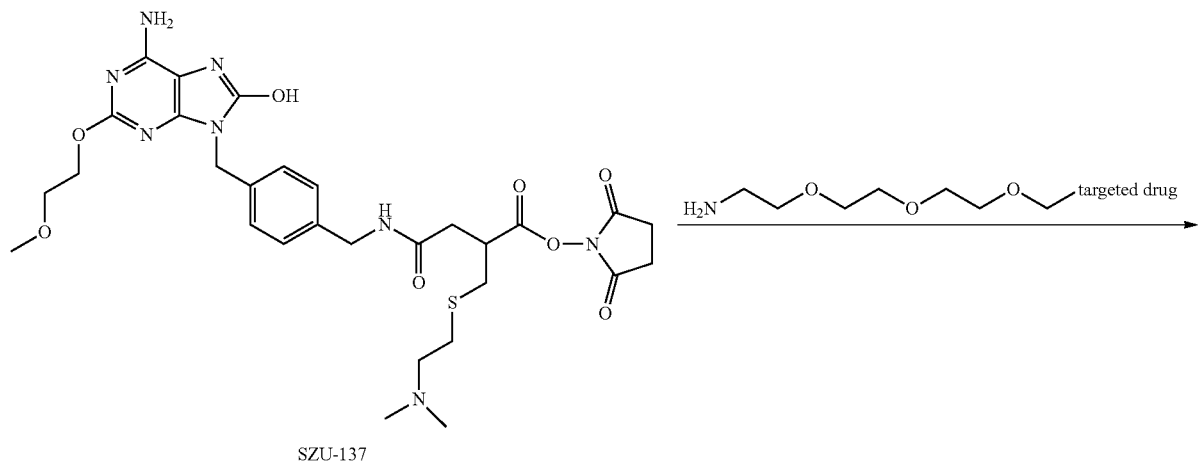
SZU-137

-continued

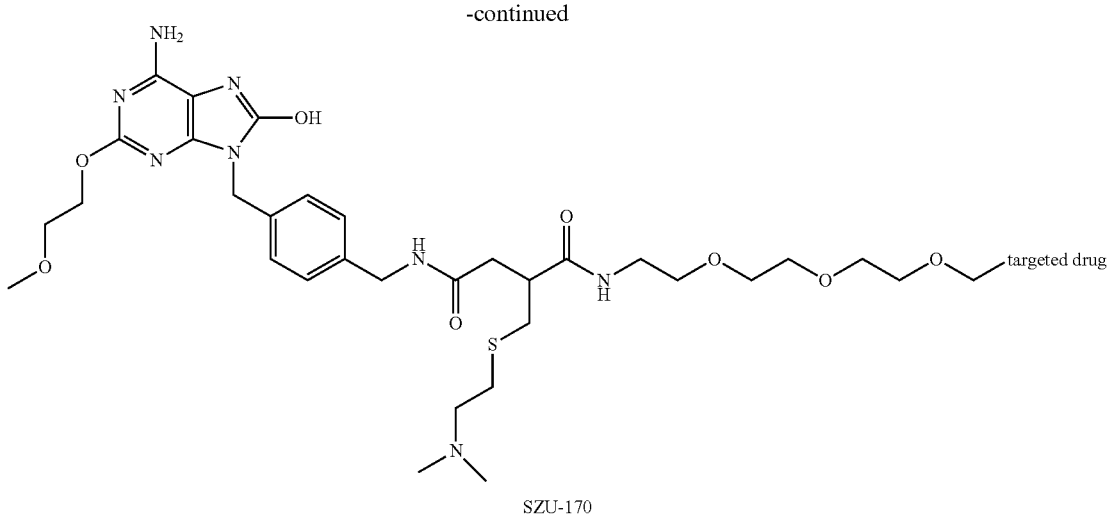

SZU-170

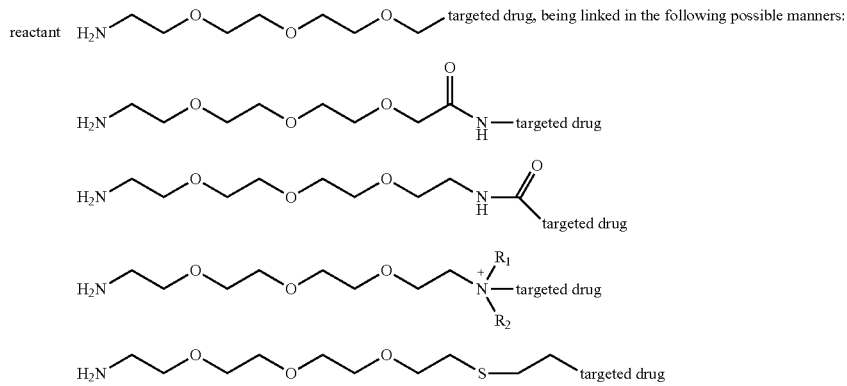

The same process as described above may also be applied to conjugating of SZU-144 or SZU-133 with targeted drugs to form immune targeted compounds. The linker may also be a simple linear alkane or other linkers replaced as desired.

Carboxyl-containing small-molecule immune agonists (such as SZU-138) can be conjugated with antibodies through addition reactions and conjugation reactions to form soluble, functional protein polypeptide conjugates, which can be formed into salts owing to the presence of the dimethylamino group, so that they can provide ionized positive charges, and thus are advantageous for increasing the therapeutic efficacy and water solubility, thereby solving the solubility problem of the conjugated products.

Furthermore, the carboxyl-containing small-molecule immune agonists as described above can also be conjugated with two different targeted drugs to form dual-targeted immune compounds.

Small-molecule immune agonists (using SZU-171 as an example) may be conjugated with targeted drugs via Synthesis Scheme III:

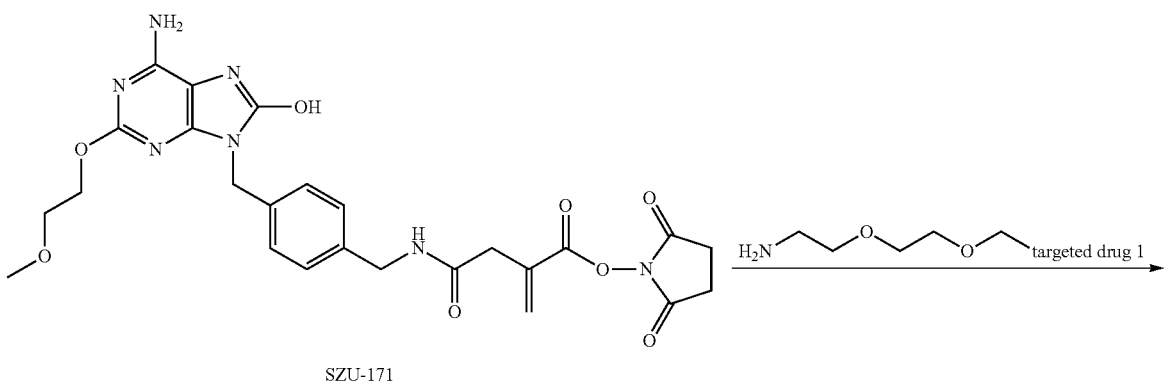

SZU-171

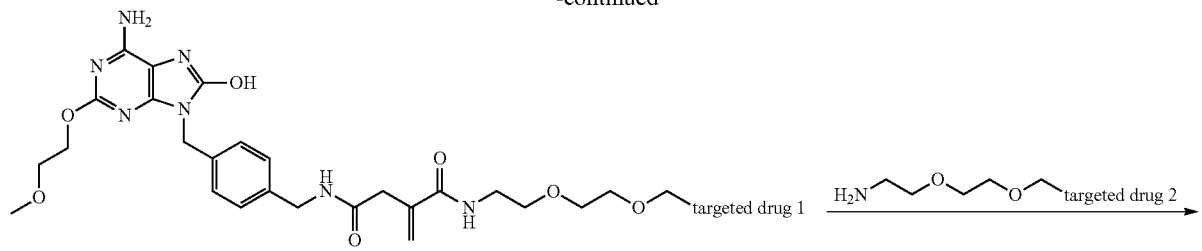
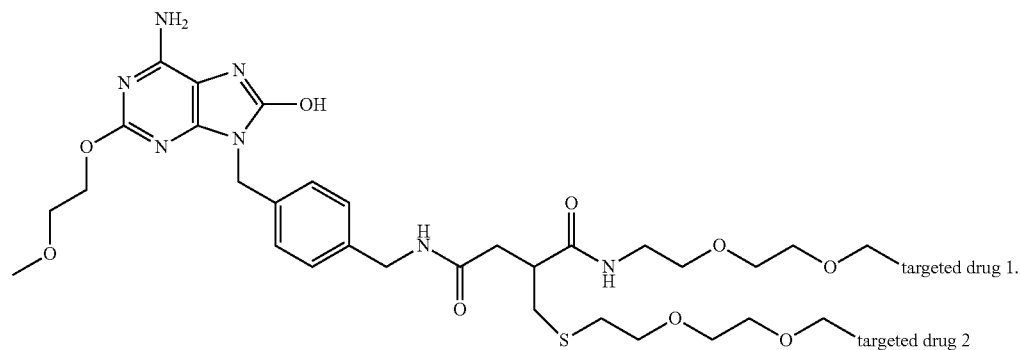
wherein the linker may vary in length
SZU-172
Products formed from small-molecule immune agonists and glutathione (using SZU-114-GSH as an example) can also be conjugated with two different targeted drugs to enhance the therapeutic efficacy.
Small-molecule immune agonists may be conjugated with targeted drugs via Synthesis Scheme IV:
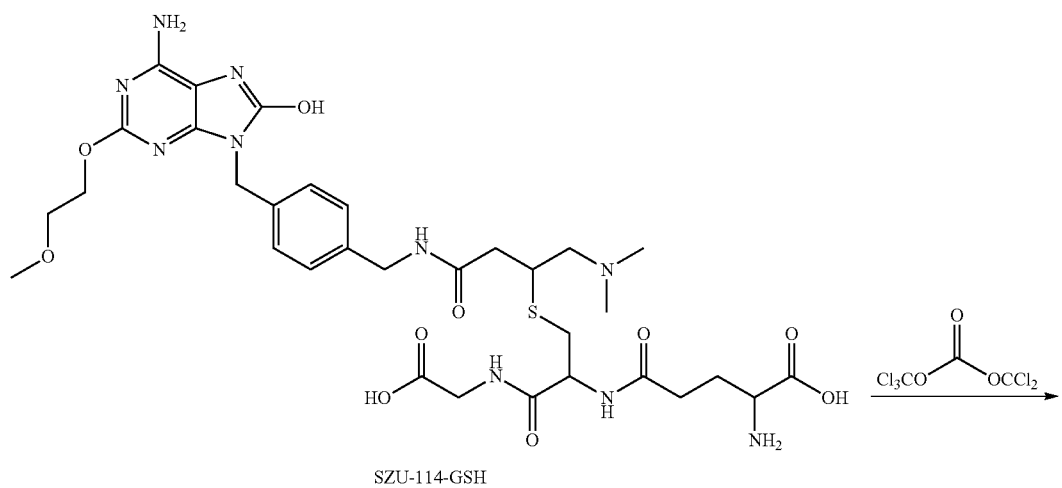
SZU-114-GSH -continued

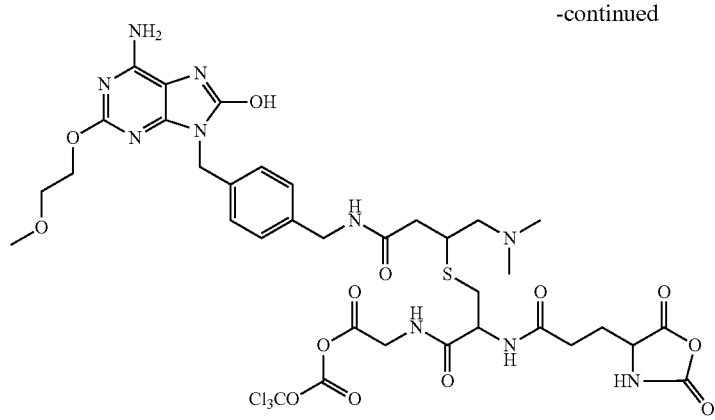

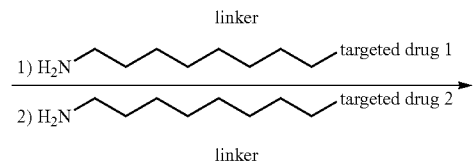

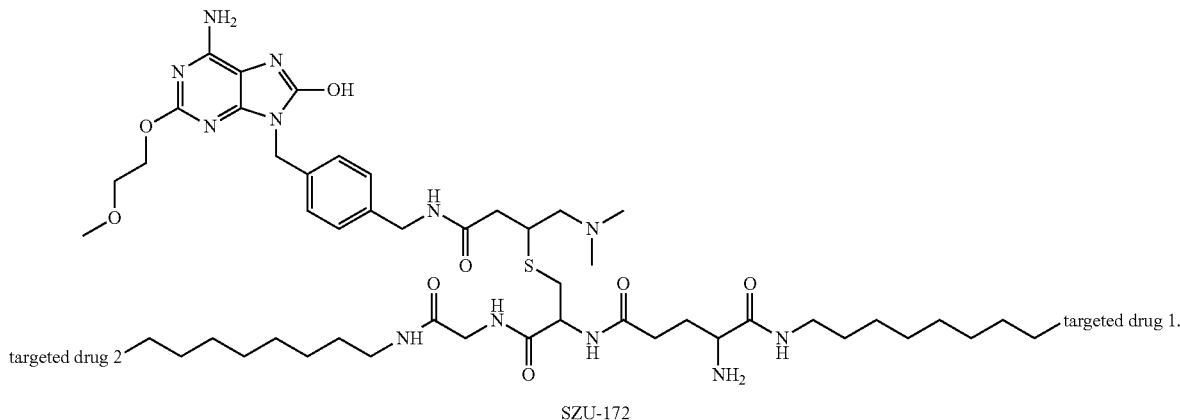

SZU-172

As used herein, the targeted drugs can either be various TKI agents and tumor targeted drugs, or antibodies such as CD3 antibody, PD-1 antibody, OX40 antibody, CD19 antibody, CD20 antibody, HER2 antibody, MUC1 antibody and antibodies against various tumor proteins and pathogens, wherein the linker may be alkane or alkoxy chains, and can be adjusted depending on the requirements for optimizing dissolution and metabolism.

Dual conjugated immune-targeted compounds as described above have the following advantages:

Being capable of forming two positive amino ionic groups (amino salts —HN$^+$— and —NH$_3^+$);

High solubility;

Dual targets, which can be adjusted and optimized if necessary, for example, with target 1 being CD3 antibody or CD122 antibody targeting T cells, and target 2 being HER2 inhibitors targeting cancer cells;

promoting infiltration of T cells into the tumor microenvironment;

enhancing the anti-tumor effects while activating immune TLR7 receptors; and forming immune targeted memory.

Small-molecule immune agonists (using SZU-166 as an example, which is a unique isocyanate small-molecule immune agonist with the merit of mild quantitative conjugate addition with amino compounds) may be conjugated with targeted drugs via Synthesis Scheme V:

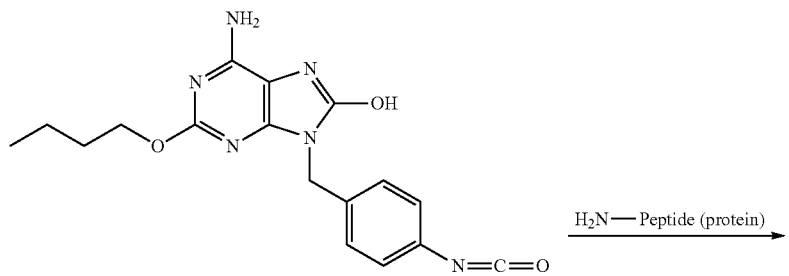

166

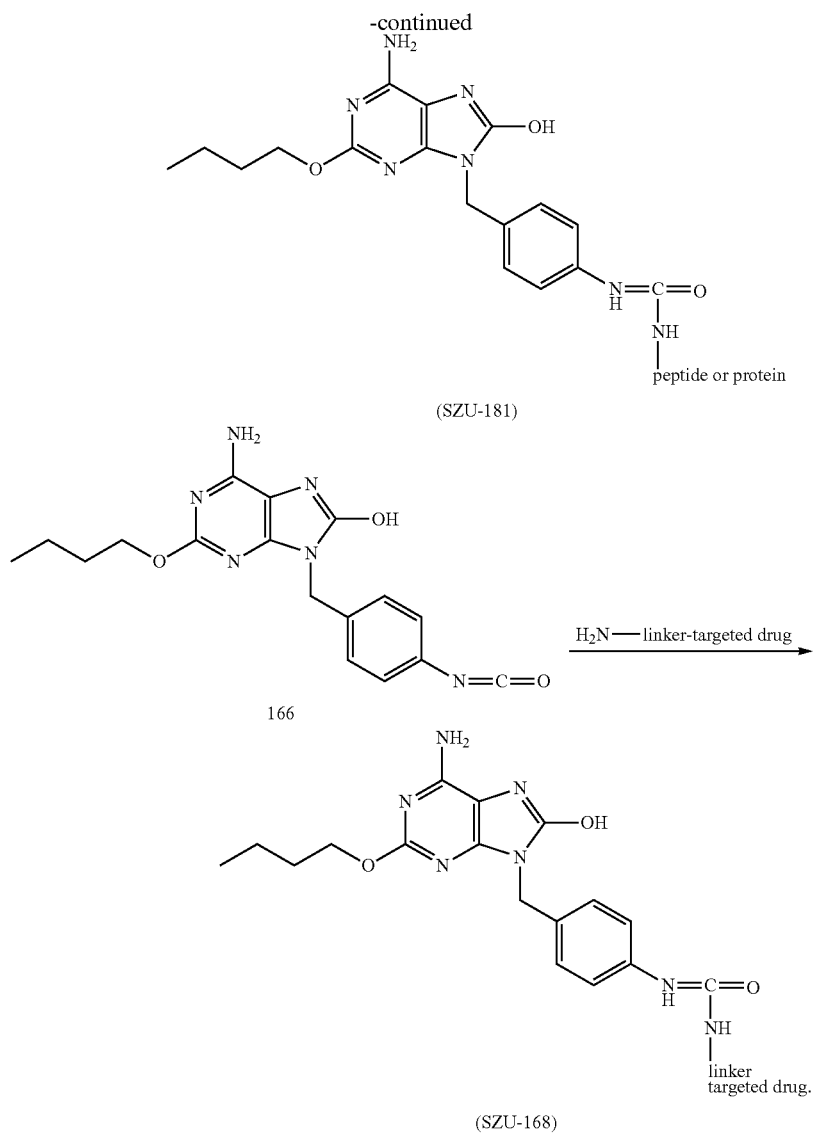

(SZU-181)

(SZU-168)

Compounds SZU-115 and SZU-160 are novel small-molecule immune agonists with Click reactive groups that mainly have two functions including: 1) after having been conjugated with macromolecules and biologically active substances, being useful in optical tracking of the conjugated product by linking to a chromogenic indicator via Click reaction; for example, when they have conjugated with proteins or targeted drugs, the cellular absorption and distribution in vivo of the proteins and targeted drugs are observed.

Small-molecule immune agonists may be conjugated with targeted drugs via Synthesis Scheme VI:

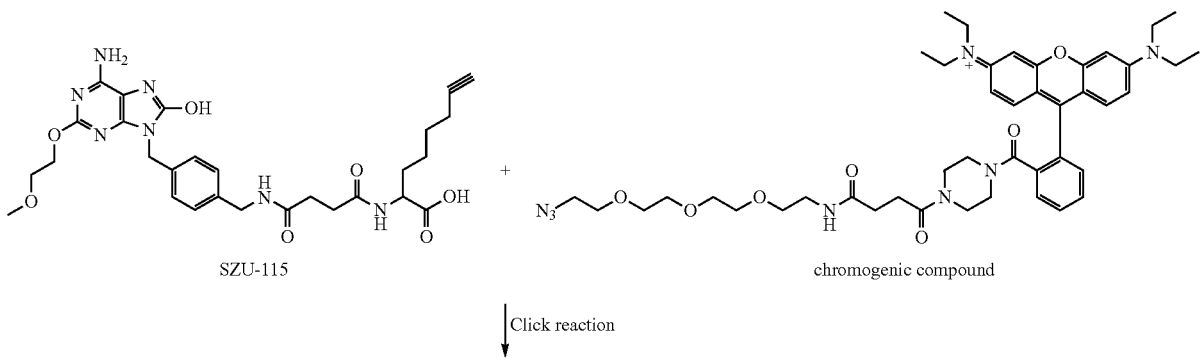

-continued
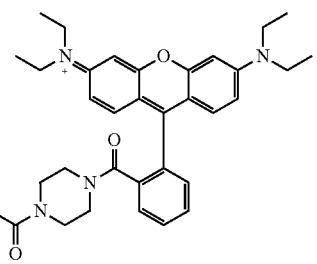
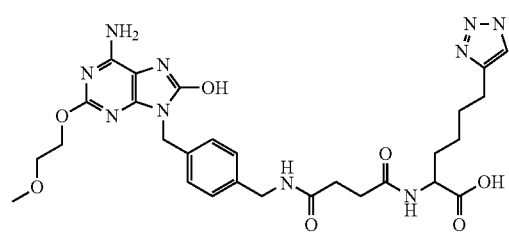
SZU-116
| conjugated with targeted drug
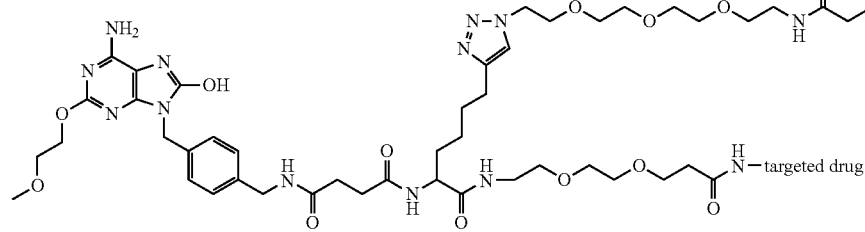
or
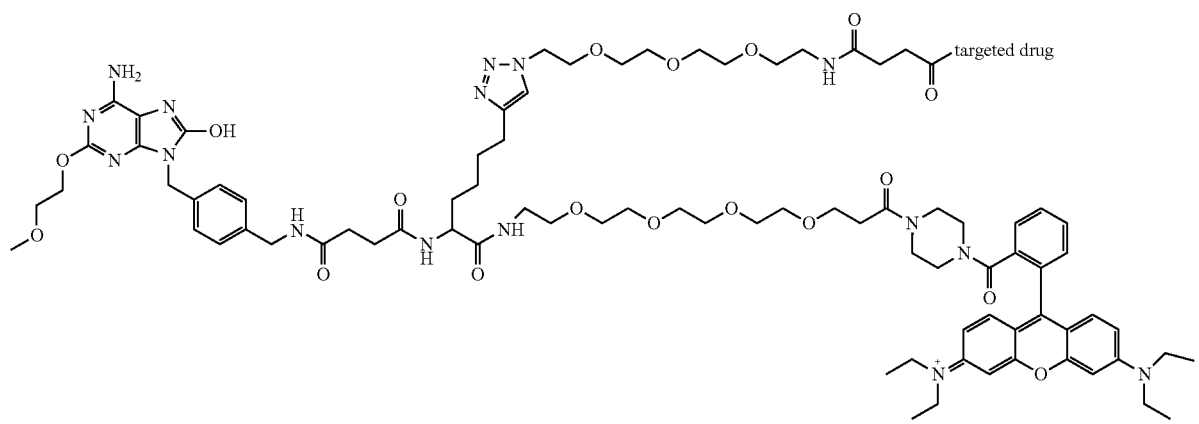

2) SZU-115 can also be simultaneously linked to antibodies and targeted drugs, thereby leading to reduced off-target effects of the antibodies, enhanced efficacy of the targeted drugs and activated antitumor immunity:

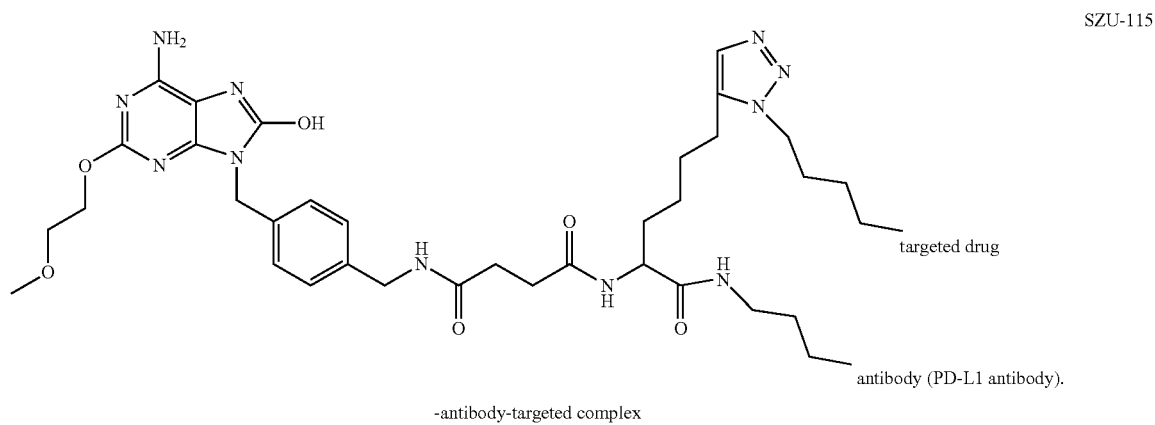 [SMILES: CCCCCn1nncc1CCCCC(NC(=O)CCC(=O)NCc1ccc(Cn2c(O)nc3c(N)nc(OCCOC)nc32)cc1)C(=O)NCCCC]

-antibody-targeted complex

Compounds SZU-136 and SZU-160 have similar action mechanisms and application effects.

Compound SZU-139 in the present invention is prepared by Click reaction of SZU-136 with ribose:

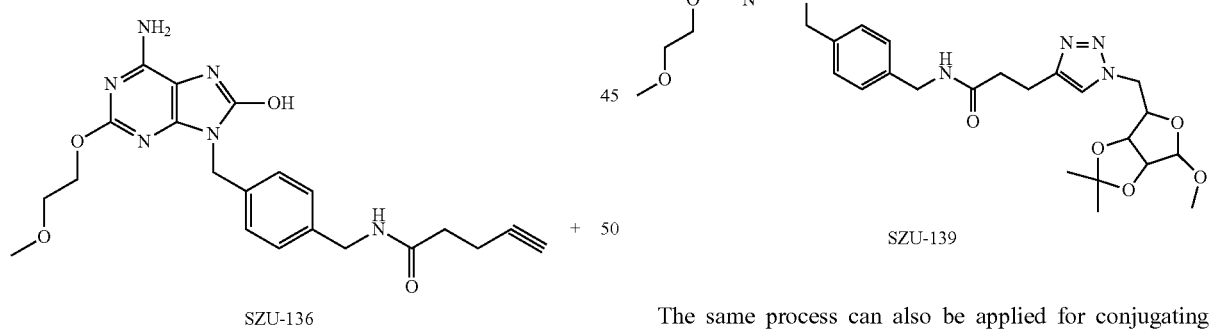

SZU-136

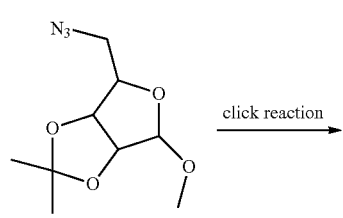

click reaction →

-continued

SZU-139

The same process can also be applied for conjugating small-molecule immune agonists with small-molecule RNAs (miRNAs). For example, miRNA21 (microRNA21) plays an important role in generation and development of tumor (Cell Death Dis. 2018 Feb. 13; 9(2):219. doi: 10.1038/s41419-017-0243-9; Proc Natl Acad Sci S U.S.A. 2015 Jun. 30; 112(26): E3355-64. doi: 10.1073/pnas.1504630112; Cancer Lett. 2017 May 1; 393: 86-93.doi: 10.1016/j.canlet.2017.02.019; https://en.wikipedia.org/wiki/MIRN21). The application of small-molecule immune agonists conjugated with pathogenic miRNAs can guide the immune system to block the occurrence of diseases at source, the changes of related proteins and the onset of related diseases.

Small-molecule immune agonists may be conjugated with targeted drugs via Synthesis Scheme VII:

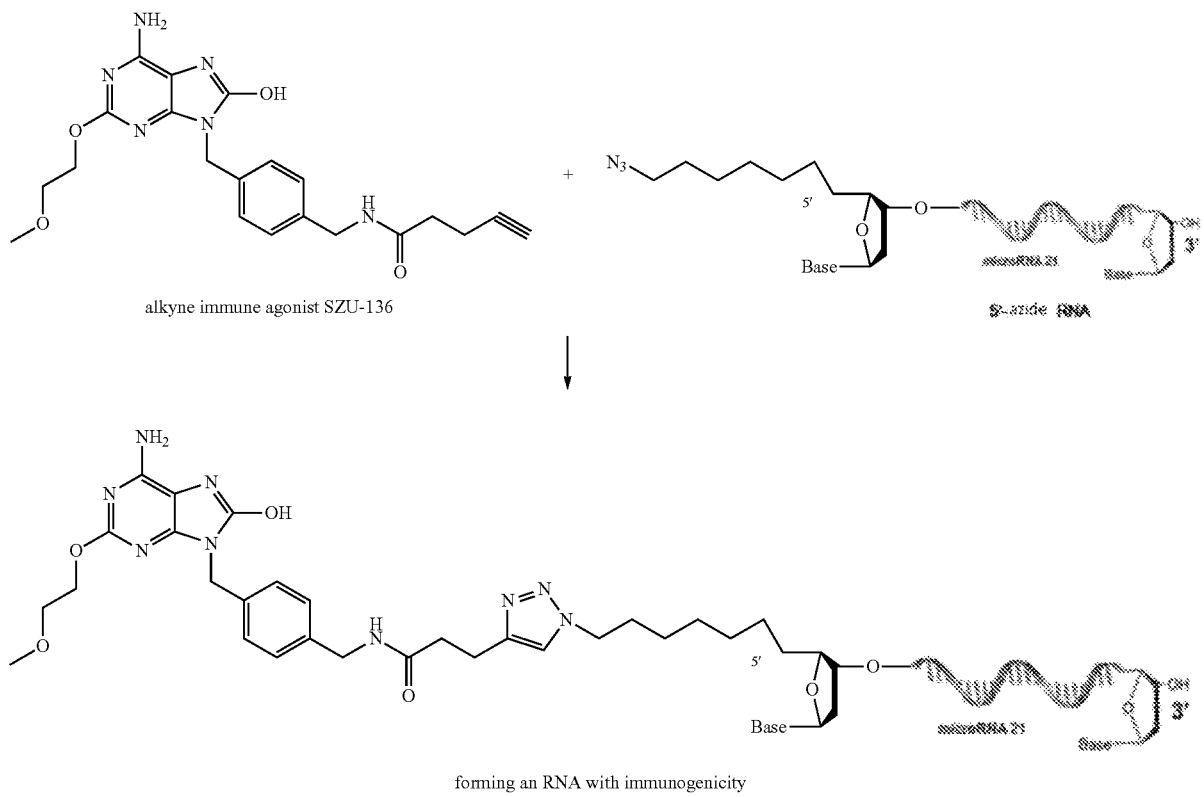

forming an RNA with immunogenicity

Synthesis of azide miRNA was described in the literature (Bioconjug Chem 2003 May-June; 14(3):697-701):

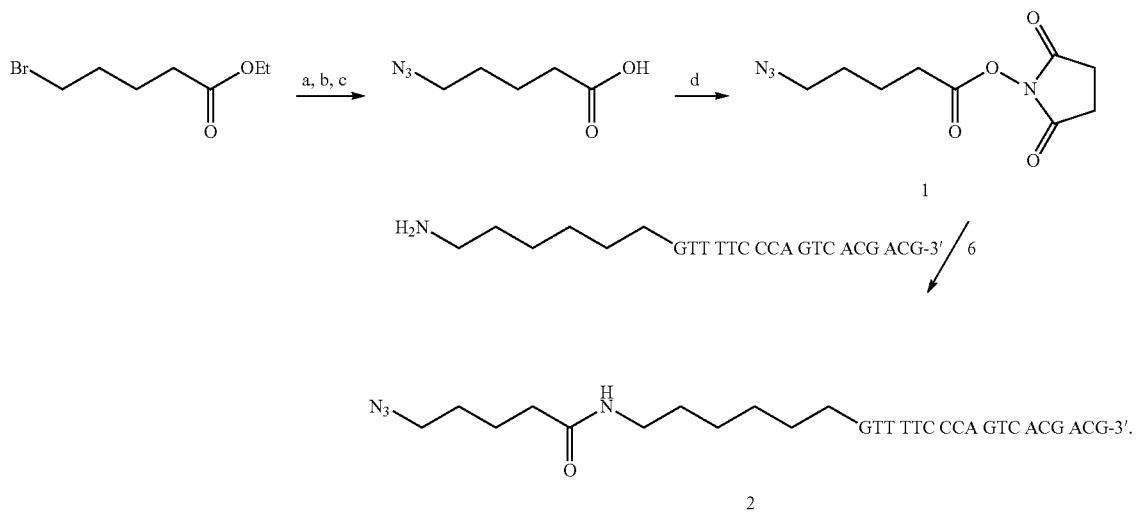

The alkyne immune agonist can be replaced with SZU-115. The carboxyl group of SZU-115 can be conjugated with Argonaute to form a conjugate, which interrupts the formation of a conjugate of miRNA and Argonaute, and is directed into the endosome of immunocytes under the action of TLR7 agonist, thus resulting in immunological elimination and memory:

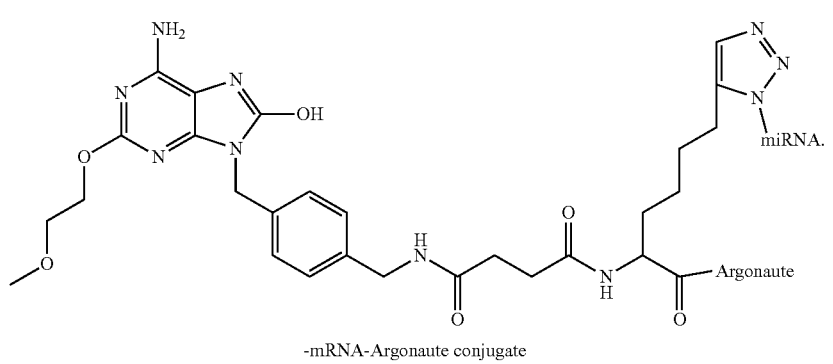

-mRNA-Argonaute conjugate

Recent studies have confirmed that pathogenic miRNAs released by tumor exosomes present an important cause of drug resistance and tumor metastasis (Proc, Natl, Acad, Sci, U, A, 2018, February, 12.pii:201717363.doi:10.1073/pnas.1717363115, J Clin Invest. 2016 Apr. 1; 126(4): 1163-72.doi: 10.1172/JCI81130); self-miRNAs generated in human bodies, especially those released from cancer cells, are generally incapable of inducing immunity. Although the target miRNAs can be specifically recognized by exogenous antisense oligonucleotide RNAs, most of them will be cleared or degraded rapidly in vivo owing to their immunogenicity. By using the above process, it is possible to transform pathogenic self-miRNAs into immunogenic miRNAs that can be recognized by innate immunity. The same process can also be applied to other pathogenic miRNAs such as miRNA30c.

An important role of miRNA is to guide the corresponding Argonaute protein to initiate target mRNA cleavage or transcriptional suppression (https://en.wikipedia.org/wiki/Argonaute).

Therefore, one of the innovative effects achieved by the TLR7 immune agonist conjugated with self-miRNAs in human bodies lies in immune targeted interference in the binding to the Argonaute protein, thereby eliminating the related pathogenicity. This effect is schematically shown in FIG. 69. In summary, the inventors have found a series of small-molecule immune agonists, which can be conjugated with targeted drugs to form novel immune targeted compounds with immunostimulatory function, thereby resulting in increased in vitro and in vivo immunostimulatory effects of the targeted drugs and improved efficacy against tumors and other diseases, conferring dual functions to the targeted drugs (bi-functional targeted drugs). Such an enhanced effect is resulted from the synergistic action of two functions: inclusion of antitumor immune factors (such as IFN-γ) and inhibition on the pathogenic targeted sites. Thus, the present invention is directed to novel high-effective targeted drugs with a combination of the two functions.

The immune targeted compounds according to the present invention act appropriately by eliminating pathogenic targets (proteins) via immune pathway as shown in FIG. 70. Immune targeted compounds formed by conjugating small-molecule immune agonists with targeted drugs are guided by the targeted drugs to the pathogenic proteins, thereby resulting in the death of the targeted cells and release of the pathogenic proteins. Further, they are guided by the immune agonists to antigen presenting cells (such as DC), in which the pathogenic proteins are cleaved, leading to degradation of these proteins. The immune targeted compounds formed by conjugating small-molecule immune agonists with targeted drugs (such as TKIs) in the present invention can overcome drug resistance and improve therapeutic efficacy.

Lysine-derived compounds SZU-104, SZU-105, SZU-112 and SZU-113 that are useful as acidic small-molecule immune agonists are amino acid derivatives having the activity of immune agonists, and can achieve the purpose of site-specific conjugation by inserting polypeptides (or antibodies) at specific sites as desired in the preparation of immunogenic polypeptides:

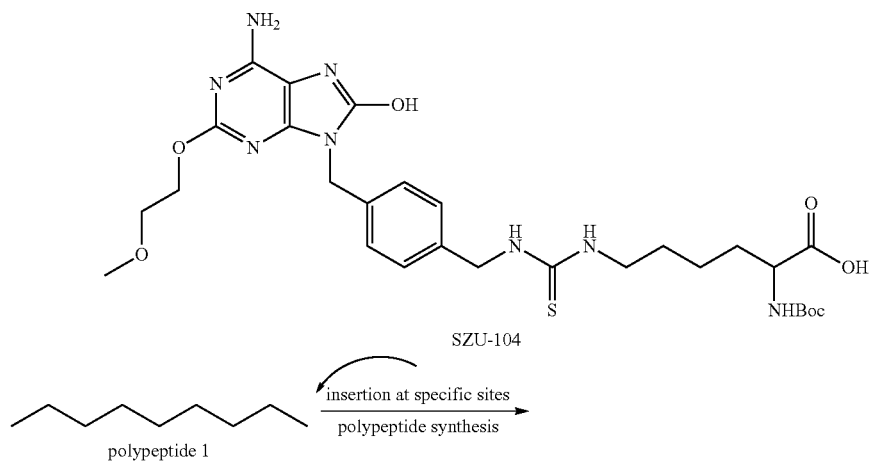

-continued

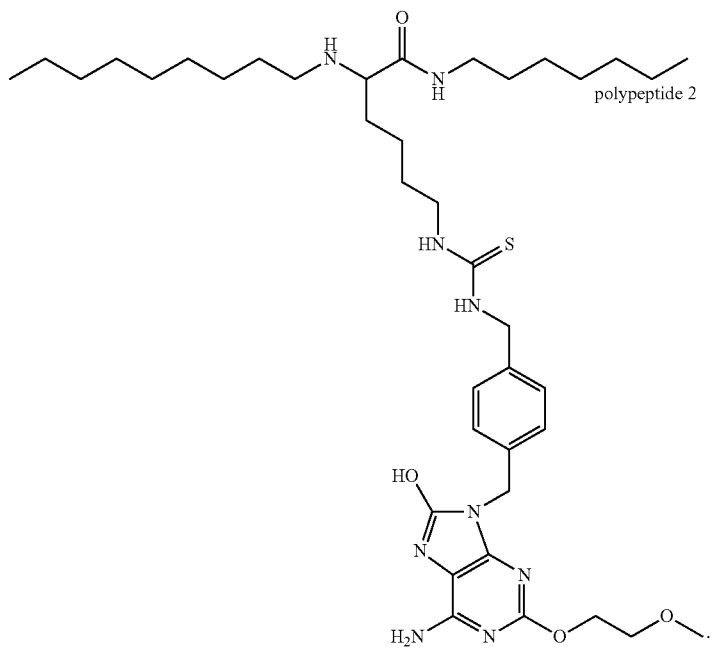

Analogous process can be performed by replacing the compound with SZU-112

SZU-161 and SZU-162, as small-molecule immune agonists suitable for conjugating with protein drugs, have a specific ultraviolet absorption peak (342 nM), and can be used typically for measuring the conjugation degree of small-molecule immune agonists conjugated with proteins drugs:

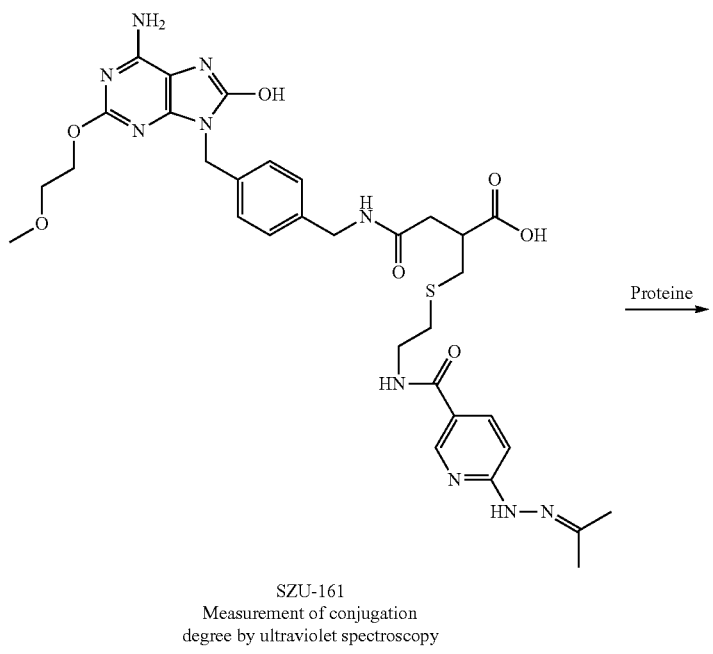

SZU-161
Measurement of conjugation
degree by ultraviolet spectroscopy

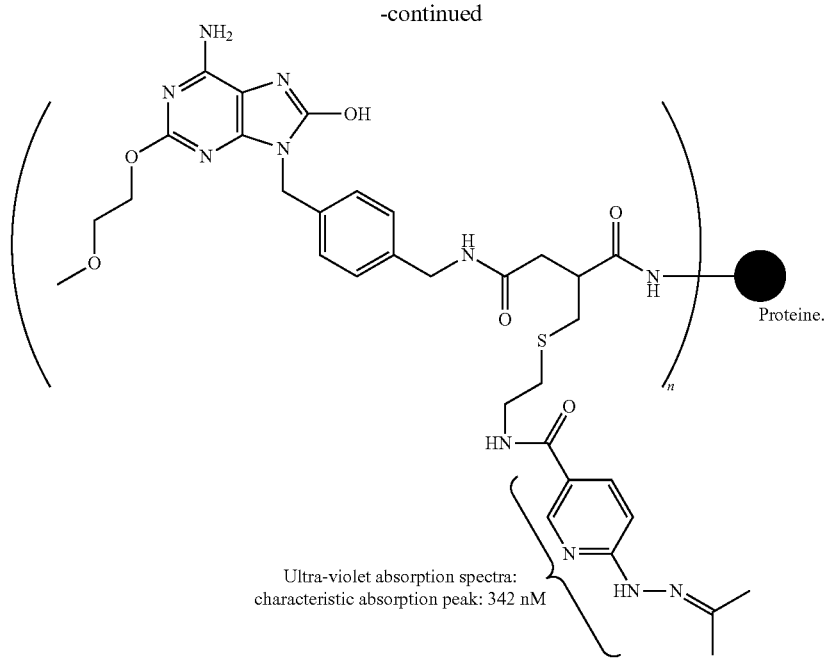

The measurement method is described as follows: 1) SZU-161 was measured for the intensity of optical absorption at 342 nM under different concentrations; standard curves of concentration and absorption were plotted to obtain the concentration-absorption relationship formula; and 2) after conjugation with protein, the conjugated protein was measured for the absorption at 342 nM under certain concentration; the resulting value was placed into the relationship formula to readily obtain the relative concentration of SZU-161 in the conjugate (i.e., conjugation degree). SZU-162 may be applied to achieve the same effect.

BRIEF DESCRIPTION OF THE DRAWINGS

The "immune cytokines" mentioned in the following figures refer to cytokines (including IFN-γ, IL-12, IL-6, and TNF-α), and their concentration levels can be used to indicate the levels of immunocyte responsiveness stimulated by the compound.

DETAILED DESCRIPTION OF THE INVENTION

Figure 1:
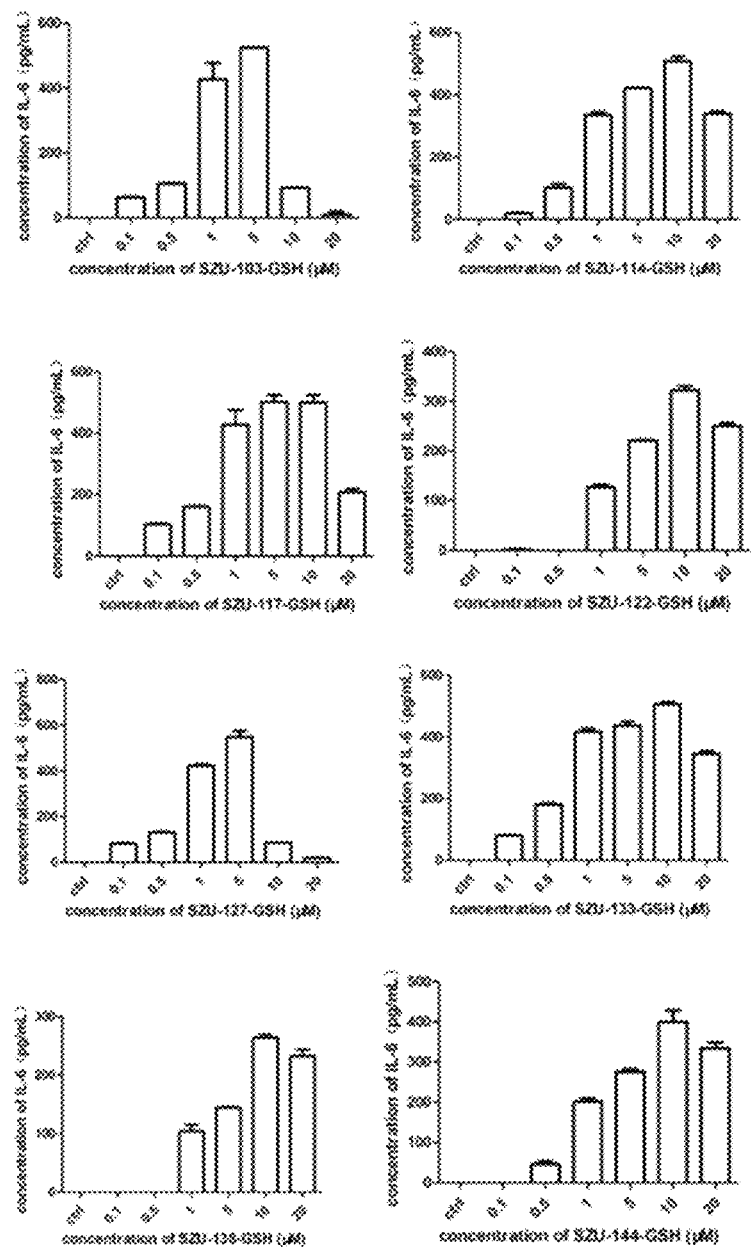
FIG. 1 shows the stimulatory effects of SZU-GSH-series compounds on immune cytokine (IL-6).
Figure 2:
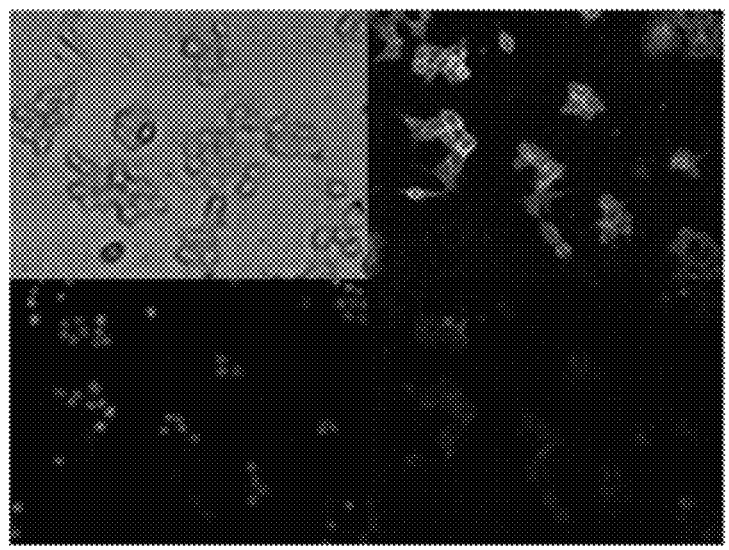
FIG. 2 shows the distribution of fluorescence-labeled SZU-116 in cells.
Figure 3:
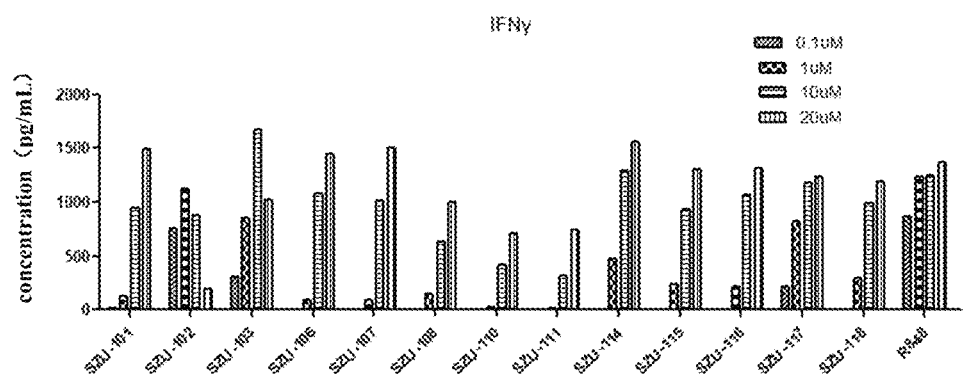
FIG. 3 shows the stimulatory effects of SZU-102, 103, 106, 107, 108, 110, 111, 114, 115, 116, 117, and 118 on immune cytokine (IFN-γ), wherein SZU-101 and R848, as the standard control, are internationally-accepted, standard small-molecule immune agonists with immunostimulatory function (the same below).
Figure 4:
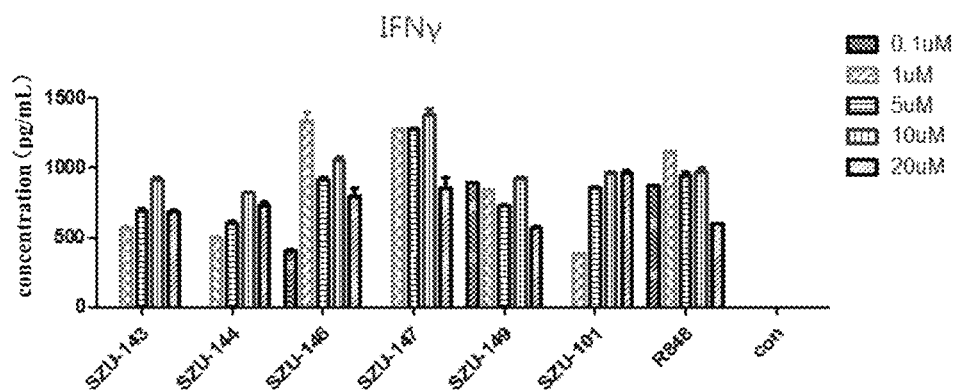
FIG. 4 shows the stimulatory effects of SZU-143, 144, 146, 147, and 149 on immune cytokine (IFN-γ), wherein "con" is PBS blank control (the same below).
Figure 5:
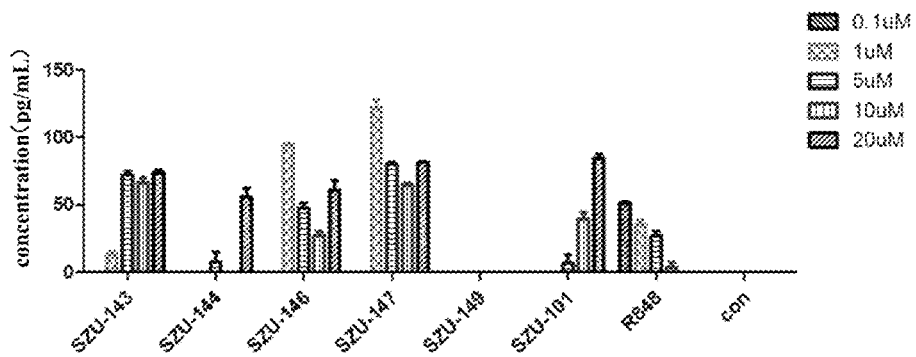
FIG. 5 shows the stimulatory effects of SZU-143, 144, 146, 147, and 149 on immune cytokine (IL-12).
Figure 6:
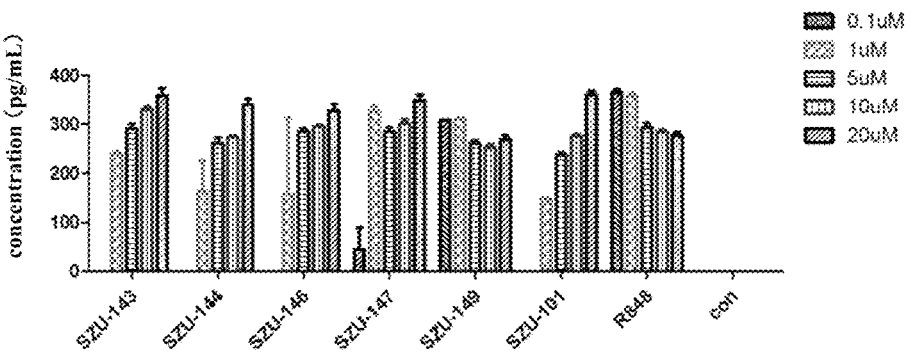
FIG. 6 shows the stimulatory effects of SZU-143, 144, 146, 147, and 149 on immune cytokine (TNF-α).
Figure 7:
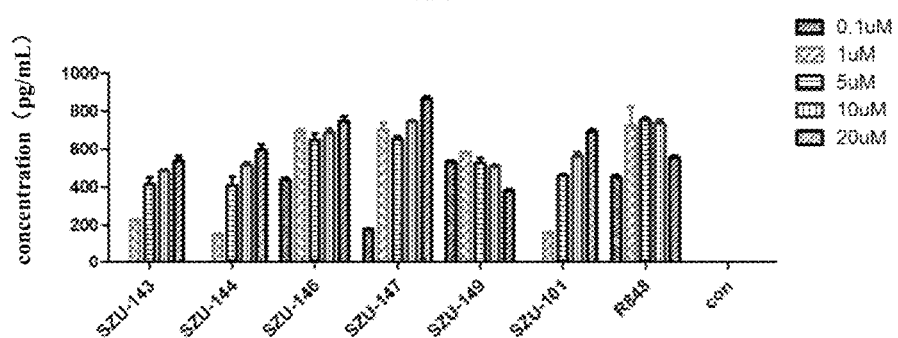
FIG. 7 shows the stimulatory effects of SZU-143, 144, 146, 147, and 149 on immune cytokine (IL-6).
Figure 8:
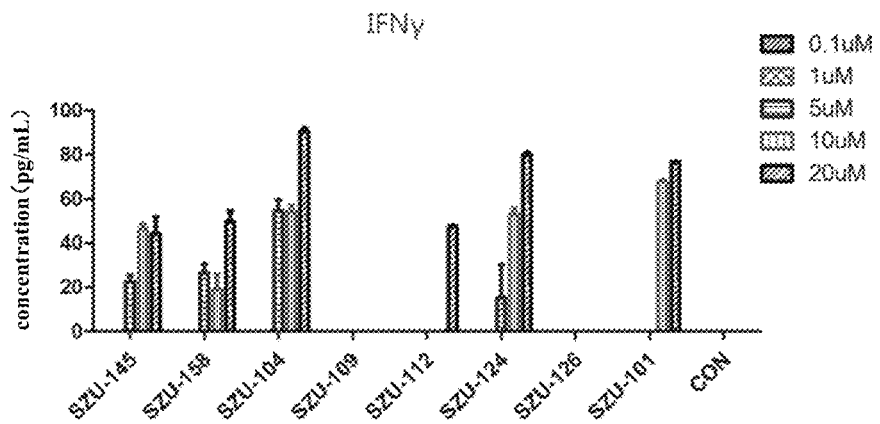
FIG. 8 shows the stimulatory effects of SZU-145, 158, 104, 109, 112, and 124 on immune cytokine (IFN-γ).
Figure 9:
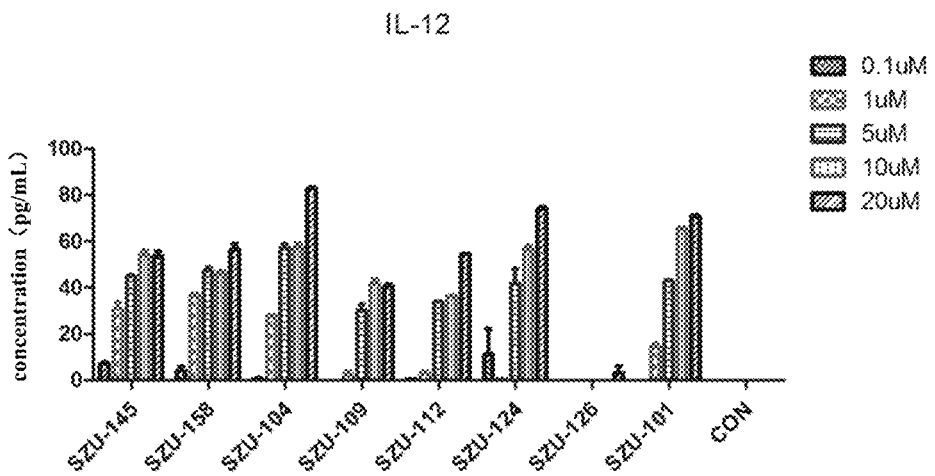
FIG. 9 shows the stimulatory effects of SZU-145, 158, 104, 109, 112, and 124 on immune cytokine (IL-12).
Figure 10:
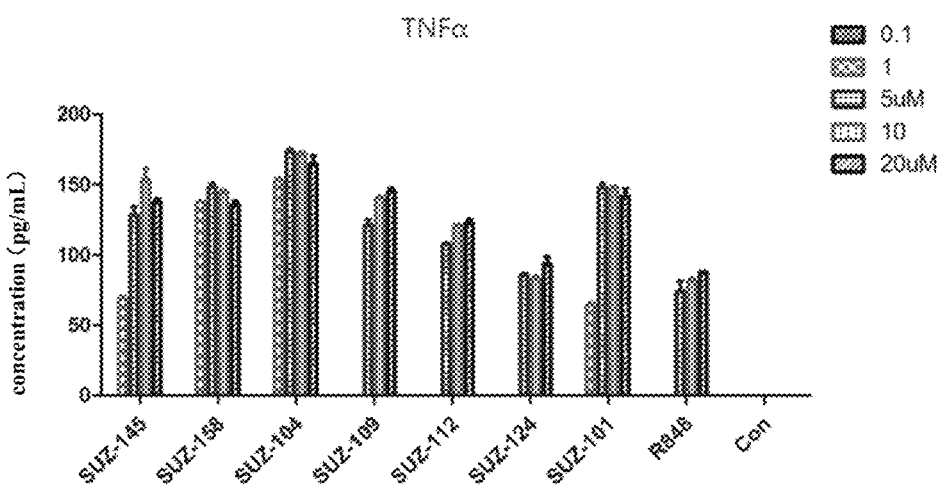
FIG. 10 shows the stimulatory effects of SZU-145, 158, 104, 109, 112, and 124 on immune cytokine (TNF-α).
Figure 11:
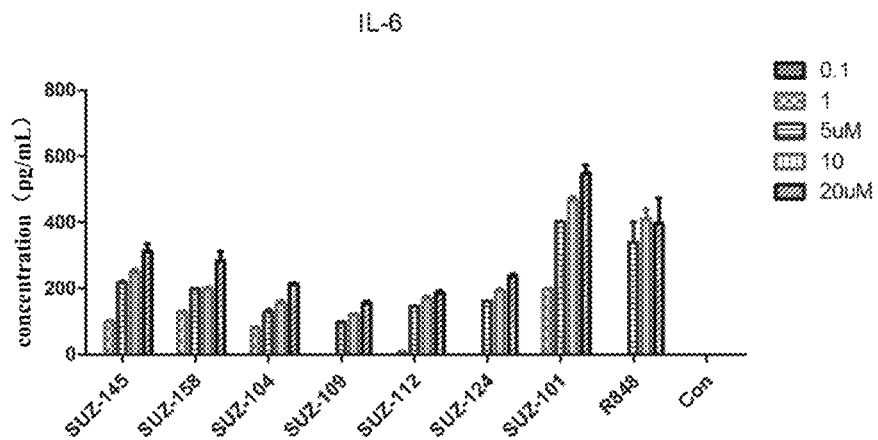
FIG. 11 shows the stimulatory effects of SZU-145, 158, 104, 109, 112, and 124 on immune cytokines (IL-6).
Figure 12:
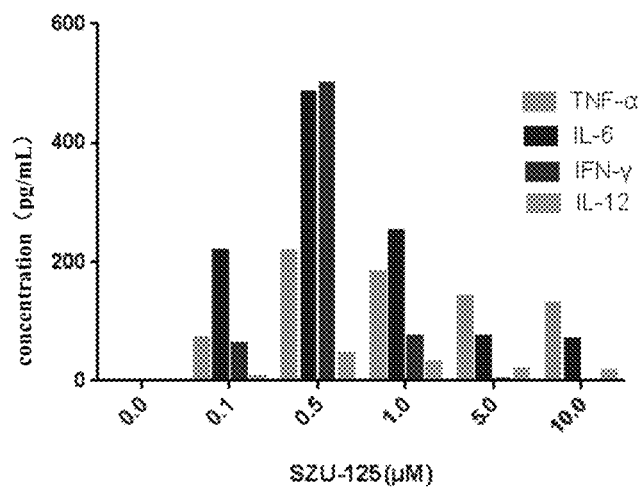
FIG. 12 shows the stimulatory effects of SZU-125 on several immune cytokines.
Figure 13:
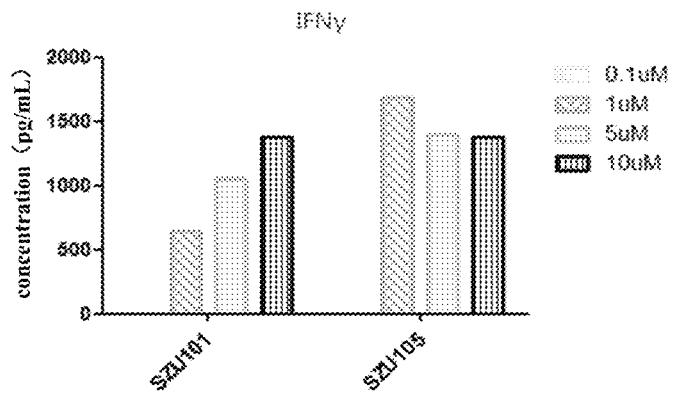
FIG. 13 shows the stimulatory effects of SZU-105 on immune cytokine (IFN-γ).
Figure 14:
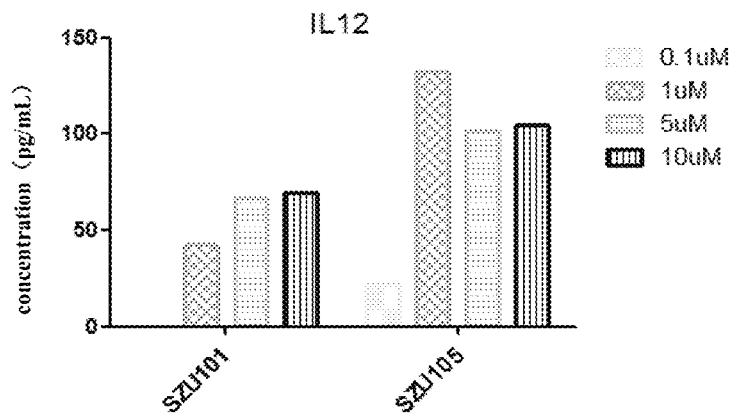
FIG. 14 shows the stimulatory effects of SZU-105 on immune cytokine (IL-12).
Figure 15:
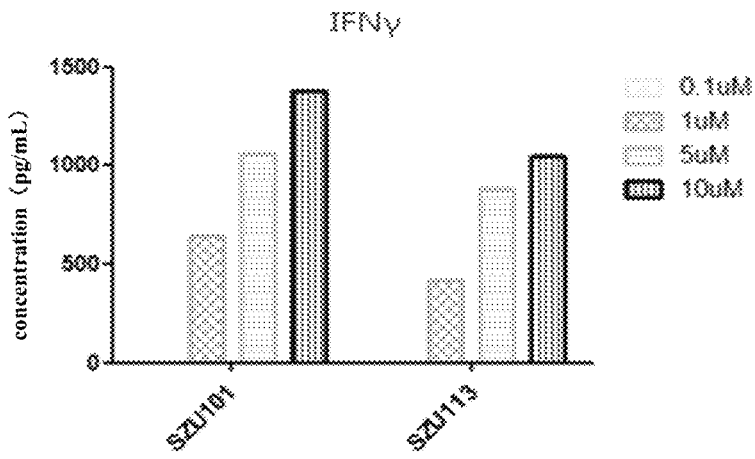
FIG. 15 shows the stimulatory effects of SZU-113 on immune cytokine (IFN-γ).
Figure 16:
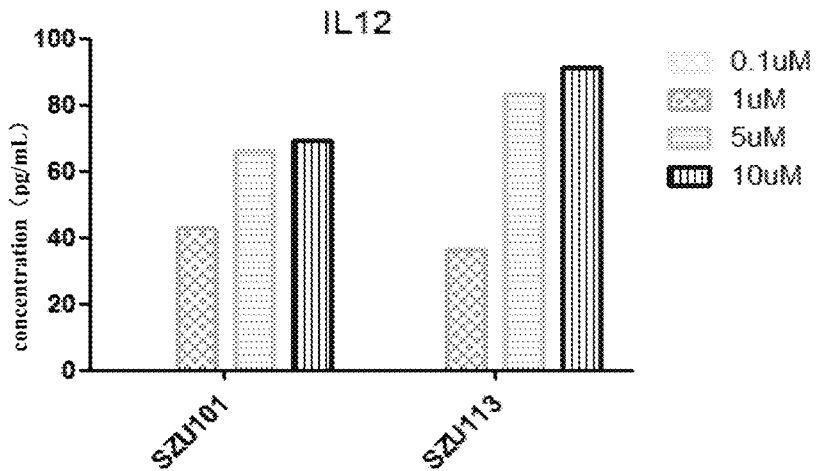
FIG. 16 shows the stimulatory effects of SZU-113 on immune cytokine (IL-12).
Figure 17:
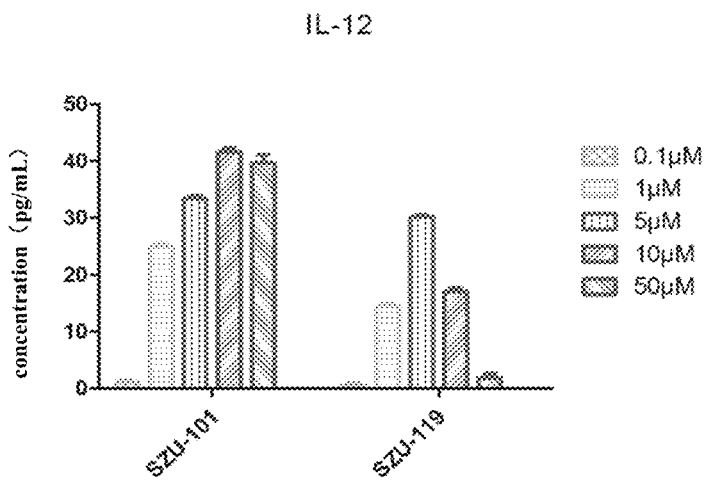
FIG. 17 shows the stimulatory effects of SZU-119 on immune cytokine (IL-12).
Figure 18:
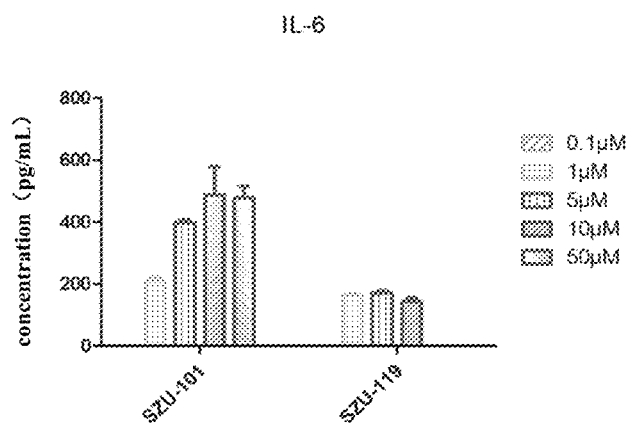
FIG. 18 shows the stimulatory effects of SZU-119 on immune cytokine (IL-6).
Figure 19:
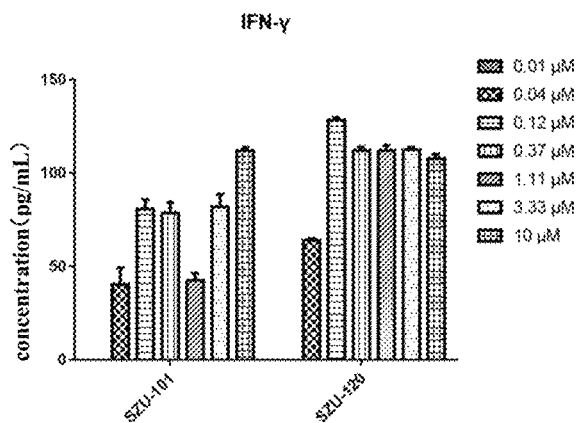
FIG. 19 shows the stimulatory effects of SZU-120 on immune cytokine (IFN-γ).
Figure 20:
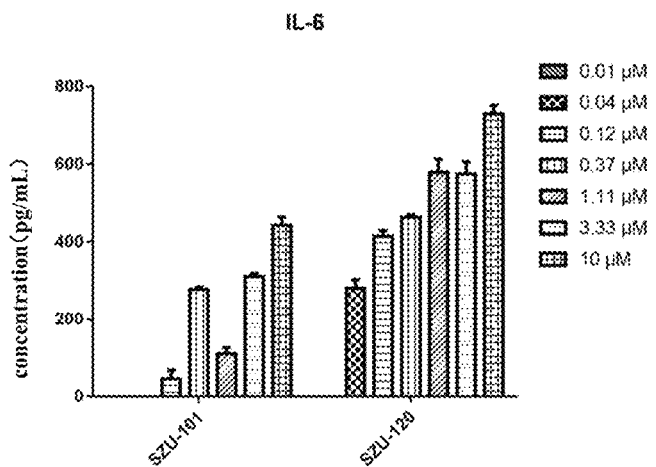
FIG. 20 shows the stimulatory effects of SZU-120 on immune cytokine (IL-6).
Figure 21:
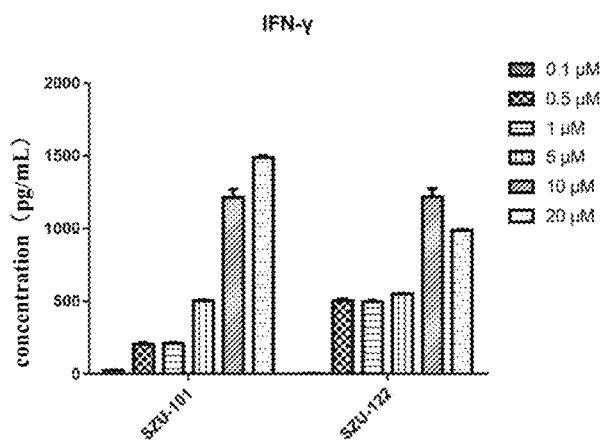
FIGS. 21-54 show the stimulatory effects of the small-molecule immune agonists SZU-122 and 127-142 according to the present invention on immune cytokines, respectively.
Figure 22:
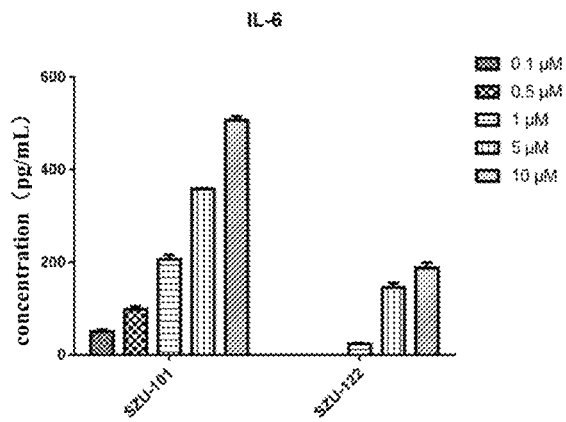
Figure 23:
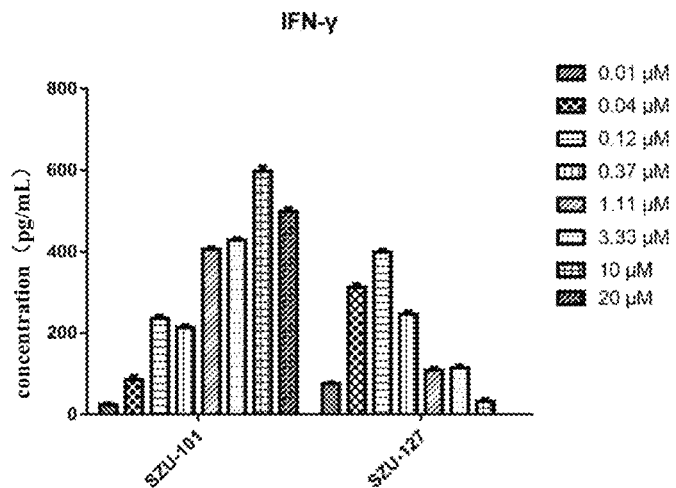
Figure 24:
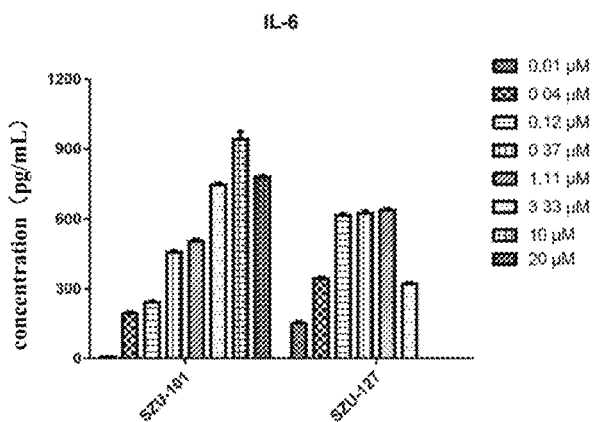
Figure 25:
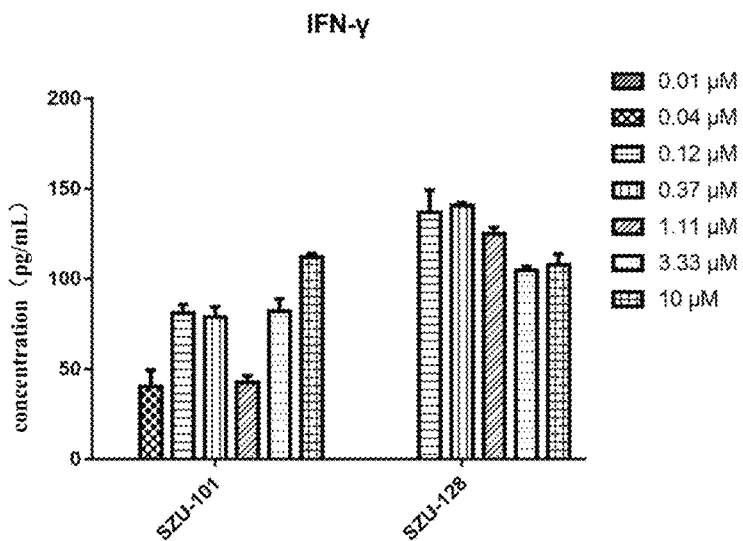
Figure 26:
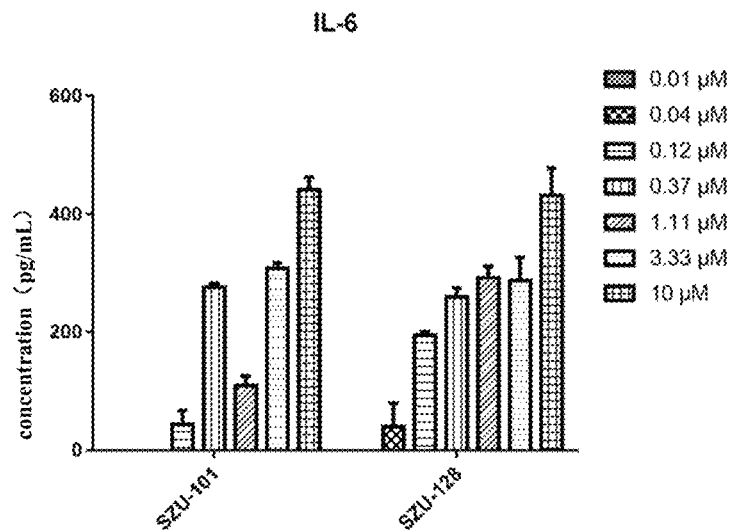
Figure 27:
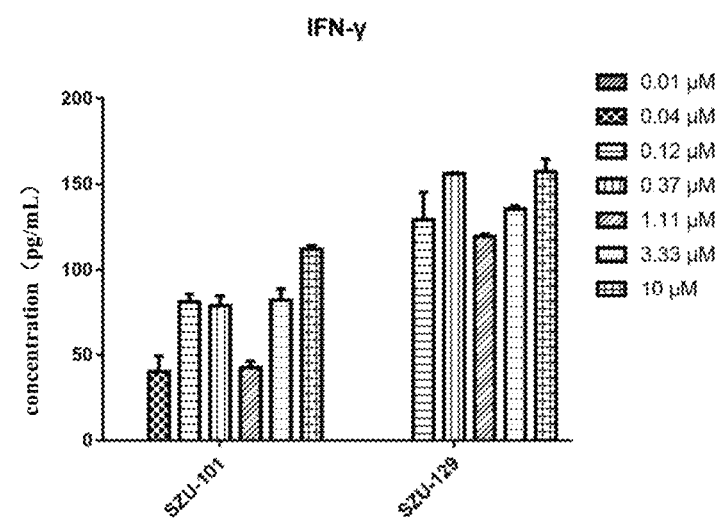
Figure 28:
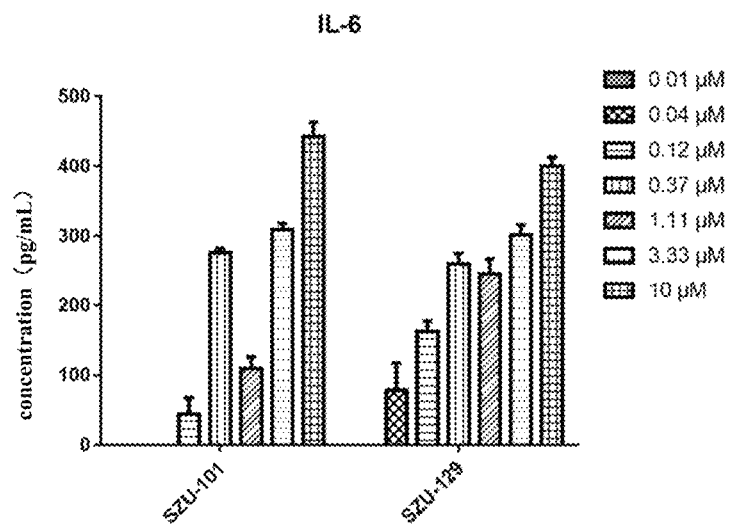
Figure 29:
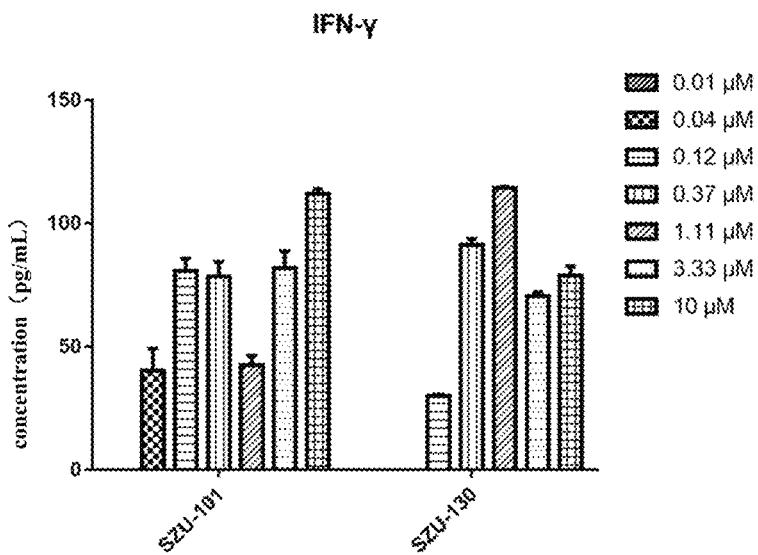
Figure 30:
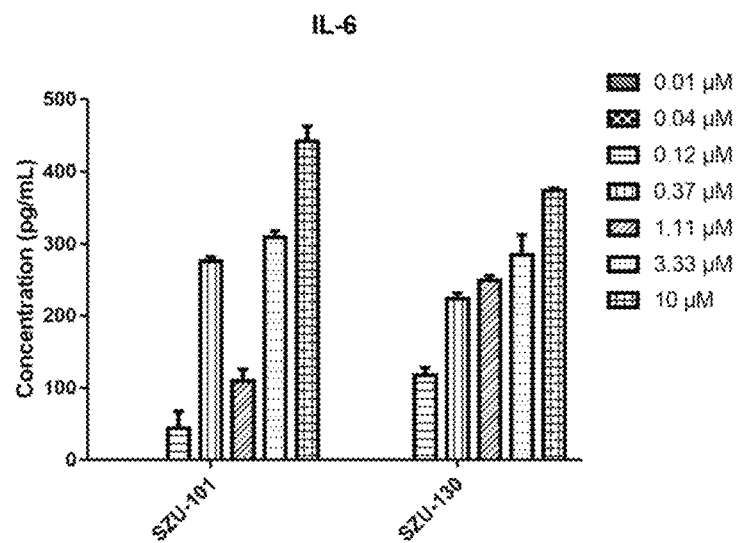
Figure 31:
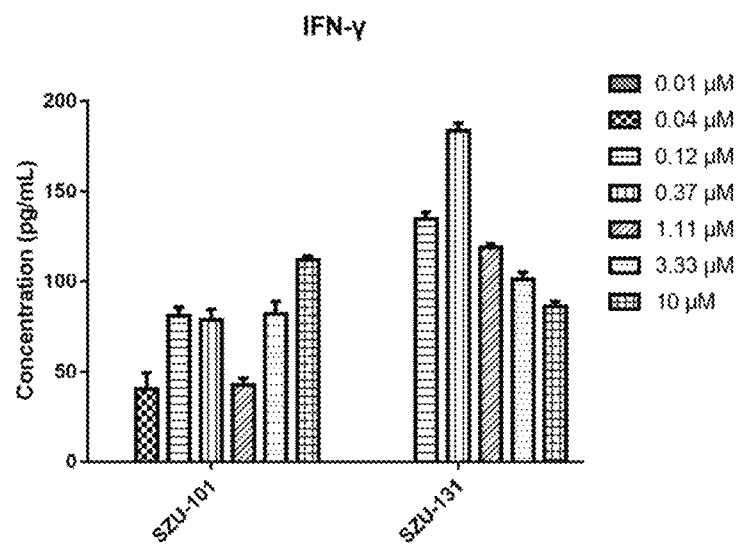
Figure 32:
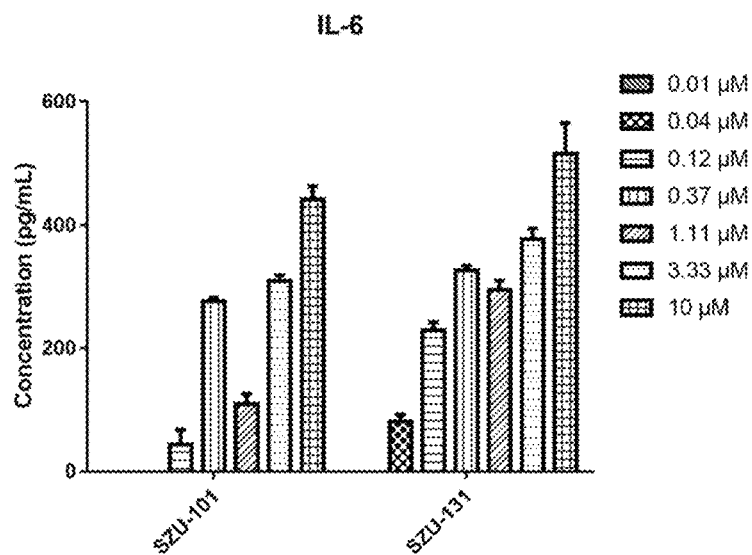
Figure 33:
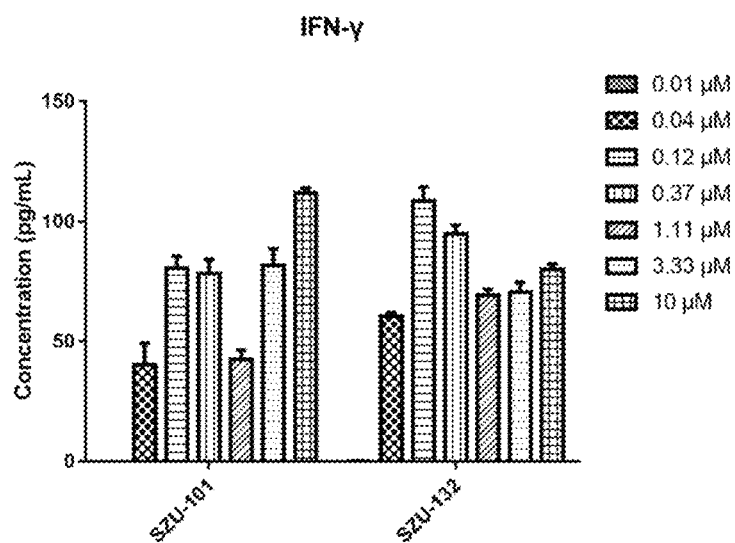
Figure 34:
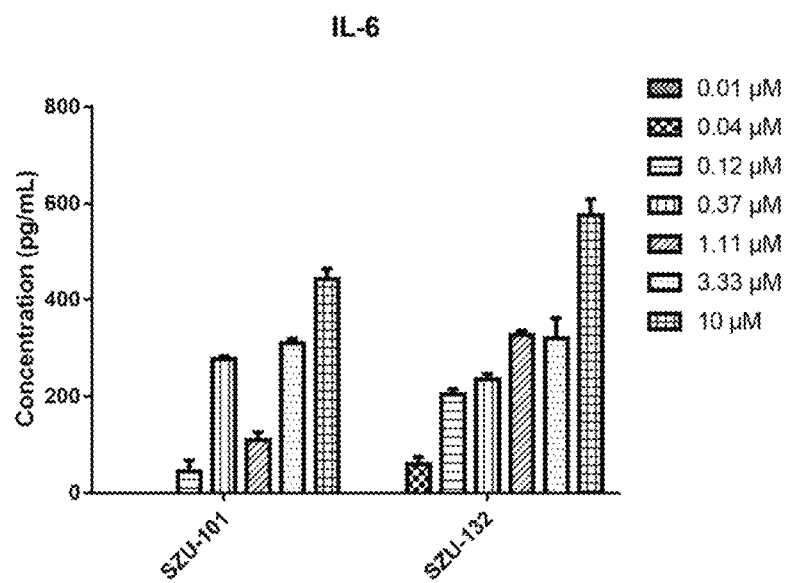
Figure 35:
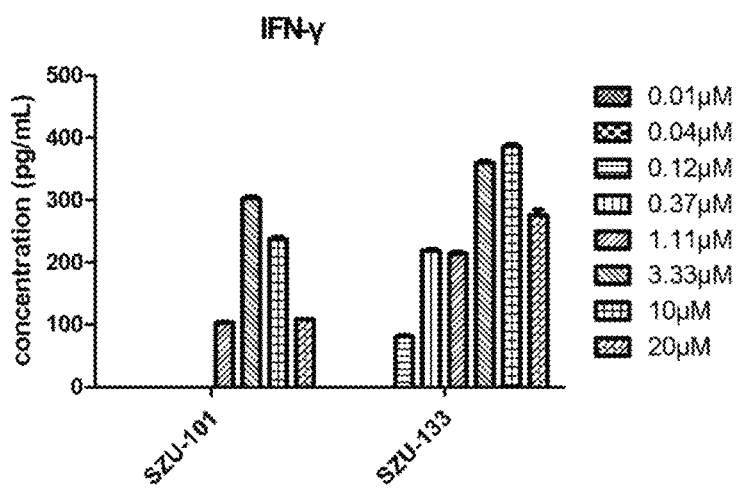
Figure 36:
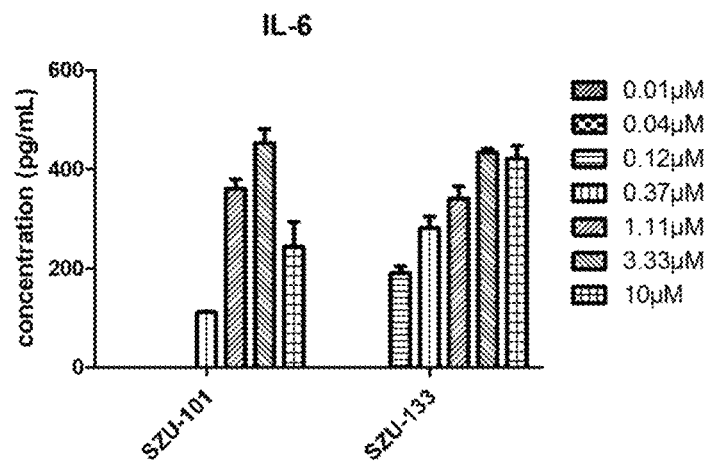
Figure 37:
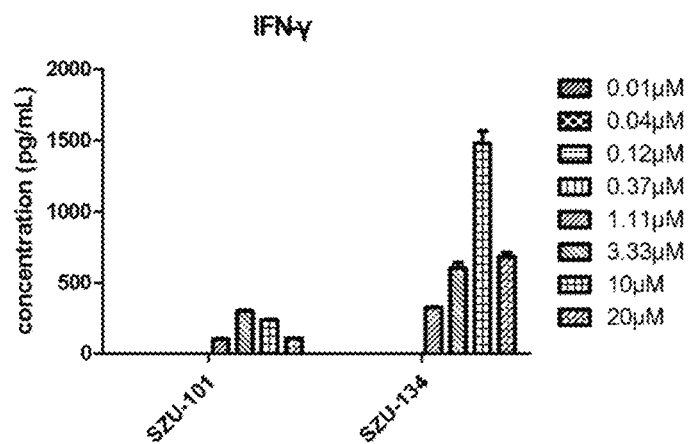
Figure 38:
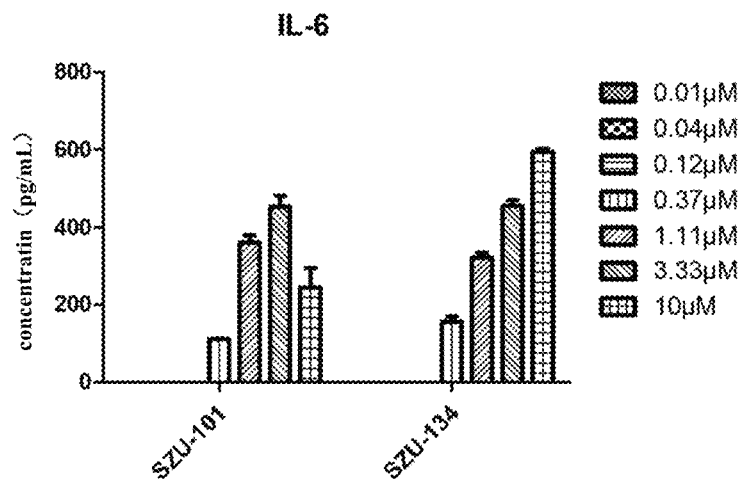
Figure 39:
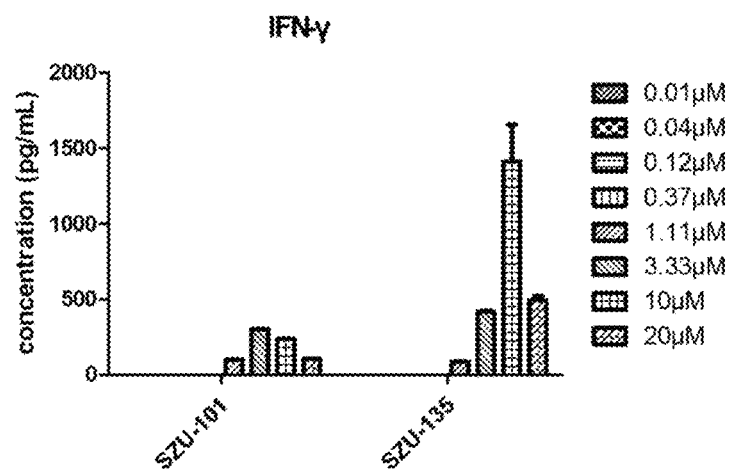
Figure 40:
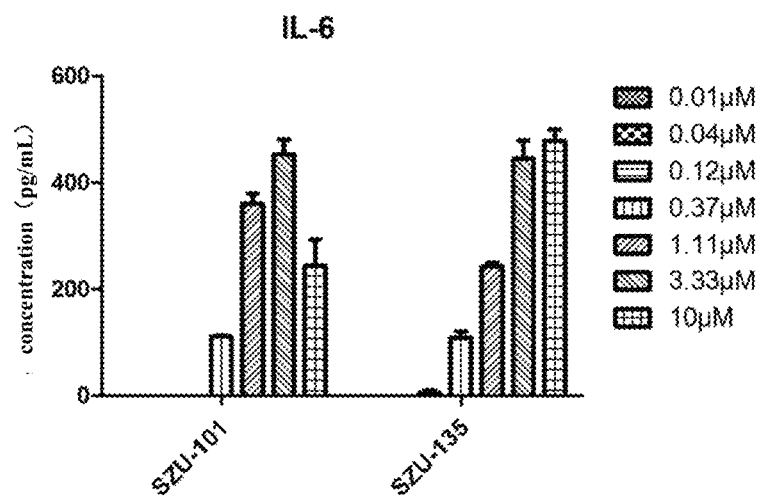
Figure 41:
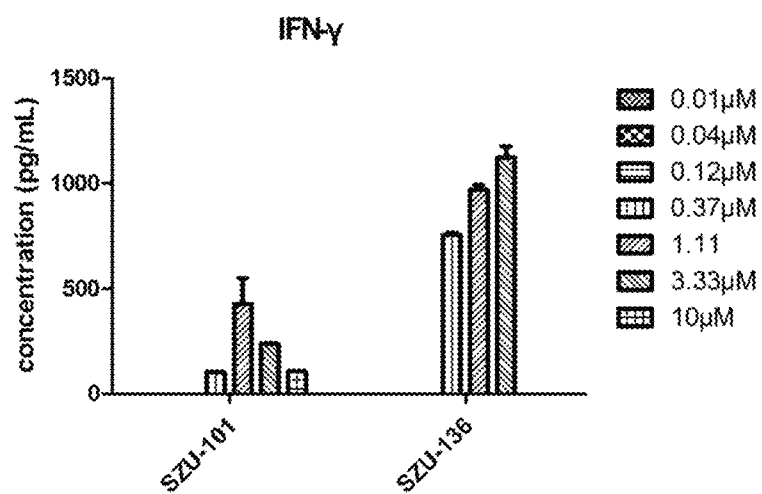
Figure 42:
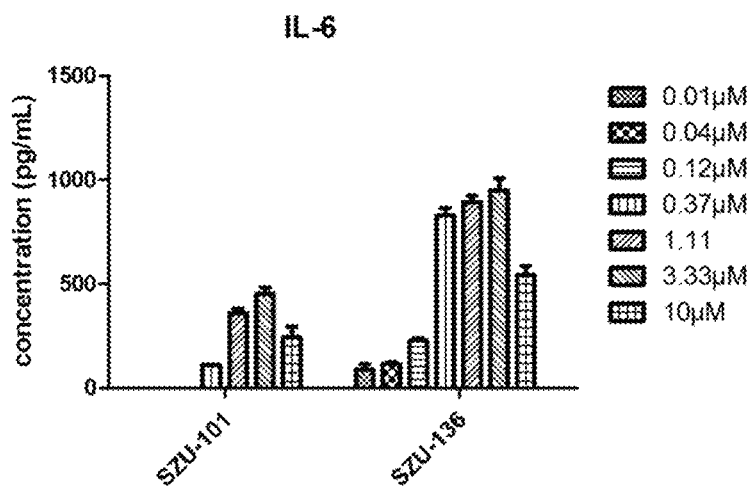
Figure 43:
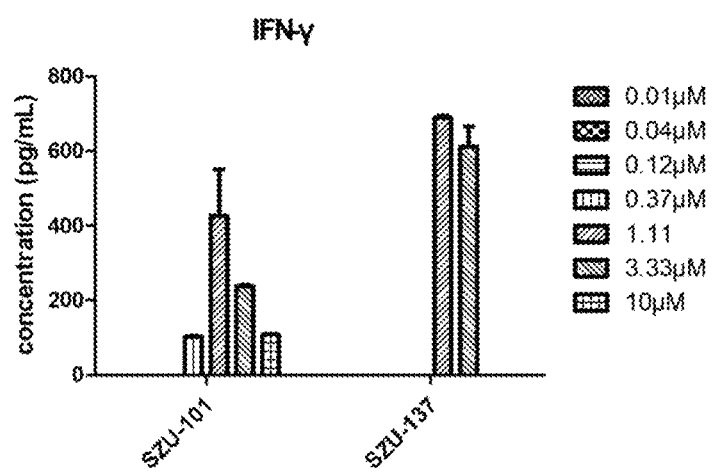
Figure 44:
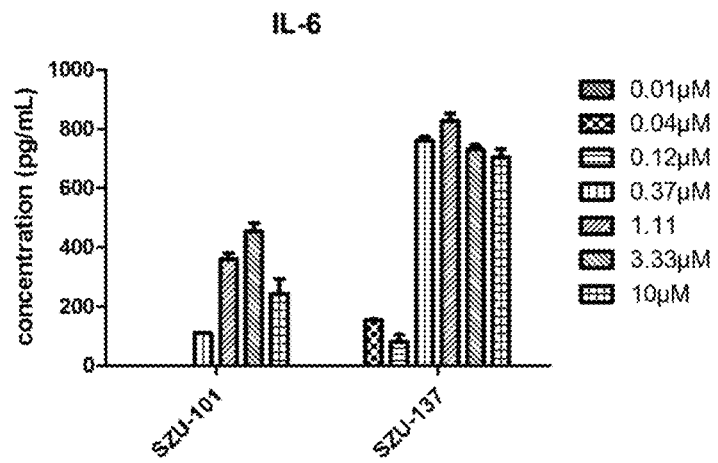
Figure 45:
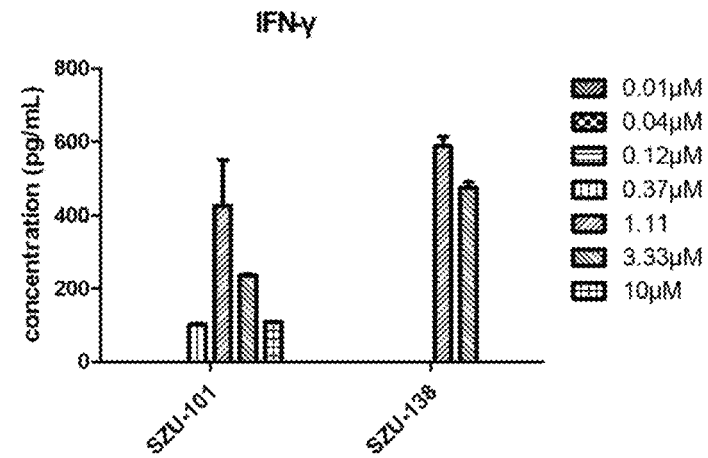
Figure 46:
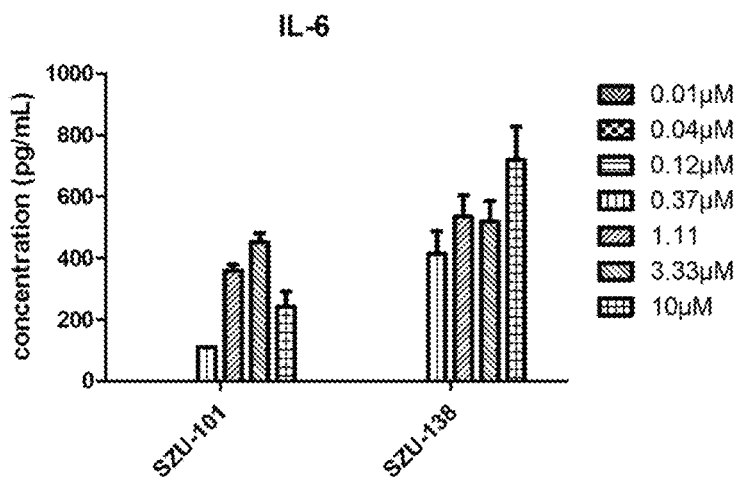
Figure 47:
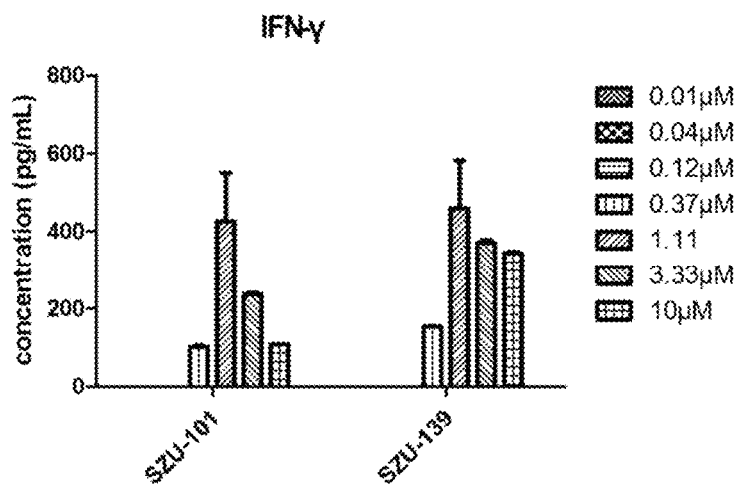
Figure 48:
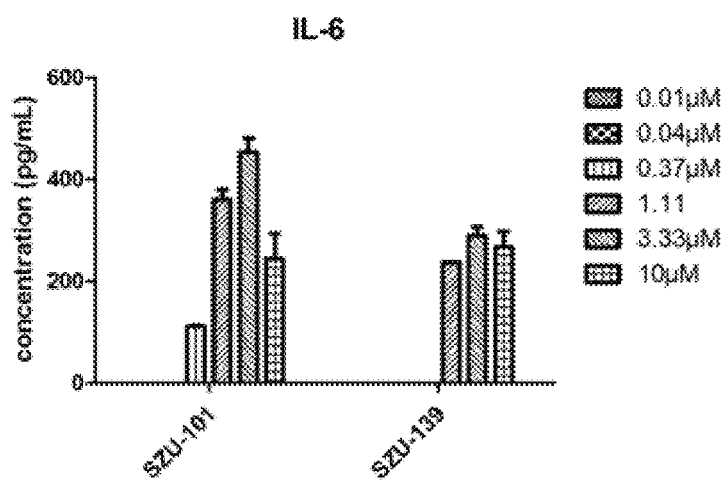
Figure 49:
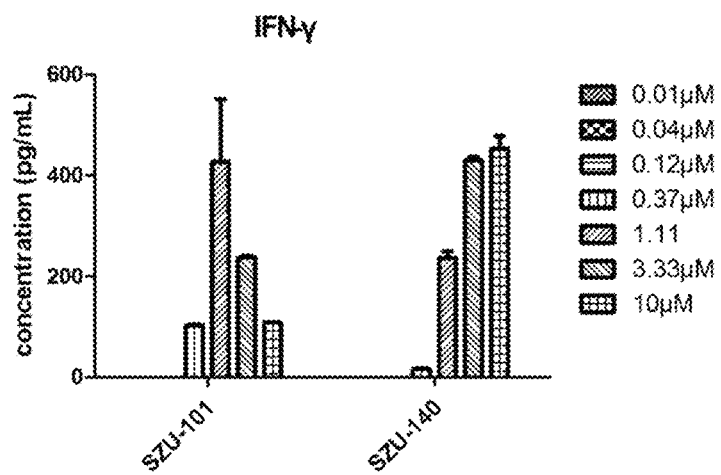
Figure 50:
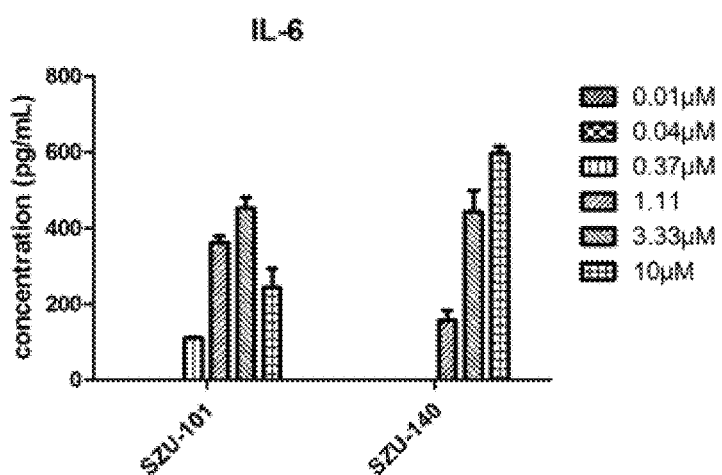
Figure 51:
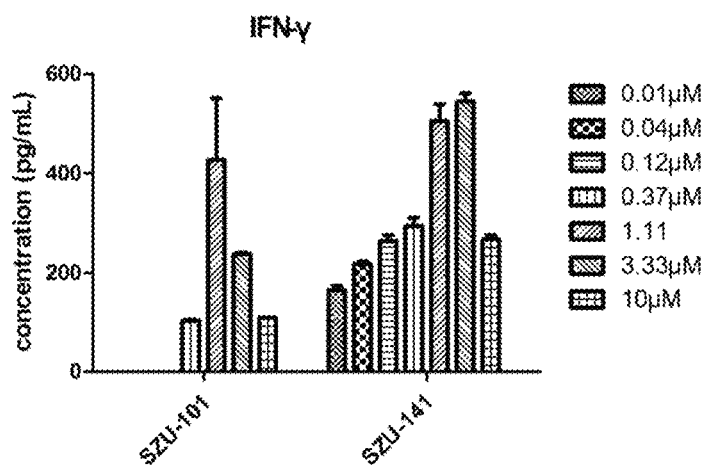
Figure 52:
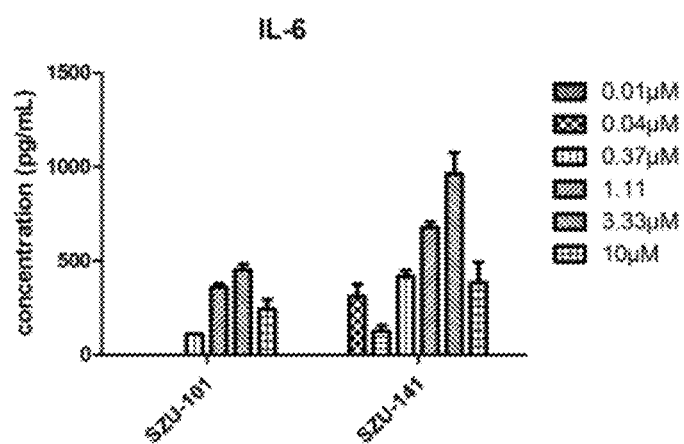
Figure 53:
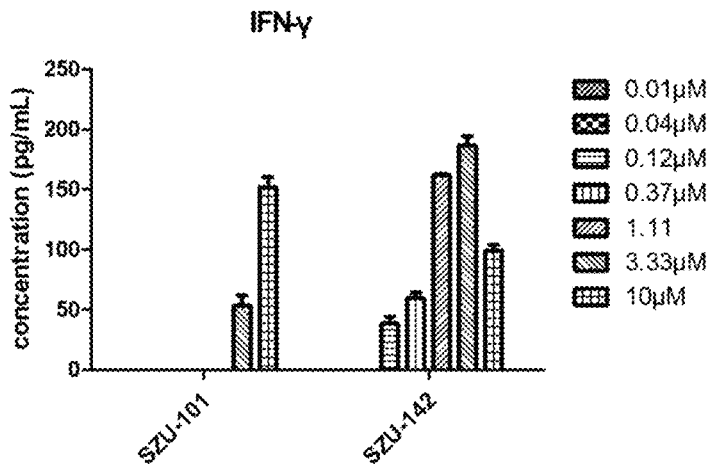
Figure 54:
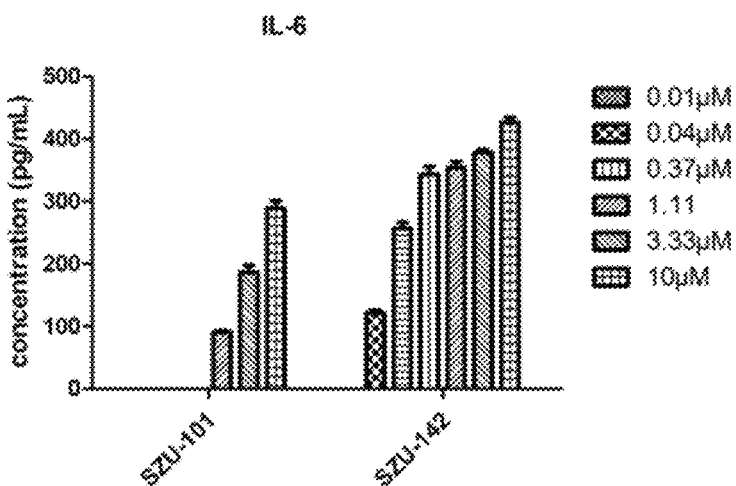
Figure 55:
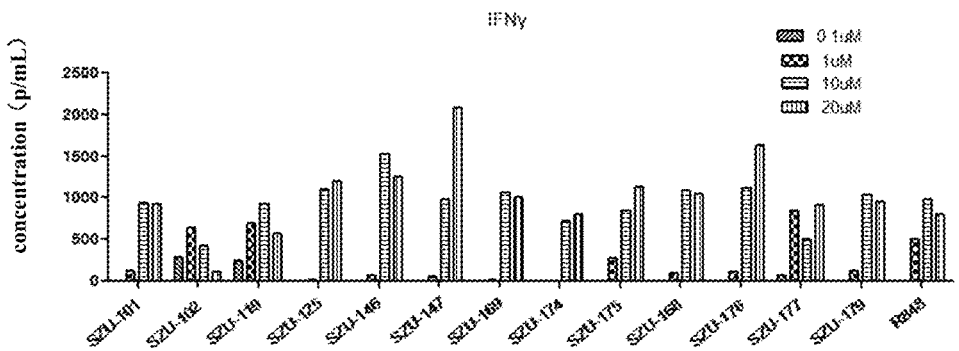
FIG. 55 shows the stimulatory effects of SZU-102, 119, 125, 146, 147, 169, 174, 175, 168, 176, 177, and 179 on immunocytes to produce IFN-γ.
Figure 56:
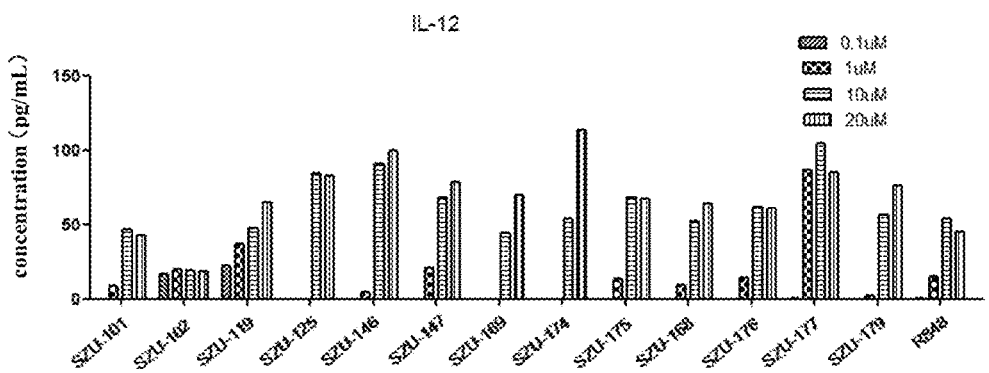
FIG. 56 shows the stimulatory effects of SZU-102, 119, 125, 146, 147, 169, 174, 175, 168, 176, 177, and 179 on immunocytes to produce IL-12.

Processes for the synthesis of the related compounds of the present invention are exemplified as follows. The exemplified synthesis processes could inspire those skilled in the art to achieve the synthesis of the novel compounds as described herein. However, synthesis of the novel compounds of the present invention is not limited to these exemplified synthesis processes.

PREPARATION EXAMPLES

SZU-112

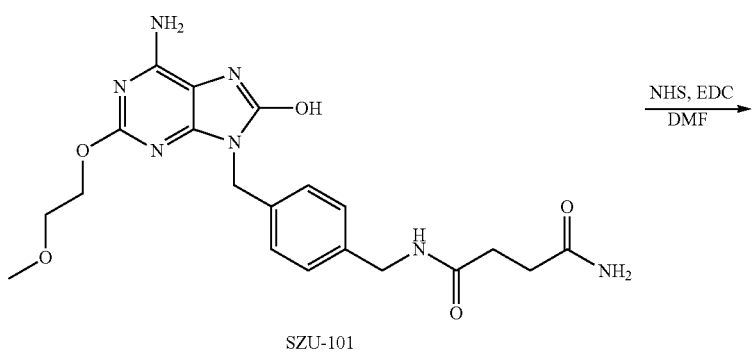

SZU-101

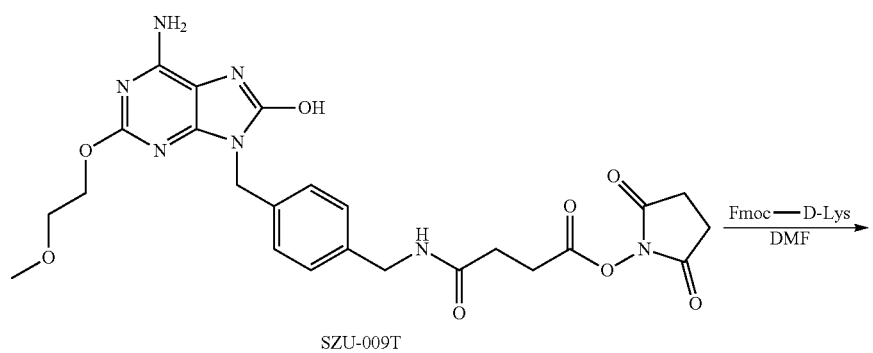

SZU-009T

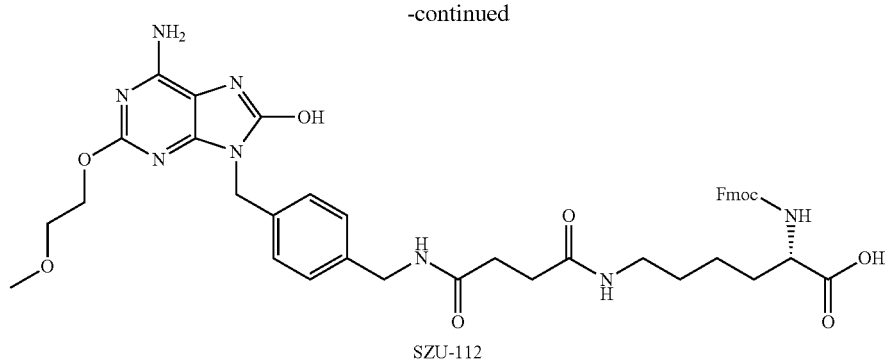

SZU-112

1 g of SZU-101, 311 mg of N-hydroxysuccinimide (NHS) and 518 mg of dichloroethane (EDC) were dissolved in 12 mL of anhydrous N,N-dimethylformamide (DMF). The mixture was reacted at room temperature for 2 hours under the protection of nitrogen atmosphere. The reaction was monitored by Thin Layer Chromatography (TLC). When the reaction was completed, the reaction solution was poured into water. The precipitate was filtered off and dried to give a crude SZU-009T, which was directly reacted in the next step.

500 mg of SZU-009T and 339 mg of Fmoc-D-lysine were dissolved in 10 mL of anhydrous DMF. The mixture was stirred at room temperature for 1 hour. After the reaction was completed, the mixture was admixed with water, and precipitated solids were filtered off with suction. The residue was purified by column chromatography (chloroform:methanol=3:1) to give a white solid (576 mg) with a yield of 78.9%, ESI-MS: m/z=795.3 [M+H]$^+$.

SZU-107

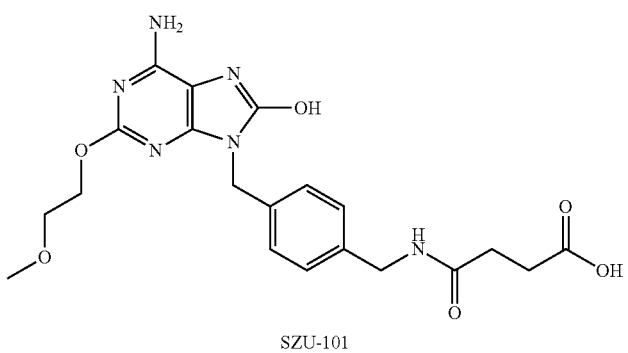

SZU-101

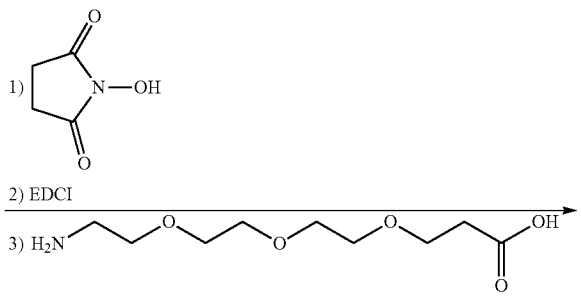

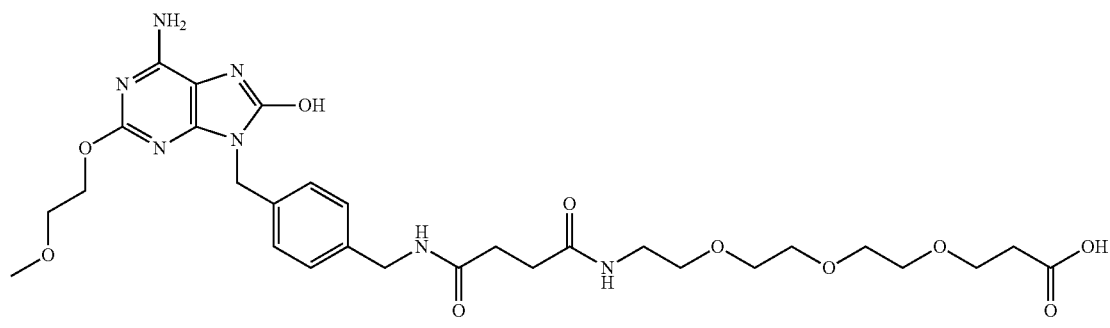

SZU-107

1 g of SZU-101 was dissolved in 20-fold weight of anhydrous DMSO. Equimoles of compounds 1), 2) and 3) were added successively. The reactants were mixed under stirring at room temperature for 12 hours, and added with 10-fold volume of water based on the reaction volume. The mixture was centrifuged to give a precipitate as a crude product, which was added into 20 mL of saturated aqueous sodium carbonate solution. The resulting mixture was stirred for 10 minutes and filtered. The filtrate was adjusted to a pH of 3 with concentrated hydrochloric acid. A pure product SZU-107 was precipitated out and dried under vacuum, with a yield of 65%. ESI-MS: m/z=647.6865 [M+H]$^+$.

SZU-113

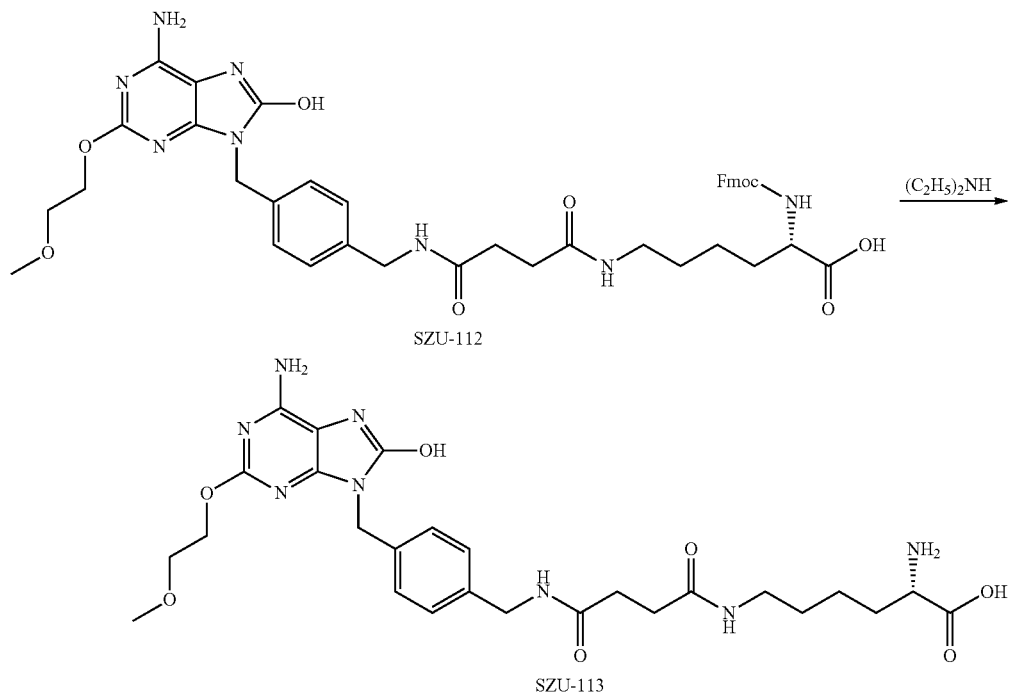

SZU-112

SZU-113

50 mg of SZU-112 was dissolved in 1 mL of diethylamine. The mixture was stirred at room temperature for 1 hour. The progress of the reaction was monitored by TLC. After the reaction was completed, diethylamine was removed under reduced pressure. The residue was washed with the addition of 1 mL of dichloromethane, then centrifuged at 10,000 rpm for 5 minutes. The supernatant was removed. The precipitate was washed again and dried under reduced pressure to give 32 mg of a white solid with a yield of 90%, ESI-MS: m/z=573.2 [M+H]$^+$.

SZU-115

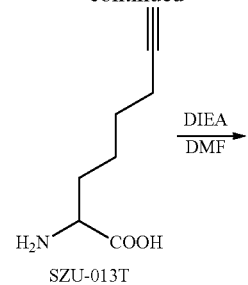

SZU-013T

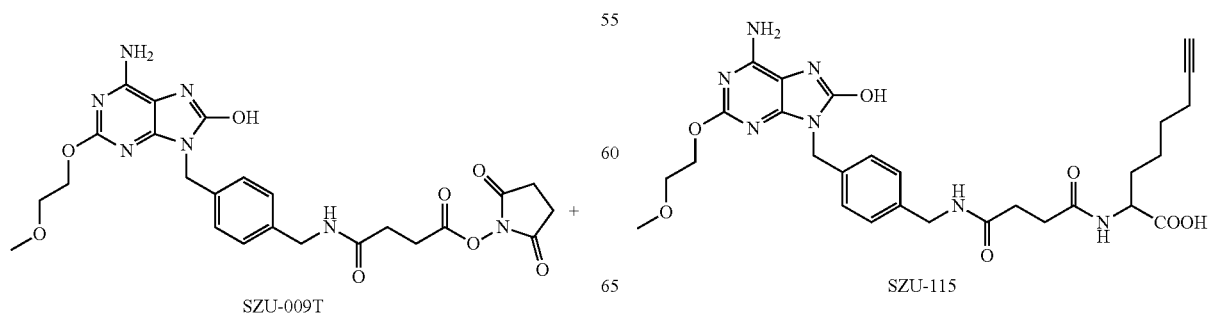

SZU-009T

SZU-115

108 mg of SZU-009T was dissolved in 2 mL of anhydrous DMF. 31 mg of SZU-013T and 100 μL of N,N-diisopropylethylamine (DIEA) were added successively. The mixture was stirred at room temperature overnight. The progress of the reaction was monitored by LC-MS. After the reaction was completed, the residue was purified by preparative liquid chromatography to give 65 mg of a white solid with a yield of 56%. ESI-MS: m/z=582.2 [M+H]$^+$.

SZU-116

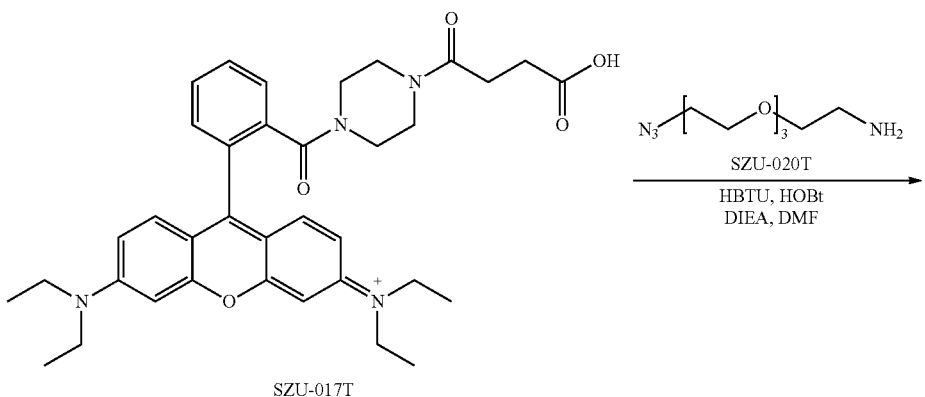

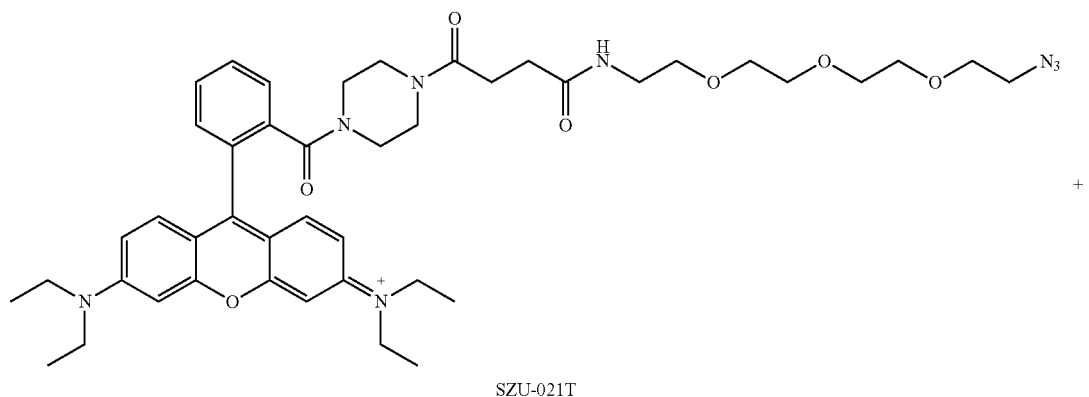

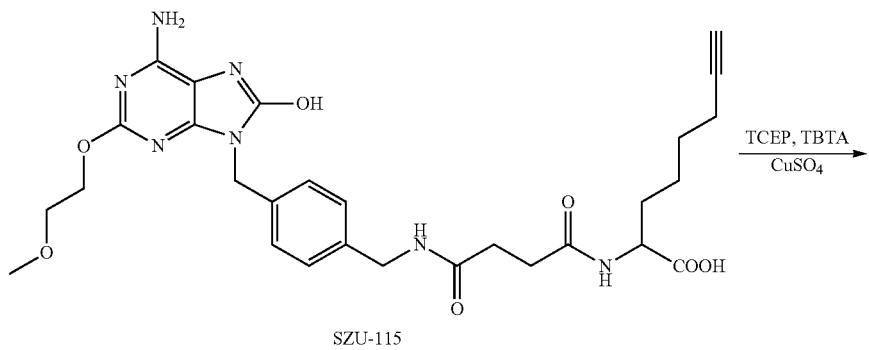

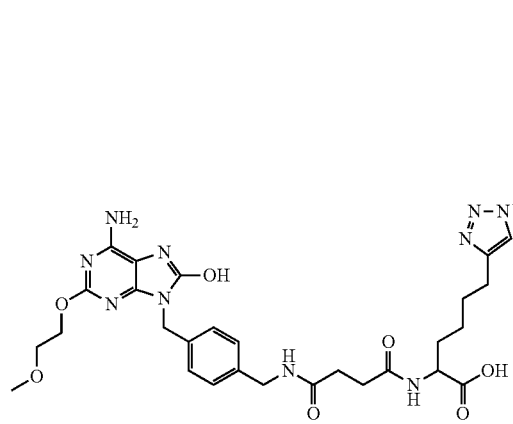
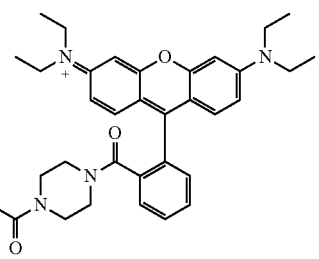

SZU-116

264 mg of SZU-017T, 324 mg of HBTU and 119 mg of 1-hydroxybenzotriazole (HOBt) was dissolved in 5 mL of anhydrous DMF. 256 μL of DIEA was added dropwise. The mixture was stirred at room temperature for 10 minutes. 5 mL of SZU-020T (230 mg) in anhydrous DMF was added and the resulting mixture was stirred at room temperature overnight. The reaction solution was poured into 100 mL of 5% HCl, and extracted with 30 mL of dichloromethane three times. The organic layers were combined and washed with saturated sodium bicarbonate solution, 5% HCl, and saturated sodium chloride solution, respectively, and dried over anhydrous sodium sulfate. The solvent was removed under reduced pressure, and the residue was purified by column chromatography (dichloromethane:methanol=50:1) to give 180 mg of a purple-red semi-solid SZU-021T with a yield of 51.6%.

28 mg of SZU-021T was dissolved in 0.1 mL of dimethyl sulfoxide (DMSO) and admixed with 0.5 mL of aqueous solution of tris(2-carboxyethyl)phosphine (TCEP) (97 mg), 0.1 mL of TBTA (18 mg) in DMSO and 0.5 mL of aqueous solution of anhydrous copper sulfate (54 mg). 20 mg of SZU-115 in 2 mL of methanol/water mixed solution was added. The mixture was stirred at room temperature for 2 hours and purified by column chromatography to give 31 mg of a purple-red solid with a yield of 66%. ESI-MS: m/z=1393.7 [M+H]$^+$.

SZU-119

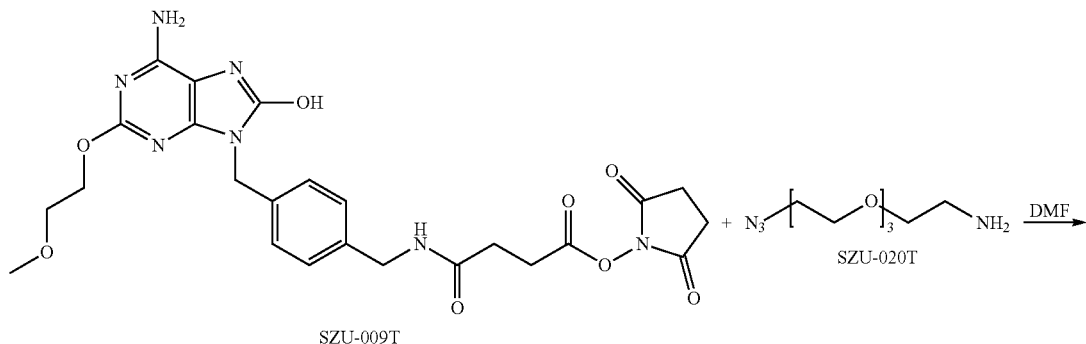

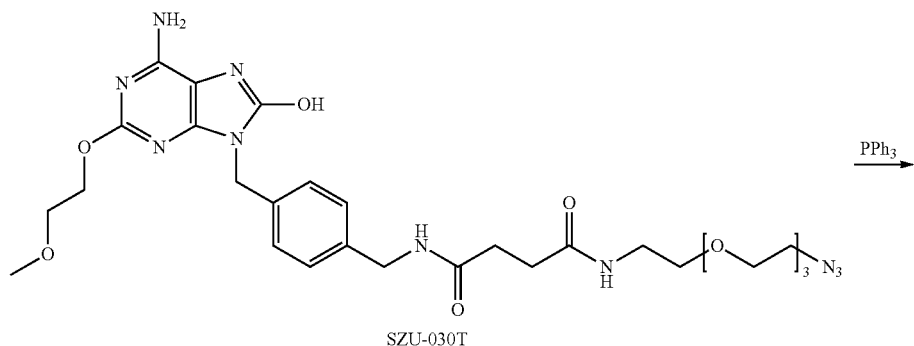

-continued

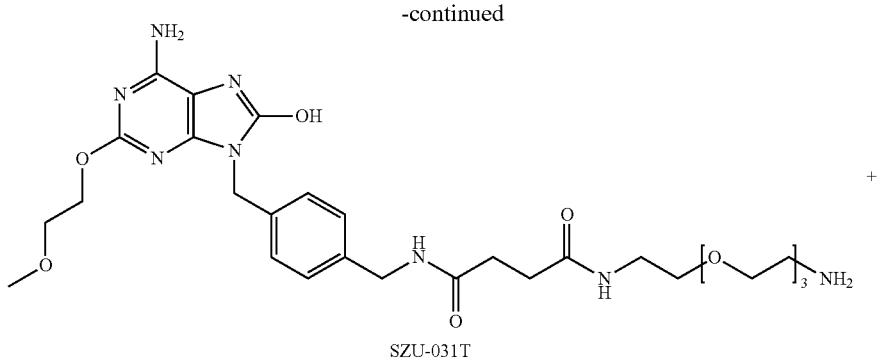

SZU-031T

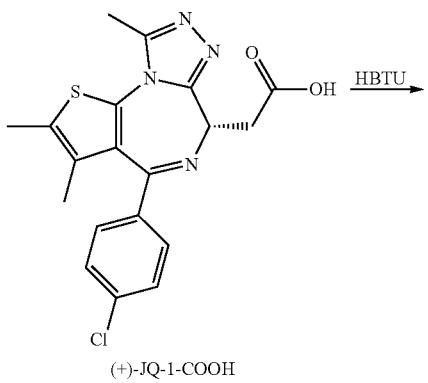

(+)-JQ-1-COOH

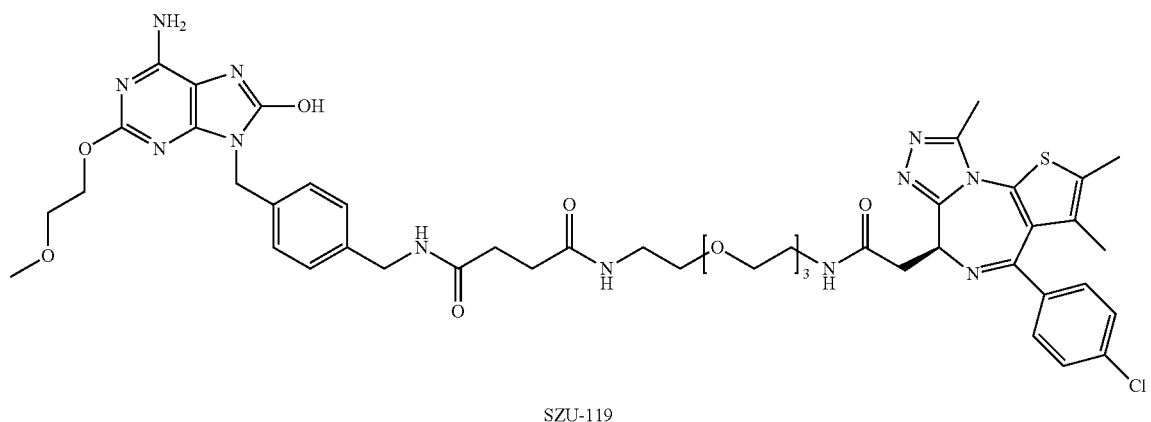

SZU-119

667 mg of SZU-009T was dissolved in 2 mL of anhydrous DMF. 300 mg of SZU-020T was added and the mixture was stirred at room temperature overnight. After the reaction was completed, the reaction solution was poured into water. A white solid was precipitated out and dried to give a crude SZU-030T.

The SZU-030T obtained in the above step was dissolved in 10 mL of anhydrous tetrahydrofuran (THF). 484 mg of triphenylphosphine was added under an ice bath. The mixture was transferred to room temperature and continued to react under stirring overnight. The progress of the reaction was monitored by LC-MS. After the reaction was completed, 20 mL of water was added. The mixture was stirred for another 30 minutes, then filtered off with suction under reduced pressure. The residue was washed with water twice and dried to give 625 mg of SZU-031T with a yield of 79% over the two steps.

71 mg of SZU-031T, 42 mg of (+)-JQ-1-COOH (JQ1, active isomer), 46 mg of HBTU were dissolved in 2 mL anhydrous DMF. Catalytic amount of 4-dimethylaminopyridine (DMAP) and N,N-diisopropylethylamine (DIPEA) were added. The mixture was stirred at room temperature for 24 hours. The progress of the reaction was monitored by LC-MS. The residue was purified by preparative liquid chromatography and lyophilized to give 27 mg of a light yellow solid with a yield of 27%. ESI-MS: m/z=1001.2 [M+H]$^+$.

SZU-124
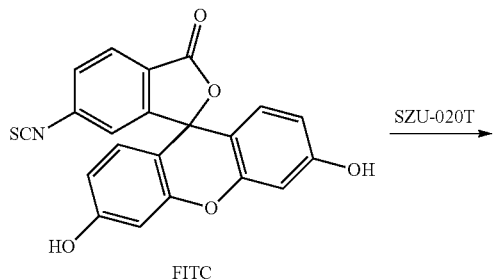
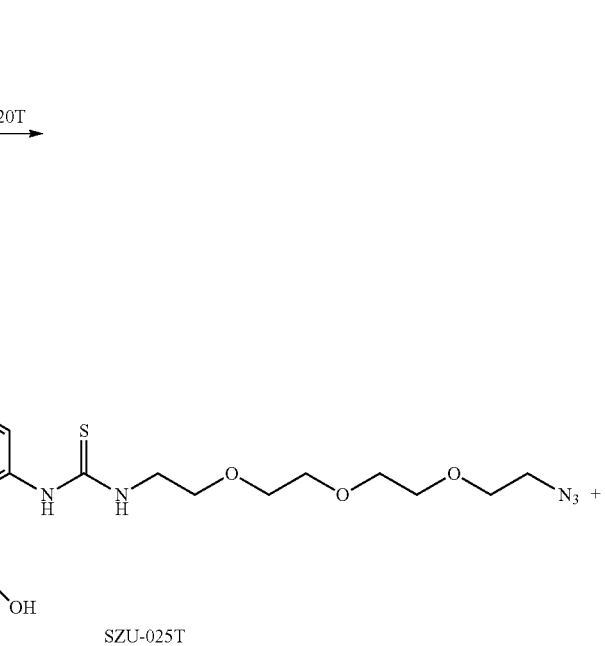
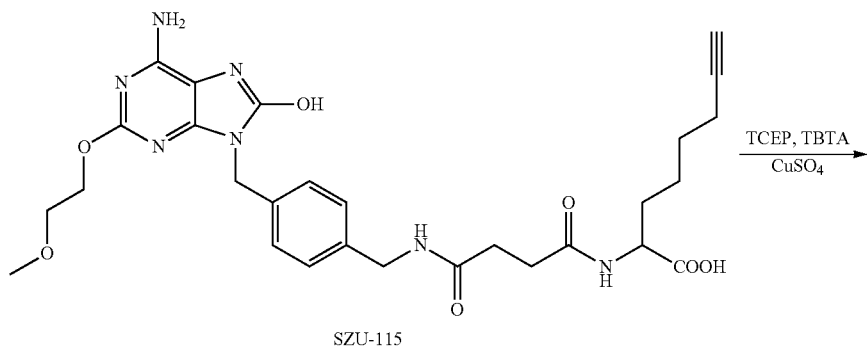
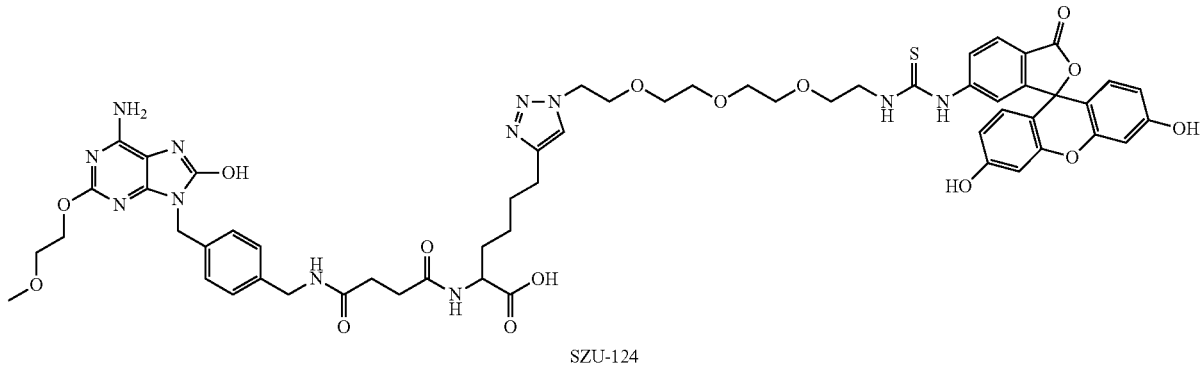
SZU-124 was prepared by the same process as SZU-116, except that SZU-017T was replaced with FITC, and a grass green semi-solid was obtained. The yield over the two steps was 31%. ESI-MS: m/z=1199.5 [M+H]$^+$.

SZU-125

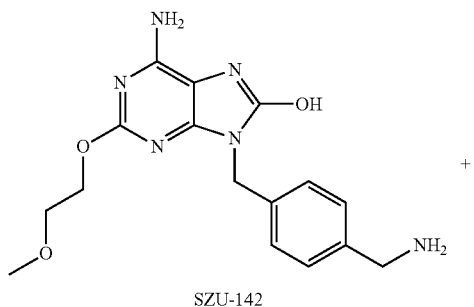

SZU-142

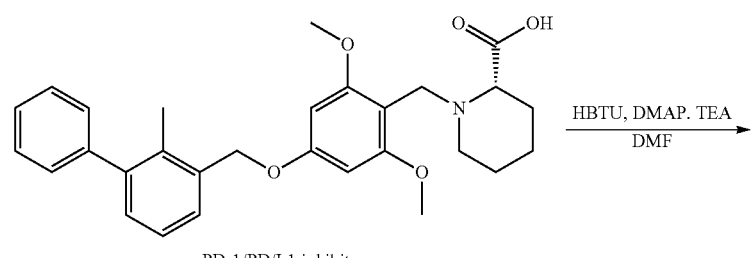

PD-1/PD/L1 inhibitor

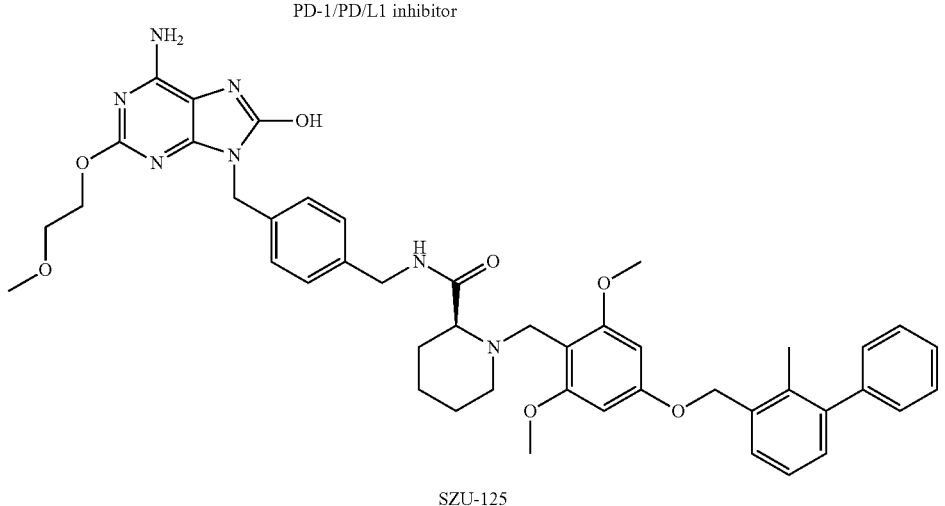

SZU-125

34 mg of SZU-008T was dissolved in 500 μL of anhydrous DMF. 53 mg of PD-1/PD-L1 inhibitor (CAS #:1675203-84-5), 43 mg of HBTU, 42 μL of triethylamine (TEA) and catalytic amount of DMAP were added successively. The mixture was stirred at room temperature for 5 hours. After the reaction was completed, the residue was purified by preparative liquid chromatography and lyophilized to give 45 mg of a white solid with a yield of 56%. ESI-MS: m/z=802.3 [M+H]$^+$.

SZU-127

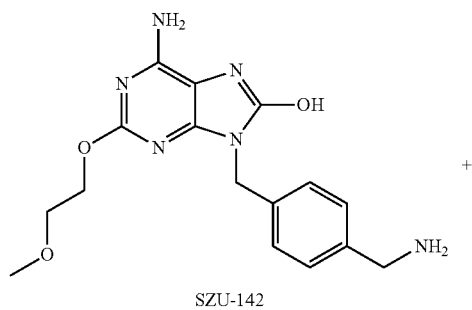

SZU-142

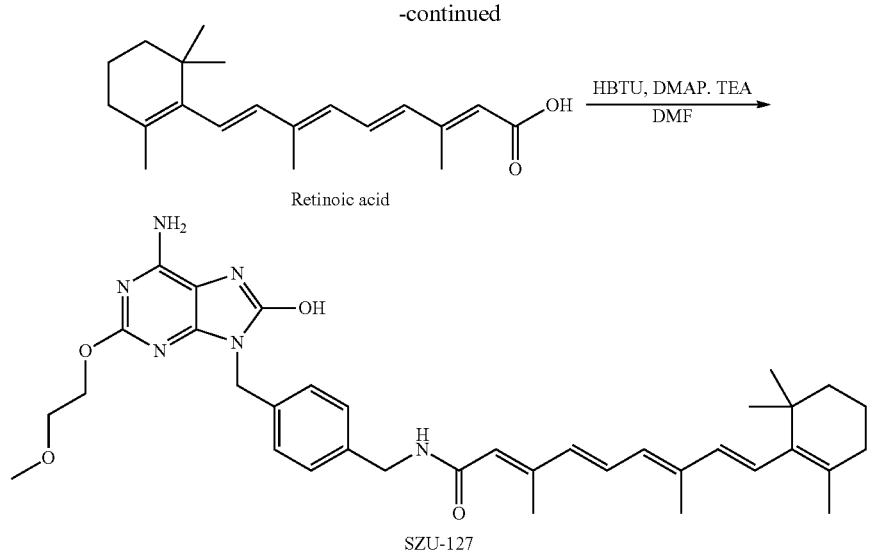

SZU-127 was prepared by the same process as SZU-125, except that the PD-1/PD-L1 inhibitor was replaced with retinoic acid, and a yellow solid was obtained. ESI-MS: m/z=627.4[M+H]$^+$.

SZU-134

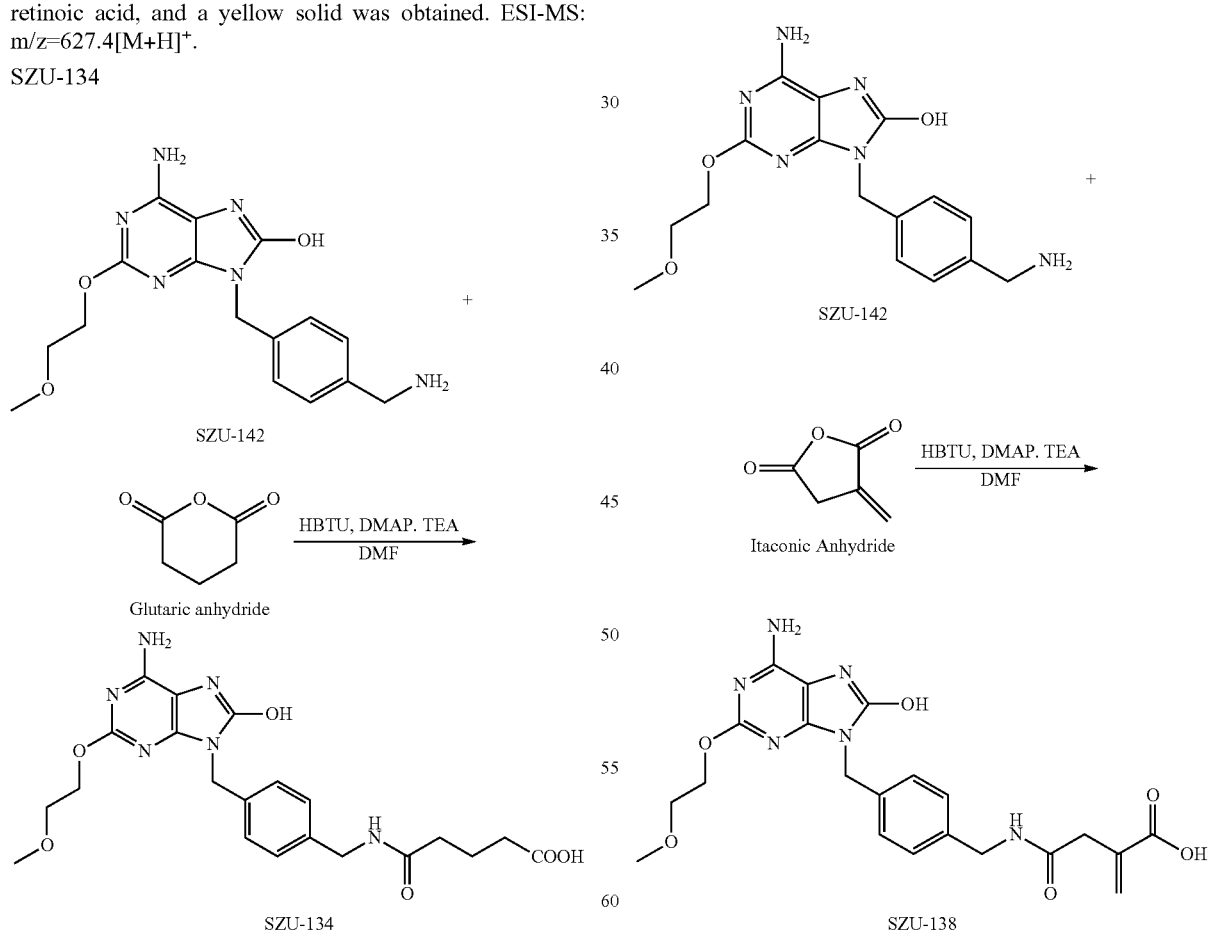

SZU-134 was prepared by the same process as SZU-125, except that the PD-1/PD-L1 inhibitor was replaced with glutaric anhydride; and a white solid was obtained. ESI-MS: m/z=459.1[M+H]$^+$.

SZU-138 was prepared by the same process as SZU-125, except that the PD-1/PD-L1 inhibitor was replaced with itaconic anhydride; and a white solid was obtained. ESI-MS: m/z=457.1[M+H]$^+$.

SZU-140
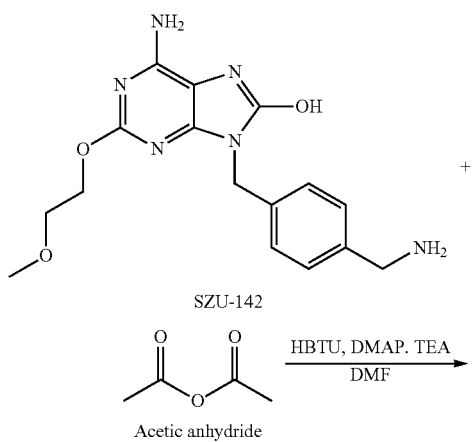
SZU-142
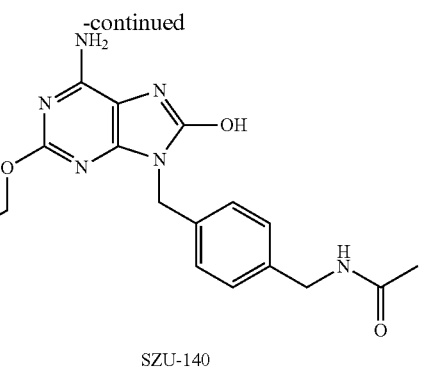
SZU-140
SZU-140 was prepared by the same process as SZU-125, except that the PD-1/PD-L1 inhibitor was replaced with acetic anhydride; and a white solid was obtained. ESI-MS: m/z=387.1[M+H]$^+$.
SZU-103-GSH
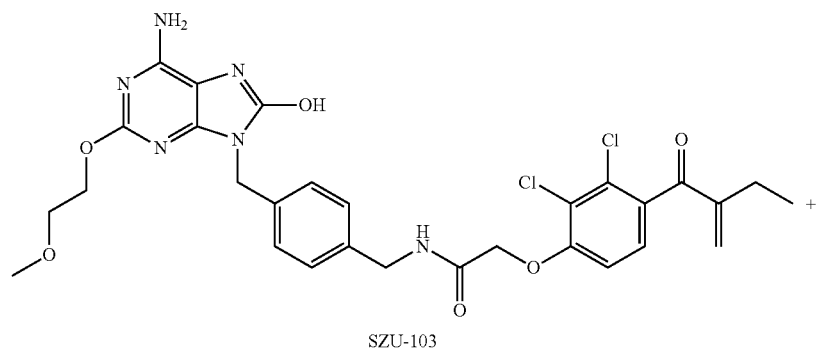
SZU-103
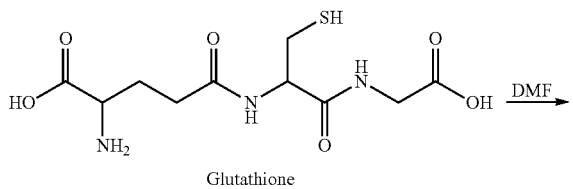
Glutathione
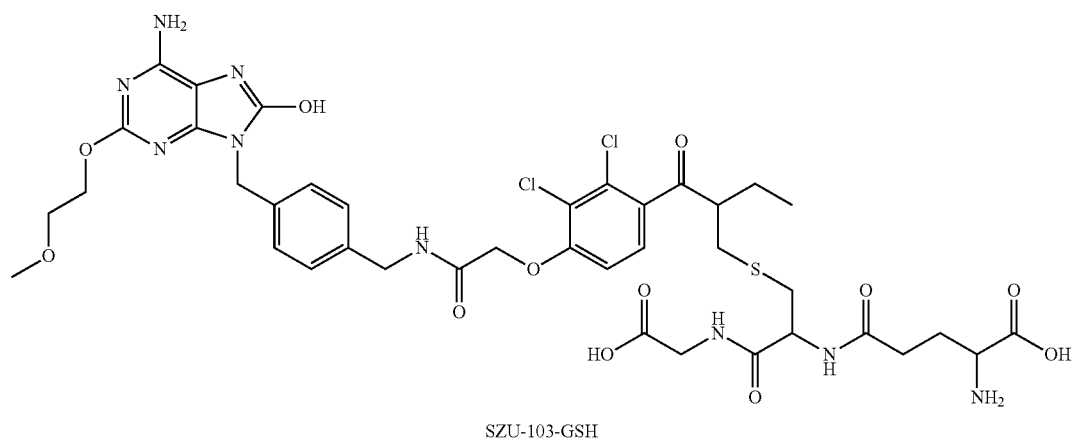
SZU-103-GSH SZU-103 and an equivalent amount of glutathione (Glutathione, GSH) were dissolved in anhydrous DMF. The mixture was stirred at room temperature overnight. The progress of the reaction was monitored by LC-MS. After the reaction was completed, the residue was purified by preparative liquid chromatography to give a white solid with a yield of 85%. ESI-MS: m/z=936.2 [M+H]⁺.

SZU-142

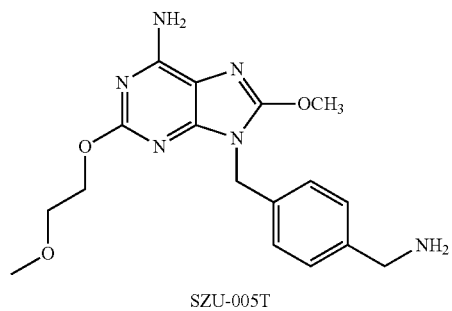

SZU-005T

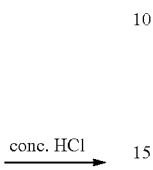

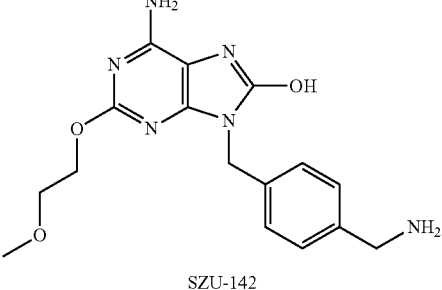

SZU-142

5 g of SZU-005T was placed in a round-bottom flask. Concentrated hydrochloric acid was added. The mixture was reacted for 12 hours. After the reaction was completed, the resulting mixture was adjusted to a pH of 3-4 with sodium hydroxide, and 4.56 g of a white solid was precipitated out, with the yield being 95%. ESI-MS: m/z=345.2[M+H]⁺.

SZU-145

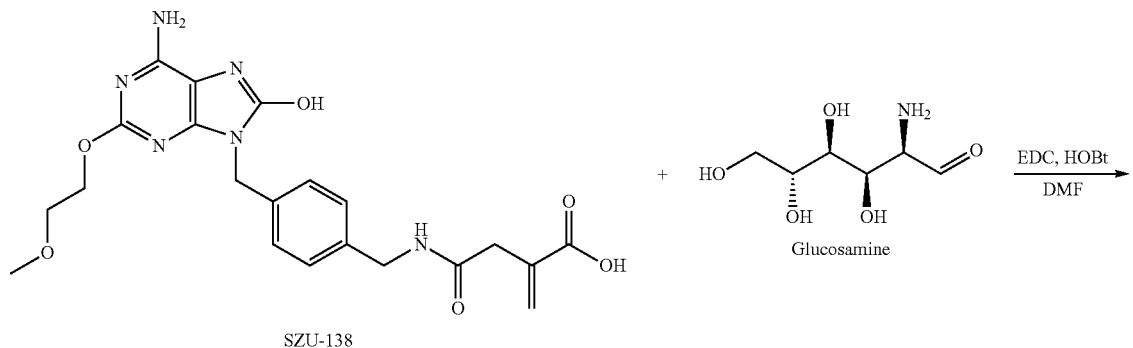

SZU-138    Glucosamine

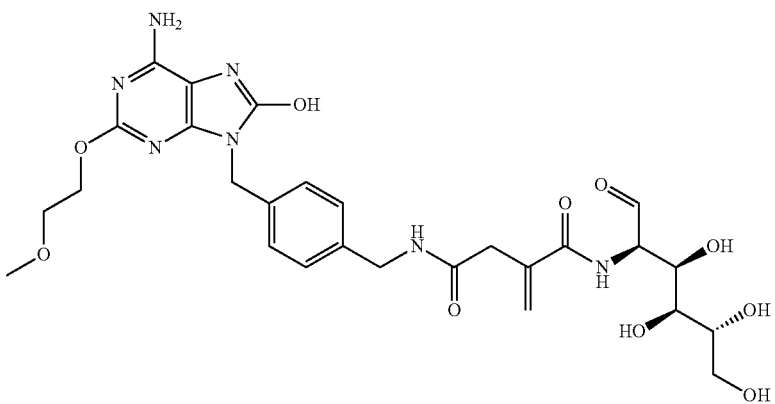

SZU-145

20 mg of SZU-138 was dissolved in 2 mL of anhydrous DMF. 8.7 mg of D-glucosamine, 9.2 mg of EDC, and 6.5 mg of HOBt were added successively. The mixture was stirred at room temperature for 2 hours. After the reaction was completed, the residue was purified by preparative liquid chromatography to give 12 mg of a white solid, with the yield being 44%, ESI-MS: m/z=618.2 [M+H]⁺.

SZU-114-GSH
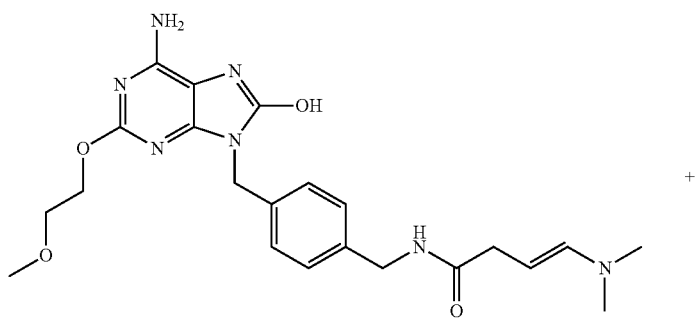
SZU-114
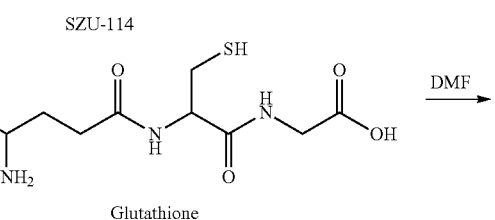
Glutathione
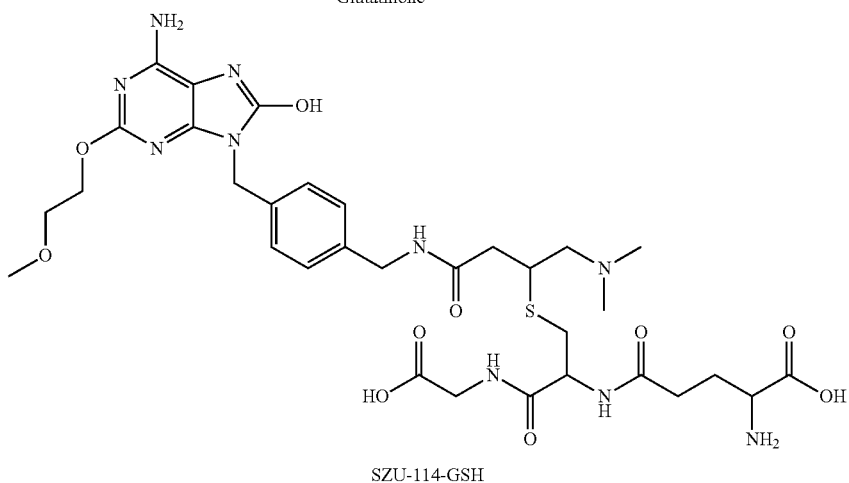
SZU-114-GSH
SZU-114-GSH was prepared by the same process as SZU-103-GSH, except that SZU-103 was replaced with SZU-114; and a white solid was obtained. ESI-MS: m/z=763.3[M+H]⁺.
SZU-117-GSH
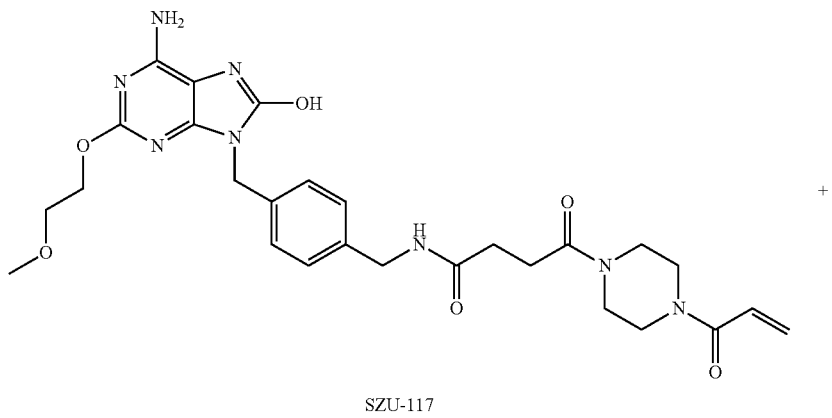
SZU-117

-continued

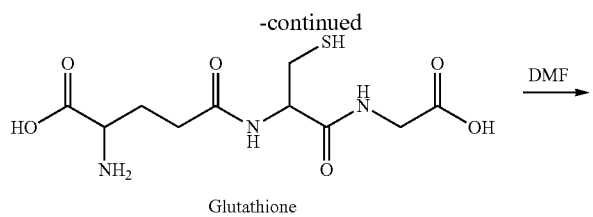

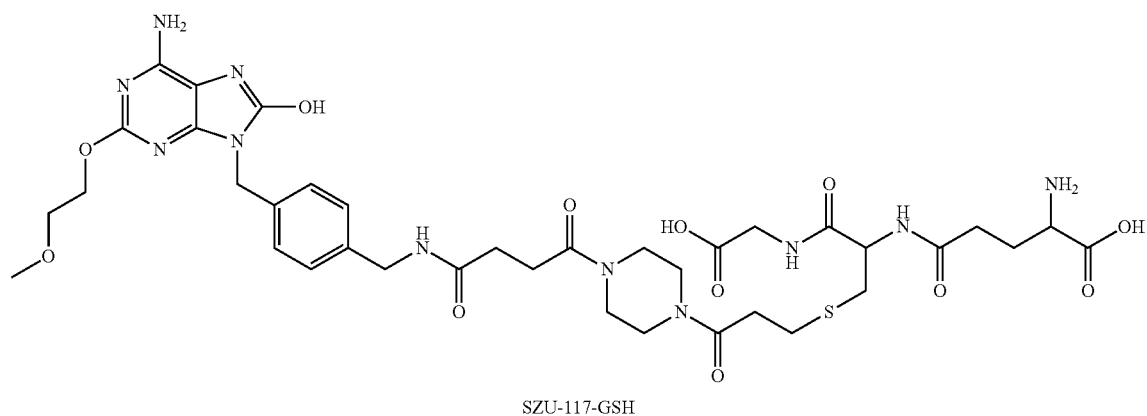

SZU-117-GSH was prepared by the same process as SZU-103-GSH, except that SZU-103 was replaced with SZU-117; and a white solid was obtained. ESI-MS: m/z=874.3[M+H]$^+$.

SZU-158

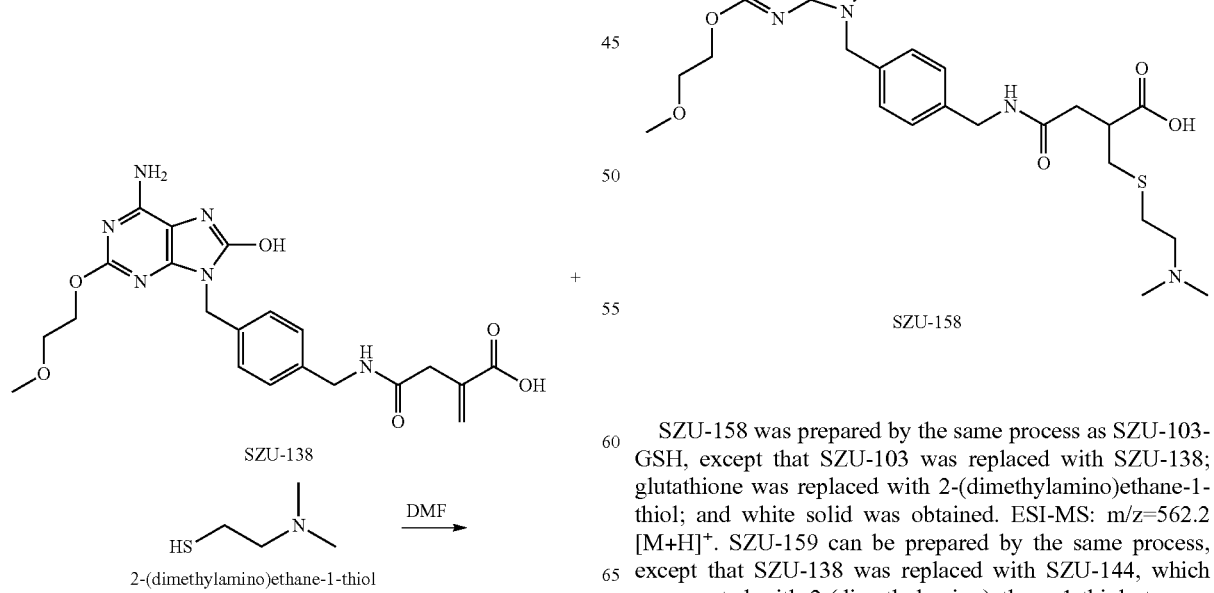

SZU-158 was prepared by the same process as SZU-103-GSH, except that SZU-103 was replaced with SZU-138; glutathione was replaced with 2-(dimethylamino)ethane-1-thiol; and white solid was obtained. ESI-MS: m/z=562.2 [M+H]$^+$. SZU-159 can be prepared by the same process, except that SZU-138 was replaced with SZU-144, which was reacted with 2-(dimethylamino)ethane-1-thiol at room temperature for 24 hours to give SZU-159.

SZU-161
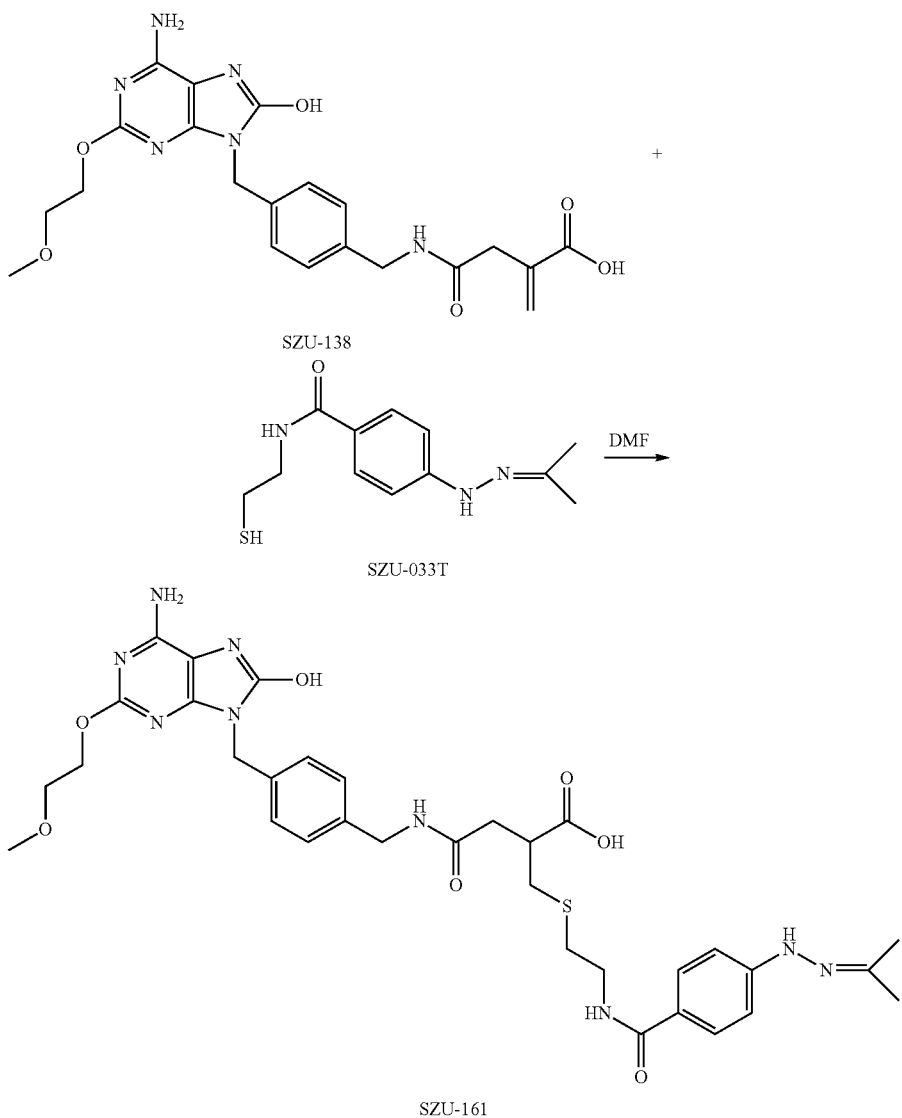
SZU-161 was prepared by the same process as SZU-103-GSH, except that SZU-103 was replaced with SZU-138; glutathione was replaced with SZU-033T; and a white solid was obtained. ESI-MS: m/z=708.4[M+H]$^+$.
SZU-162
SZU-162 was prepared by the same process as SZU-161. ESI-MS: m/z=695.81[M+H]$^+$.
SZU-160
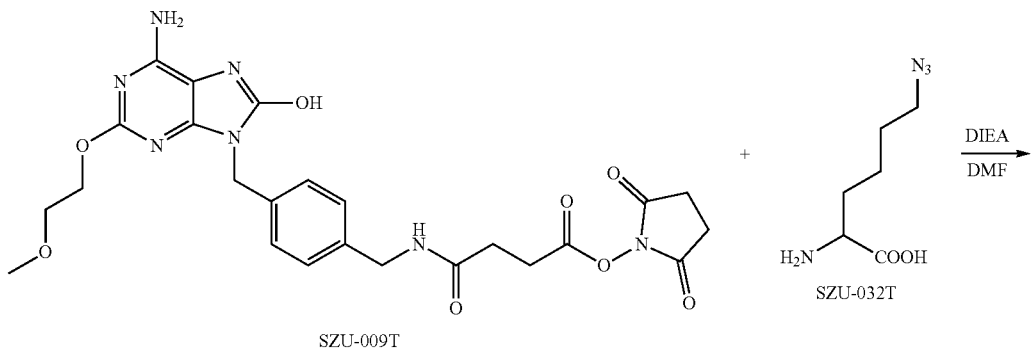

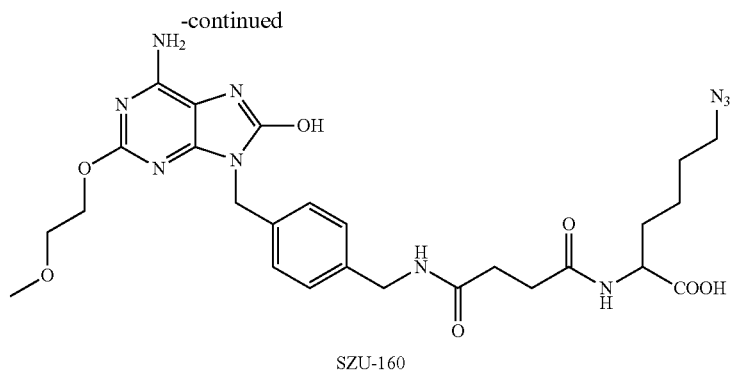

SZU-160

SZU-160 was prepared by the same process as SZU-115, except that SZU-013T was replaced with SZU-032T; and a white solid was obtained. ESI-MS: m/z=599.3[M+H]$^+$.

SZU-114

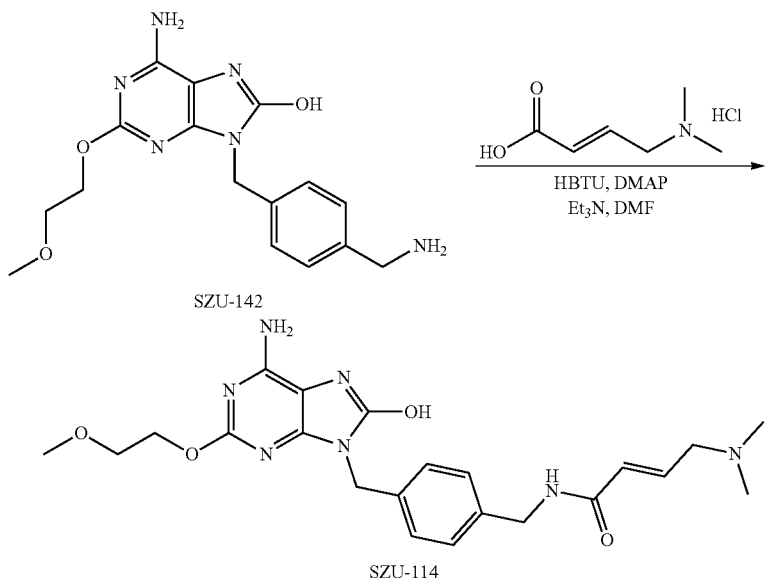

HBTU, DMAP and TEA were added to the anhydrous DMF solution of TL-008 at 0° C. The mixture was stirred at room temperature for 0.5 hour. Then trans-4-dimethylaminocrotonic acid hydrochloride was added at 0° C. The resulting mixture was reacted at room temperature for 24 hours. The reaction solution was poured into water and filtered off with suction to give a crude product, which was purified by liquid phase separation to obtain a pure product (ESI-MS: m/z=456.6 [M+H]$^+$).

SZU-117

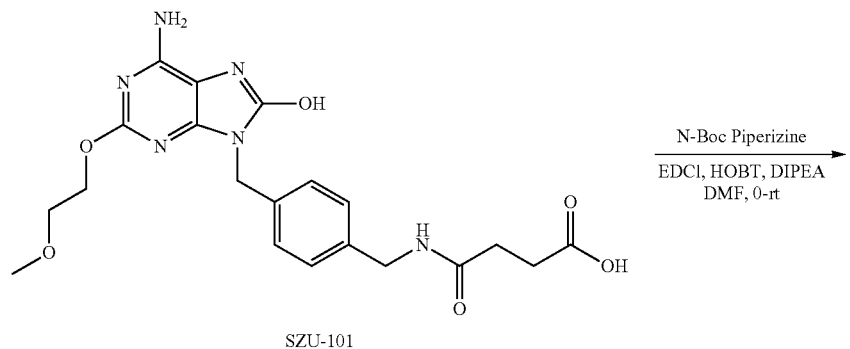

SZU-101

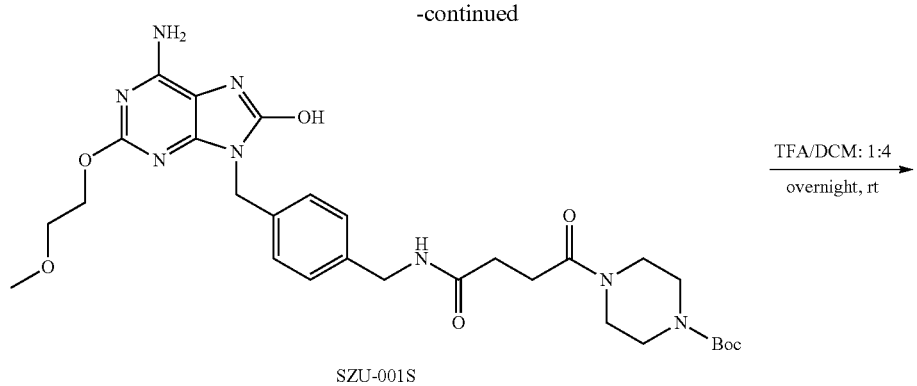

SZU-001S

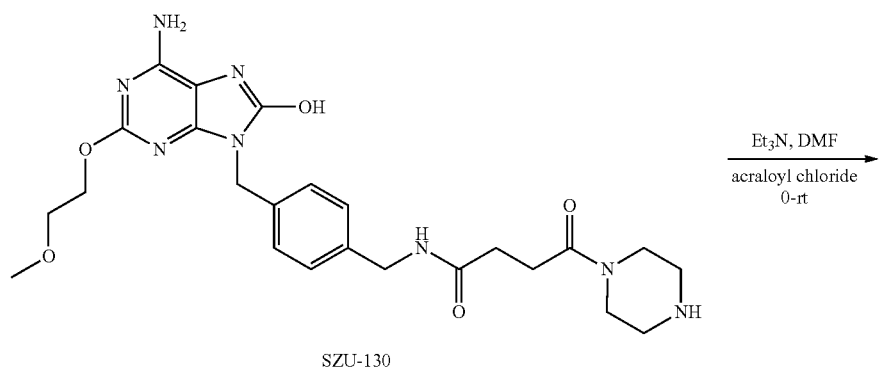

SZU-130

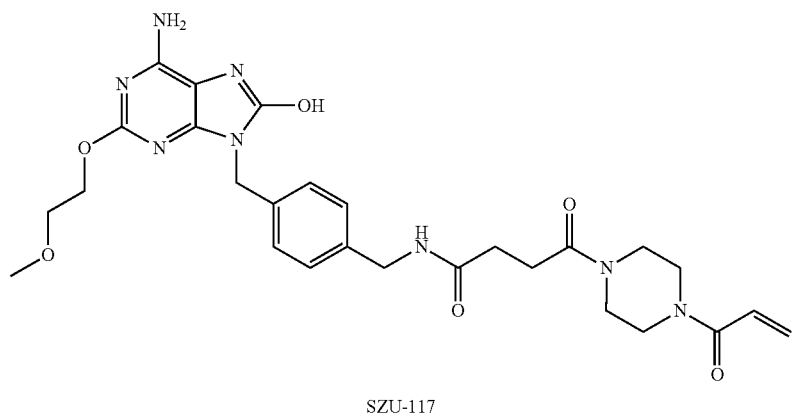

SZU-117

Synthesis of SZU-001S:

1-(3-dimethylaminopropyl)-3-ethylcarbodiimide hydrochloride (EDCI), HOBt and DIPEA were added to the anhydrous DMF solution of SZU-101 at 0° C. The mixture was stirred at room temperature for 0.5 hour. Then N-Boc piperazine was added at 0° C. The resulting mixture was reacted at room temperature for 24 hours. The reaction solution was poured into water and filtered off with suction to give a crude product, which was purified by liquid phase separation to obtain a pure product (ESI-MS: m/z=613.4 [M+H]$^+$).

Synthesis of SZU-130:

Trifluoroacetic acid was added dropwise to the dichloromethane solution of SZU-001S. After stirring for 2 hours, the reaction solution was concentrated under reduced pressure. Then 5 mL ethanol and 2N HCl solution were added to give a hydrochloride salt. After the solvent was removed under reduced pressure, diethyl ether or dichloromethane was added, and then solvent was removed again under reduced pressure. This procedure was repeated several times to give a pure solid product (ESI-MS: m/z=513.5 [M+H]$^+$).

Synthesis of SZU-117:

TEA and acryloyl chloride were added successively to the anhydrous DMF solution of SZU-130 at 0° C. After stirring at room temperature for 2 h, the reaction solution was poured into water and filtered off with suction to give a crude product, which was purified by liquid phase separation to obtain a pure product (ESI-MS: m/z=567.7[M+H]$^+$).

SZU-118

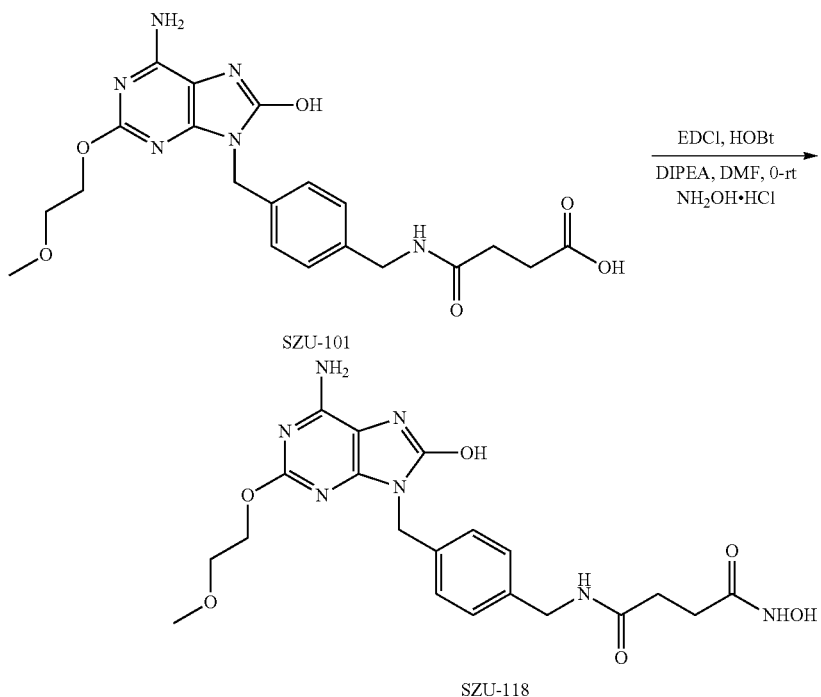

EDCI and HOBt were added to the anhydrous DMF solution of SZU-101. After stirring for 15 min, DIPEA was added at 0° C. The mixture was reacted at room temperature for 0.5 hour, and then hydroxylamine hydrochloride was added at 0° C. The resulting mixture was reacted at room temperature overnight. The reaction solution was poured into water and filtered off with suction to give a crude product, which was purified by liquid phase separation to obtain a pure product (ESI-MS: m/z=460.4 [M+H]$^+$).

SZU-120

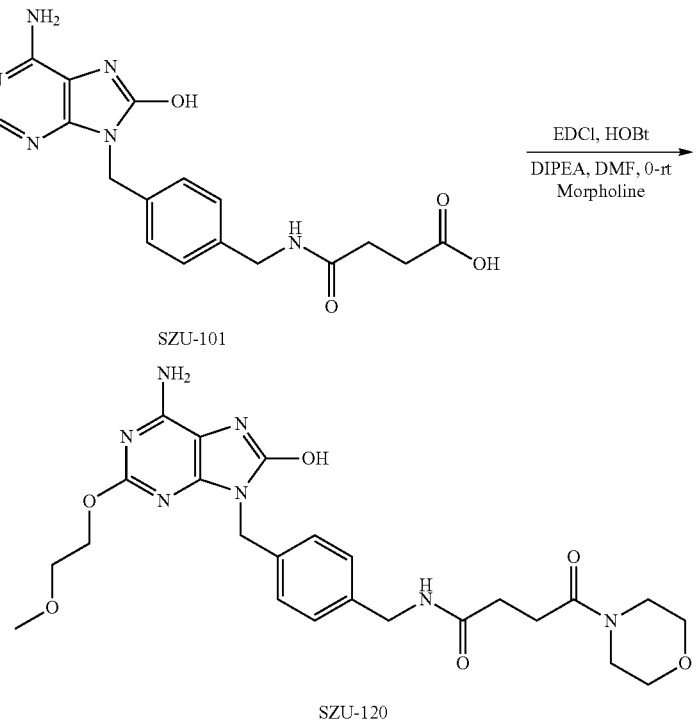

EDCI and HOBt were added to the anhydrous DMF solution of SZU-101. After stirring for 15 minutes, DIPEA was added at 0° C. The mixture was reacted at room temperature for 0.5 hour, and then morpholine was added at 0° C. The resulting mixture was reacted at room temperature overnight. The reaction solution was poured into water and filtered off with suction to give a crude product, which was purified by liquid phase separation to obtain a pure product (ESI-MS: m/z=514.5[M+H]⁺).
SZU-122

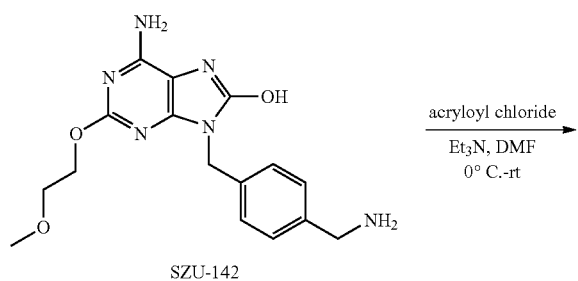

SZU-142 acryloyl chloride
———————→
Et₃N, DMF
0° C.-rt

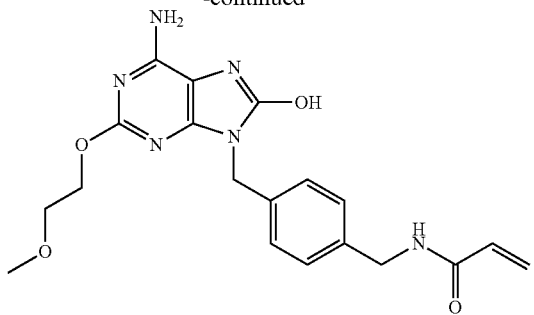

SZU-122

TEA and acryloyl chloride were added successively to the anhydrous DMF solution of SZU-142 at 0° C. After stirring at room temperature for 2 hours, the reaction solution was poured into water and filtered off with suction to give a crude product, which was purified by liquid phase separation to obtain a pure product (ESI-MS: m/z=399.4[M+H]⁺).
SZU-128

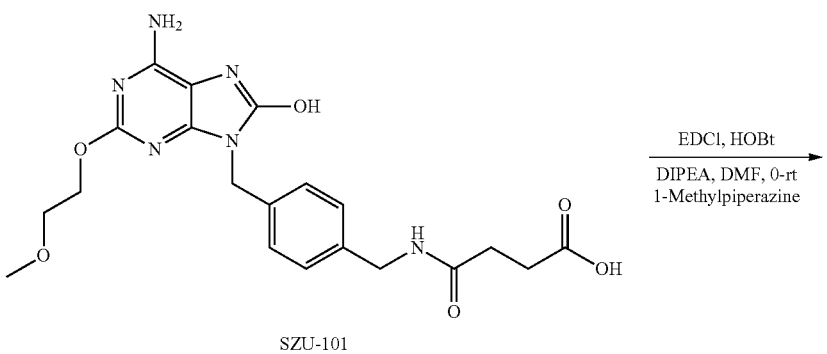

SZU-101

EDCl, HOBt
————————→
DIPEA, DMF, 0-rt
1-Methylpiperazine

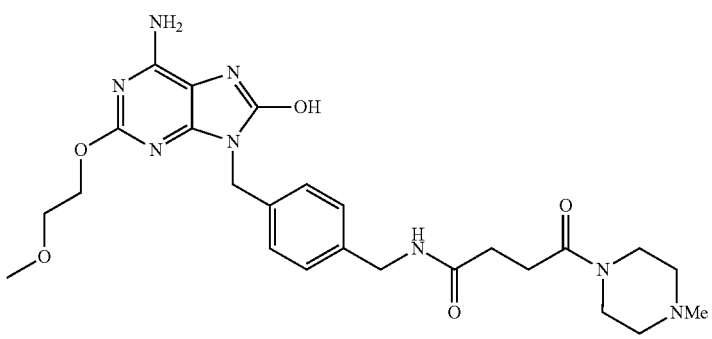

SZU-128

EDCI and HOBt were added to the anhydrous DMF solution of SZU-101. After stirring for 15 minutes, DIPEA was added at 0° C. The mixture was reacted at room temperature for 0.5 hour, and then 1-methylpiperazine was added at 0° C. The resulting mixture was reacted at room temperature overnight. The reaction solution was poured into water and filtered off with suction to give a crude product, which was purified by liquid phase separation to obtain a pure product (ESI-MS: m/z=527.7 [M+H]⁺).

SZU-129

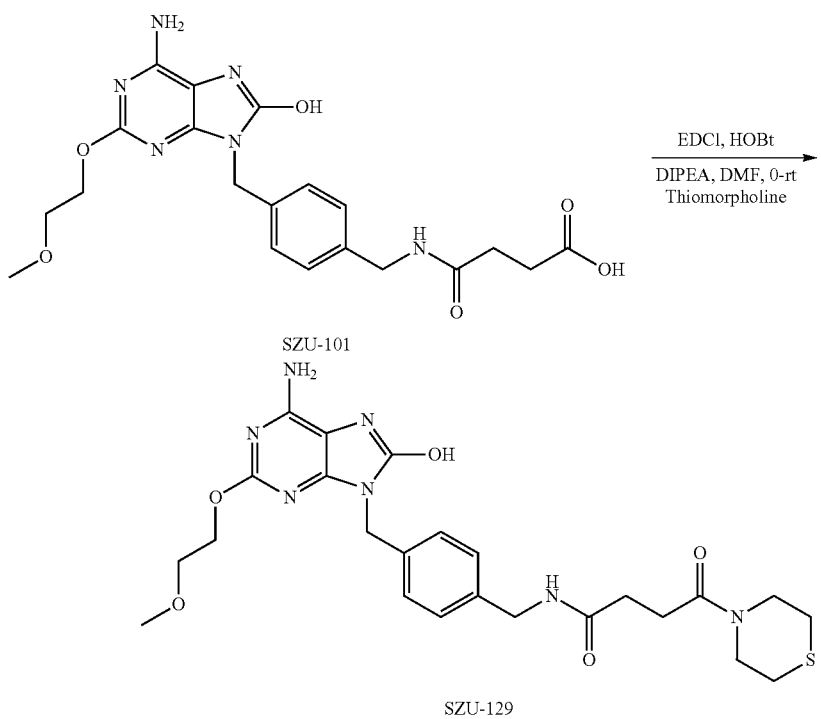

EDCI and HOBt were added to the anhydrous DMF solution of SZU-101. After stirring for 15 min, DIPEA was added at 0° C. The mixture was reacted at room temperature for 0.5 hour, and then thiomorpholine was added at 0° C. The resulting mixture was reacted at room temperature overnight. The reaction solution was poured into water and filtered off with suction to give a crude product, which was purified by liquid phase separation to obtain a pure product (ESI-MS: m/z=530.6 [M+H]$^+$).

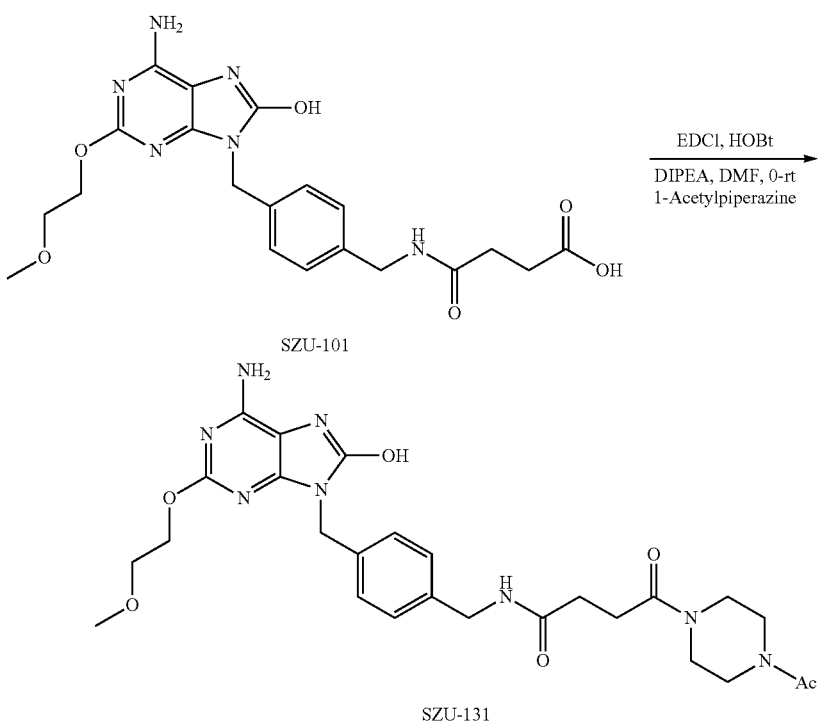

EDCI and HOBt were added to the anhydrous DMF solution of SZU-101. After stirring for 15 min, DIPEA was added at 0° C. The mixture was reacted at room temperature for 0.5 hour, and then 1-acetylpiperazine was added at 0° C. The resulting mixture was reacted at room temperature overnight. The reaction solution was poured into water and filtered off with suction to give a crude product, which was purified by liquid phase separation to obtain a pure product (ESI-MS: m/z=555.6 [M+H]$^+$).
SZU-132

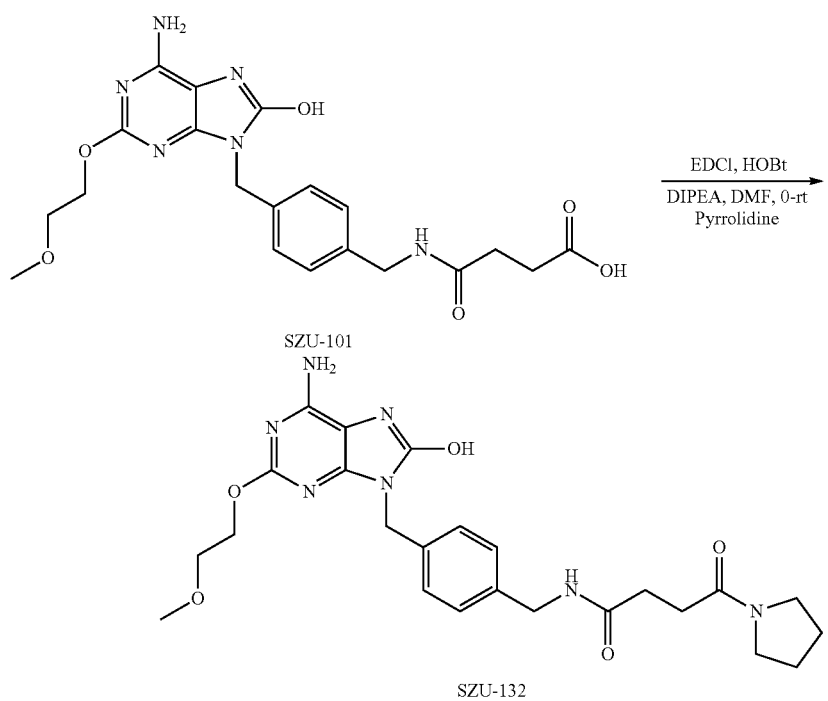

EDCI and HOBt were added to the anhydrous DMF solution of SZU-101. After stirring for 15 min, DIPEA was added at 0° C. The mixture was reacted at room temperature for 0.5 hour, and then pyrrolidine was added at 0° C. The resulting mixture was reacted at room temperature overnight. The reaction solution was poured into water and filtered off with suction to give a crude product, which was purified by liquid phase separation to obtain a pure product (ESI-MS: m/z=498.5 [M+H]$^+$).
SZU-133

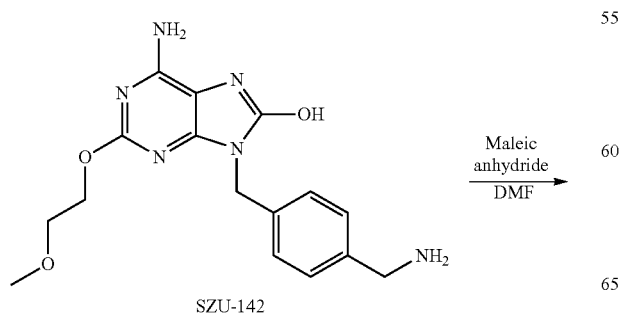

Maleic anhydride was added to the anhydrous DMF solution of SZU-142. After the resulting solution was reacted overnight, the reaction solution was poured into water and filtered off with suction to give a crude product, which was purified by liquid phase separation to obtain a pure product (ESI-MS: m/z=443.3 [M+H]$^+$).

SZU-143

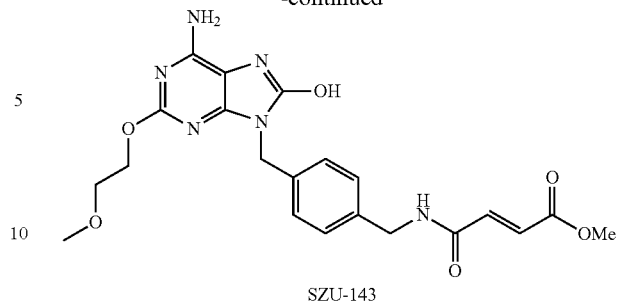

SZU-143

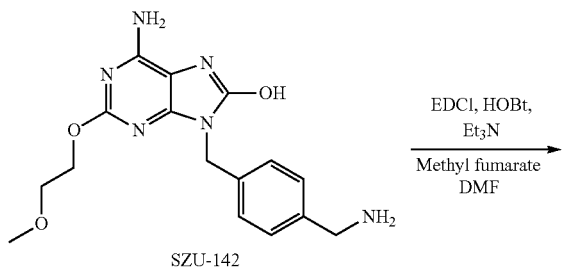

SZU-142

EDCl and HOBt were added to the anhydrous DMF solution of monomethyl fumarate. After stirring for 15 min DIPEA was added at 0° C. The resulting solution was reacted at room temperature for 0.5 hour, and then SZU-142 was added at 0° C. The resulting mixture was reacted at room temperature overnight. The reaction solution was poured into water and filtered off with suction to give a crude product, which was purified by high performance liquid chromatography (HPLC) to obtain a pure product (ESI-MS: m/z=457.4 [M+H]⁺).

SZU-144

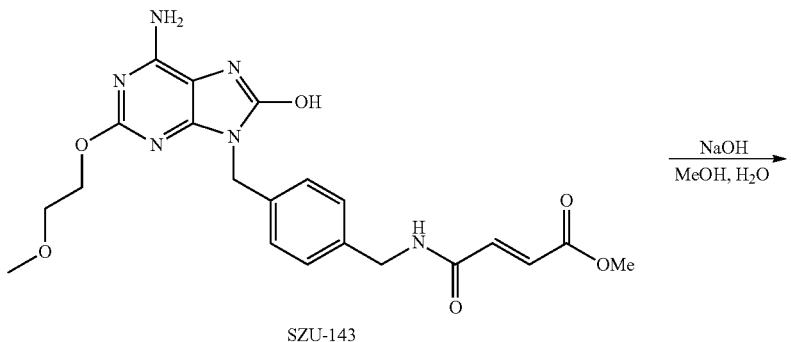

SZU-143

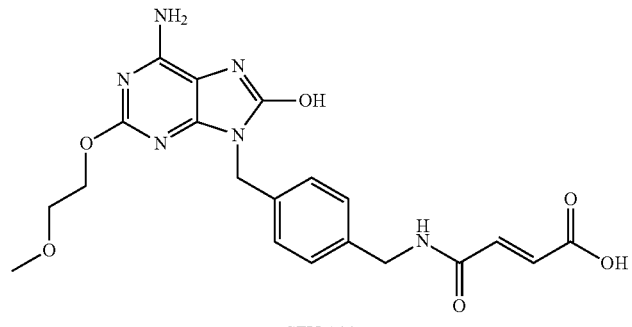

SZU-144

Sodium hydroxide (1.1 equivalent amount) was added to the methanol/water (1:1) mixed solution of SZU-143. After stirring at room temperature for 8 hours, the reaction solution was neutralized with 1N HCl solution after the reaction was completed, and then filtered off with suction and washed with water to give a crude product, which was purified by high performance liquid chromatography (HPLC) to obtain a pure product (ESI-MS: m/z=443.5[M+H]⁺).

SZU-146

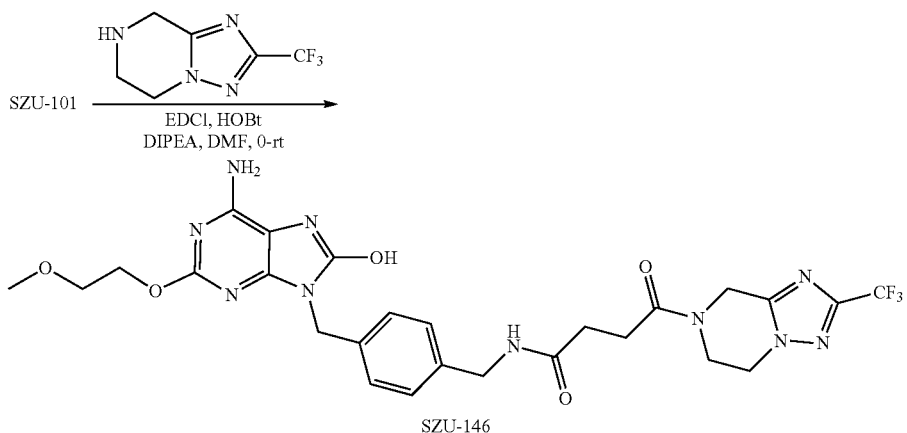

EDCI and HOBt were added to the anhydrous DMF solution of SZU-101. After stirring for 15 minutes, DIPEA was added at 0° C. The resulting solution was reacted at room temperature for 0.5 hour, and then 3-(trifluoromethyl)-5,6,7,8-tetrahydro-[1,2,4]triazolo[4,3-a]pyrazine (intermediate of Fuzuopali) was added at 0° C. The resulting mixture was reacted at room temperature overnight. The reaction solution was poured into water and filtered off with suction to give a crude product, which was purified by liquid phase separation to obtain a pure product (ESI-MS: m/z=619.6 [M+H]$^+$).

SZU-147

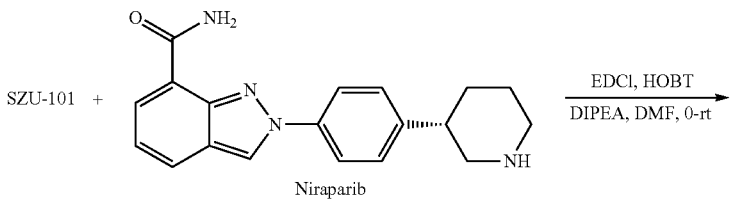

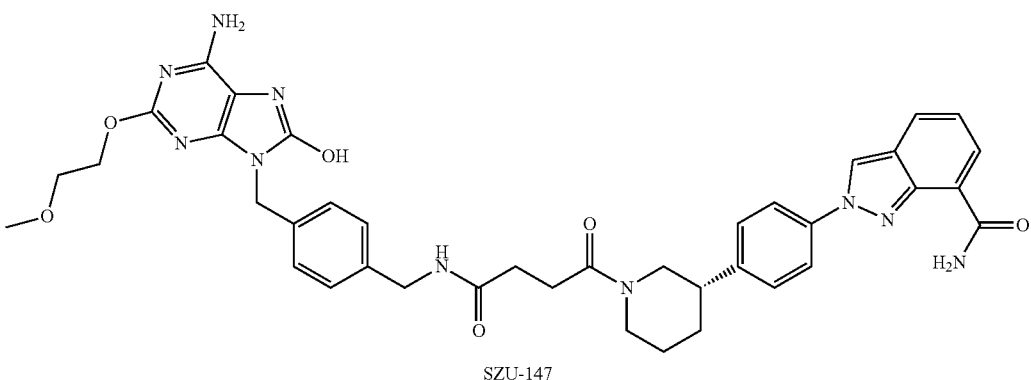

Equimoles of EDCI and HOBt were added to the anhydrous DMF solution of SZU-101. After stirring for 15 minutes, DIPEA was added at 0° C. The resulting solution was reacted at room temperature for 0.5 hour, and then an equimole of Niraparib was added at 0° C. The resulting mixture was reacted at room temperature overnight. The reaction solution was poured into water and filtered off with suction to give a crude product, which was purified by high-performance liquid chromatograph (HPLC) to obtain a pure product SZU-147 (ESI-MS: m/z=747.77[M+H]$^+$).

SZU-148
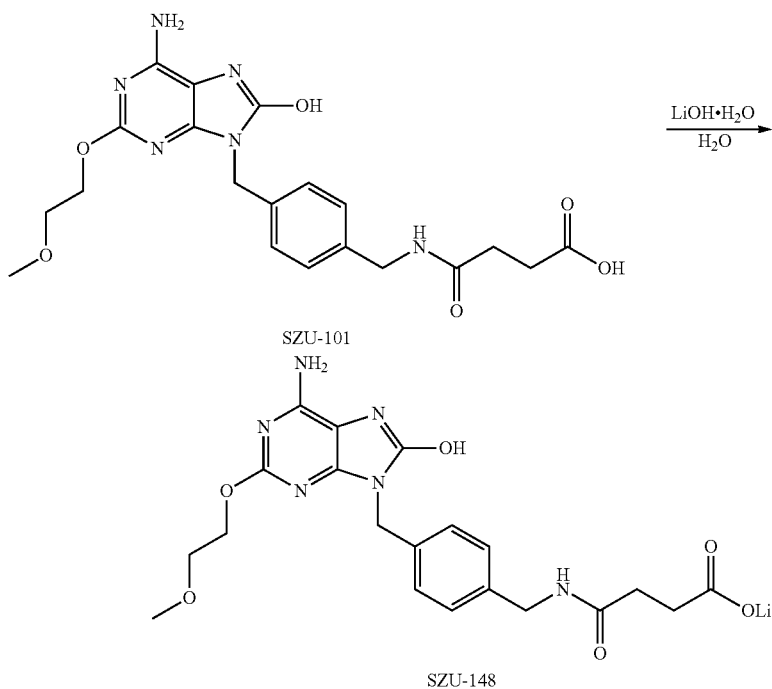
Lithium hydroxide and SZU-101 (in 1:1 ratio) were added to water. The resulting solution was stirred for 2-3 hours, and then lyophilized to remove the solvent to obtain a pure product.
SZU-150, 151, 152 and 153
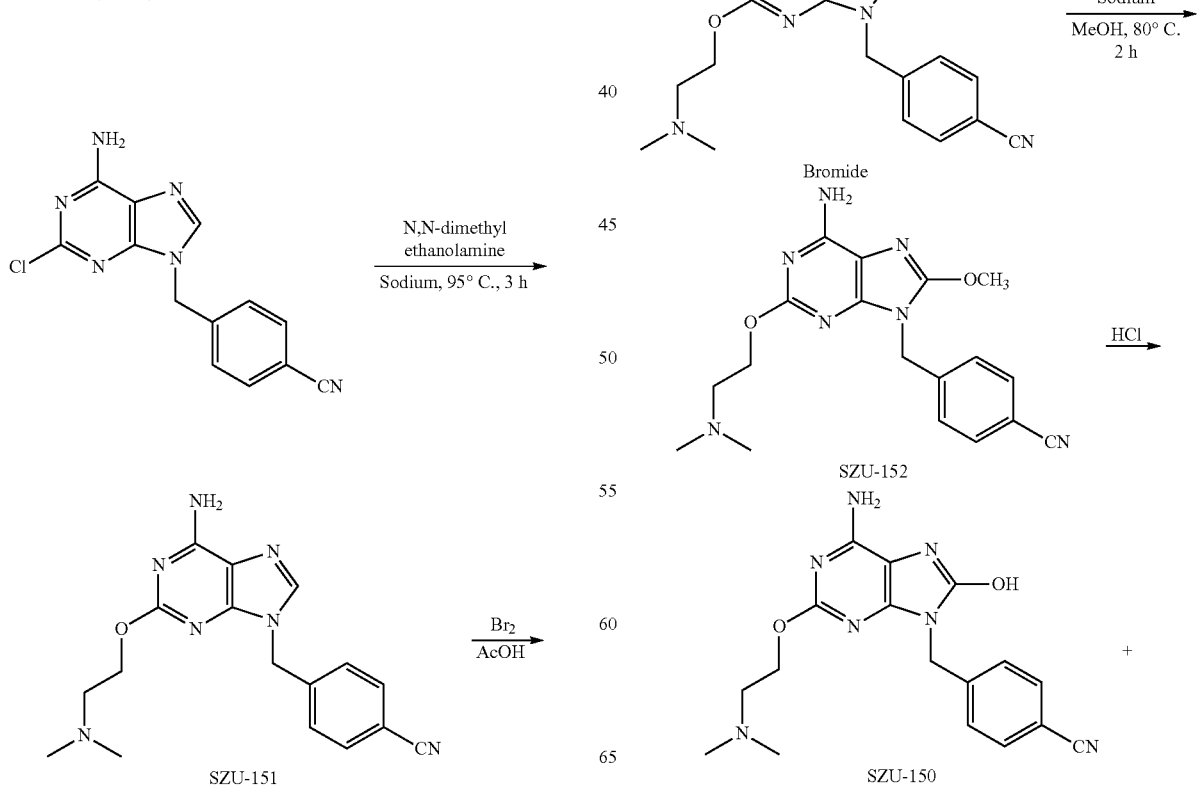

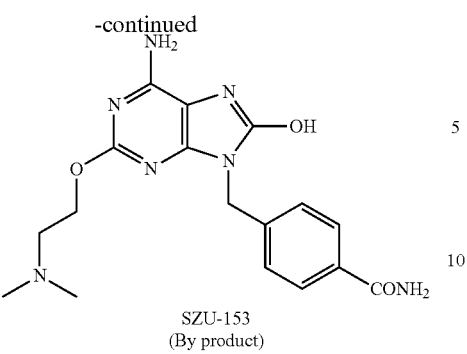

SZU-153
(By product)

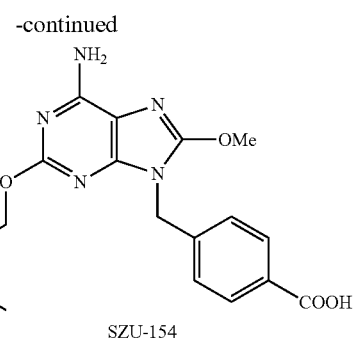

SZU-154

Synthesis of SZU151:

After sodium salt was formed by adding metal Na to N,N-dimethylethanolamine, the starting materials were added to the reaction solution, heated to 95° C. and reacted for 3 hours. The solvent was removed under reduced pressure, and then water was added. The reaction solution was filtered off with suction to give a solid, which was washed with water to have a pH of 7-8 and dried under reduced pressure to obtain a pure product SZU-151.

Synthesis of SZU-152:

Bromine was added dropwise slowly to the acetic acid solution of SZU-151. After stirring overnight, the reaction solution was neutralized with NaHCO$_3$. Small amount of ethanol was added into the obtained viscous compound. Subsequently, sodium thiosulfate solution was added to remove the remaining bromine. The reaction solution was filtered off with suction and dried to give a solid, and then 10% NaOH solution was added. The resulting solution was further filtered off with suction and dried under reduced pressure. The residue was purified by preparative liquid chromatography to obtain a bromide.

Metal Na was added to methanol. After stirring, the starting materials were added. The mixture was heated to 80° C. and reacted for 2 hours. Methanol was removed under reduced pressure. The resulted mixture was neutralized with HCl, filtered off with suction and dried under reduced pressure to give a solid SZU-152.

Synthesis of SZU-150 and SZU-153:

SZU-152 was added to HCl and stirred for 12 h. The solvent was removed under reduced pressure. The residue was separated by preparative liquid chromatography to give a compound SZU-150 (ESI-MS: 354.5 [M+H]$^+$) and SZU-153 (ESI-MS: m/z=372.4 [M+H]$^+$).

SZU-154

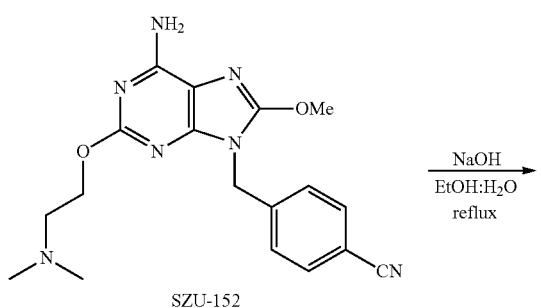

SZU-152

NaOH was added to the ethanol/water (1:1) mixed solution of SZU-152 and refluxed overnight. The resulting solution was concentrated under reduced pressure, adjusted to have a pH of 3, and purified by preparative liquid chromatography to give a pure product SZU-154 (ESI-MS: m/z=387.5 [M+H]$^+$).

SZU-155

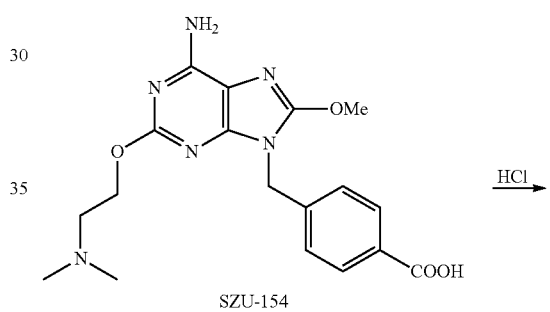

SZU-154

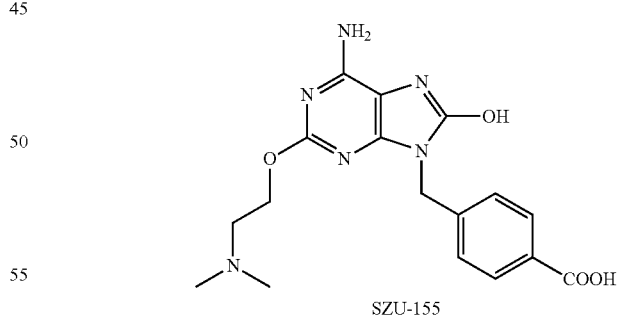

SZU-155

SZU-154 was dissolved in concentrated HCl and stirred overnight. The solvent was removed under reduced pressure. The residue was purified by preparative liquid chromatography to give a pure product SZU-155 (ESI-MS: m/z=373.5 [M+H]$^+$).

SZU-104
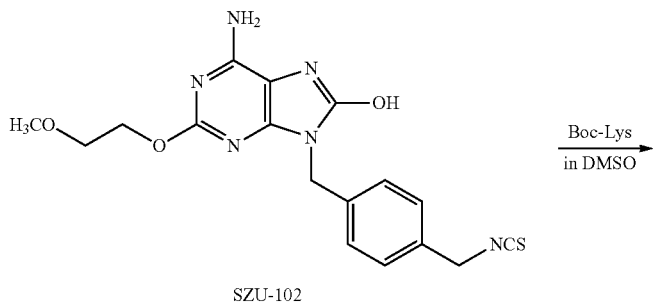
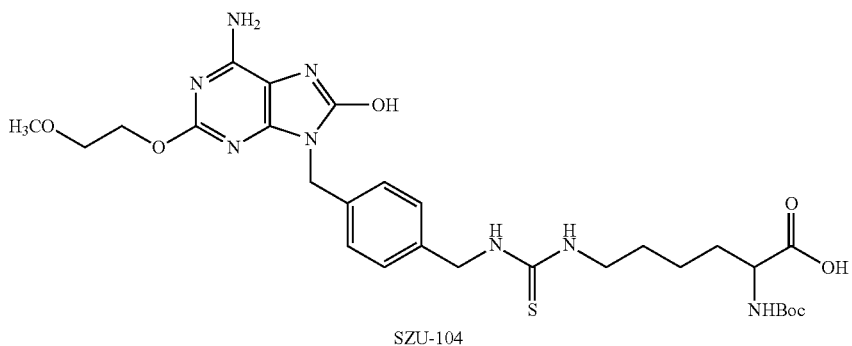
50 mg of SZU-102 was dissolved in 0.5 mL of DMSO. 41 mg of tert-butoxycarbonyl (Boc)-protected lysine was added. The mixture was stirred at room temperature overnight. After the reaction was completed, DMSO was removed by lyophilization. The residue was purified by preparative liquid chromatography to give 69 mg of a white solid with a yield of 85%. ESI-MS: m/z=633.7 [M+H]$^+$.
SZU-105
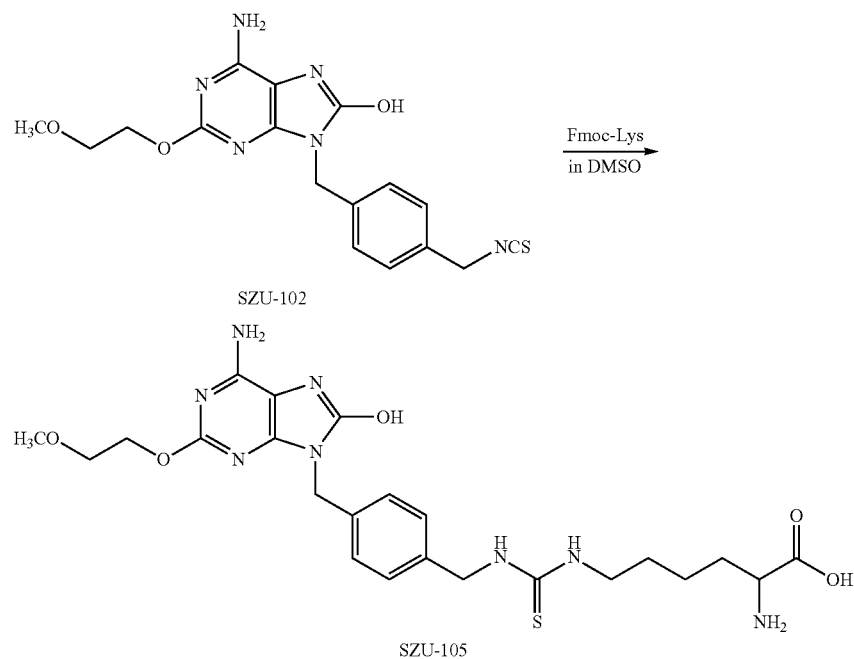

50 mg of SZU-102 was dissolved in 0.5 mL of DMSO. 47 mg of Boc-protected lysine was added. The resulting mixture was stirred at room temperature overnight. After the reaction was completed, DMSO was removed by lyophilization. The residue was purified by preparative liquid chromatography to give 68 mg of white solid with a yield of 83%. ESI-MS: m/z=533.6 [M+H]$^+$.
SZU-108

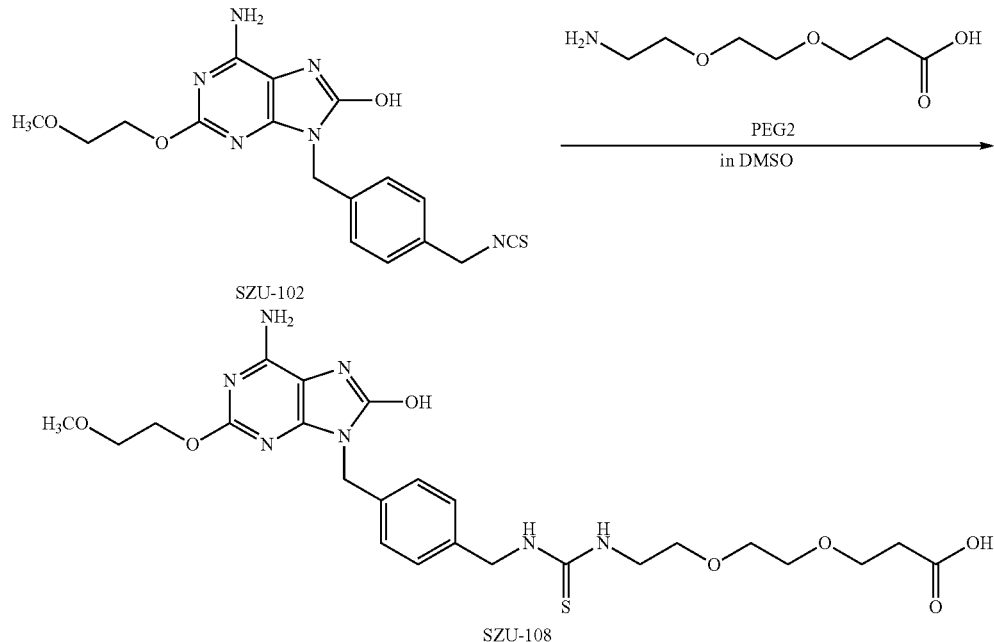

109 mg of SZU-102 was dissolved in 1 mL of DMSO. 50 mg of PEG2 was added. The resulting mixture was stirred at room temperature overnight. After the reaction was completed, DMSO was removed by lyophilization. The residue was purified by preparative liquid chromatography to give 125 mg of a white solid with a yield of 79%. ESI-MS: m/z=564.6 [M+H]$^+$.
SZU-109

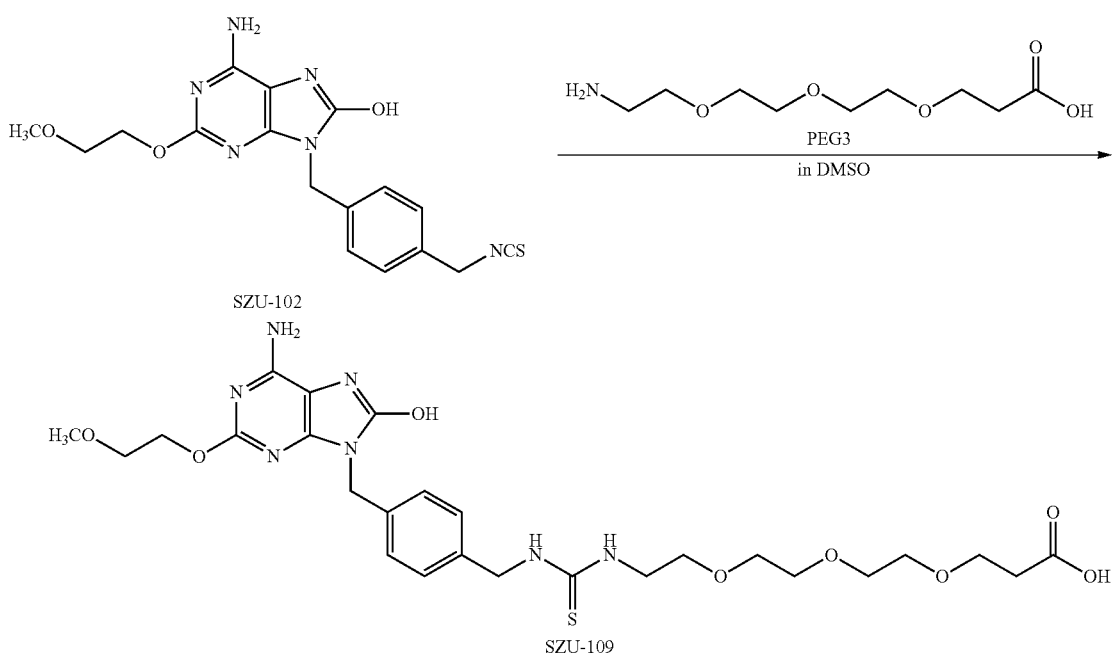

87 mg of SZU-102 was dissolved in 0.9 mL of DMSO. 50 mg of PEG3 was added. The mixture was stirred at room temperature overnight. After the reaction was completed, DMSO was removed by lyophilization. The residue was purified by preparative liquid chromatography to give 105 mg of a white solid with a yield of 77%. ESI-MS: m/z=608.7 [M+H]⁺.
SZU-110

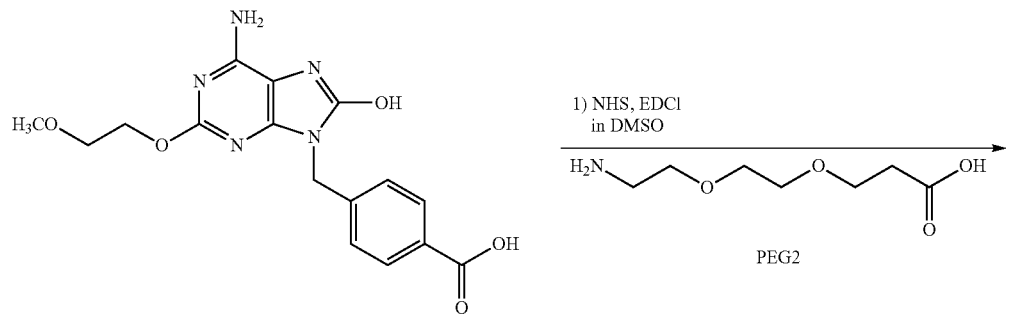

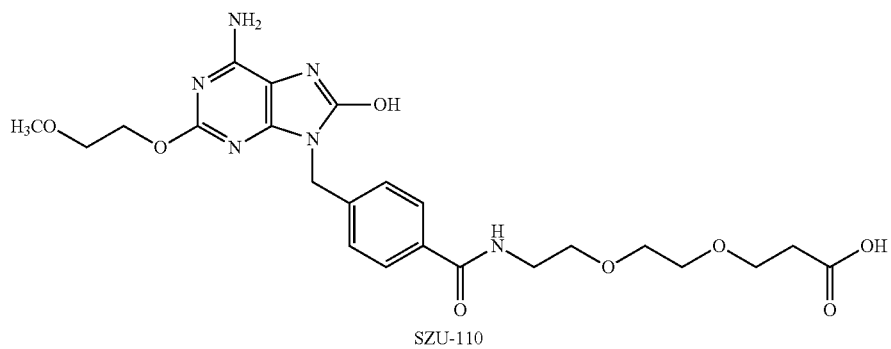

193 mg of a carboxylic compound was dissolved in 2 mL of DMSO. 100 mg of EDCI and 59 mg of N-hydroxysuccinimide (NHS) were added successively. After stirring at room temperature for 2 hours, the reaction solution was added with 50 mg of PEG2 and stirred at room temperature overnight. After the reaction was completed, DMSO was removed by lyophilization. The residue was purified by preparative liquid chromatography to give 203 mg of white solid with a yield of 73%. ESI-MS: m/z=519.5 [M+H]⁺.
SZU-111

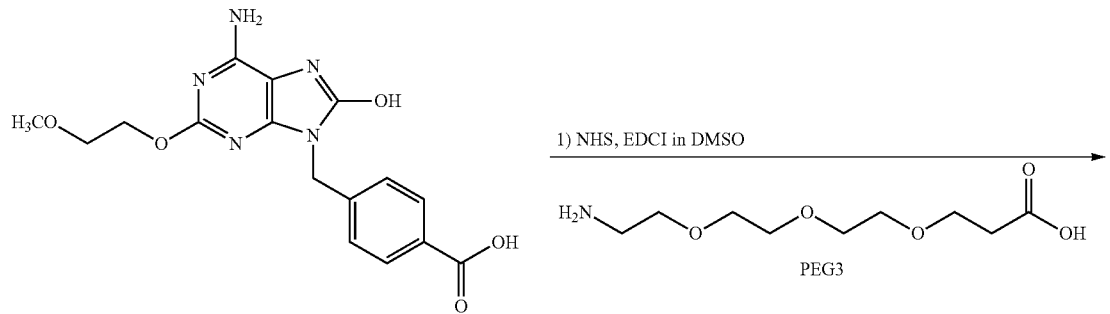

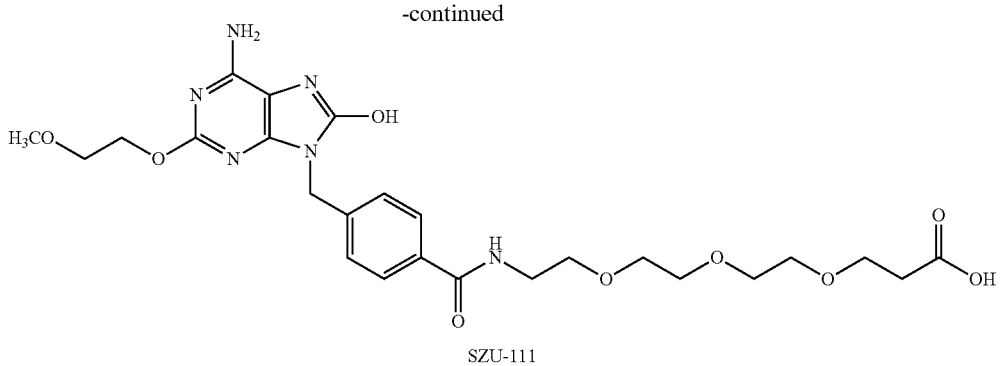

SZU-111

155 mg of a carboxylic compound was dissolved in 1.5 mL of DMSO. 79 mg of EDCI and 47 mg of NHS were added successively. After stirring at room temperature for 2 hours, the reaction solution was added with 50 mg of PEG3 and stirred at room temperature overnight. After the reaction was completed, DMSO was removed by lyophilization. The residue was purified by preparative liquid chromatography to give 174 mg of a white solid with a yield of 72%. ESI-MS: m/z=563.6 [M+H]$^+$.

SZU-149 and SZU-163

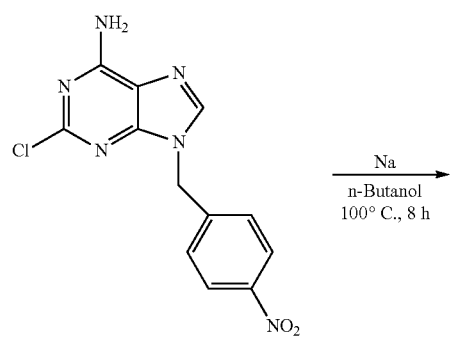

a

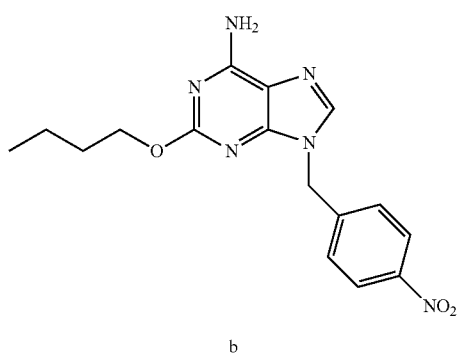

b

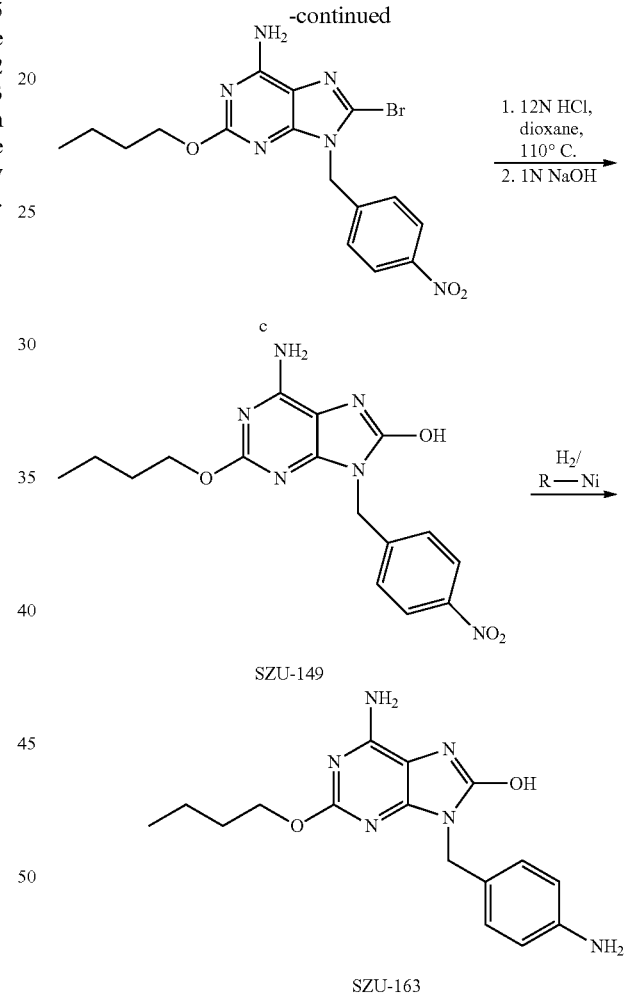

SZU-149

SZU-163

0.5 g of metal Na was added slowly to 100 mL of anhydrous n-butanol at 0° C. After 30 minutes, 3 g of reactant a was added. The resulting mixture was stirred at 100° C. for 8 hours, cooled to room temperature and poured into a large amount of water. A yellow solid was precipitated out, filtered, washed with tetrahydrofuran three times, and dried to obtain 2.5 g of product b.

2.5 g of the product b was mixed with 100 mL of chloroform and stirred homogeneously. 10 mL of bromine was added. The resulting solution was reacted at room temperature for 24 hours and filtered to obtain 2.2 g of product c, which was mixed with 60 mL of dioxane. Then 10 mL of concentrated hydrochloric acid was added. The mixture was reacted at 110° C. for 12 hours. The reaction mixture was poured into 600 mL of water and a crude solid product was precipitated out, which was filtered, dissolved in 60 mL of 1N NaOH, cooled and neutralized to a pH of 4 with hydrochloric acid. A pure product was precipitated out and then dried to give 1 g of SZU-149 with a yield of 55%. MS (ESI): m/z: [M+Na]381.42.

0.5 g of SZU-149 was dissolved in anhydrous methanol. 0.5 g of Raney Nickel was added. The resulting solution was subjected to hydrogenation reaction for 24 hours under 3 atmospheric pressures in hydrogen, filtered, and distilled under reduced pressure to give 0.4 g of a pure product SZU-163 with a yield of 89%; MS (ESI): m/z: [M+H] 329.41.

SZU-166 and SZU-181

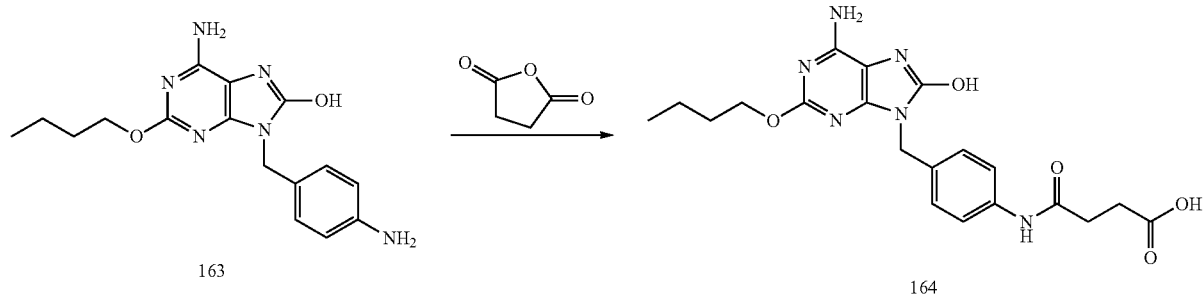

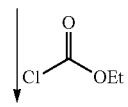

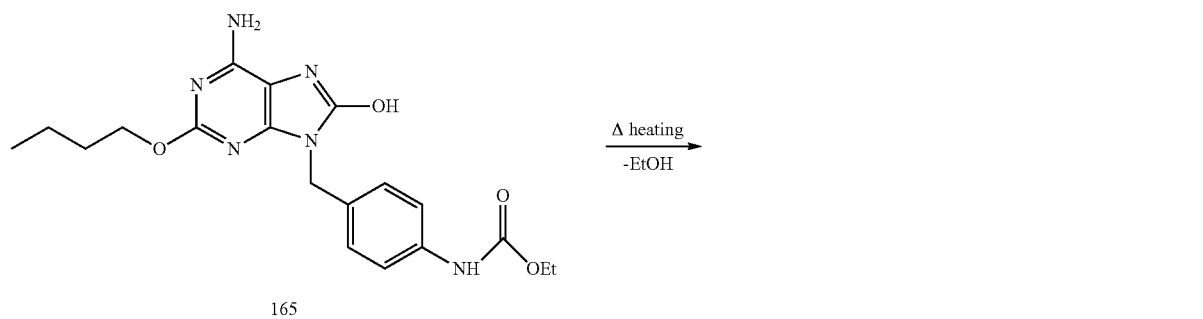

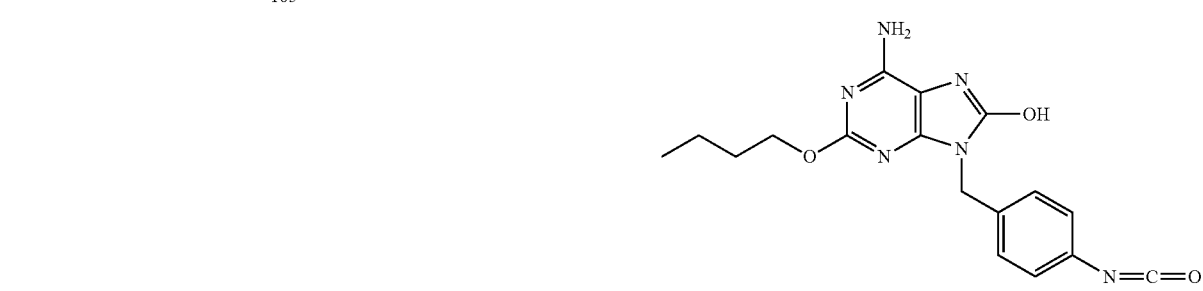

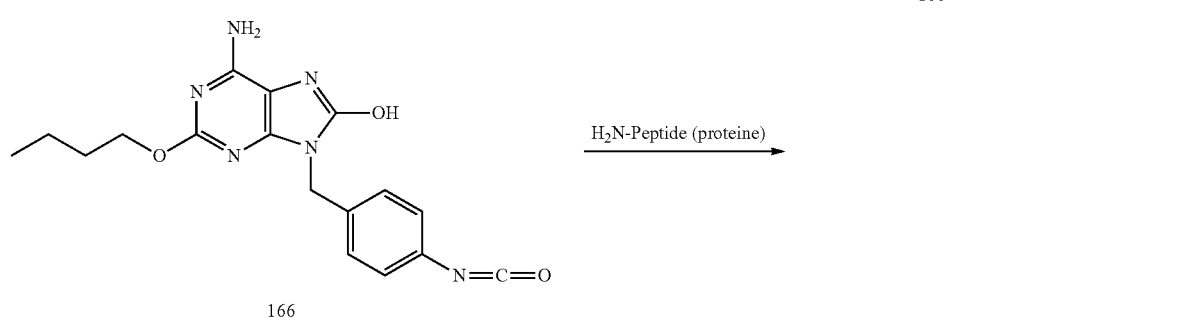

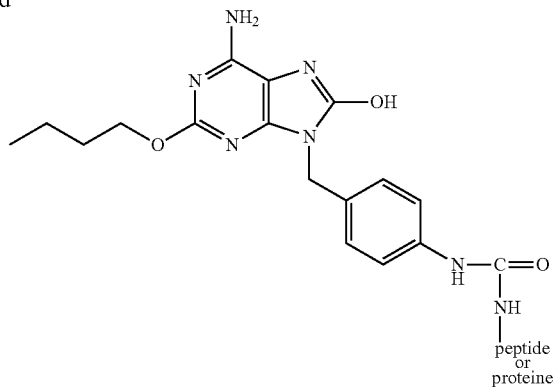

181

Synthesis of SZU-166:
1.5 g of SZU-163 was dissolved in 30 mL of DMSO. 1 mL of triethylamine and 0.5 g of ethyl chloroformate were added. The mixture was stirred at room temperature for 2 hours. The reaction mixture was distilled under vacuum to a small volume, cooled to room temperature, and added with 30 mL of ethyl acetate. A solid was precipitated out, filtered, washed with ethyl acetate, and dried to give 0.75 g of a pure product SZU-166 with a yield of 46%; MS (ESI): m/z: [M+H] 355.40.

Synthesis of SZU-181 (Conjugate Formed by Conjugating SZU-166 with Hepatitis B PreS Antigen Epitope):

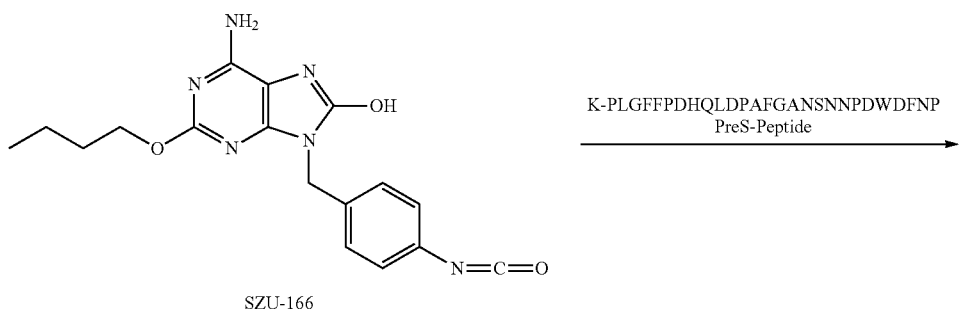

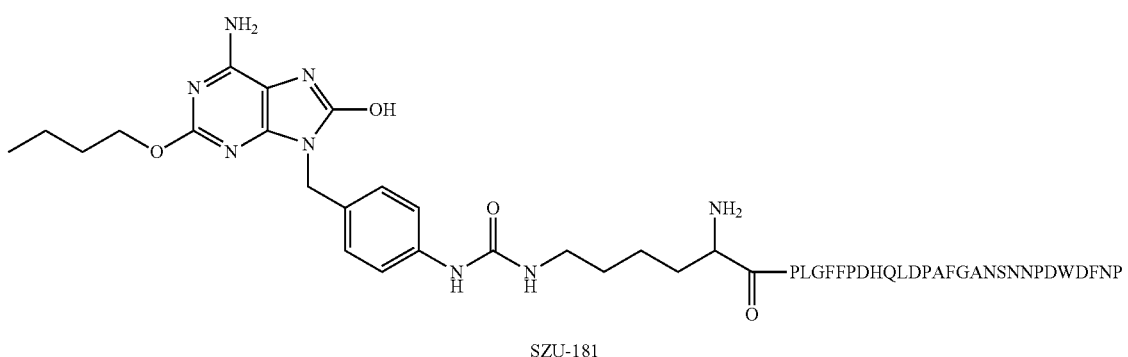

A mixture of SZU-166 (10 mg) and PreS-peptide (90 mg) was dissolved in 3 mL of DMF. 0.2 mL of triethylamine was added. The mixture was reacted under stirring at 20° C. for 24 hours. 3 mL of dichloromethane was added. The precipitated product was separated by centrifugation to give a crude product, which was purified by HPLC, and lyophilized to give 65 mg of SZU-181. Molecular weight determined by mass spectrometry: 3512.80: (1756.3×2), (1170.9×3).

SZU-136 and SZU-139

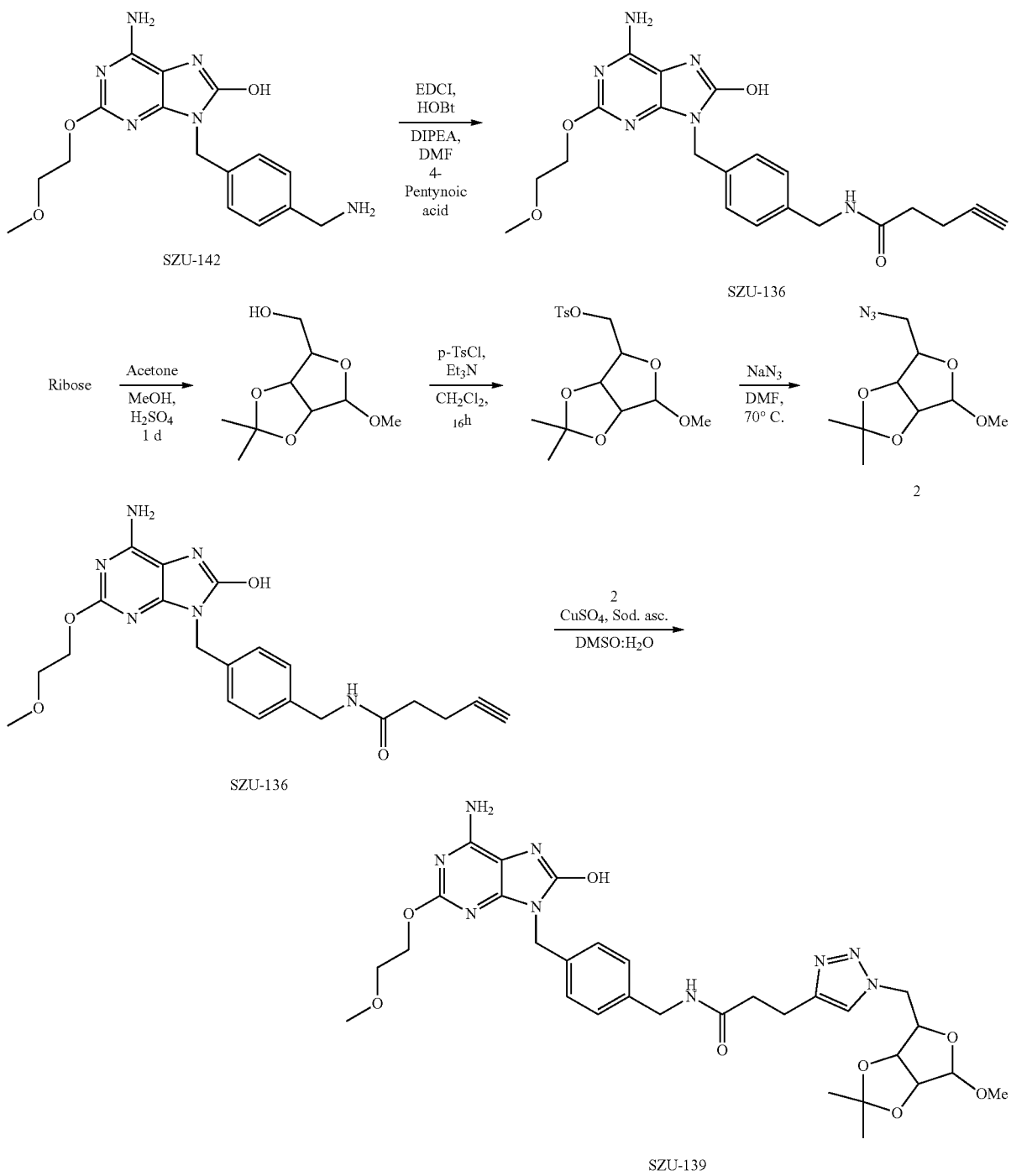

EDCI and HOBt were added to an equimole of 4-pentynoic acid in DMF. After 15 minutes, triethylamine was added. The mixture was reacted under stirring at 0° C. for 15 minutes, and then the reaction was continued under stirring at room temperature for 30 minutes.

Subsequently, an equimole of TL -008 was added. The resulting mixture was reacted at room temperature overnight. The reaction solution was poured into water. The precipitated product was filtered and dried under vacuum to give SZU-136 with a yield of 87%; MS (ESI): m/z: [M+1] 425.51.

SZU-136, azide compound 2 and sodium ascorbate in equimolar amounts were added to the solution of DMSO and water (1:1). The resulting solution was stirred at room temperature overnight, added with 10-fold volume of water and filtered. The obtained product was purified by HPLC, and dried to obtain SZU-139 with a yield of 77%; MS (ESI): m/z: [M+1] 654.72.

SZU-169
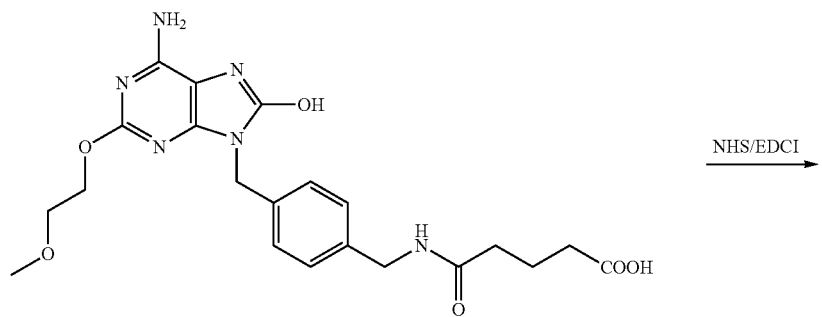
SZU-134
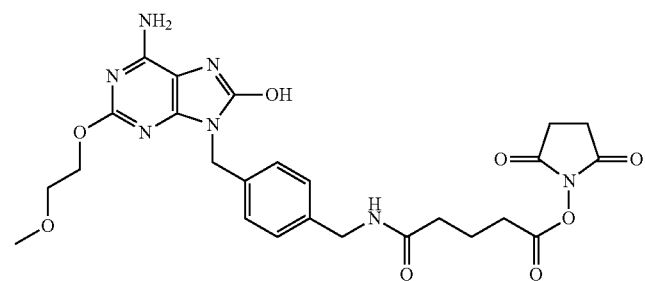
active ester
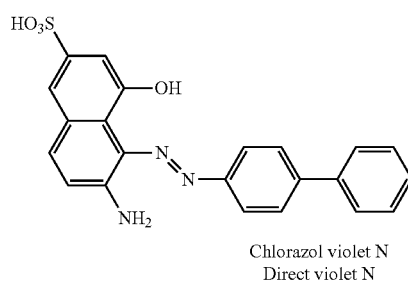
Chlorazol violet N
Direct violet N
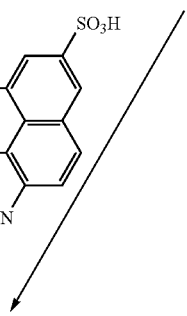
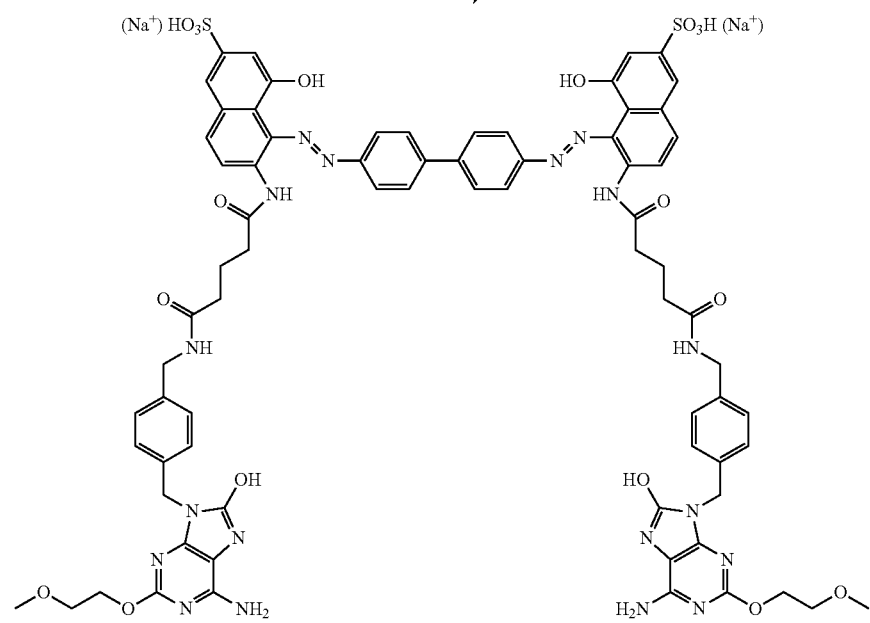
SZU-169

SZU-134 was dissolved in DMSO. Equimoles of NHS and EDCI were added. After stirring for 10 minutes, an equimole of Direct violet N (OX40 agonist) was added. The reactants were reacted in a closed vessel at room temperature for 3 days. 20-fold amount of water was added. Solid was precipitated out and filtered, and then 2N NaOH was added. The mixture was stirred at 10° C. for 30 minutes and filtered. The filtrate was acidified with 2N hydrochloric acid to have a pH of 1 and gave a precipitated solid product SZU-169 with a yield of 52%; MS (ESI): m/z: [M+2Na] 1611.64.

SZU-174

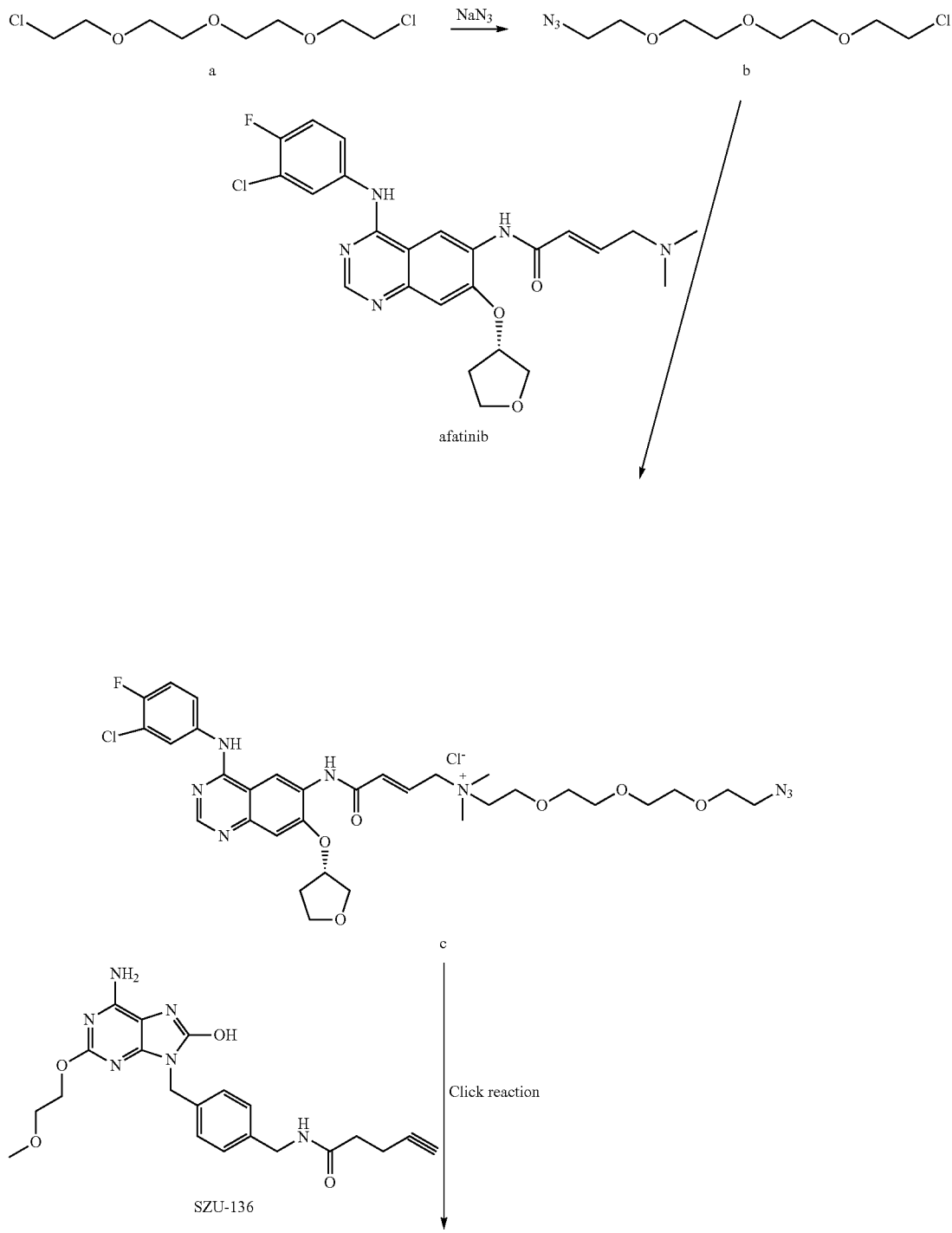

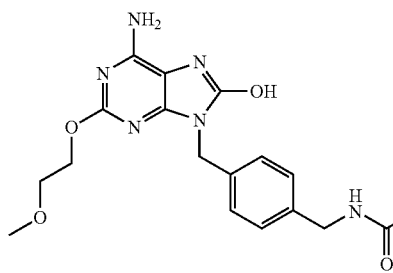
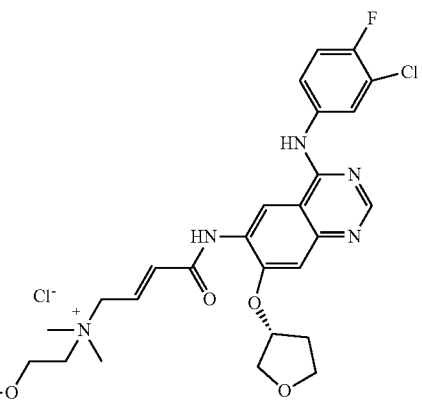

SZU-174

The reactant a was dissolved in small amount of DMF. One-fold equivalent amount of sodium azide was added. The mixture was reacted under stirring at room temperature for 24 hours. The reaction mixture was added with 10-fold volume of water and extracted with ethyl acetate. The extracted phase was washed with water three times. The solvent was distilled off under reduced pressure to obtain product b with a yield of 90%.

100 mg of Afatinib and 50 mg of the product b were dissolved in 15 mL of DMF. Trace amount of NaI was added. The mixture was reacted at 60° C. for 24 hours. 100 mL of n-butanol was added to the reaction mixture, which was subjected to distillation under reduced pressure to a small volume (about 5 mL), cooled to room temperature, and added with 50 mL of ethyl acetate. A solid product c was precipitated out and dried under vacuum to give 118 mg of product c; MS (ESI): m/z: [M+H] 688.21.

100 mg of the product c, 60 mg SZU-136, 10 mg of copper sulfate, and 30 mg of vitamin C were added to the solution of DMSO and water (1:1). The resulting solution was stirred at room temperature overnight, added with 10-fold volume of water and filtered. The obtained product was purified by HPLC, and dried to obtain 105 mg of SZU-174 with a yield of 65%; MS (ESI): m/z: [M+1] 1112.70.

SZU-158-PD-1

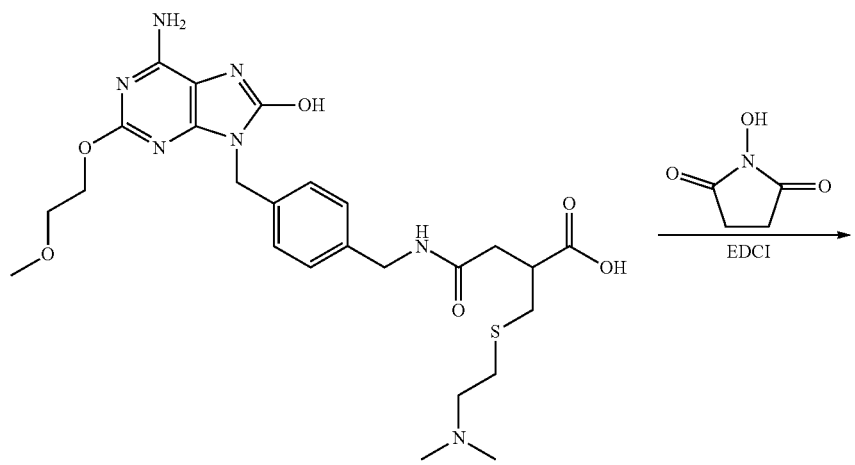

SZU-158

-continued

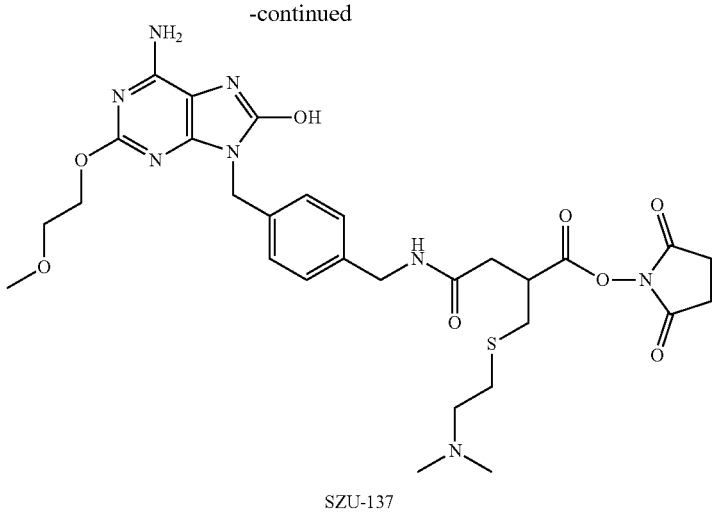

SZU-137

↙ PD-1 antibody

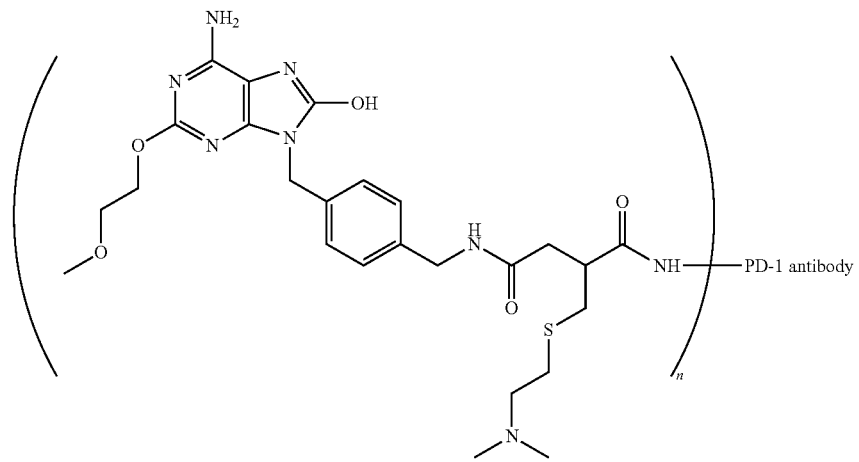

SZU-158-PD-1
wherein n = a numerical value ranging from 1 to 5

Figure 58:
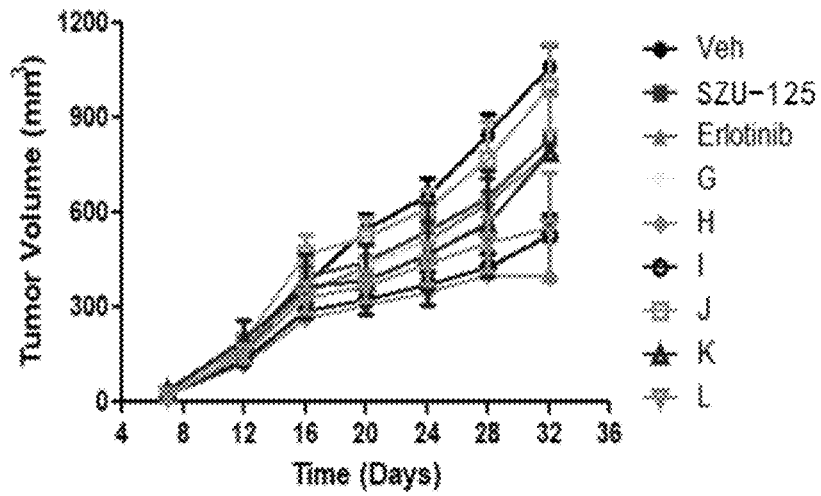
FIG. 58 shows the anti-tumor (B16) activity of novel immune targeted compounds in vivo: Veh (untreated control), G (PD-L1 antibody), H (SZU-178), I (SZU-158-PD-L1), J (SZU-158-OX40), K (PD-1 antibody), and L (SZU-158-PD-1).
Figure 59:
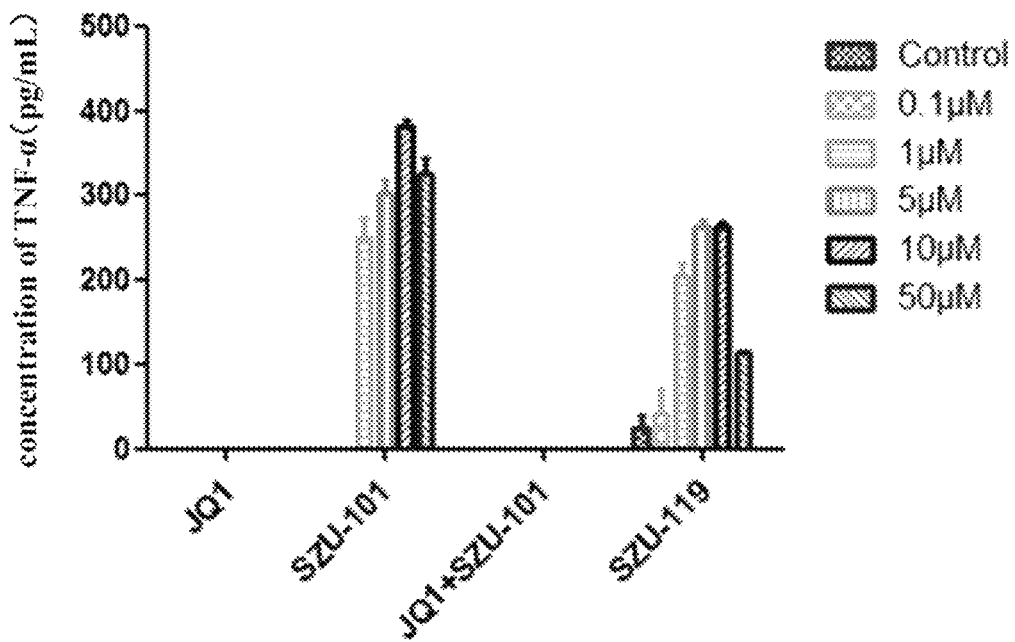
FIG. 59 shows the inhibition of JQ1 on the activity of SZU-101 as a TLR7 agonist; wherein SZU-119 retains the activity of TLR7 agonist for stimulating immune cytokine.
Figure 60:
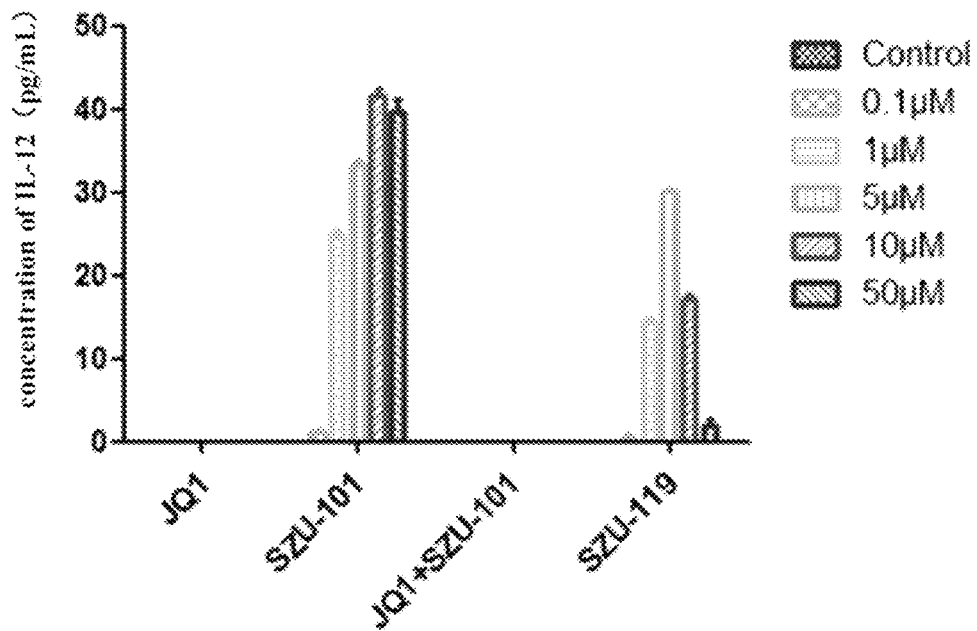
FIG. 60 shows the inhibition of JQ1 on the activity of SZU-101 as a TLR7 agonist, wherein SZU-119 retains the activity of TLR7 agonist for stimulating immune cytokine.
Figure 61:
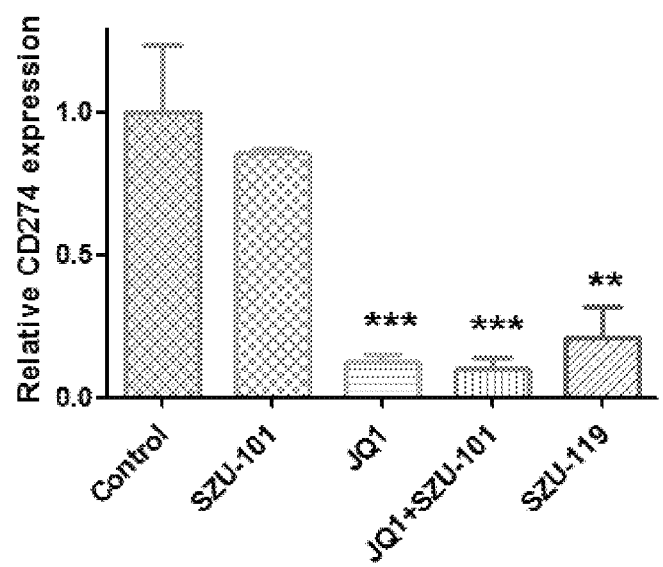
FIG. 61 shows that SZU-119 retains the inhibitory activity of JQ1 against CD274 (PD-L1) on B16 cells, wherein "control" represents blank control.
Figure 62:
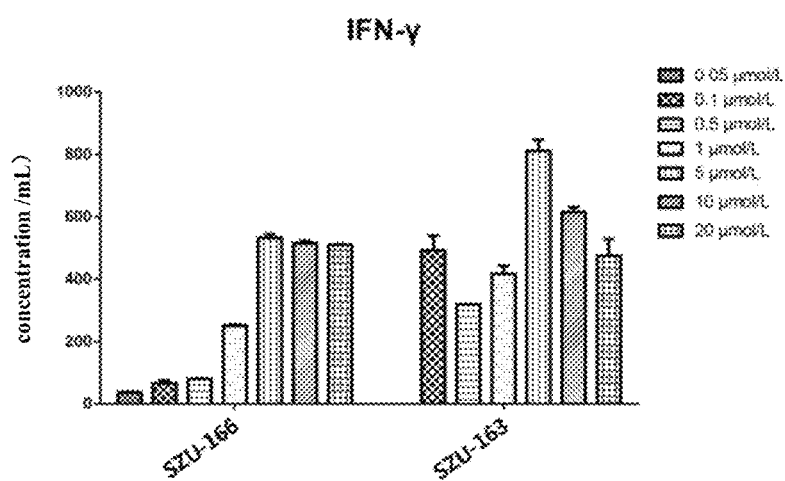
FIG. 62 shows the stimulatory effects of SZU-163 and SZU-166 on immunocytes to produce IFN-γ.
Figure 63:
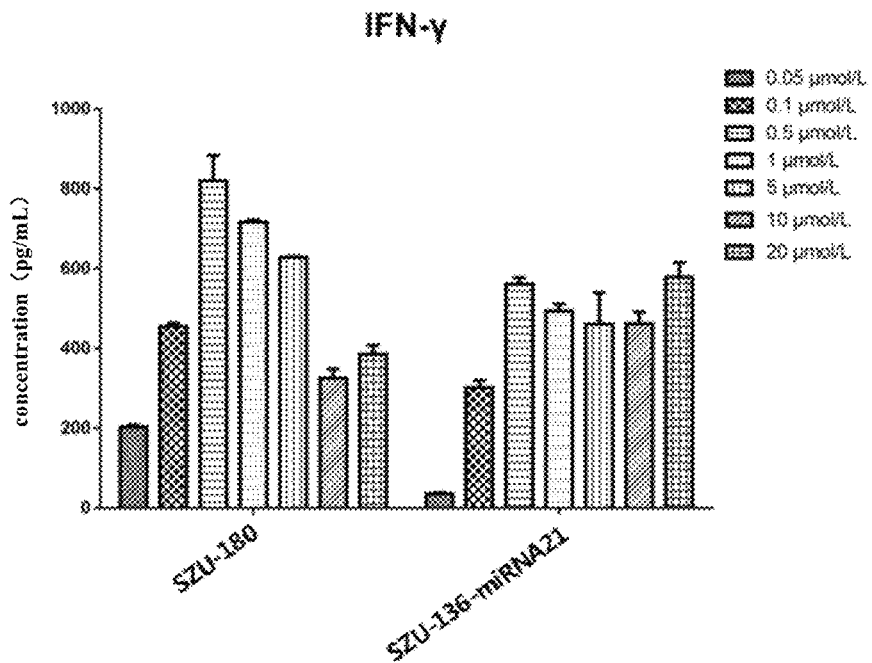
FIG. 63 shows the stimulatory effects of SZU-180 and SZU-136-miRNA21 on immunocytes to produce IFN-γ. 35
Figure 64:
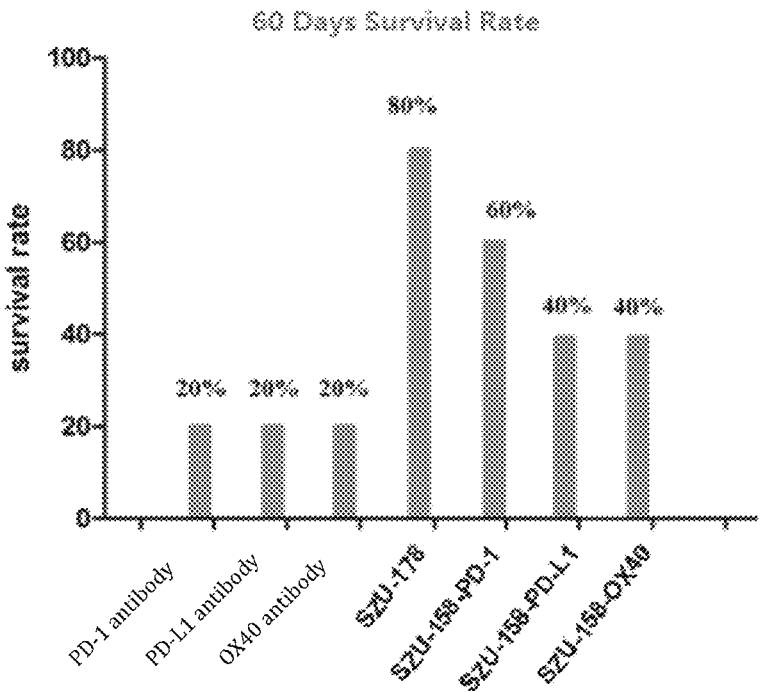
FIG. 64 shows the anti-tumor (4T1) survival rates of PD-1 antibody, PD-L1 antibody, OX40 antibody and their SZU-158 conjugates and SZU-178.
Figure 65:
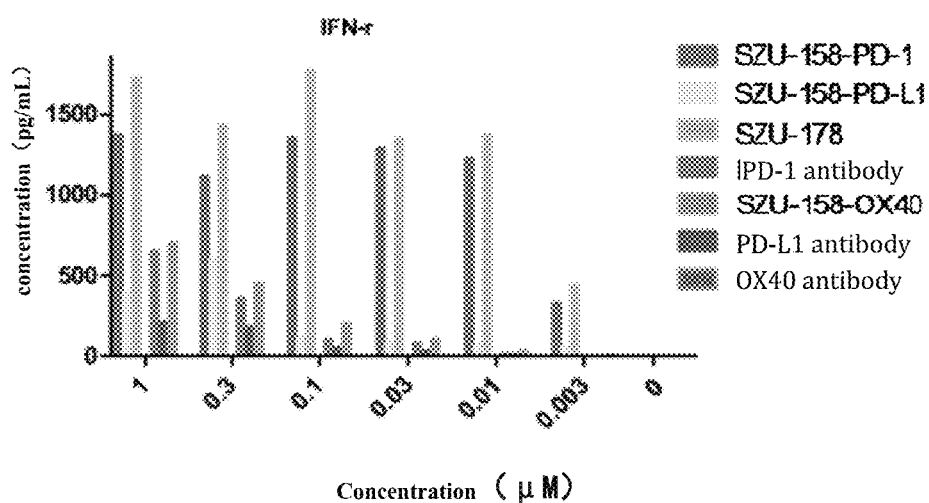
FIG. 65 shows the stimulatory effects of PD-1 antibody, PD-L1 antibody, OX40 antibody, and their SZU-158 conjugates and SZU-178 on immunocytes to produce IFN-γ.
Figure 66:
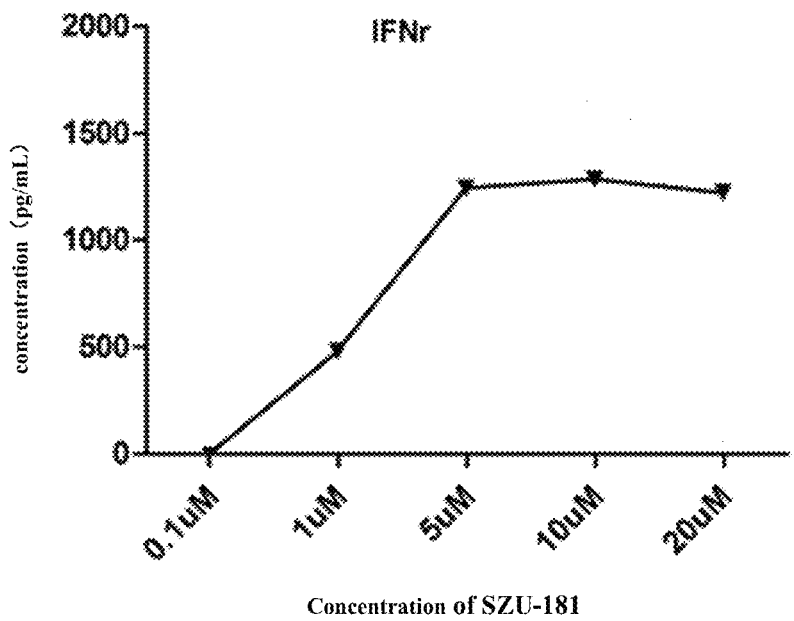
FIG. 66 shows the stimulatory effects of SZU-181 on immunocytes to produce IFN-γ.
Figure 67:
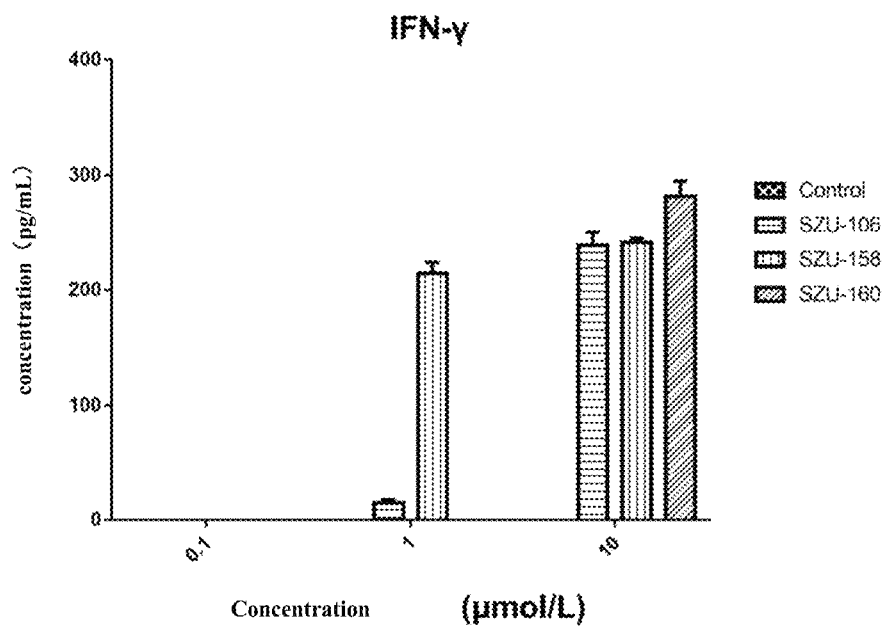
FIG. 67 shows the stimulatory effects of SZU-106, SZU-158, and SZU-160 on immunocytes to produce IFN-γ, wherein "control" represents PBS blank control.
Figure 68:
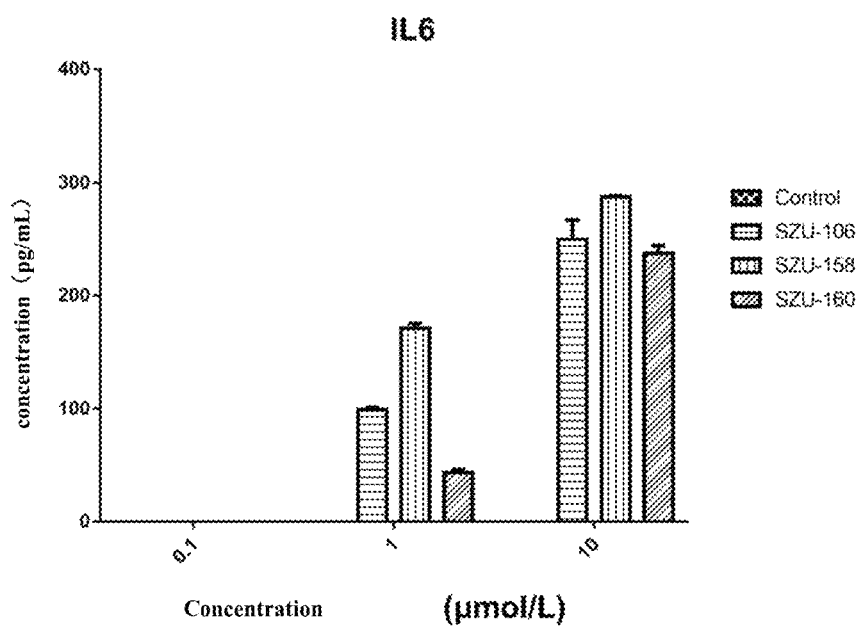
FIG. 68 shows the stimulatory effects of SZU-106, SZU-158, and SZU-160 on immunocytes to produce IL-6, where "control" represents blank control.
Figure 69:
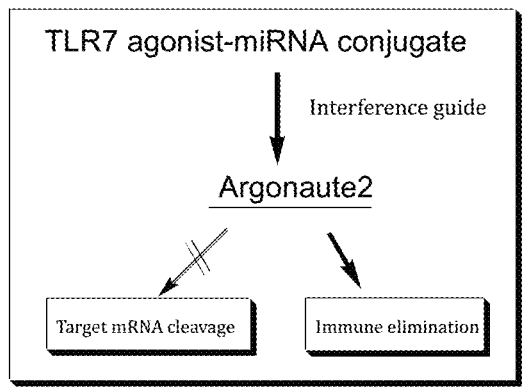
FIG. 69 is a schematic diagram showing the functioning mechanism of TLR7 small-molecule immune agonist conjugated with self-miRNAs in human bodies for immune-targeted interference in the binding of agonist to protein, thereby eliminating protein-related pathogenicity.
Figure 70:
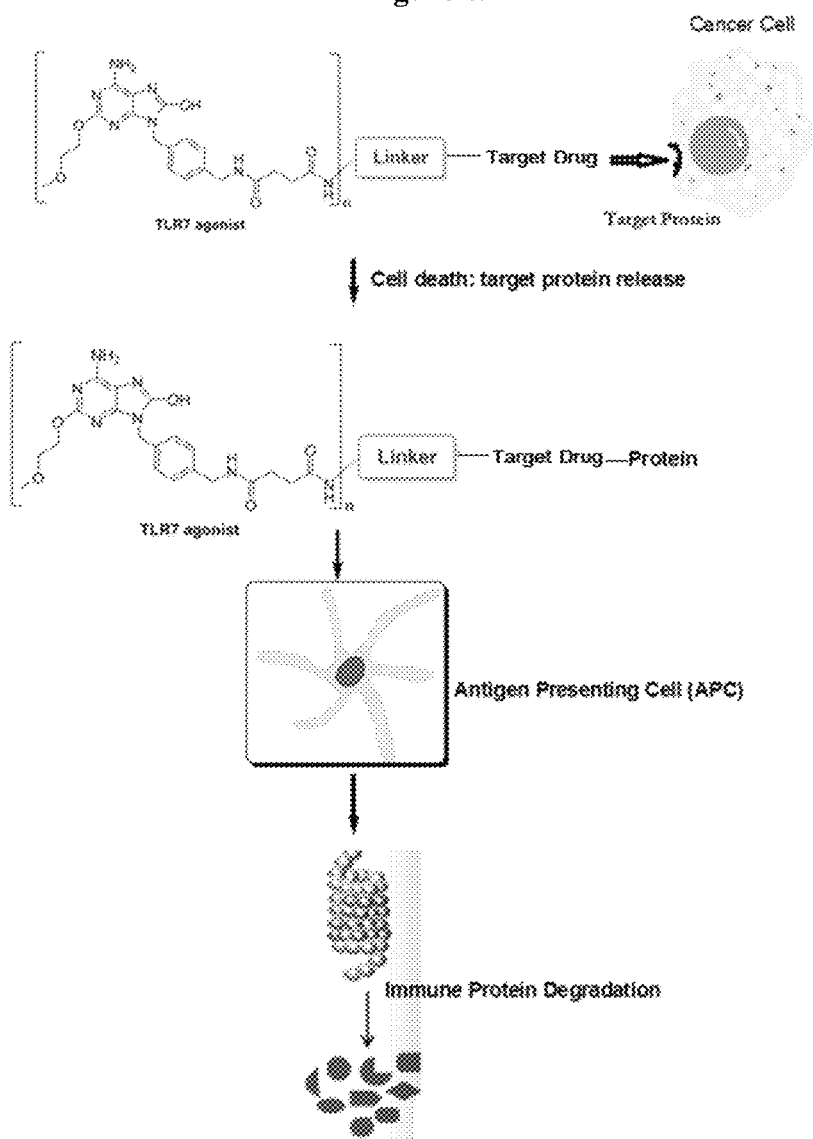
FIG. 70 is a schematic diagram showing the functioning mechanism of the immune targeted compound of the present invention for eliminating pathogenic targets (proteins) via immune pathway.

5 mg of SZU-158 was dissolved in 0.5 mL of DMSO. Equimoles of NHS and EDCI were added. The mixture was stirred at room temperature for 4 hours. 20 mg of PD-1 antibody (purchased from Bioxcell, J43) in 0.5 mL of PBS was added. The mixture was stirred in a closed vessel at 15° C. overnight. The mixed reaction solution was filtered with a filter membrane to obtain a SZU-158-PD-1 conjugate product, which was lyophilized to obtain 18 mg of a white solid SZU-158-PD-1. The conjugation degree determined by mass spectrometry is n=4 (SZU-158-PD-1 has immunocytokine activities as shown in FIGS. 58 and 65, and antibody functions as shown in FIGS. 58, 64 and 65).

SZU-158-OX40
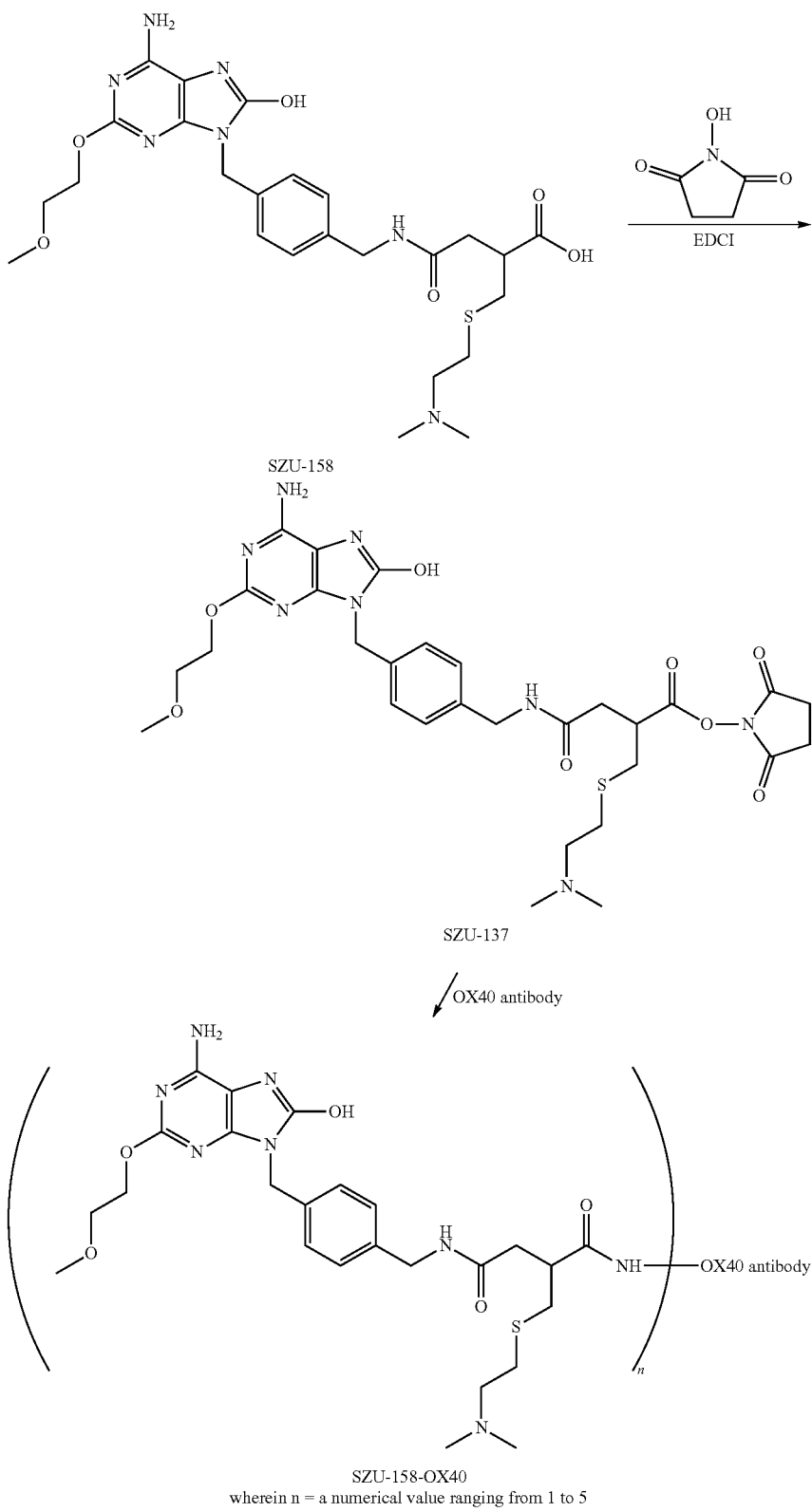
5 mg of SZU-158 was dissolved in 0.5 mL of DMSO. Equimoles of NHS and EDCI were added. The mixture was stirred at room temperature for 4 hours. 20 mg of OX40 antibody (purchased from Bioxcell, OX-86) in 0.5 mL of PBS was added. The resulting mixture was stirred in a closed vessel at 15° C. overnight. The mixed reaction solution was filtered with a filter membrane to obtain SZU-158-OX40 conjugate product, which was lyophilized to obtain 17 mg of a white solid SZU-158-OX40. The conjugation degree determined by mass spectrometry is n=4 (SZU-158-OX40 has immunocytokine activities as shown in FIGS. 58 and 65, and antibody functions as shown in FIGS. 58, 64 and 65).

SZU-158-PD-L1

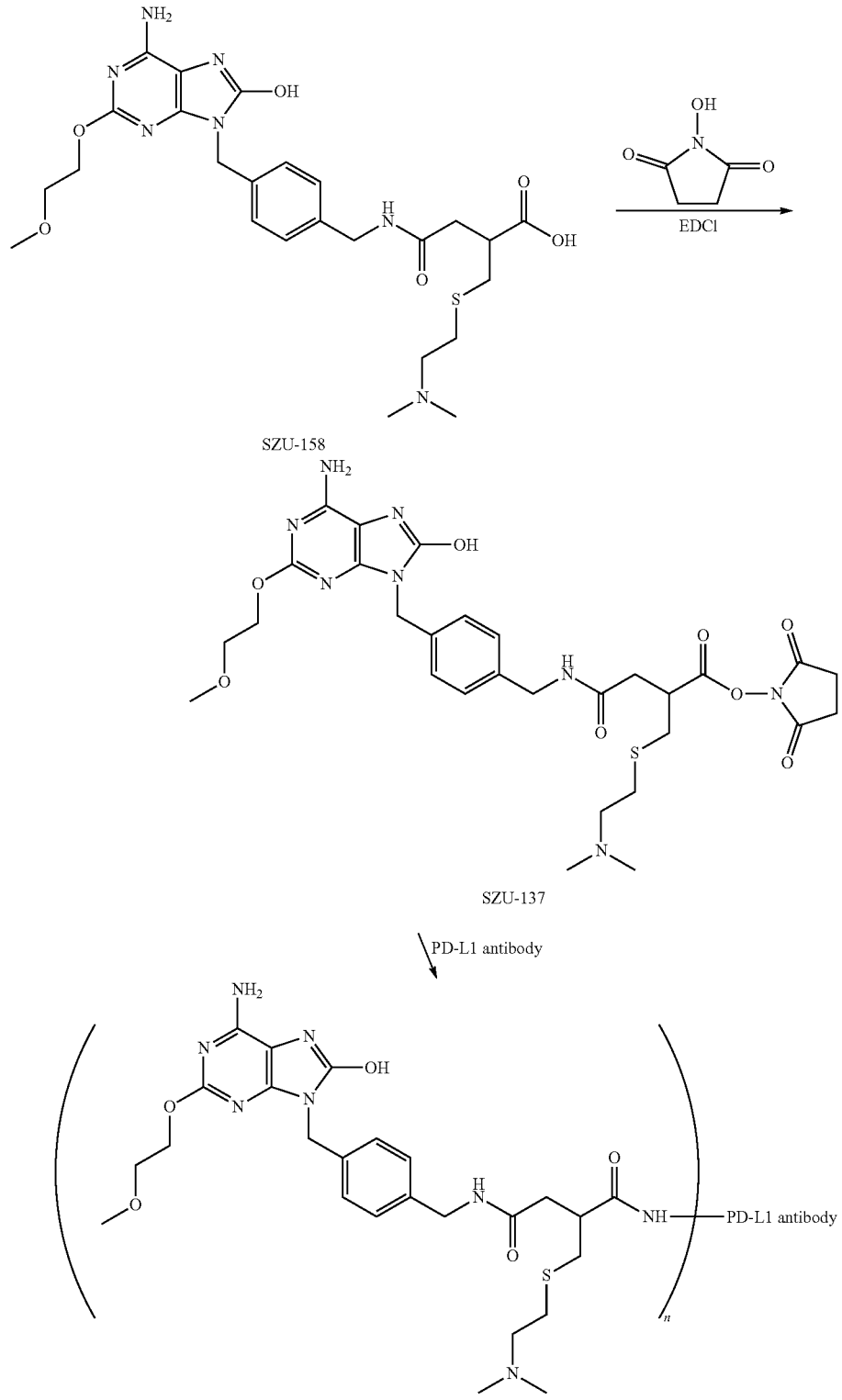

SZU-158-PD-L1
wherein n = a numerical value ranging from 1 to 5

5 mg of SZU-158 was dissolved in 0.5 mL of DMSO. Equimoles of NHS and EDCI were added. The mixture was stirred at room temperature for 4 hours. 20 mg of PD-L1 antibody (purchased from Bioxcell, 10F.9G2) in 0.5 mL of PBS was added. The mixture was stirred in a closed vessel at 15° C. overnight. The mixed reaction solution was filtered with a filter membrane to obtain SZU-158-PD-L1 conjugate product, which was lyophilized to obtain 15 mg of a white solid SZU-158-PD-L1. The conjugation degree determined by mass spectrometry is n=4 (SZU-158-PD-L1 has immunocytokine activities as shown in FIGS. 58 and 65, and antibody functions as shown in FIGS. 58, 64 and 65).

The novel immune-targeted compounds formed by conjugating SZU-158 with an antibody, owing to the presence of dimethylamino group, can form a salt and result in an ionized positive charge, which is advantageous for improving the therapeutic efficacy and water solubility.

SZU-168 and SZU-175

Vemu-1, a precursor of Vemurafenib, is purchased from WuXi AppTec.

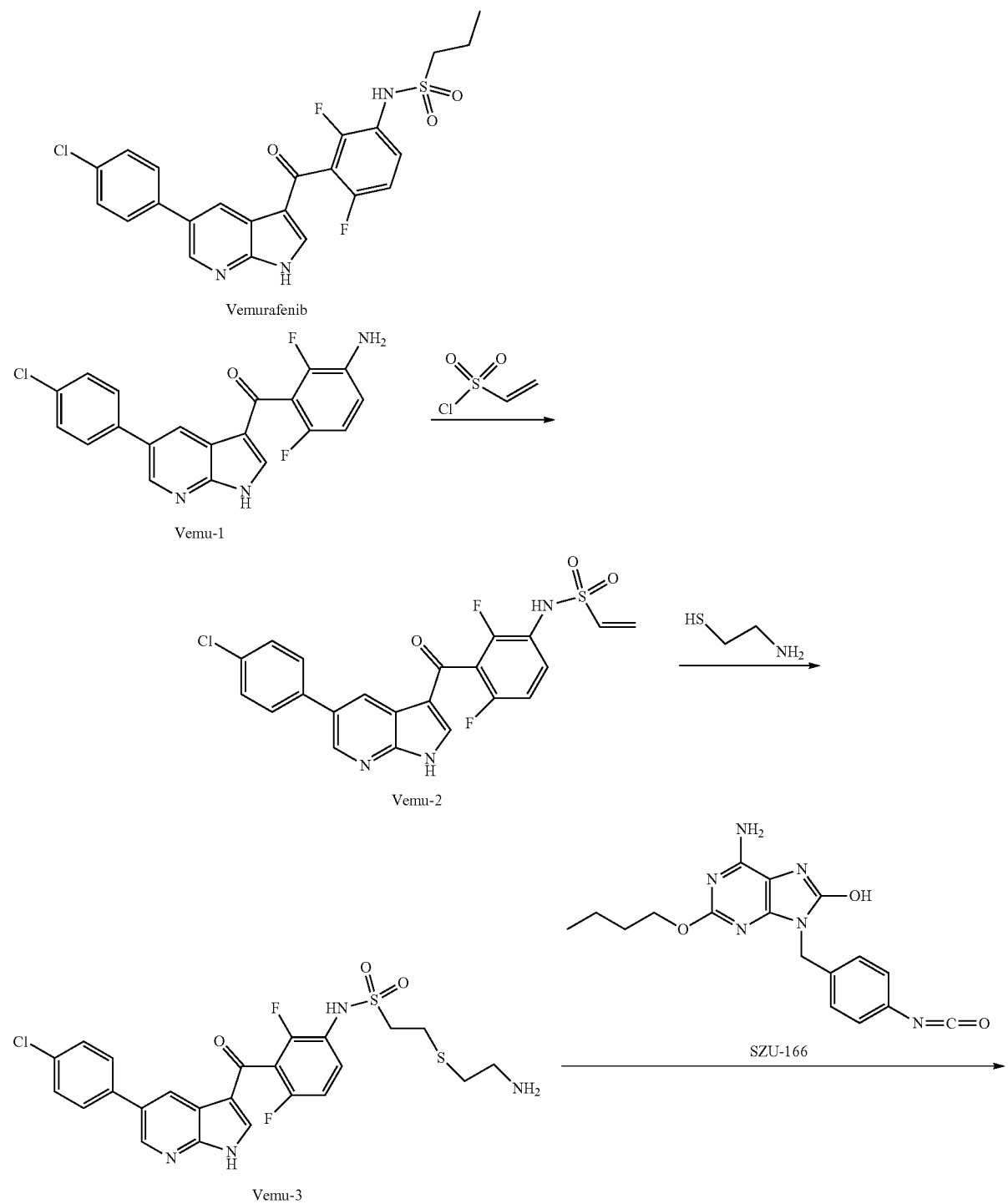

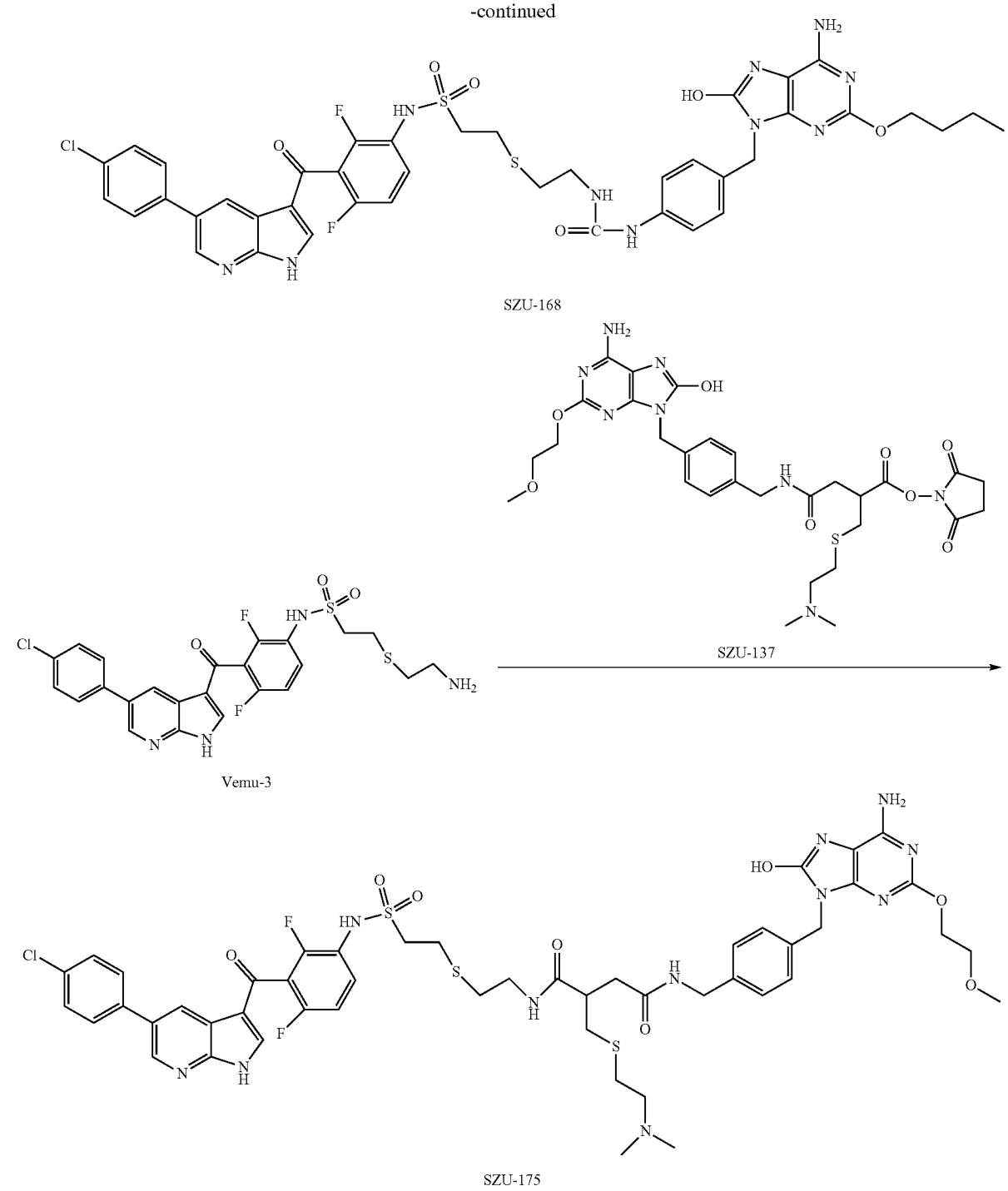

Vemu-1 was dissolved in DMF. 2-fold moles of triethylamine were added. The mixture was cooled to 0° C. and then added with 1-fold mole of vinylsulfonyl chloride. The resulting mixture was warmed slowly to room temperature, stirred for 8 hours, and then added with 10-fold volume of ice-water. The mixture was stirred thoroughly for 1 hour and adjusted with saturated $Na_2CO_3$ to have a pH of 8. The precipitated solid was filtered, washed with water twice, and dried to give Vemu-2. 1 g of Vemu-2 was dissolved in 30 mL of DMF. 0.33 g of mercaptoethylamine was added. The mixture was stirred at room temperature for 12 hours. The reaction mixture was distilled off the solvent under reduced pressure to obtain crude Vemu-3, which was purified by silica gel column chromatography to obtain 0.98 g of a pure product Vemu-3 with a yield of 85%; MS (ESI): m/z: [M+1] 552.04.

0.3 g of Vemu-3 was dissolved in 10 mL of DMSO. 0.2 g of SZU-166 was added. The mixture was reacted under stirring at 40° C. for 8 hours, and then added with 100 mL of water. The reaction solution was centrifuged to give precipitated crude product, which was dissolved in 20 mL of glacial acetic acid. After filtration, the filtrate was added with 100 mL of water and a pure product SZU-168 was precipitated, which was dried to 0.33 g; MS (ESI): m/z: [M+1] 906.41.

1 g of SZU-158 was dissolved in 10 mL of DMSO. 0.2 g of NHS (N-hydroxysuccinimide) and 0.33 g of EDCI (1-(3-dimethylaminopropyl)-3-ethylcarbodiimide hydrochloride) were added. The mixture was left under stirring at room temperature overnight to obtain SZU-137. 0.9 g of Vemu-3 was added and stirring was continued at room temperature for another 12 hours. The mixture was added with 100 mL of water and filtered to give a crude product, which was re-crystallized with acetic acid to obtain 1.22 g of SZU-175 acetate; MS(ESI): m/z: [M+1] 1095.81.

SZU-176

Intermediate of Osimertinib was purchased from WuXi AppTec.

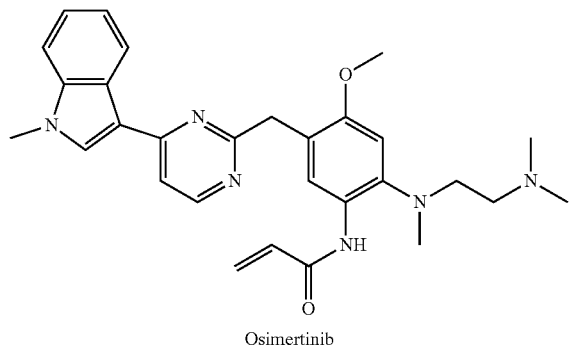
Osimertinib

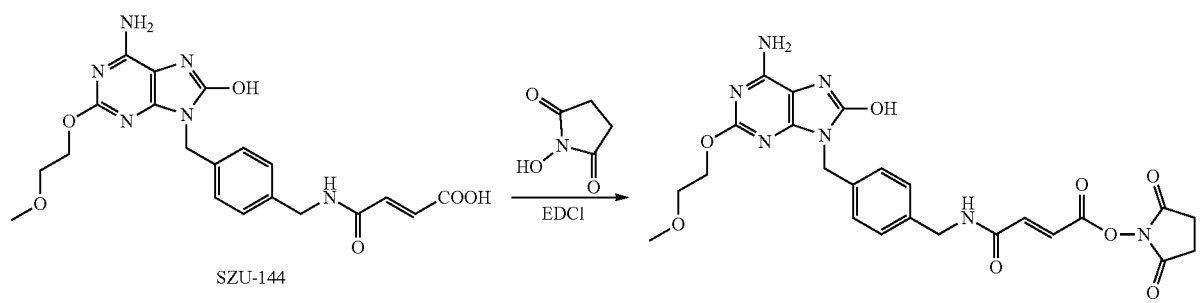
SZU-144

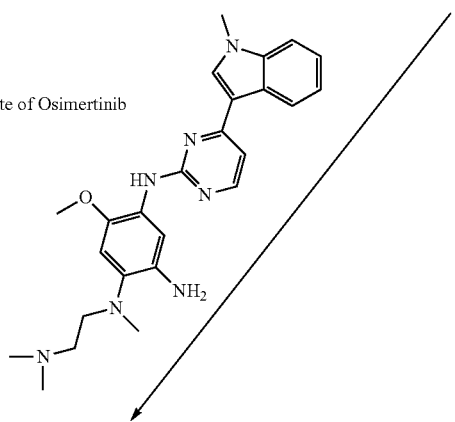
Intermediate of Osimertinib

-continued

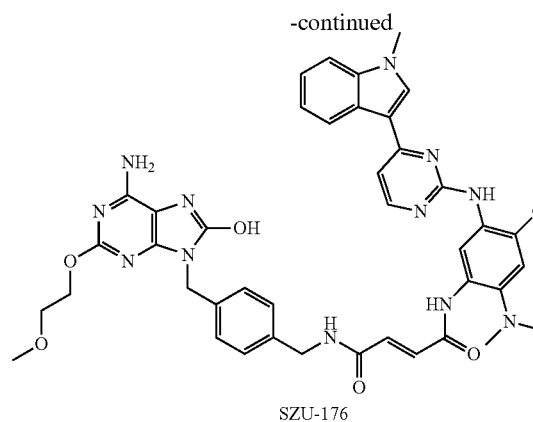

SZU-176

1 g of SZU-144 was dissolved in 10 mL of DMSO. 0.26 g of NHS and 0.4 g of EDCI were added. The mixture was left under stirring at room temperature overnight. 1 g of intermediate of Osimertinib was added, and then the stirring was continued at room temperature for another 12 hours. The mixture was added with 100 mL of water and filtered to give a crude product, which was re-crystallized with acetic acid to obtain 1.5 g of SZU-176 acetate; MS (ESI): m/z: [M+1] 870.81.

SZU-177

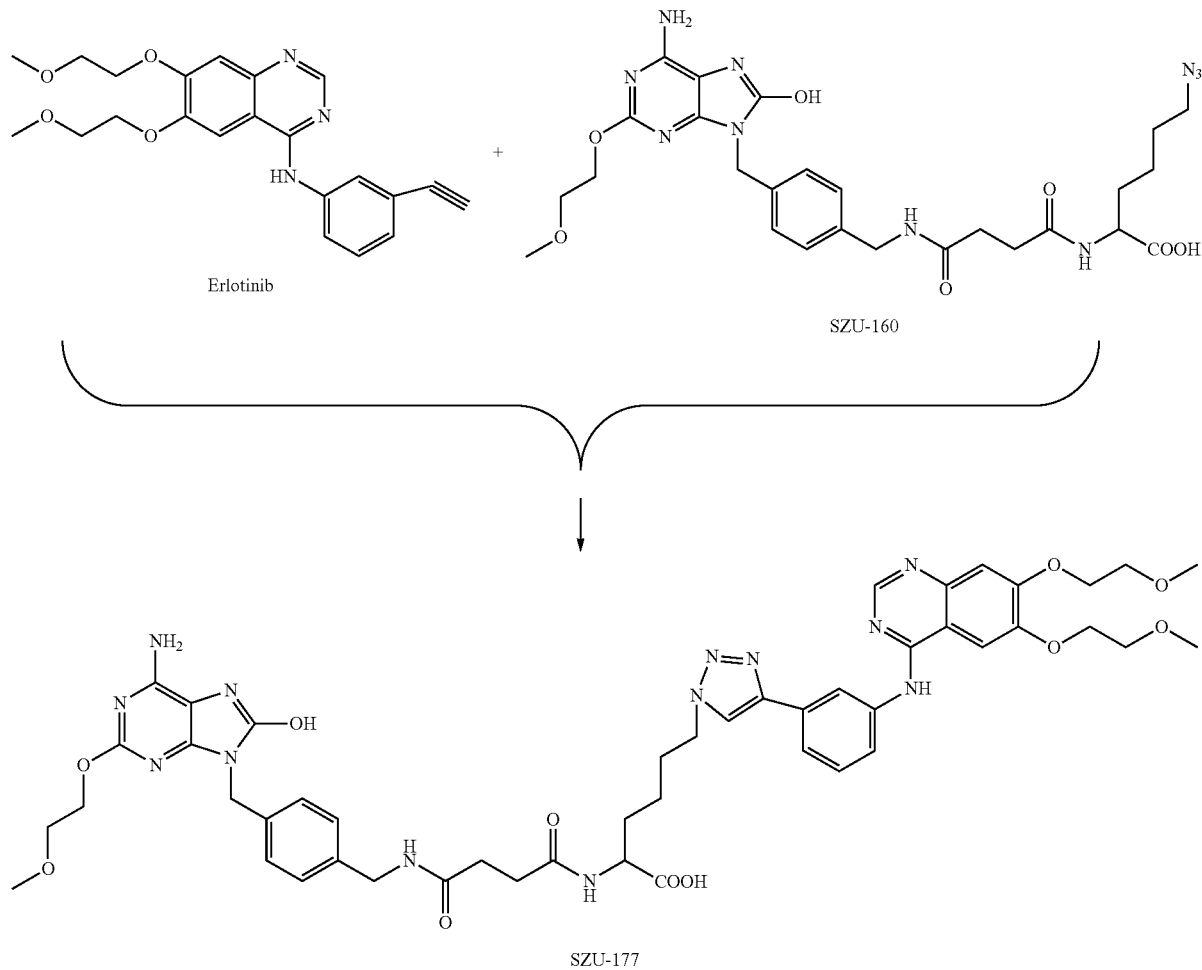

100 mg of Erlotinib, 150 mg of SZU-160, 20 mg of copper sulfate and 20 mg of vitamin C were added to a solution (10 mL) of DMSO and water (1:1). The mixture was left under stirring at room temperature overnight. 10-fold volume of water was added. The reaction solution was filtered, purified by HPLC and dried to give 176 mg of SZU-177 with a yield of 70%; MS (ESI): m/z: [M+1] 993.10.

SZU-178

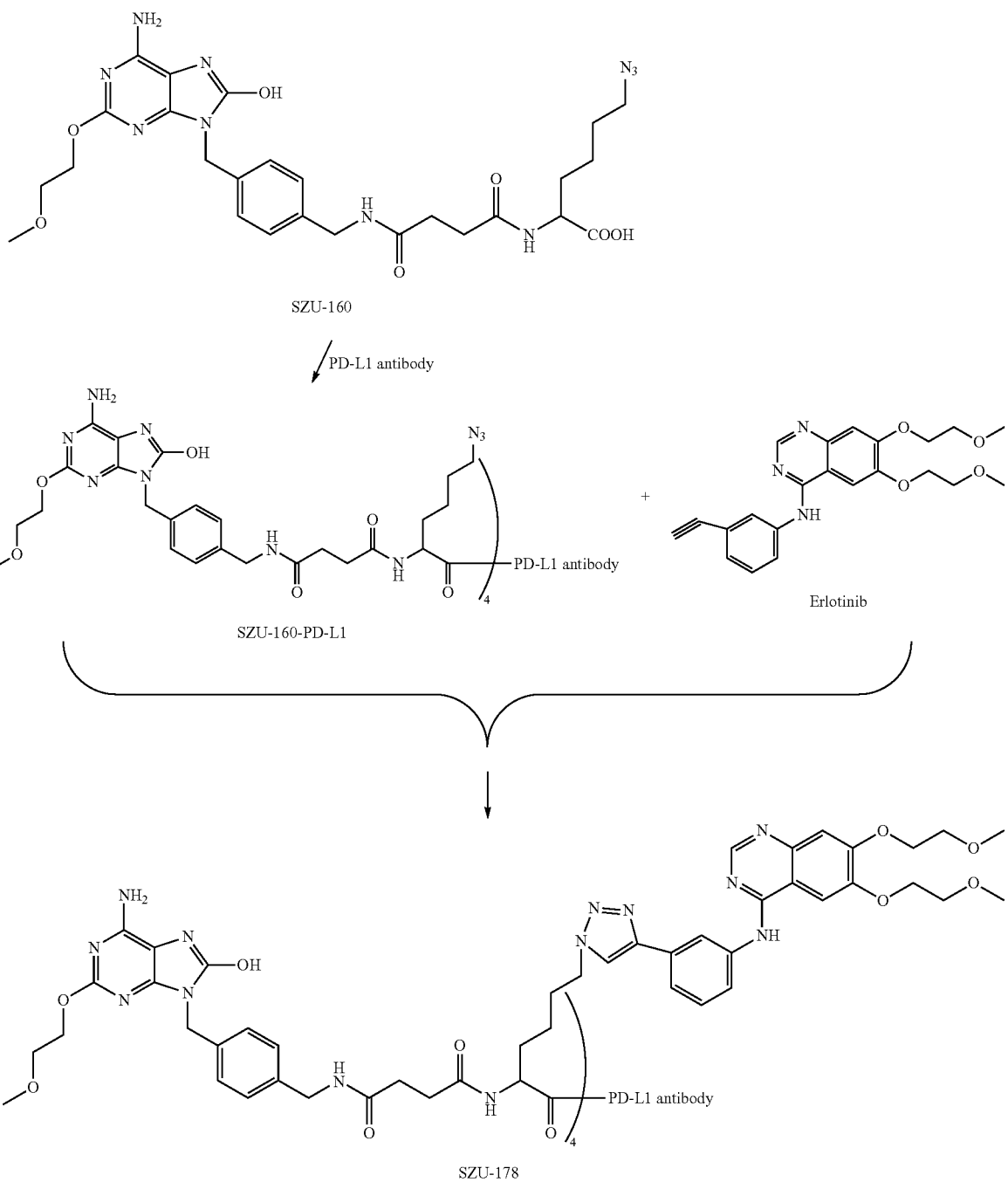

3.5 mg of SZU-160 was dissolved in 0.5 mL of DMSO. Equimoles of NHS and EDCI were added. The mixture was left under stirring at room temperature for 4 hours. 20 mg of PD-L1 antibody (purchased from Bioxcell, 10F.9G2) in 0.5 mL of PBS was added. The mixture was stirred in a closed vessel at 15° C. overnight. The mixed reaction solution was filtered with a filter membrane to obtain a solution of SZU-160-PD-L1 antibody conjugate product. 2.5 mg of Erlotinib, 2 mg of sodium ascorbate, and 2 mg of copper sulfate were added. The mixture was reacted under stirring at room temperature for 12 hours. The reaction solution was filtered with filter membrane and lyophilized to give 12 mg of a white solid SZU-178 (i.e., SZU-160-Erlotinib-PD-L1 conjugate formed by conjugating SZU-178 with Erlotinib and PD-L1 antibody). The conjugation degree determined by mass spectrometry is n=4 (SZU-178 has immune cytokine stimulation and anti-tumor functions as shown in FIGS. 58, 64 and 65).

SZU-136-miRNA21

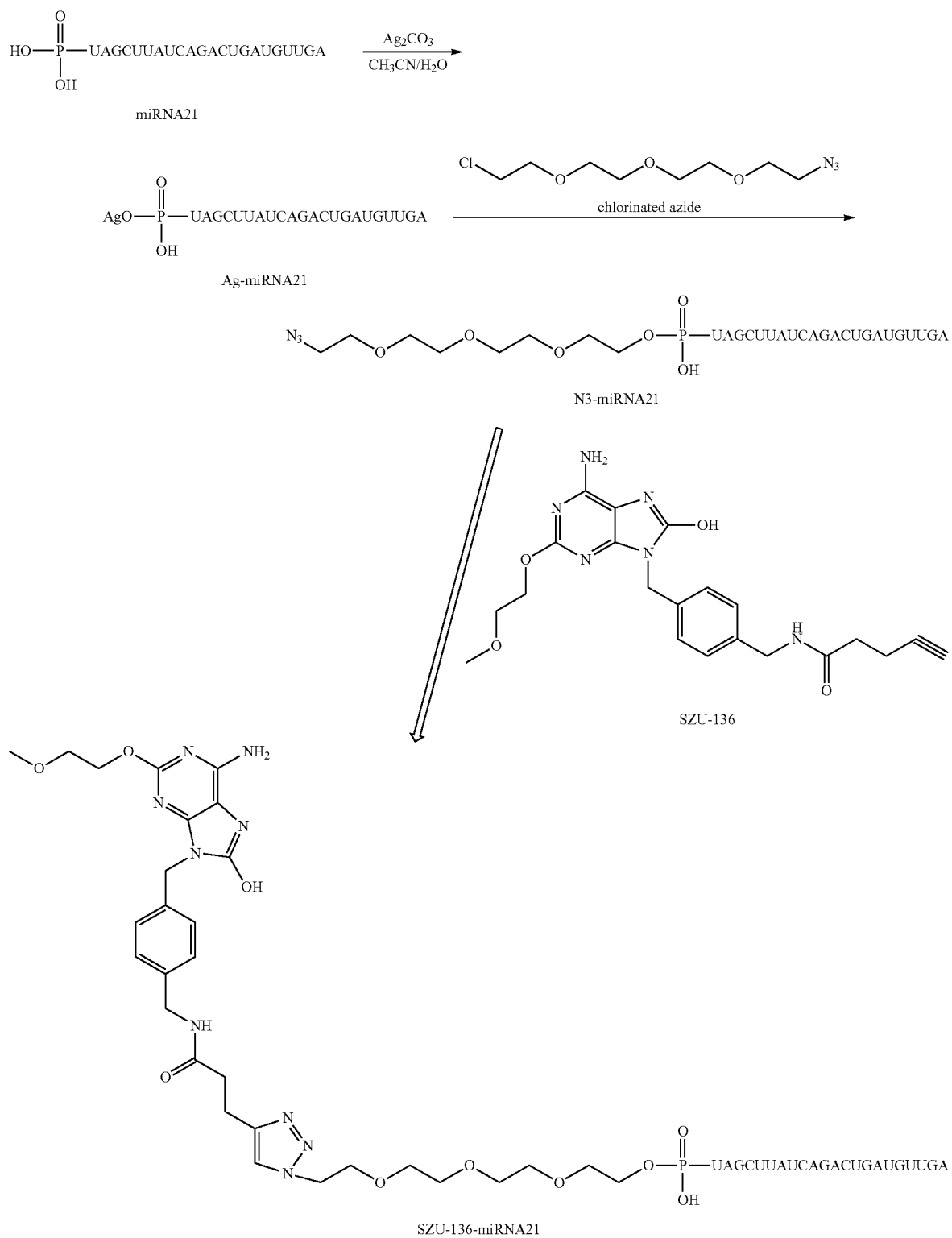

71 mg of miRNA21 (purchased from Suzhou Jima Gene Co., Ltd.) was dissolved in 10 mL of acetonitrile and water (1:1) solvent. 14 mg of $Ag_2CO_3$ was added. The mixture was stirred at room temperature for 12 hours. The solvent was distilled off under reduced pressure to give 69 mg of Ag-miRNA21 (96%), which was mixed with 5 mg of chlorinated azide in 20 mL of acetonitrile. The mixture was heated under reflux for 4 hours, cooled to room temperature, and added with 50 mL of water. The resulting mixture was stirred for 15 minutes and filtered. The filtrate was distilled under reduced pressure to a small volume (10 mL). 50 mL of tetrahydrofuran was added. After stirring for 10 minutes, the solution was centrifuged to give precipitate, which was dried under vacuum to obtain 45 mg of N3-miRNA21 (yield 61%). MS (ESI): m/z: [M+Na] 7307.42.

40 mg of N3-miRNA21, 3 mg of SZU-136, 2 mg of copper sulfate and 2 mg of vitamin C were mixed and added to a solution (10 mL) of DMSO and water (1:1). The mixture was stirred at room temperature overnight. The product was purified by HPLC, lyophilized, and dried under vacuum to give 14 mg of SZU-136-miRNA21 (i.e., the conjugate formed by conjugating SZU-136 with miRNA21) with a yield of 33%; MS (ESI): m/z: [M+Na] 7731.86.

SZU-179

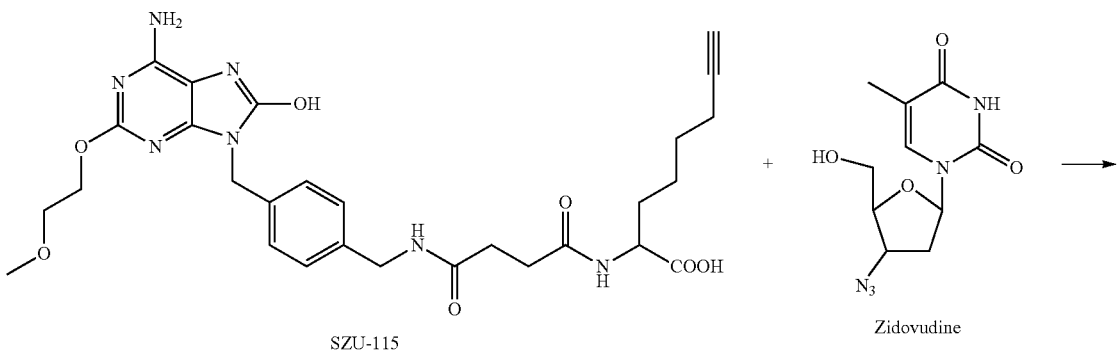

SZU-115        Zidovudine

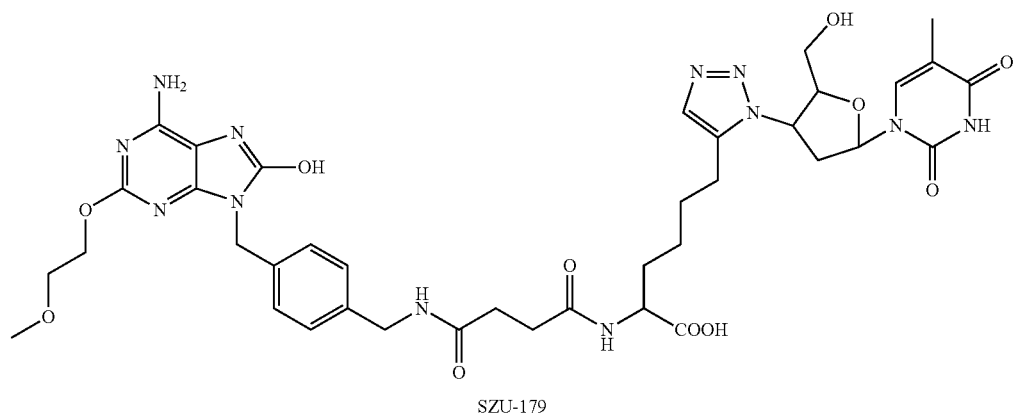

SZU-179

580 mg of SZU-115, 267 mg of Zidovudine, 25 mg of copper sulfate and 25 mg of sodium ascorbate were admixed and added to a solution (25 mL) of DMSO and water (1:1). The mixture was stirred at room temperature overnight and added with 10-fold volume of water. The reaction solution was distilled under vacuum to a small volume (about 10 mL) and added with 30 mL of water. The mixed solution was adjusted to a pH of 10 with 5% NaOH and filtered. The filtrate was adjusted to a pH of 5 with glacial acetic acid and gave precipitated product, which was filtered and dried under vacuum to obtain 728 mg of SZU-179 with a yield of 86%; MS (ESI): m/z: [M+Na] 871.42.

SZU-115-PD-L1-Targeted Drug (i.e., the Conjugate Formed by Conjugating SZU-115 with PD-L1 Antibody and Targeted Drug)

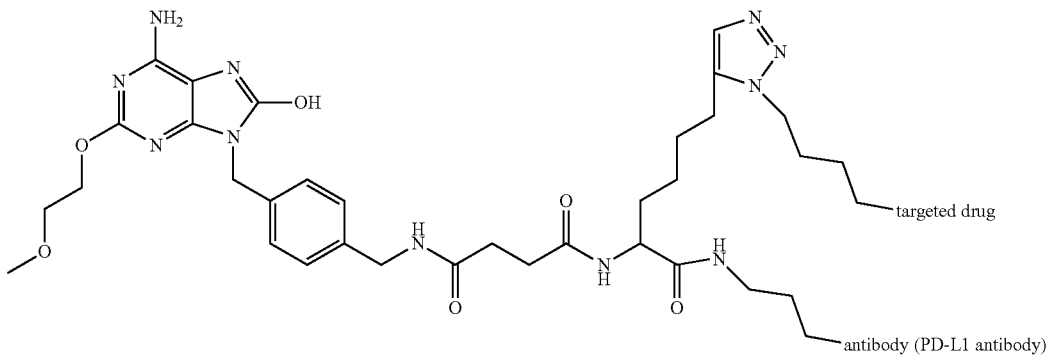

Conjugate of SZU-115-Antibody-Targeted Drug
SZU-180

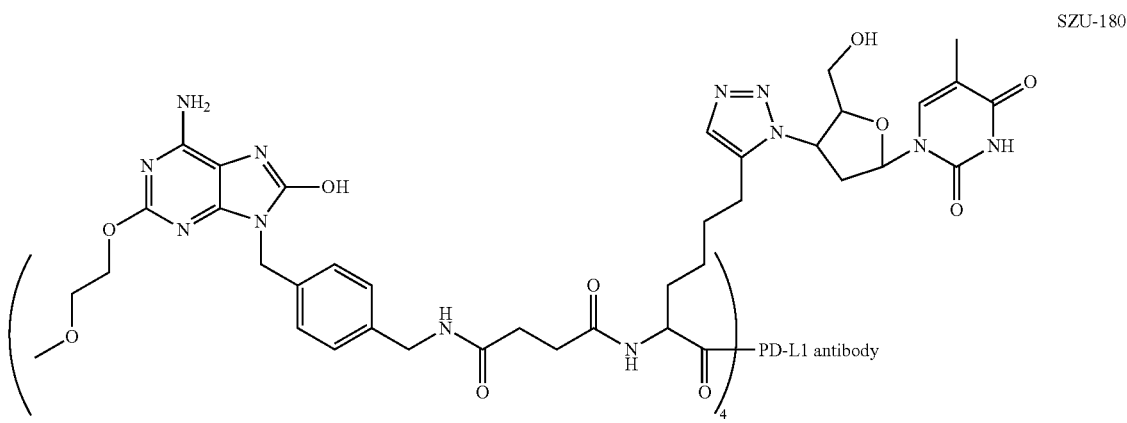

The PD-L1 antibody was conjugated by the same process as in the preparation of SZU-178, and Click reaction was conducted by the same process as in the preparation of SZU-179, to obtain SZU-180. The resulting product can be used for the treatment of AIDS.

EFFECT EXAMPLES

Effect Example 1: Detection of the Immunostimulatory Effects of the SZU-Series Small-Molecule Immune Agonists and Novel Immune Targeted Compounds of the Present Invention on Spleen Lymphocytes 1. Extraction of Spleen Lymphocytes (1) BALB/c or $C_{57}BL/6$ mouse spleens were collected, ground in a small dish containing Mouse Lymphocyte Separation Medium, and filtered through a filter membrane (with a pore size of 0.22 μm) to obtain a cell suspension, which was treated by centrifugation to obtain lymphocytes. The isolated lymphocytes were placed in a 15 mL centrifuge tube, into which 10 mL of 1640 complete medium was added. The mixture was mixed uniformly and centrifuged at 250 g for 10 minutes. The supernatant was discarded.

(2) The cells were re-suspended with 1 mL of erythrocyte lysate. After 1 minute of lysis, 4 mL of 1640 complete medium was added for termination. The tube was centrifuged at 1,000 rpm for 5 minutes. The supernatant was discarded.

(3) The cells were re-suspended with 2 mL of 1640 complete medium, counted, and then seeded into 24-well plates at a density of $1\times10^6$ cells per well.

2. Preparation of the Samples

The spleen lymphocytes seeded into the 24-well plates were stimulated with different concentrations of the SZU-series small-molecule immune agonists and novel immune targeted compounds. The 24-well plate was transferred into an incubator. After 24 hours of stimulation, the supernatant was gently aspirated, i.e. samples to be tested by ELISA (Enzyme-Linked Immunosorbent Assay). The concentrations and concentration gradients were dependent on individual requirements of each tested sample.

3. ELISA Test (1) Coating: 10× coating buffer was diluted to 1× and then used to dilute the capture antibody. The diluted capture antibody was added into a 96-well microtiter plate, 100 μl per well. The plate was sealed with plastic wrap and placed at 37° C. for 2 to 4 hours or at 4° C. in refrigerator overnight. The liquid contents were aspirated out of each well of the plate. Then the plate was washed with washing buffer (PBST: PBS solution with 5‰ Tween-20) three times and dried by patting.

(2) Blocking: diluted blocking solution was added, 200 μl per well; the plate was sealed with plastic wrap and blocked at room temperature for 1 hour. Then the plate was washed with PBST three times and dried by patting.

(3) Loading samples: 12 standard samples were arranged, wells in duplicate for each concentration of a standard sample, with the highest concentration of the standard sample being 2,000 pg/mL. The samples were diluted with dilution buffer to the desired concentration. The standard samples have the following successive concentrations: 2,000 pg/mL, 1,000 pg/mL, 500 pg/mL, 250 pg/mL, 125 pg/mL, 62.5 pg/mL, 31.5 pg/mL, 15.75 pg/mL, 7.875 pg/mL, 3.9375 pg/mL, 1.96875 pg/mL, and 0 pg/mL. The supernatant samples obtained by stimulating spleen lymphocytes with different concentrations of drugs were added into the corresponding wells, wells in triplicate per sample. Blank control wells and negative control wells were also arranged and labeled accordingly. The 96-well microtiter plate loaded with the standard samples and tested samples was sealed with plastic wrap and incubated at room temperature for 2 hours or at 4° C. in refrigerator overnight. The liquid contents were aspirated out of each well. The plate was washed with PBST three times and dried by patting.

(4) Secondary antibody: the testing antibody was diluted with dilution buffer to the desired concentration, and added to the plate at 100 μl per well, and incubated at room temperature for 1 hour. The liquid contents were aspirated out of each well of the plate. Then the plate was washed with PBST five times and dried by patting.

(5) Enzyme-labeled antibodies: Avidin-HRP was diluted with dilution buffer to the desired concentration, and added to the plate at 100 μl per well, and then incubated at room temperature for 30 minutes. The liquid contents were aspirated out of each well of the plate. Then the plate was washed with PBST five times and dried by patting.

(6) Color development: 100 μl of 3,3',5,5'-tetramethylbenzidine (TMB) chromogenic solution was added to each well, and then incubated at room temperature in the dark for 15 minutes.

(7) Termination: after the completion of color development, 50 μl of stop solution was added to each well, wherein the stop solution was 1 mol/L $H_2SO_4$.

(8) Detection: the 96-well microtiter plate after termination was placed into a full-wavelength microplate reader, and the absorbance values were read at the wavelength of 450 nm. The data were exported and plotted as a standard curve with software; and a linear regression equation was derived. The concentrations of the immune factors (INF-γ, IL-6, etc.) produced by immunocytes were calculated. Specific results of the experiments are given in the figures attached hereto.

Effect Example 2: Anti-Tumor Effects of the Novel Immune Targeted Compounds of the Present Invention 1. Tumor Treatment Protocol in Mice (1) BALB/c or C57BL/6 mice of 6-8 weeks old were weighed and anesthetized with pentobarbital sodium (50 mg/kg i.p). Hair was removed from the tumor implantation site (on the back). The mice were immobilized with sticky tapes.

(2) Surgical sites were sterilized by using cotton swabs dipped into 75% alcohol. Small incisions of about 1 cm at the tumor implantation sites were made and injected with 100 μl of cancer cell suspension ($5\times10^4$ CT26 cells, B16 cells or 4T1 cells). The incisions were sealed with surgical thread and sterilized. After the operations, 50,000 units of ampicillin/100 μL/mouse were injected intraperitoneally for 3 consecutive days.

2. Administration

Figure 57:
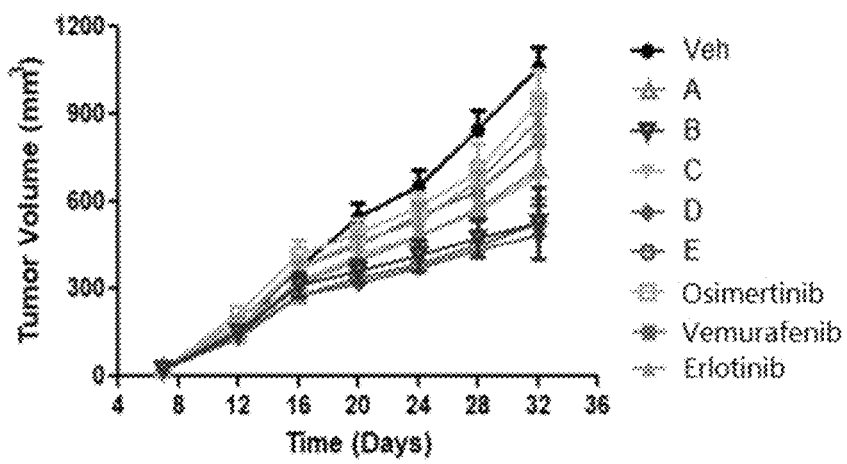
FIG. 57 shows the anti-tumor (CT26) activity of novel immune targeted compounds in vivo: Veh (untreated control), A (SZU-177), B (SZU-175), C (SZU-174), D (SZU-147), and E (SZU-176).

The mice were administered with PBS blank control, the immune agonists or novel immune targeted compounds, respectively. The dosages were determined according to the actual needs (following the principle of effective and safe dosages). The respective substance was dissolved in an appropriate solvent, and the volume of each administration was 100 μL; the mice in each group were administered via intraperitoneal injection. Each group was administered on day 7, 15, 22, and 29 after tumor implantation; and the tumor sizes were measured regularly. The mice were euthanized when the tumor size reached 1500 $mm^3$ or had a weight higher than 15% of their body weights. The results of tumor suppression and survival rates were shown in FIGS. 57, 58 and 64. It can be seen that the groups of mice treated with the novel immune targeted compounds according to the present invention have significantly higher anti-tumor effect.

Methods for testing the biological activities of the novel small-molecule immune agonists and novel immune targeted compounds of the present invention are not limited to the above test methods, and other known or accepted activity testing methods may also be used. Analogously, the schematic diagrams of activities in the present invention are not limited to the illustrated schematic diagrams, while these schematic diagrams can inspire those skilled in the art to achieve the application effects of the novel small-molecule immune agonists and novel immune targeted compounds according to the present invention.

The invention claimed is:

1. A small-molecule immune agonist that is a SZU-series compound selected from the group consisting of:

SZU-104

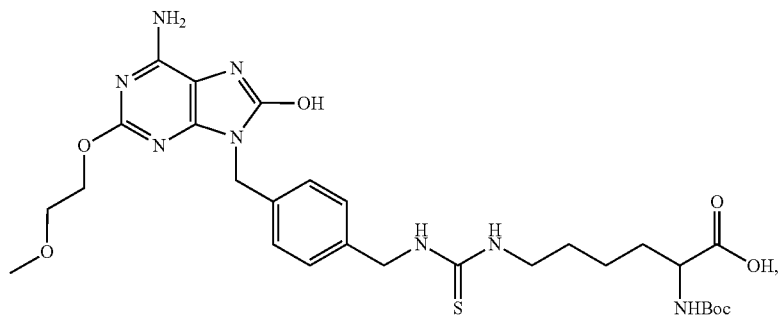

SZU-105

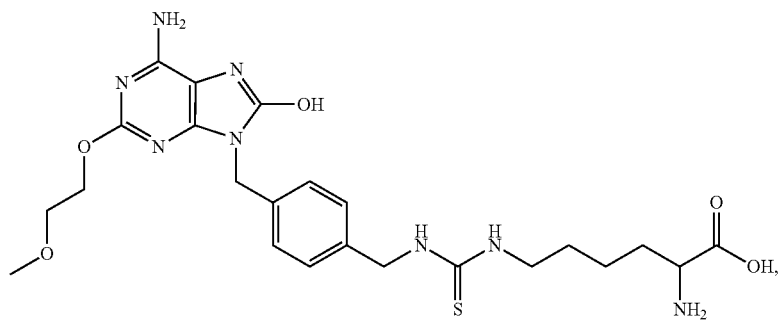

SZU-107

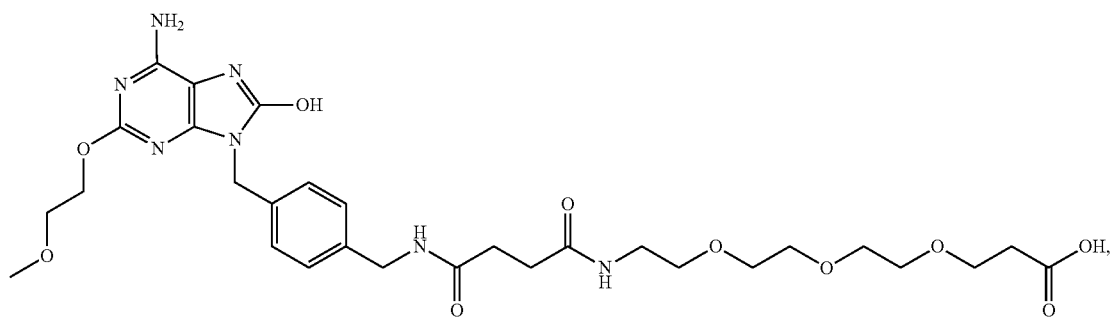

SZU-108

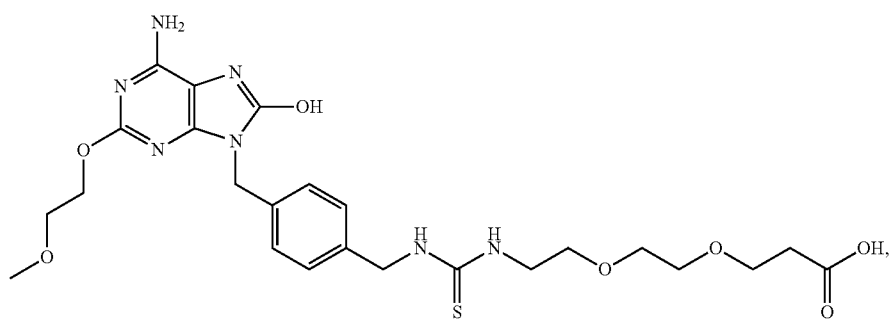

-continued
SZU-109
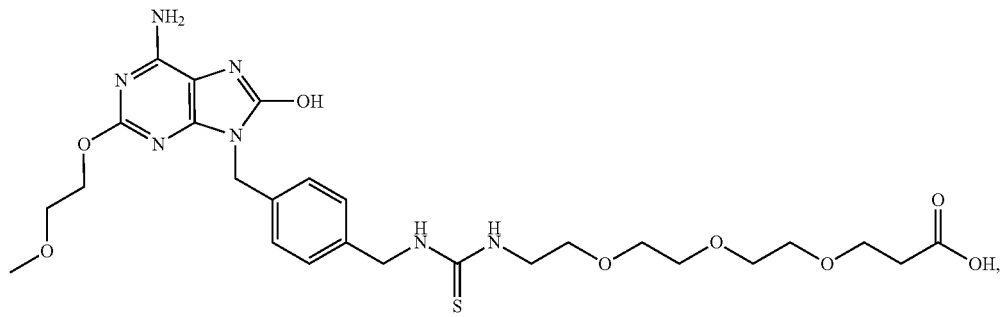
SZU-110
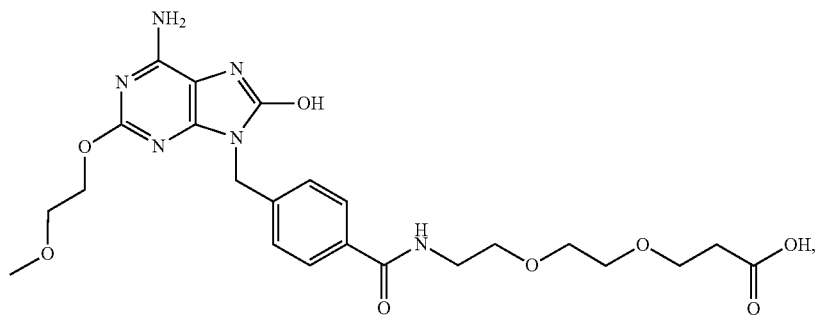
SZU-111
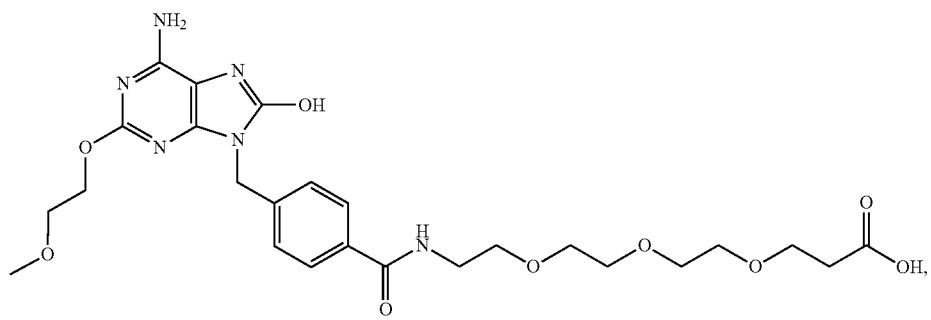
SZU-112
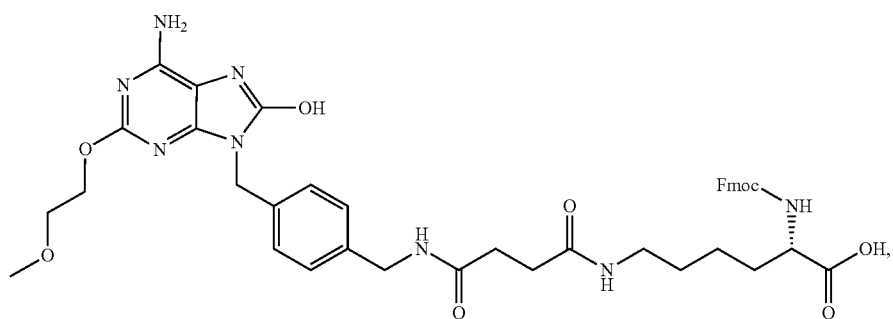
SZU-113
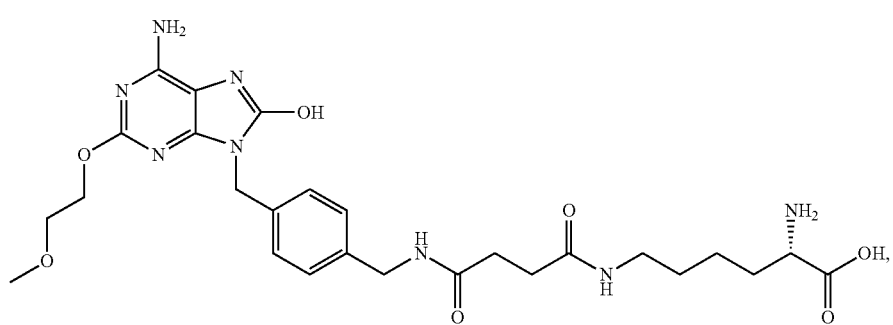

-continued
SZU-115
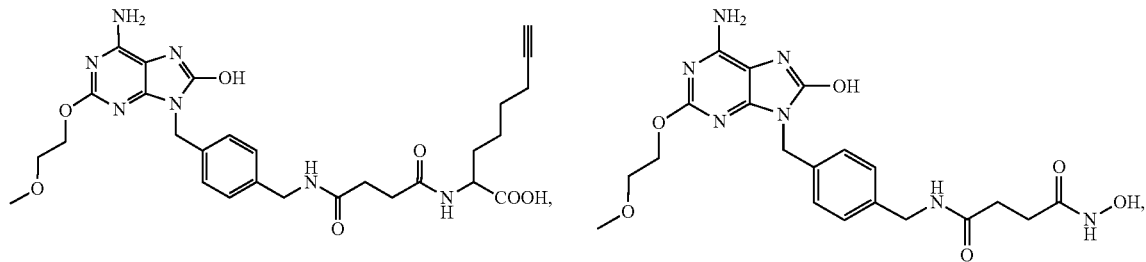
SZU-118
SZU-120
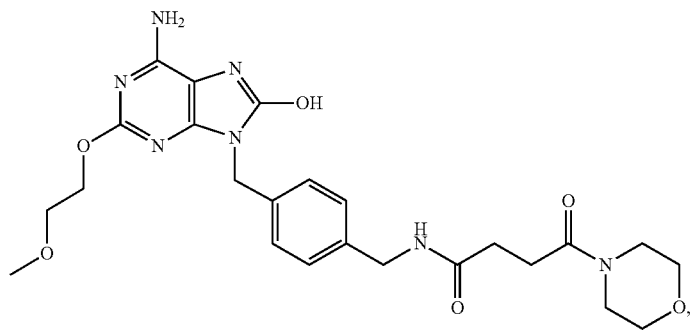
SZU-127
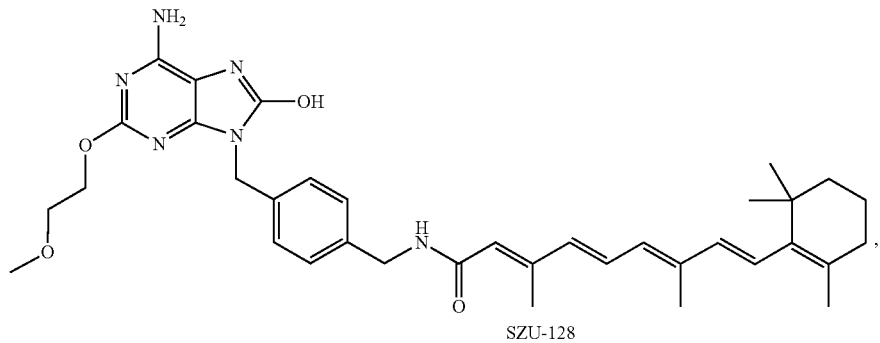
SZU-128
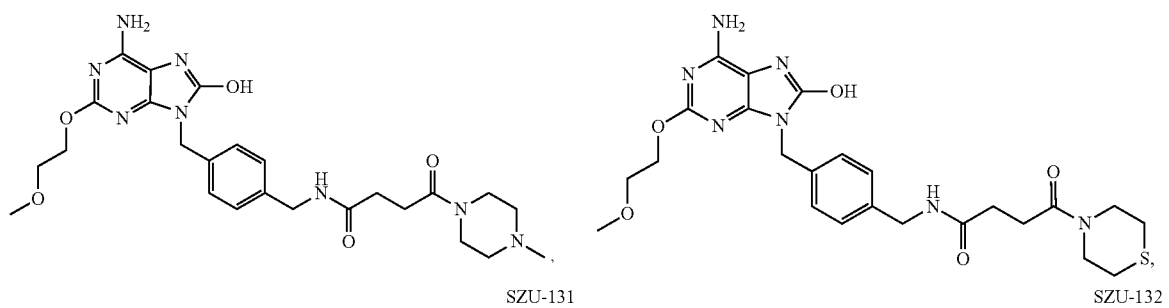
SZU-129
SZU-131
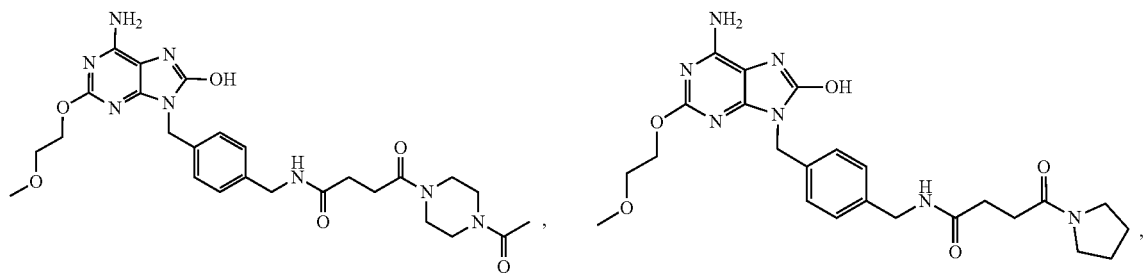
SZU-132

-continued
SZU-133
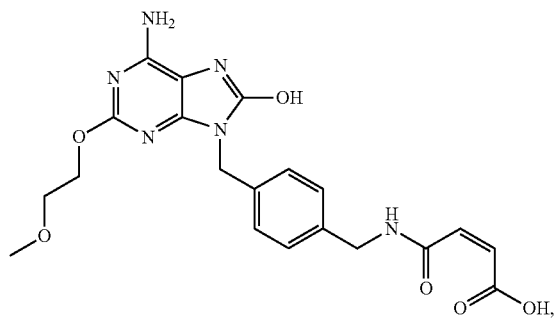
SZU-134
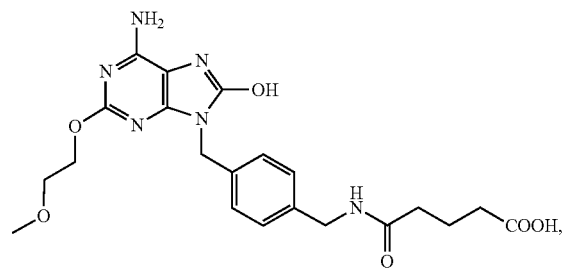
SZU-135
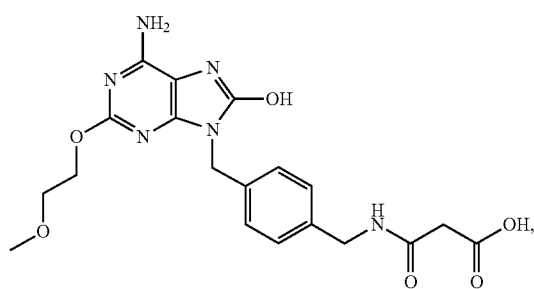
SZU-136
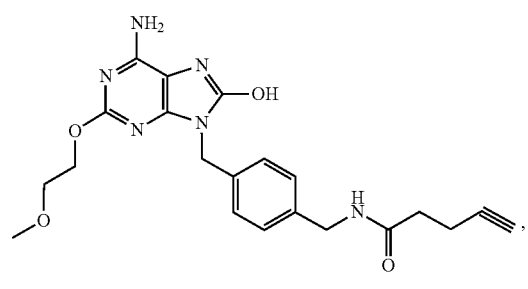
SZU-137
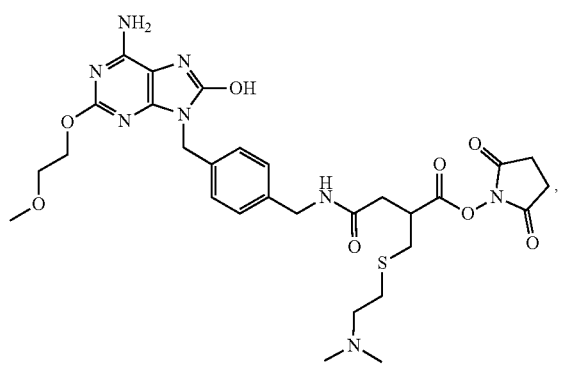
SZU-138
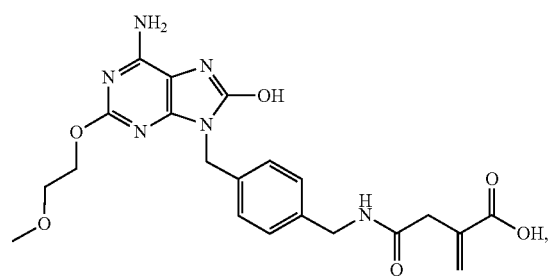
SZU-139
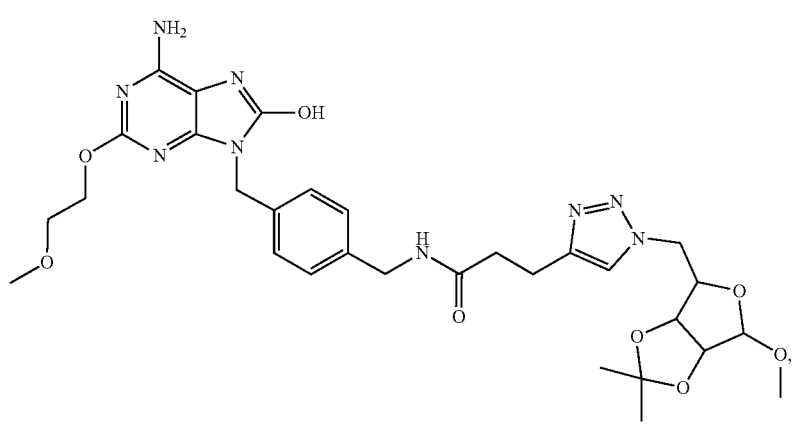

187 188
-continued
SZU-140
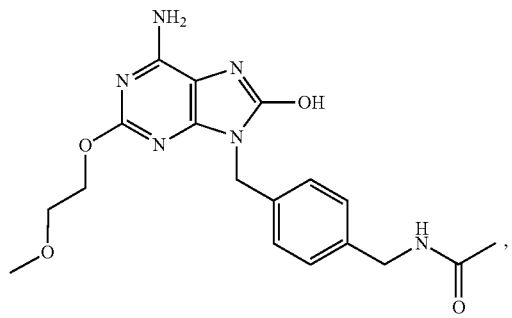
SZU-143
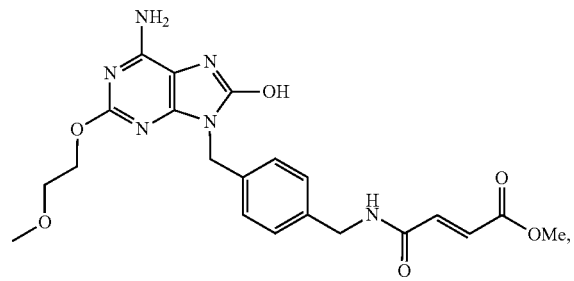
SZU-144
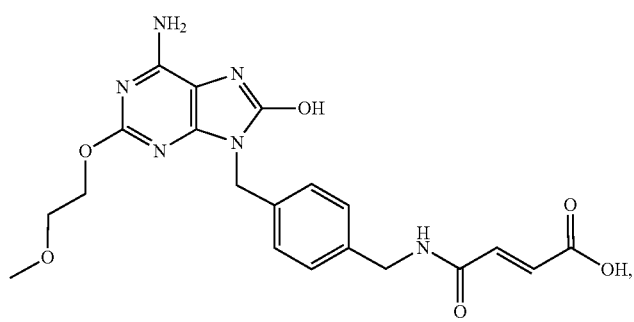
SZU-145
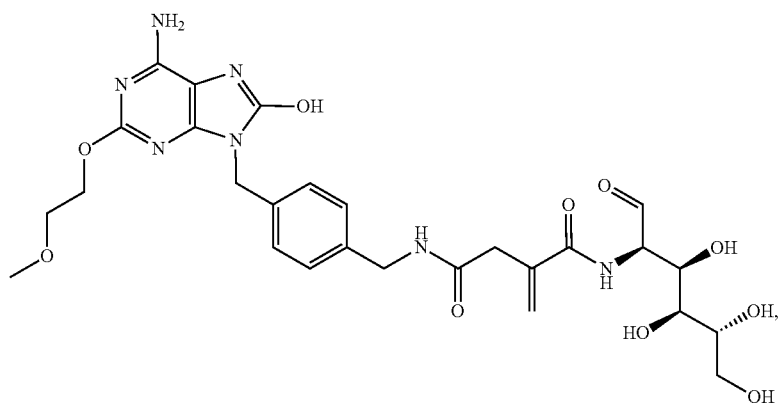
SZU-149
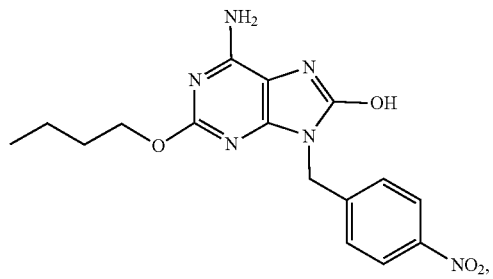

189  190
SZU-158  SZU-159
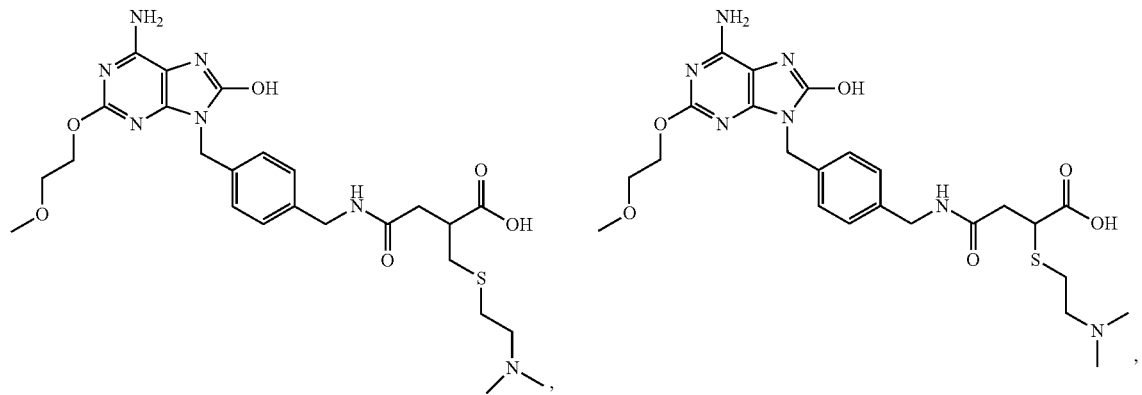
SZU-160  SZU-161
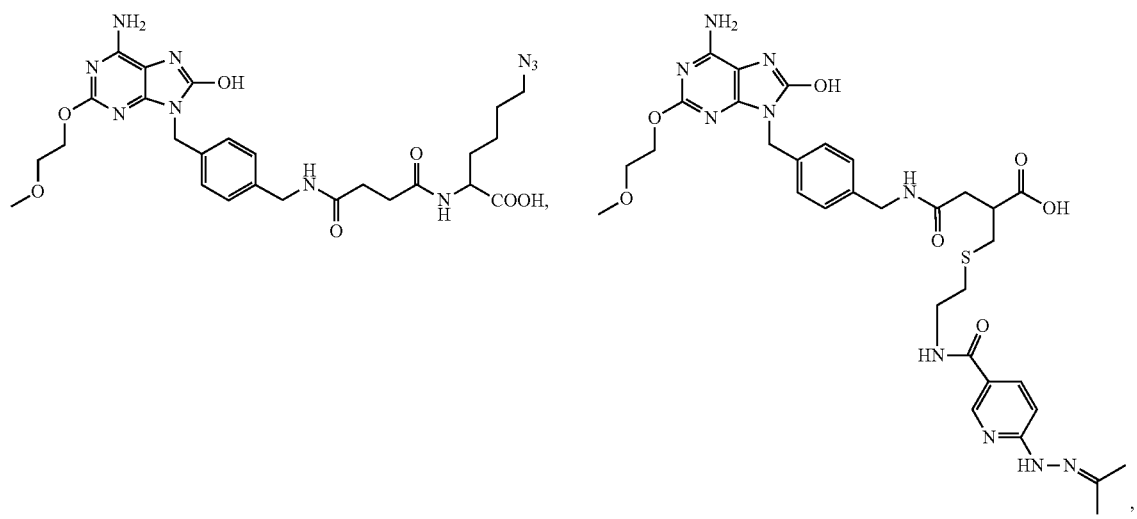
SZU-162
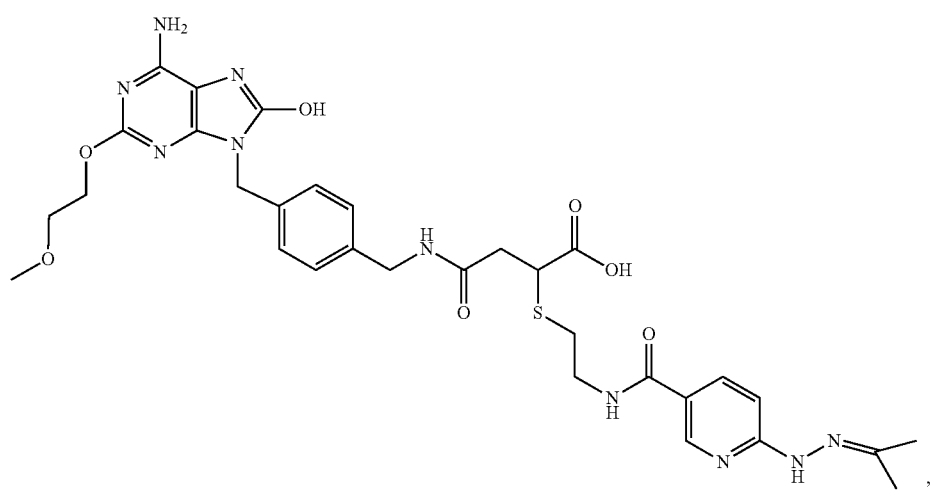

SZU-163
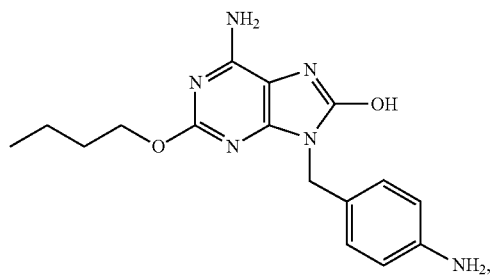
SZU-166
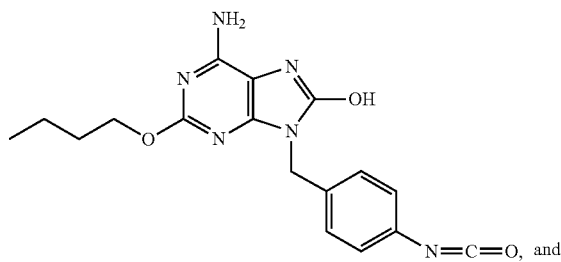
, and
SZU-171
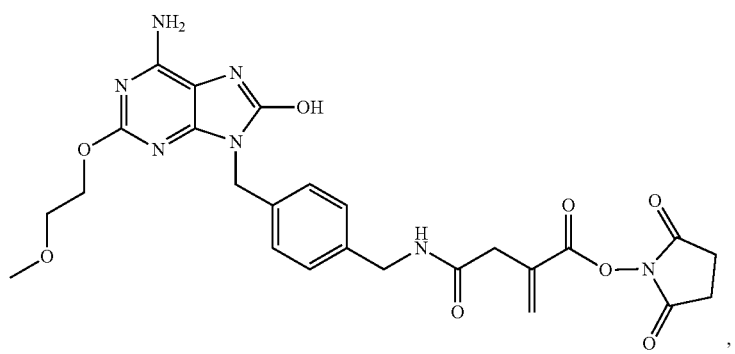
or a pharmaceutically acceptable salt thereof.
2. A method of inducing immunomodulation in a subject in need thereof, the method comprising administering to the subject the small-molecule immune agonist or pharmaceutically acceptable salt thereof according to claim 1 and a compound selected from:
SZU-101
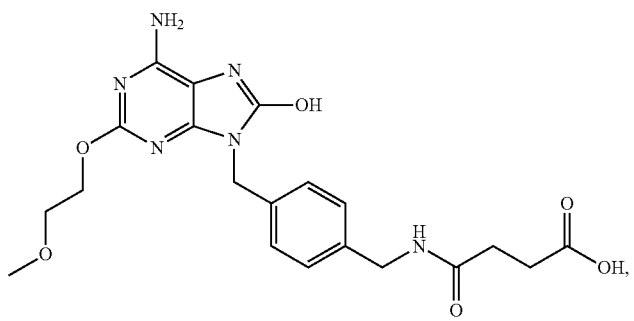
SZU-103
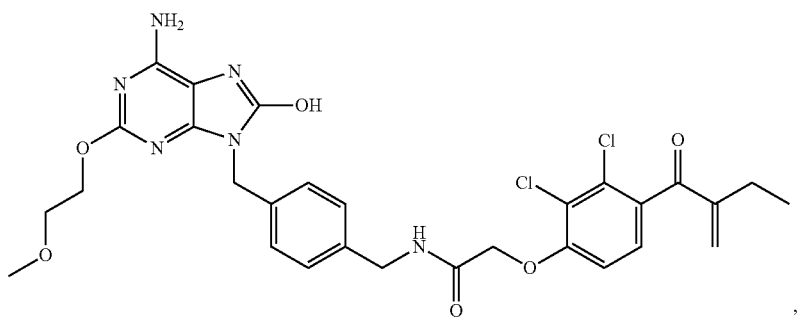
, -continued
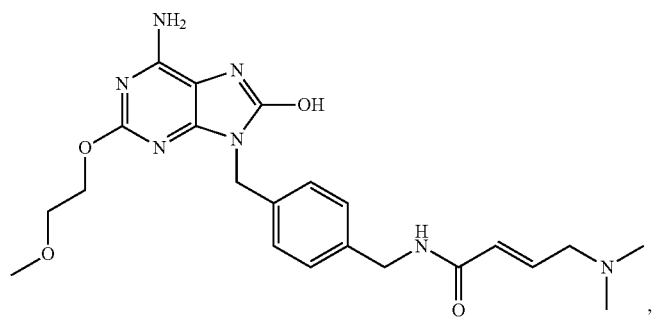
SZU-114
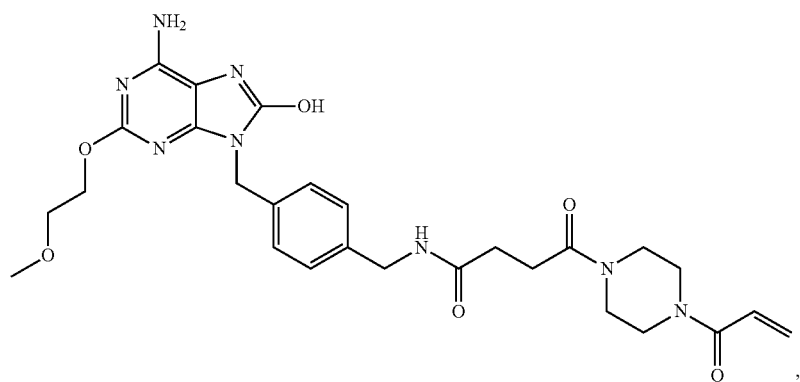
SZU-117
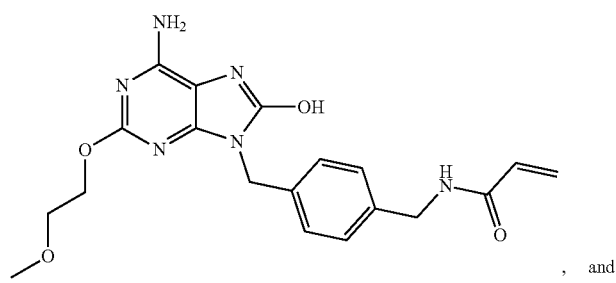
SZU-122
, and
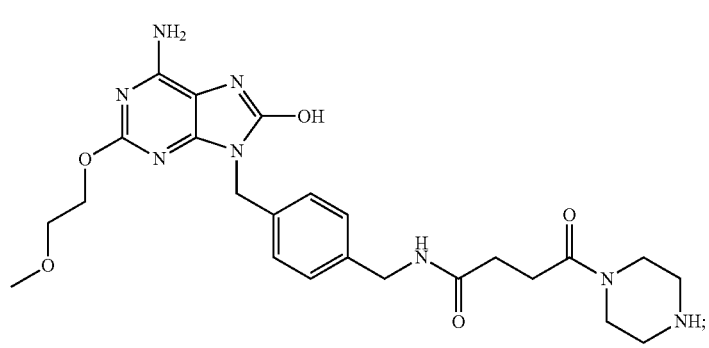
SZU-130

3. A method for treating a tumor or for defending against a virus in a subject in need thereof, the method comprising administering to the subject the small-molecule immune agonist or pharmaceutically acceptable salt thereof according to claim 1 and a compound selected from:
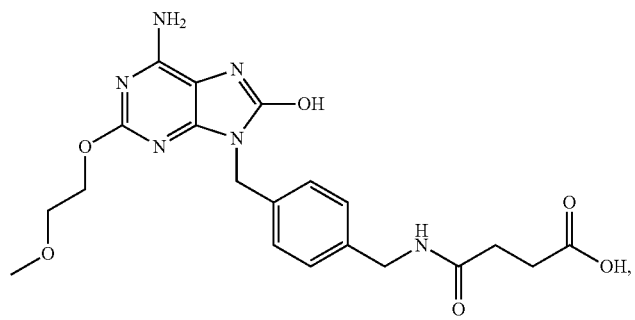
SZU-101
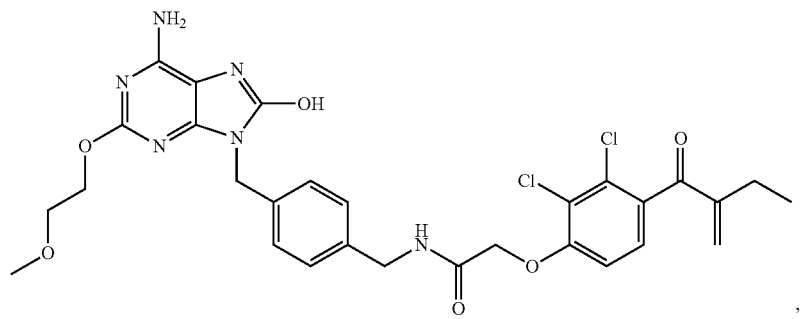
SZU-103
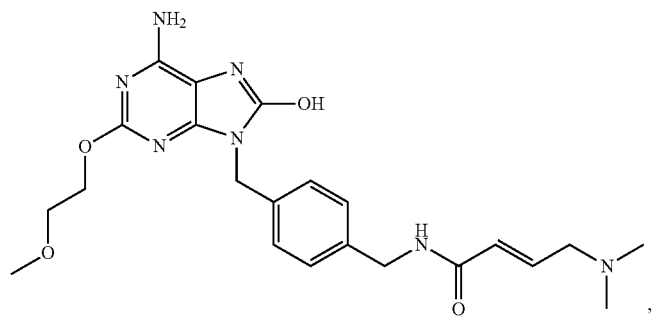
SZU-114
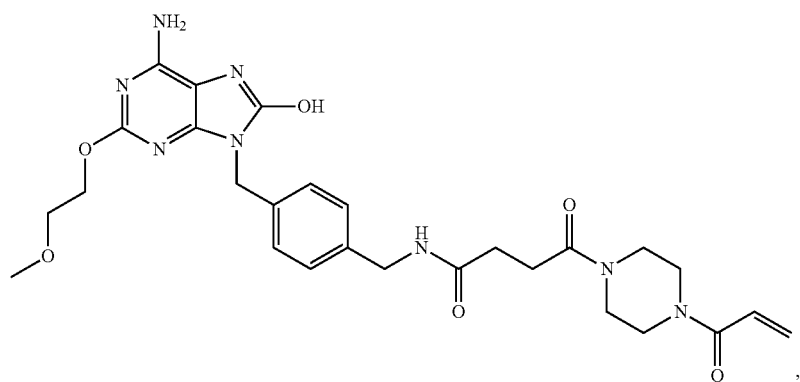
SZU-117

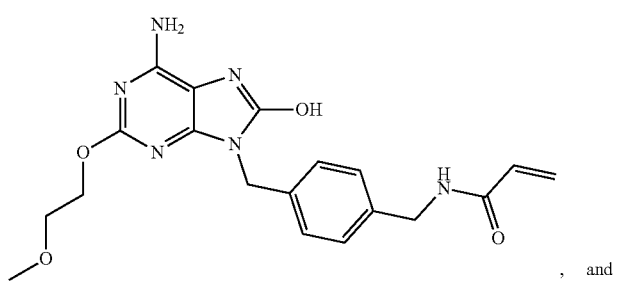
SZU-122
, and
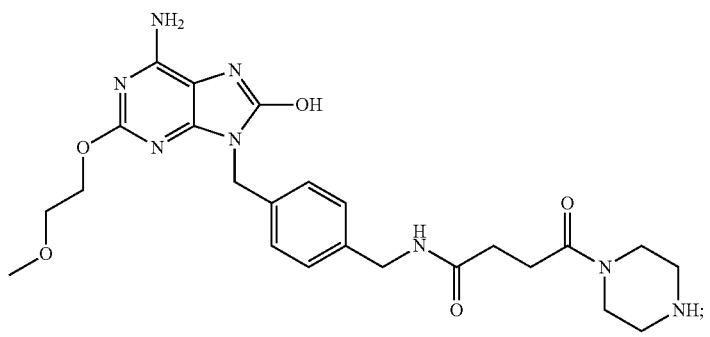
SZU-130
* * * * *